(12) United States Patent
Hallow et al.

(10) Patent No.: US 12,144,795 B2
(45) Date of Patent: Nov. 19, 2024

(54) CANNABIDIOL COMPOSITIONS HAVING MODIFIED CANNABINOID PROFILES

(71) Applicant: PURISYS LLC, Athens, GA (US)

(72) Inventors: Daniel M. Hallow, Bishop, GA (US); Jun He, Watkinsville, GA (US); Mark C. Dobish, Watkinsville, GA (US); Denis Petrovic, Schaffhausen (CH); Gnel Mkrtchyan, Watkinsville, GA (US)

(73) Assignee: PURISYS LLC, Athens, GA (US)

( * ) Notice: Subject to any disclaimer, the term of this patent is extended or adjusted under 35 U.S.C. 154(b) by 538 days.

(21) Appl. No.: 17/273,643

(22) PCT Filed: Sep. 5, 2019

(86) PCT No.: PCT/US2019/049810
§ 371 (c)(1),
(2) Date: Mar. 4, 2021

(87) PCT Pub. No.: WO2020/051371
PCT Pub. Date: Mar. 12, 2020

(65) Prior Publication Data
US 2022/0218651 A1 Jul. 14, 2022

Related U.S. Application Data

(60) Provisional application No. 62/727,442, filed on Sep. 5, 2018, provisional application No. 62/882,177, filed on Aug. 2, 2019.

(51) Int. Cl.
*A61K 31/352* (2006.01)
*A61K 31/05* (2006.01)

(52) U.S. Cl.
CPC ............ *A61K 31/352* (2013.01); *A61K 31/05* (2013.01)

(58) Field of Classification Search
CPC .. A61K 31/352; A61K 31/05; C07B 2200/13; C07C 2601/16; C07C 37/00; C07C 37/14; C07C 37/84; C07C 39/23; C07C 37/62
See application file for complete search history.

(56) References Cited

U.S. PATENT DOCUMENTS 9,956,185 B2    5/2018  Guy et al.
2010/0016418 A1 1/2010  Guy et al.
(Continued)

FOREIGN PATENT DOCUMENTS

JP    2009-510078 A    3/2009
JP    2018-522944 A    8/2018
(Continued)

OTHER PUBLICATIONS

Ones et al: "Cannabidiol", Acta Cryst., vol. 33, 1977, pp. 3211-3214. (Year: 1977).*

(Continued)

*Primary Examiner* — Deborah D Carr
(74) *Attorney, Agent, or Firm* — Alston & Bird LLP

(57) ABSTRACT

The present disclosure relates to the preparation of a highly pure cannabidiol compound by a novel synthesis route. The cannabidiol compound can be prepared by an acid-catalyzed reaction of a di-halo olivetol with menthadienol, followed by two crystallization steps. The highly pure cannabidiol compound is produced in high yield, stereospecificity, or both, and shows exceedingly low levels of Δ-9-tetrahydrocannabinol at the time of preparation and after storage.

20 Claims, 65 Drawing Sheets

(56) References Cited

U.S. PATENT DOCUMENTS

2011/0082195 A1    4/2011  Guy et al.
2017/0008868 A1*   1/2017  Dialer ...................... A61P 3/10

FOREIGN PATENT DOCUMENTS

WO    WO 2007/041167    4/2007
WO    WO 2017/011210    1/2017

OTHER PUBLICATIONS

Jones et al., "Cannabidiol," Acta Cryst., B33:3211-3214, (Jan. 1, 1977).
WIPO Application No. PCT/US2019/049810, PCT International Preliminary Report on Patentability mailed Mar. 18, 2021.
WIPO Application No. PCT/US2019/049810, PCT International Search Report and Written Opinion of the International Searching Authority mailed Apr. 3, 2020.

* cited by examiner

| | NQS1803 | | |
|---|---|---|---|
| Atom number | Proton chemical shift (ppm) | Carbon chemical shift (ppm) | NOE |
| 1 | | 156.1 | |
| 2,4 | 6.015 | 106.5 | OH,α,β |
| 3 | | 140.1 | |
| 4a | | 156.1 | |
| 6 | | 149.2 | |
| 6a | 3.029 | 43.7 | 7,8,10,10a,13 |
| 7 | 1.66/1.60 | 29.6 | 6a,8,10a,13 |
| 8 | 2.10/1.918 | 30.5 | 6a,7,10 |
| 9 | | 130.1 | |
| 10 | 5.092 | 126.8 | 6a,8,10a,11 |
| 10a | 3.829 | 35.6 | 6a,7,10,13 |
| 10b | | 114.3 | |
| 11 | 1.598 | 23.1 | 10 |
| 12 | 1.587 | 19.3 | |
| 13 | 4.491/4.406 | 109.4 | 6a,7,10a |
| OH-1,4a | 8.640 | | 2,4 |
| α | 2.301/2.301 | 35.1 | 2,4 |
| β | 1.469/1.469 | 30.5 | 2,4 |
| γ | 1.25/1.25 | 31.2 | |
| δ | 1.286/1.286 | 22.2 | |
| ε | 0.859 | 14.2 | |

| | |
|---|---|
| Particle Name:<br>Cannabidiol (CBD)<br>Particle RI:<br>1.530<br>Dispersant Name: | Accessory Name:<br>Scirocco 2000<br>Absorption:<br>0.01<br>Dispersant RI:<br>1.000 | Analysis model:<br>General purpose (fine)<br>Size range:<br>0.050 to 2000.000 um<br>Weighted Residual:<br>0.145 % | Sensitivity:<br>Enhanced<br>Obscuration:<br>2.19 %<br>Result Emulation:<br>Off |
| Concentration:<br>0.0014 %Vol<br>Specific Surface Area:<br>0.282 m²/g | Span:<br>2.831<br>Surface Weighted Mean D[3,2]:<br>21.305 um | Uniformity:<br>0.912<br>Vol Weighted Mean D[4,3]:<br>52.676 um | Result units:<br>Volume |
| d(0.1): 10.493 um | d(0.5): 36.575 um | d(0.9): 114.044 um | |

FIG. 8C

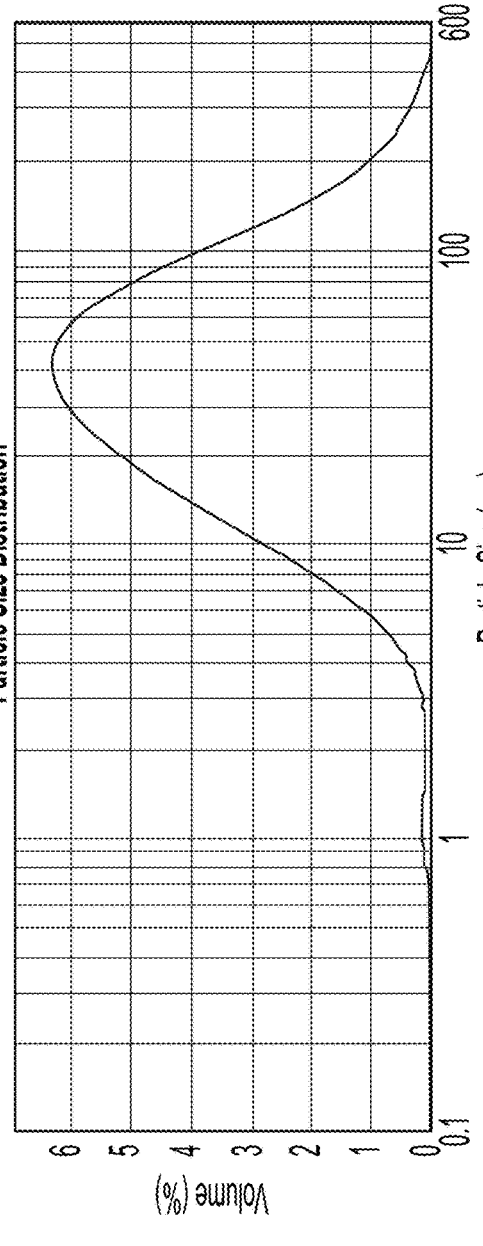

FIG. 8D

| Particle Name: Cannabidiol (CBD) | Accessory Name: Scirocco 2000 | Analysis model: General purpose (fine) | Sensitivity: Enhanced |
|---|---|---|---|
| Particle RI: 1.530 | Absorption: 0.01 | Size range: 0.050 to 2000.000 um | Obscuration: 1.83 % |
| Dispersant Name: | Dispersant RI: 1.000 | Weighted Residual: 0.276 % | Result Emulation: Off |
| d(0.1): 2.579 um | | d(0.5): 5.980 um | d(0.9): 15.181 um |

| Analysis | |
|---|---|
| SOP Analysis: 3.0 | SOP Fill Holes: True |
| SOP Segmentation: None | SOP Trash Size: 10 |
| SOP Optic(s) used: 5x | |
| Result | |
| CE Diameter Minimum (μm): 2.16 | CE Diameter D[v, 0.1]: 22.98 |
| CE Diameter Maximum (μm): 142.17 | CE Diameter D[v, 0.5]: 60.39 |
| CE Diameter D[4,3] (μm): 63.67 | CE Diameter D[v, 0.9]: 111.2 |
| CE Diameter D[3,2] (μm): 44.19 | CE Diameter STDV (μm): 13.20 |
| Particles Counted: 19696 | CE Diameter RSD (%): 91.34 |

| Analysis | |
|---|---|
| SOP Analysis: 3.0 | SOP Fill Holes: True |
| SOP Segmentation: None | SOP Trash Size: 10 |
| SOP Optic(s) used: 5x | |
| Result | |
| CE Diameter Minimum (μm): 2.16 | CE Diameter D[v, 0.1]: 41.3 |
| CE Diameter Maximum (μm): 193.90 | CE Diameter D[v, 0.5]: 103.2 |
| CE Diameter D[4,3] (μm): 102.1 | CE Diameter D[v, 0.9]: 157.7 |
| CE Diameter D[3,2] (μm): 75.06 | CE Diameter STDV (μm): 21.05 |
| Particles Counted: 5154 | CE Diameter RSD (%): 118.00 |

| Analysis | |
|---|---|
| SOP Analysis: 3.0 | SOP Fill Holes: True |
| SOP Segmentation: None | SOP Trash Size: 10 |
| SOP Optic(s) used: 5x | |
| Result | |
| CE Diameter Minimum (µm): 2.16 | CE Diameter D[v, 0.1]: 14.87 |
| CE Diameter Maximum (µm): 124.91 | CE Diameter D[v, 0.5]: 52.07 |
| CE Diameter D[4,3] (µm): 54.22 | CE Diameter D[v, 0.9]: 96.89 |
| CE Diameter D[3,2] (µm): 32.15 | CE Diameter STDV (µm): 7.95 |
| Particles Counted: 51760 | CE Diameter RSD (%): 93.43 |

| Analysis | |
|---|---|
| SOP Analysis: 3.0 | SOP Fill Holes: True |
| SOP Segmentation: None | SOP Trash Size: 10 |
| SOP Optic(s) used: 5x | |
| Result | |
| CE Diameter Minimum (μm): 2.16 | CE Diameter D[v, 0.1]: 15.93 |
| CE Diameter Maximum (μm): 49.83 | CE Diameter D[v, 0.5]: 32.47 |
| CE Diameter D[4,3] (μm): 32.08 | CE Diameter D[v, 0.9]: 44.9 |
| CE Diameter D[3,2] (μm): 26.28 | CE Diameter STDV (μm): 8.99 |
| Particles Counted: 5088 | CE Diameter RSD (%): 87.82 |

| Analysis | |
|---|---|
| SOP Analysis: 3.0 | SOP Fill Holes: True |
| SOP Segmentation: None | SOP Trash Size: 10 |
| SOP Optic(s) used: 5x | |
| Result | |
| CE Diameter Minimum (μm): 2.16 | CE Diameter D[v, 0.1]: 20.76 |
| CE Diameter Maximum (μm): 165.74 | CE Diameter D[v, 0.5]: 51.78 |
| CE Diameter D[4,3] (μm): 55.55 | CE Diameter D[v, 0.9]: 93.77 |
| CE Diameter D[3,2] (μm): 38.68 | CE Diameter STDV (μm): 11.57 |
| Particles Counted: 44801 | CE Diameter RSD (%): 91.81 |

Analysis

SOP Analysis: 3.0  SOP Fill Holes: True

SOP Segmentation: None  SOP Trash Size: 10

SOP Optic(s) used: 5x

Result

CE Diameter Minimum (µm): 2.16  CE Diameter D[v, 0.1]: 8.236

CE Diameter Maximum (µm): 49.97  CE Diameter D[v, 0.5]: 19.88

CE Diameter D[4,3] (µm): 23.41  CE Diameter D[v, 0.9]: 43.32

CE Diameter D[3,2] (µm): 15.77  CE Diameter STDV (µm): 4.78

Particles Counted: 126623  CE Diameter RSD (%): 70.59

| Analysis | |
|---|---|
| SOP Analysis: 3.0 | SOP Fill Holes: True |
| SOP Segmentation: None | SOP Trash Size: 10 |
| SOP Optic(s) used: 10x | |
| Result | |
| CE Diameter Minimum (µm): 1.09 | CE Diameter D[v, 0.1]: 4.189 |
| CE Diameter Maximum (µm): 8.49 | CE Diameter D[v, 0.5]: 6.767 |
| CE Diameter D[4,3] (µm): 6.491 | CE Diameter D[v, 0.9]: 8.132 |
| CE Diameter D[3,2] (µm): 5.958 | CE Diameter STDV (µm): 2.07 |
| Particles Counted: 37474 | CE Diameter RSD (%): 50.07 |

CANNABIDIOL COMPOSITIONS HAVING MODIFIED CANNABINOID PROFILES

CROSS-REFERENCE TO RELATED APPLICATIONS

This application is a 35 U.S.C. § 371 national stage of International Application No. PCT/US2019/049810, filed Sep. 5, 2019, which claims the benefit of priority to U.S. Provisional Application No. 62/727,442, filed Sep. 5, 2018 and U.S. Provisional Application No. 62/882,177, filed Aug. 2, 2019, which are herein incorporated by reference in their entirety for all purposes.

FIELD

The subject matter described herein relates to the preparation of a highly purified cannabidiol compound by novel synthesis routes. The highly purified cannabidiol compound is produced in high yield, stereospecificity, or both, and shows exceedingly low levels of Δ-9-tetrahydrocannabinol at the time of preparation and after storage.

BACKGROUND

More than 100 phytocannabinoids have been isolated to date. See Pertwee, et al. "Hand book of *Cannabis*," Oxford University Press, First Edition 2014, ISBN 978-0-19-966268-5. Phytocannabinoids are cannabinoids that originate from nature and can be found in the *Cannabis* plant. These compounds have been investigated based, in part, on their availability from a natural source. The term "cannabinoids" generally refers to not only the chemical substances isolated from *C. sativa* L exhibiting the typical C21 terpenophilic skeleton, but also to their derivatives and transformation products.

In addition to the historical and anecdotal medicinal use of cannabinoids, the FDA has approved cannabinoid based products, such as MARINOL and a number of other regulatory agencies have approved SATIVEX. Many other cannabinoids are being investigated by the mainstream pharmaceutical industry for various indications. Examples of cannabinoids either approved for clinical use or in clinical trials include EPIDIOLEX (e.g., cannabidiol) for Dravet Syndrome and Lennox-Gastaut Syndrome; cannabidivarin for epilepsy; and tetrahydrocannabidivarin for diabetes.

Considerable research has been directed towards the preparation of cannabinoids via a synthetic route, thereby eliminating the need to obtain the material through the extraction of natural resources. However, often preparations that contain cannabinoids also contain Δ-9-tetrahydrocannabinol. It is generally accepted that Δ-9-tetrahydrocannabinol causes the "high" typically observed in recreational *Cannabis* use, serving as the primary psychoactive ingredient in marijuana. One of the main complications in synthesizing cannabinoids has been the uncontrolled conversion of intermediate compounds to cyclized products, such as Δ-9-tetrahydrocannabinol. The noncrystalline nature of cannabinoids has further limited their availability purity. Accordingly, a stock of pure synthetic material is necessary to investigate the pharmacological effects of cannabinoids, as well as to facilitate accurately reproducible doses of the active ingredient to be used for its pharmacological properties.

The present disclosure relates to the preparation of a cannabidiol compound using a novel synthesis route to produce a highly purified cannabidiol compound in high yield, stereospecificity, or both, with exceedingly low levels of Δ-9-tetrahydrocannabinol at the time of preparation and after storage.

BRIEF SUMMARY

In one aspect, the subject matter described herein is directed to a composition comprising cannabidiol and delta-9-tetrahydrocannabinol, wherein said delta-9-tetrahydrocannabinol is present in an amount less than 10 ppm.

Another aspect of the subject matter described herein is a composition comprising cannabidiol and delta-9-tetrahydrocannabinol, wherein said delta-9-tetrahydrocannabinol is present in an amount less than 10 ppm upon storage for 2 years or less.

Another aspect of the subject matter described herein is a composition comprising cannabidiol and less than 10 ppm delta-9-tetrahydrocannabinol, wherein the ratio of cannabidiol to delta-9-tetrahydrocannabinol is less than 1:0.00001 as measured by HPLC.

Another aspect of the subject matter described herein is a formulation comprising cannabidiol and delta-9-tetrahydrocannabinol, wherein said delta-9-tetrahydrocannabinol is present in an amount less than 10 ppm, and a pharmaceutically acceptable excipient.

Another aspect of the subject matter described herein is a method of preparing crystalline cannabidiol characterized by a X-ray powder diffraction pattern substantially as depicted in FIG. 11A and having less than 10 ppm delta-9-tetrahydrocannabinol, comprising crystalizing the cannabidiol from isooctane.

Another aspect of the subject matter described herein is a method of preparing a cannabidiol composition, comprising
  contacting di-halo olivetol with menthadienol in the presence of a protic acid catalyst to prepare di-halo cannabidiol;
  contacting the di-halo cannabidiol with a reducing agent to prepare a first cannabidiol composition;
  contacting the first cannabidiol composition with a first solvent;
  crystallizing a second cannabidiol composition from said first solvent; and
  recrystallizing a crystalline cannabidiol composition having less than 10 ppm delta-9-tetrahydrocannabinol from a second solvent.

Another aspect of the subject matter described herein is a method of recrystallizing cannabidiol from a mixture of cannabinoids to prepare a composition comprising cannabidiol and less than 10 ppm delta-9-tetrahydrocannabinol, said method comprising,
  contacting said mixture of cannabinoids, for example, cannabidiol and THC, with isooctane to form a solution;
  heating said solution to about 40° C.;
  cooling the solution to about 32° C.;
  seeding said solution at about 32° C. with (−)-Cannabidiol to prepare a suspension;
  allowing said suspension to warm to about 32° C. with stirring;
  cooling the suspension to about −20° C.;
  separating a solid material from said suspension;
  washing the solid material with isooctane at about −20° C.; and
  drying the solid material to obtain a crystalline composition comprising cannabidiol and less than 10 ppm delta-9-tetrahydrocannabinol.

Another aspect of the subject matter described herein is a method of treating a disease in a subject comprising,
administering to said subject a composition comprising a therapeutic amount of cannabidiol and an amount of delta-9-tetrahydrocannabinol, wherein said amount of delta-9-tetrahydrocannabinol is less than about 20 µg per day.

These and other aspects are further described herein.

BRIEF DESCRIPTION OF THE FIGURES

FIG. 8C shows the particle size distribution result analysis report for crude cannabidiol produced by Protocol 3, which did not undergo recrystallization (sample 8).

FIG. 8D shows the particle size graph for the sample analyzed in FIG. 8C.

DETAILED DESCRIPTION

Figure 1:
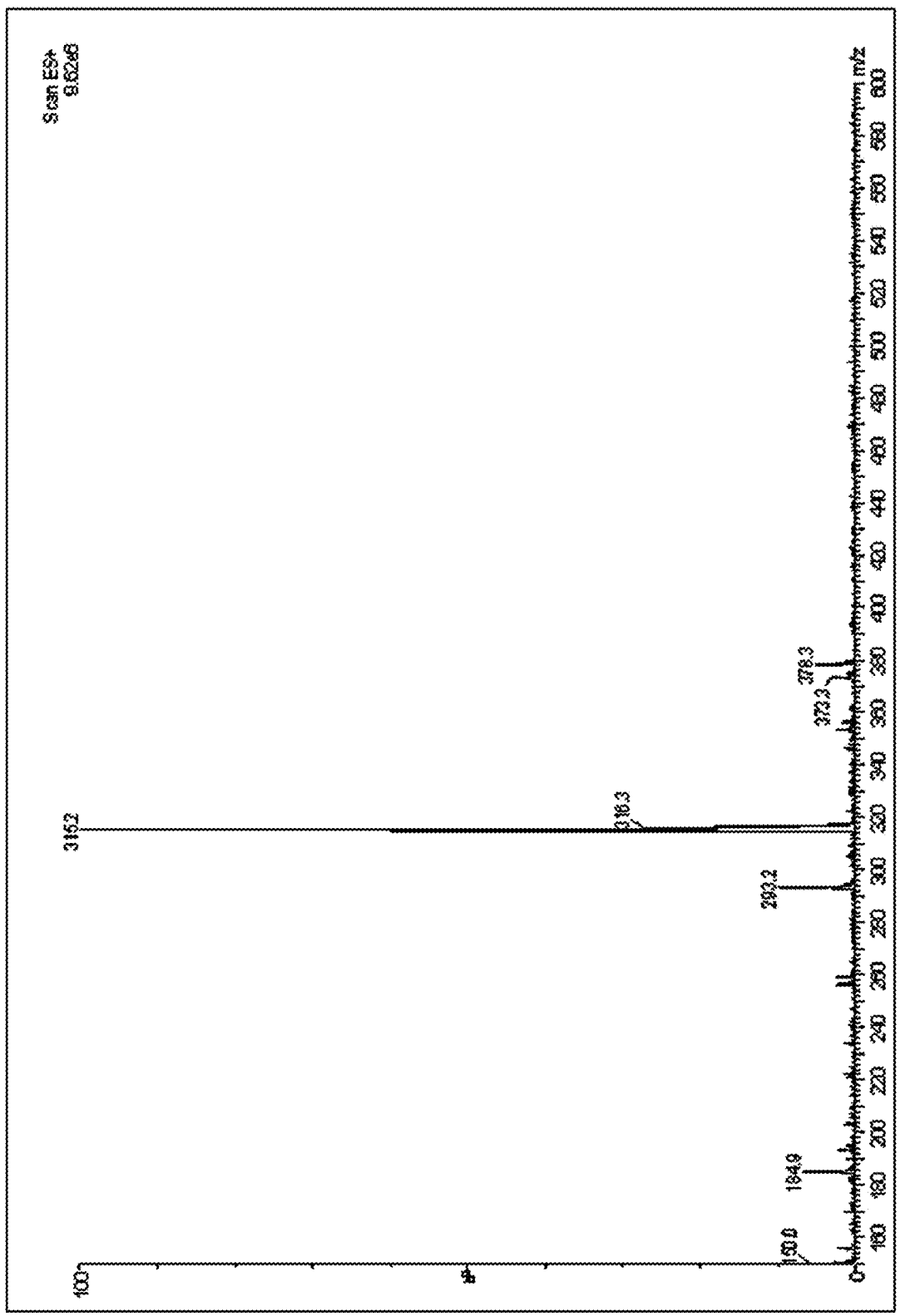
FIG. 1 shows a Liquid Chromatography Mass Spectrum of cannabidiol generated by Protocol 1. The sample underwent recrystallization in n-heptane before analysis.

Disclosed herein are novel synthesis routes to produce a highly purified cannabidiol compound in high yield, stereospecificity, or both. The highly purified cannabidiol compound shows exceedingly low levels of Δ-9-tetrahydrocannabinol at the time of preparation and after storage. The synthetic routes yield new compositions having heretofore unattainable levels of cannabidiol and Δ-9-tetrahydrocannabinol and optionally other cannabinoids such that the composition exhibits unexpected properties, such as low-levels of THC and long-term stability that maintains low-levels of THC over extended periods of time. Such long-term stability whereby the level of Δ-9-tetrahydrocannabinol remains below 10 ppm is advantageous as the level of Δ-9-tetrahydrocannabinol would be expected to increase over time. Any pharmaceutical preparation containing cannabidiol would potentially have increasing levels of Δ-9-tetrahydrocannabinol such that the preparation may not be suitable for administration. In particular, such levels of Δ-9-tetrahydrocannabinol may limit the amount of cannabidiol that can be administered because Δ-9-tetrahydrocannabinol accumulates in the body and would reach unwanted levels, e.g., above about 20 μg per day.

Many different routes to produce cannabinoids and related compounds have been reported. One route involves variations on the Lewis-acid catalyzed Friedel Crafts alkylation of olivetol with menthadienol. For example, U.S. Pat. No. 5,227,537 describes a reaction of equimolar quantities of olivetol and menthadienol in the presence of p-toluenesulfonic acid catalyst which resulted in a 44% yield of cannabidiol after purification by column chromatography. U.S. Pat. No. 7,674,922 describes a similar reaction using a Lewis acid catalyst instead of p-toluenesulfonic acid which results in the formation of significant amounts of the unwanted cannabidiol isomer along with cannabidiol. The reaction route described in the '922 patent resulted in a 47% yield of the desired cannabidiol, a 17.9% yield of the cannabidiol, and 23% of unreacted olivetol.

In addition, U.S. Pat. No. 3,562,312 describes improved selectivity for the formation of cannabidiol by reacting 6-carbethoxyolivetol with a slight excess of menthadienol in methylene chloride in the presence of dimethylformamide, dineopentylacetal as catalyst. This route resulted in a 42% yield of cannabidiol-carboxylic acid ethyl ester after purification by chromatography.

Another route for the preparation of cannabidiols involves the use of carboxylic acid esters as protecting/directing groups on olivetol analogues. See, e.g., Crombie, L. et al., in *J. Chem. Research* (S) 114, (M), pp 1301-1345 (1977). In a first step, alkylresorcyl esters (e.g., 6-alkyl-2,4-di-hydroxy-benzoic esters) are condensed with unsaturated hydrocarbons, alcohols, ketones, or derivatives thereof such as enol esters, enol ethers and ketals, in high yields to give the corresponding 3-substituted 6-alkyl-2,4-dihydroxybenzoic esters. These routes of preparation have been referred to as acid-catalyzed terpenylation. In a second step, the intermediates with an ester function obtained in the first step are subjected to a decarboxylating hydrolysis, which forms the ester-free cannabinoids.

For example, improvements in selectivity have been achieved by protecting the 4 position of the olivetol related compounds with a carboxylic acid ester. The '922 patent describes the preparation of ethyl cannabidiolate in 82% yield and 93.3% (AUC) purity. After NaOH hydrolysis, however, the route resulted in a 57.5% yield and 99.8% purity (AUC). The '922 patent also describes the need to purify the cannabidiols formed, e.g., Δ-9-tetrahydrocannabinol, by esterification of the free hydroxyl followed by purification of the cannabidiol ester, e.g., Δ-9-tetrahydrocannabinol ester. Purification was performed by crystallization followed by hydrolysis of the ester to Δ-9-tetrahydrocannabinol. Such steps were required to achieve a purity necessary for pharmaceutical use.

The art demonstrates the difficulties of manufacturing cannabidiol compounds in high yield, high stereospecificity, or both. The causes of these difficulties can include the non-crystalline nature of the materials, which renders them difficult or impossible to separate and purify without chromatography. Also, the aromatic portion of the cannabidiol molecule is sensitive to oxidation. As such, the presence of oxidized cannabidiol products, including cannabidiol quinone derivatives (CBQ), require additional investigation. Abnormal-cannabidiol (Ab-CBD), a regioisomer of cannabidiol, is another impurity often found in synthetic cannabidiol compositions.

The processes of the present disclosure provide a number of advantages over current methods for synthesizing pure cannabidiol compositions. As described in the art, the Lewis acid catalyzed condensation of olivetol or olivetolate esters with menthadienol to prepare cannabidiol or cannibidiolate esters suffers from poor selectivity, low yields, and mixtures of isomers requiring tedious purification procedures. The processes of the present disclosure can achieve high yield, high purity or both without the need to use organo-aluminum Lewis acid catalysts. The processes of the present disclosure, for instance, can use a wide selection of catalysts, such as p-toluenesulfonic acid. In the present disclosure, moreover, both of the 4 and 6 positions of olivetol can be blocked with a halogen selected from the group consisting of Br, F, I and Cl. The position can be blocked to control the conversion and prevent the formation of unwanted cannabidiol isomers. In addition, the process can be designed, such as by using excess equivalents of menthadienol relative to a halogen substituted olivetol, to form the corresponding halogen substituted cannabidiol in high yield, high selectivity, or both. The halogen substituted cannabidiol can also remain stable and not undergo uncontrolled conversion to one or more cyclized products. The halogen substituted cannabidiol can also be easily converted to cannabidiol by contacting it with a suitably selected reducing agent under mild conditions.

As previously described, the non-crystalline nature of cannabidiol has limited its ability to undergo purification processes. It is generally accepted that the difficulty in crystallizing a substance is oftentimes related to the material's solubility. The processes of the present disclosure demonstrate that in a suitable solvent and under the conditions described herein, cannabidiol can be recrystallized in high yield with exceedingly low levels of Δ-9-tetrahydrocannabinol. It is further shown that these cannabidiol compositions are relatively free of cannabidiol quinone and abnormal-cannabidiol impurities.

As described herein, re-crystallization of a cannabidiol composition can purge THC to exceedingly low levels. When coupled with the synthetic routes disclosed herein, the recrystallization has been shown to achieve an enriched cannabidiol composition having as low as about 1.9 ppm THC and a modified cannabidiol profile. The data disclosed herein show that the synthetic steps involved in the preparation of the cannabidiol compositions provide desirably low levels of THC, which levels can be further lowered through the re-crystallization process under the parameters disclosed. The synthetic methods involve particular reagents, solvents and conditions, such as counter-intuitively the use of warmer temperatures, that surprisingly attain the desired cannabidiol compositions without substantial conversion to the degradant, THC. The compositions also possess high stability as shown by the data disclosed herein.

The cannabidiol compositions disclosed herein additionally exhibit reduced levels of olivetol. It has been observed that olivetol purges poorly during crystallization. Advantageously, it has been discovered that the present methods can reduce the amount of olivetol impurities in crude cannabidiol with activated carbon prior to crystallization. As such, the combined recrystallization and activated carbon applications in the methods disclosed herein provide cannabidiol compositions in both high yields and purity.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used herein, "stable" in relation to a solution or composition is intended to mean that the CBD is not readily decomposing to degradants beyond a maximum specified level under certain parameters. Advantageously, the compositions described herein maintain levels of THC below about 10 ppm over extended periods of time.

As used herein, "CBD" refers to cannabidiol, including all stereoisomers. In certain embodiments, the cannabidiol is (1'R,2'R)-5'-methyl-4-pentyl-2'-(prop-1-en-2-yl)-1',2',3',4'-tetrahydro-[1,1'-biphenyl]-2,6-diol, which is also referred to herein as (−)-Cannabidiol.

As used herein, "Dibromo-CBD" refers to 3,5-dibromo-5-methyl-4-pentyl-T-(prop-1-en-2-yl)-1',2',3',4'-tetrahydro-[1,1'-biphenyl]-2,6-diol.

As used herein, "CBQ" refers to cannabidiol quinone derivatives.

As used herein, "Ab-CBD" refers to abnormal cannabidiol.

As used herein, "IPC" refers to In Process Control.

As used herein, "API" refers to Active Pharmaceutical Ingredient.

As used herein, "cCBD" refers to crude cannabidiol.

As used herein, "pCBD" refers to pure cannabidiol.

As used herein, "AAC" refers to accelerated ageing conditions.

As used herein, "HT-PXRD" refers to high throughput powder X-ray diffraction.

As used herein, "NMT" refers to "not more than."

As used herein, "FIO" refers to "for information only."

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human.

As used herein, the term "therapeutic amount" refers to an amount of a therapeutic agent, compound, formulation, material, or composition, as described herein effective to achieve a particular biological result. Such results may include, but are not limited to, the inhibition of a disease as determined by any means suitable in the art.

As used herein, the term "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

As used herein. "r.h." refers to relative humidity.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, "plant extract" refers to compositions prepared from solvent extractions from the whole *Cannabis* plant or parts thereof.

As used herein, "substantially free" refers to trace amounts or levels of about 1% w/w or less. As used herein, "essentially free" refers to levels that are below trace. In certain embodiments, essentially free refers to amounts not detectable by standard techniques.

Additional definitions are provided below.

II. Compositions

As used herein, 0.0001% of a composition is equivalent to 1 PPM, or 1 part per million, of that composition. For example, a 150 g sample of a composition comprising cannabidiol and 5 ppm delta-9-tetrahydrocannabinol contains 0.0005% or 0.00075 g delta-9-tetrahydrocannabinol. In certain embodiments, compositions described herein can contain 99.9999% cannabidiol, and 0.1 ppm of THC or other component. In certain embodiments, compositions described herein can contain 99.999% cannabidiol, and 1.0 ppm of THC or other component. In certain embodiments, compositions described herein can contain 99.99% cannabidiol, and 10 ppm of THC or other component. The amounts of the components described herein can be determined by any known method, for example, HPLC.

In embodiments, the subject matter described herein is directed to a composition comprising cannabidiol and delta-9-tetrahydrocannabinol, wherein said delta-9-tetrahydrocannabinol is present in an amount less than 10 ppm. In embodiments, the delta-9-tetrahydrocannabinol is present in an amount less than 9 ppm, 8 ppm, 7 ppm, 6 ppm, 5 ppm, 4 ppm, 3 ppm, 2 ppm or 1 ppm. In embodiments, the delta-9-tetrahydrocannabinol is present in an amount from about 0.1 ppm to about 9 ppm, from about 0.1 ppm to about 8 ppm, from about 0.1 ppm to about 7 ppm, from about 0.1 ppm to about 6 ppm, from about 0.1 ppm to about 5 ppm, from about 0.1 ppm to about 4 ppm, from about 0.1 ppm to about 3 ppm, from about 0.1 ppm to about 2 ppm, from about 0.1 ppm to about 1 ppm, or from about 0.2 ppm to about 8 ppm, or from about 0.3 ppm to about 7 ppm, or from about 0.4 ppm to about 6 ppm, or from about 0.5 ppm to about 5 ppm, or from about 0.5 ppm to about 4 ppm, or from about 0.5 ppm to about 6 ppm, or from about 0.5 ppm to about 5 ppm. In embodiments, the subject matter described herein is directed to a composition comprising cannabidiol, delta-9-tetrahydrocannabinol and CBQ, wherein said delta-9-tetrahydrocannabinol is present in an amount less than 0.001% w/w.

In embodiments, the compositions exhibit enhanced stability. In certain embodiments, the compositions comprise cannabidiol and delta-9-tetrahydrocannabinol, wherein said delta-9-tetrahydrocannabinol is present in an amount less than 10 ppm upon storage for 2 years or less, or upon storage for 1 year or less, or upon storage for 6 months or less. In certain embodiments, the compositions comprise cannabidiol and delta-9-tetrahydrocannabinol, wherein said delta-9-tetrahydrocannabinol is present in an amount less than 10 ppm upon storage for at least 1 month, at least 2 months, at least 3 months, at least 4 months, at least 5 months, at least 6 months, at least 9 months, or at least 12 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 1 month. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 2 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 3 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 4 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 5 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 6 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 9 months. In certain embodiments, the compositions comprise cannabidiol and delta-9-tetrahydrocannabinol, wherein said delta-9-tetrahydrocannabinol is present in an amount of about 1 ppm, 2 ppm, 3 ppm, 4 ppm, 5 ppm, 6 ppm, 7 ppm, 8 ppm, or 9 ppm upon storage for at least 12 months. In certain embodiments, samples are stable after storage under room temperature and 60% relative humidity. In certain embodiments, samples are stable after storage under room temperature and 60% relative humidity. In certain embodiments, samples are stable after storage under 40° C. and 75% relative humidity. In certain embodiments, samples are stable after storage in acidic, basic, oxidative, photodegradation, and elevated stress conditions. In embodiments, upon the storage duration mentioned above, the delta-9-tetrahydrocannabinol is present in an amount from about 0.1 ppm to about 9 ppm, from about 0.1 ppm to about 8 ppm, from about 0.1 ppm to about 7 ppm, from about 0.1 ppm to about 6 ppm, from about 0.1 ppm to about 5 ppm, from about 0.1 ppm to about 4 ppm, from about 0.1 ppm to about 3 ppm, from about 0.1 ppm to about 2 ppm, from about 0.1 ppm to about 1 ppm, or from about 0.2 ppm to about 8 ppm, or from about 0.3 ppm to about 7 ppm, or from about 0.4 ppm to about 6 ppm, or from about 0.5 ppm to about 5 ppm, or from about 0.5 ppm to about 4 ppm, or from about 0.5 ppm to about 6 ppm, or from about 0.5 ppm to about 5 ppm.

In embodiments, the subject matter described herein is directed to a composition comprising cannabidiol, delta-9-tetrahydrocannabinol and CBQ, wherein said delta-9-tetrahydrocannabinol is present in an amount less than 10 ppm and CBQ is present in an amount less than 10 ppm. In embodiments, the subject matter described herein is directed to a composition comprising cannabidiol, delta-9-tetrahydrocannabinol and CBQ, wherein said delta-9-tetrahydrocannabinol is present in an amount less than 0.001% w/w and CBQ is present in an amount less than 0.001% w/w. In embodiments, the subject matter described herein is directed to a composition comprising cannabidiol, delta-9-tetrahydrocannabinol and CBQ, wherein said delta-9-tetrahydrocannabinol is present in an amount from about 0.00001% w/w to about 0.001% w/w and CBQ is present in an amount from about 0.00001% to about 0.001% w/w. In certain embodiments, the subject matter described herein is directed to a composition comprising cannabidiol, delta-9-tetrahydrocannabinol and CBQ, wherein said delta-9-tetrahydrocannabinol is present in an amount from about 0.001% w/w to about 5 PPM and CBQ is present in an amount from about 0.001% w/w to about 5 PPM.

In embodiments, the compositions comprise cannabidiol, delta-9-tetrahydrocannabinol and CBQ, wherein said delta-9-tetrahydrocannabinolis is present in an amount less than 10 ppm and the CBQ is present in an amount less than 10 ppm upon storage for 2 years or less, or upon storage for 1 year or less, or upon storage for 6 months or less.

In embodiments, the compositions comprise cannabidiol, delta-9-tetrahydrocannabinol and CBQ, wherein said delta-9-tetrahydrocannabinolis is present in an amount less than 10 ppm and the CBQ is present in an amount less than 10 ppm upon storage for at least 1 month, at least 2 months, at least 3 months, at least 4 months, at least 5 months, at least 6 months, at least 9 months, or at least 12 months.

In embodiments, the compositions comprise cannabidiol and less than 10 ppm delta-9-tetrahydrocannabinol, wherein the ratio of cannabidiol to delta-9-tetrahydrocannabinol is less than 1:0.0001 as measured by HPLC.

In embodiments, the compositions comprise cannabidiol and less than 10 ppm delta-9-tetrahydrocannabinol, wherein the ratio of cannabidiol to delta-9-tetrahydrocannabinol is less than 1:0.0001 as measured by HPLC, and less than 10 ppm CBQ, wherein the ratio of cannabidiol to CBQ is less than 1:0.0001 as measured by HPLC.

In embodiments, the subject matter described herein is directed to a composition comprising cannabidiol and delta-9-tetrahydrocannabinol, wherein the delta-9-tetrahydrocannabinol is present in an amount less than 10 ppm, wherein the cannabidiol is an amorphous solid or a crystalline material. In embodiments, the subject matter described herein is directed to a composition comprising cannabidiol, delta-9-tetrahydrocannabinol, and CBQ, wherein the delta-9-tetrahydrocannabinol is present in an amount less than 10 ppm and CBQ is present in an amount less than 10 ppm, wherein the cannabidiol is an amorphous solid or a crystalline material. In embodiments, the cannabidiol is crystalline.

Figure 11A:
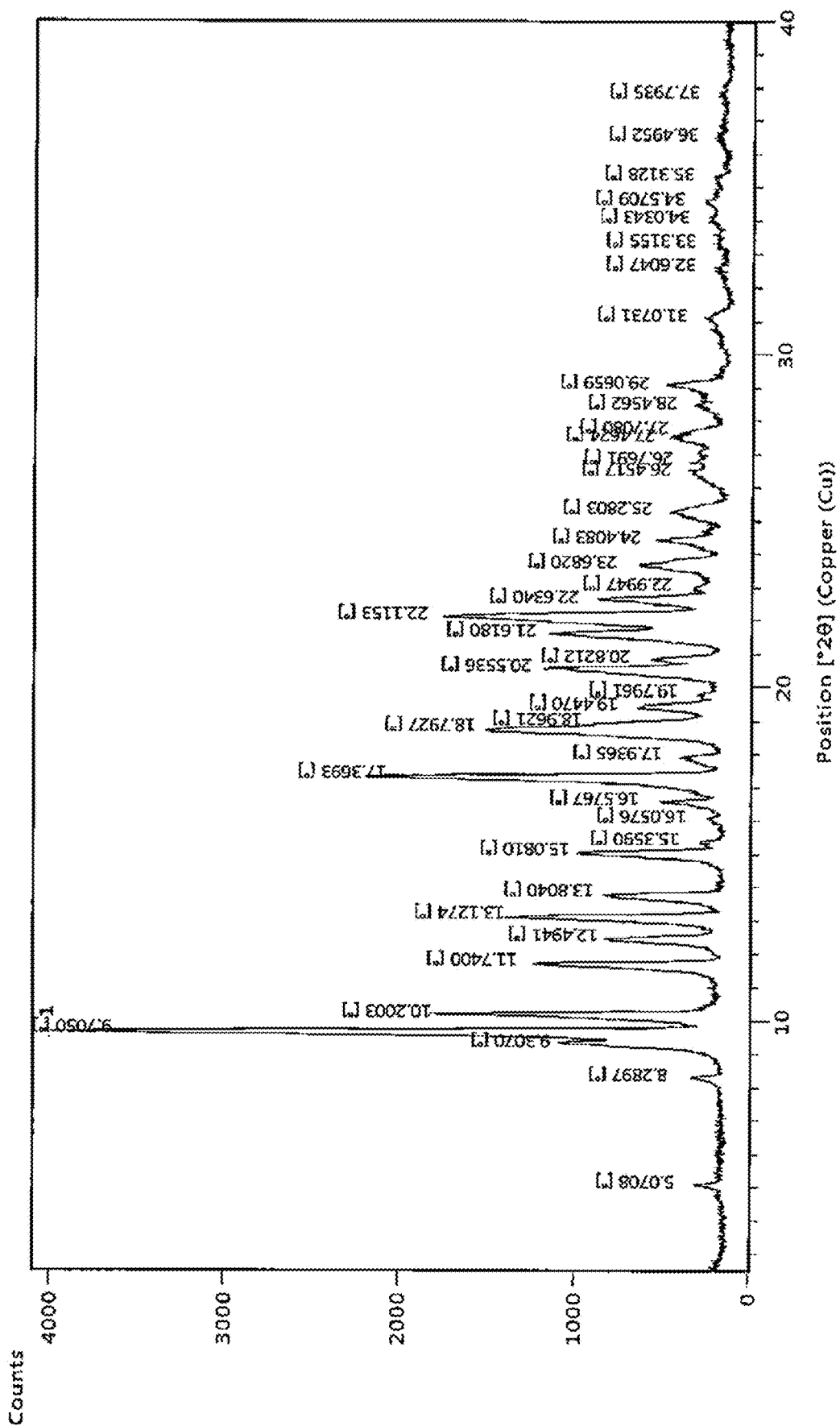
FIG. 11A shows an x-ray pattern of cannabidiol produced by Protocol 1 (sample 9), which underwent recrystallization in isooctane.

When the composition is crystalline, the cannabidiol can be crystalline polymorph Form A. The crystalline polymorph Form A has a X-ray powder diffraction pattern substantially as depicted in FIG. 11A. The crystalline polymorph Form A exhibits a characteristic X-ray powder diffraction pattern with characteristic peaks expressed in 2θ±0.07 at 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

When the composition is crystalline, the cannabidiol can be crystalline polymorph Form A. The crystalline polymorph Form A comprises at least one X-ray powder diffraction peak in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

When the composition is crystalline, the cannabidiol can be crystalline polymorph Form A. The crystalline polymorph Form A comprises at least two X-ray powder diffraction peaks in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

When the composition is crystalline, the cannabidiol can be crystalline polymorph Form A. The polymorph Form A comprises at least three X-ray powder diffraction peaks in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

When the composition is crystalline, the cannabidiol can be crystalline polymorph Form A. The polymorph Form A exhibits a characteristic X-ray powder diffraction pattern having peaks in degrees 2θ±0.07 2θ at 9.70, 11.74, 15.08, 17.36, and 18.79.

When the composition is crystalline, the cannabidiol can be crystalline polymorph Form A. The polymorph Form A exhibits a characteristic X-ray powder diffraction pattern having peaks in degrees 2θ±0.07 2θ at 9.70, 11.74, 12.49, 13.12, 13.80, 15.08, 17.36, 18.79, 20.55, and 22.11.

Figure 12:
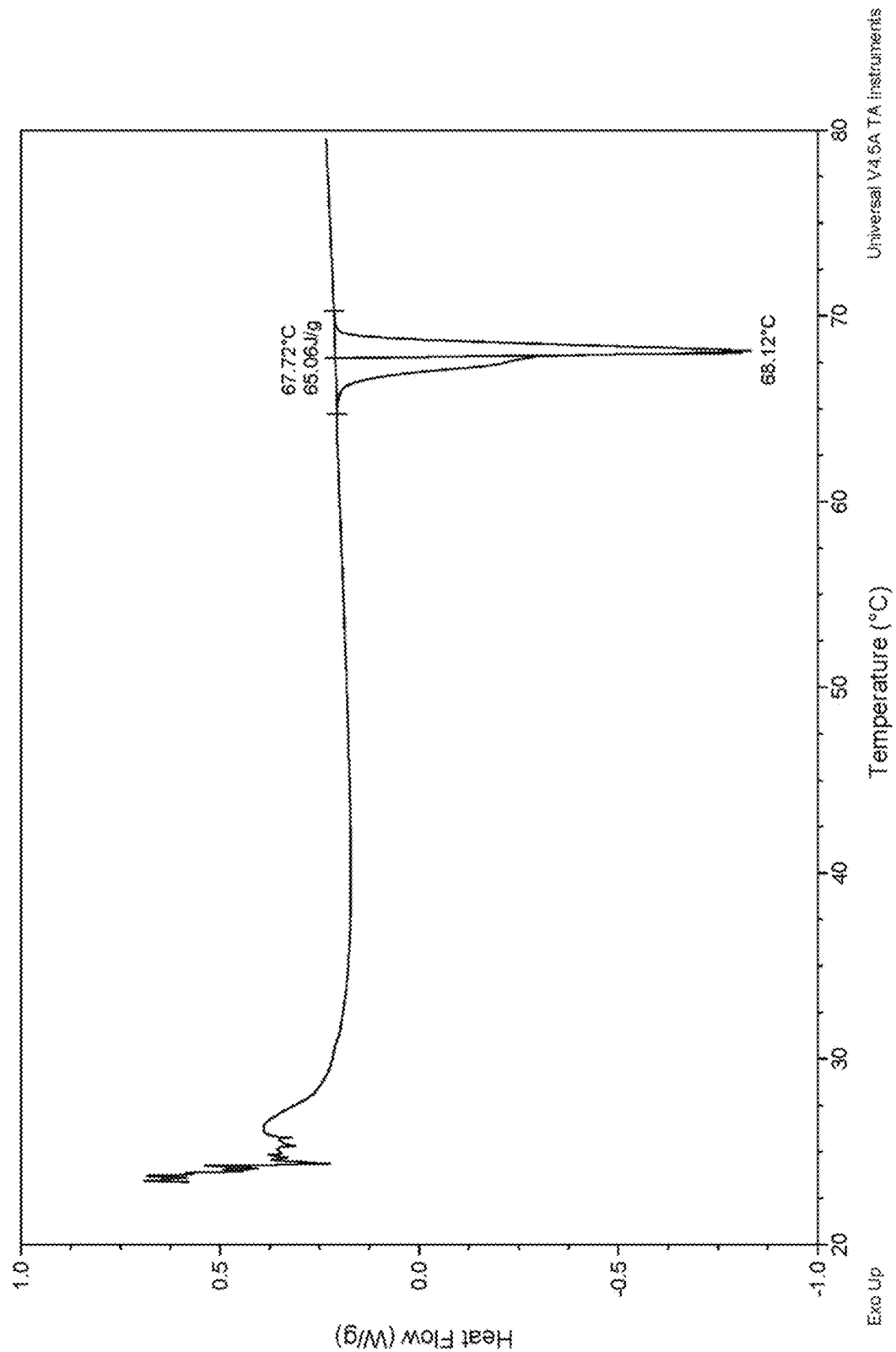
FIG. 12 shows a Differential Scanning calorimetry thermogram of cannabidiol sample 2. This sample was produced by Protocol 3 and underwent recrystallization in isooctane.

When the composition is crystalline, the cannabidiol can be crystalline polymorph Form A characterized by a differential scanning calorimetry thermogram as set forth in FIG. 12. The crystalline polymorph Form A is characterized by a differential scanning calorimetry thermogram with an endotherm having an onset of about 67.72° C. and a peak at about 68.12° C.

The compositions described herein are preferably devoid of *Cannabis* plant extract material. That is, the compositions contain cannabinoids but it is preferred that the compositions expressly do not contain the myriad of undesirable materials that can be contained in an extract from *Cannabis*. Advantageously, the cannabidiol is produced synthetically.

Other cannabinoids that can be present include compounds selected from the group consisting of cannabinol, cannabigerol, delta-8-tetrahydrocannabinol, cannabichromene, cannabicyclol, cannabiyarin, tetrahydrocannabivarin, cannabidivarin, cannabichromevarin, cannabigerovarin, cannabielsoin, cannabicitran, 3,5-dibromo-5'-methyl-4-pentyl-2'-(prop-1-en-2-yl)-1',2',3',4'-tetrahydro-[1,1'-biphenyl]-2,6-diol, 3-bromo-5'-methyl-4-pentyl-2'-(prop-1-en-2-yl)-1',2',3',4'-tetrahydro-[1,1'-biphenyl]-2,6-diol, 4,6-di-bromo olivetol, 4-bromo-5-pentylbenzene-1,3-diol, abnormal cannabidiol (ab-CBD), cannabidiol quinone derivatives (CBQ), 3,5-dibromo-5'-methyl-2'-(prop-1-en-2-yl)-4-propyl-1',2',3',4'-tetrahydro-[1,1'-biphenyl]-2,6-diol, 3,5-dibromo-4-ethyl-5'-methyl-2'-(prop-1-en-2-yl)-1',2',3', 4'-tetrahydro-[1,1'-biphenyl]-2,6-diol, 3-bromo-4-ethyl-5'-methyl-2'-(prop-1-en-2-yl)-1',2',3',4'-tetrahydro-[1,1'-biphenyl]-2,6-diol, 4,6-dibromo-5-propylbenzene-1,3-diol, 4-bromo-5-propylbenzene-1,3-diol, 4,6-dibromo-5-ethylbenzene-1,3-diol, 4-bromo-5-ethylbenzene-1,3-diol, 5'-methyl-2'-(prop-1-en-2-yl)-4-propyl-1',2',3',4'-tetrahydro-[1,1'-biphenyl]-2,6-diol, and 4-ethyl-5'-methyl-2'-(prop-1-en-2-yl)-1',2',3',4'-tetrahydro-[1,1'-biphenyl]-2,6-diol.

Unexpectedly, re-crystallization as described fully herein provides an extraordinary level of purging of THC from the compositions. In certain embodiments, the amount of THC in the compositions containing cannabidiol has been reduced at least 50% w/w, at least 60% w/w, at least 70% w/w, at least 80% w/w, at least 90% w/w, at least 91% w/w, at least 92% w/w, at least 93% w/w, at least 94% w/w, at least 95% w/w, at least 96% w/w, at least 97% w/w, at least 98% w/w, at least 99% w/w, up to about 99.999% w/w reduction in THC levels. Thus, the methods of recrystallizing as set forth herein can include reducing THC in the above amounts. In certain embodiments, the purged compositions contain at least 99.99% cannabidiol and THC at about 10 ppm, or THC at about 9.9 ppm, or THC at about 9.8 ppm, or THC at about 9.7 ppm, THC at about 9.6 ppm, or THC at about 9.5 ppm, or THC at about 9.4 ppm, or THC at about 9.3 ppm, THC at about 9.2 ppm, or THC at about 9.1 ppm, or THC at about 9.0 ppm, or THC at about 8.9 ppm, THC at about 8.8 ppm, or THC at about 8.7 ppm, or THC at about 8.6 ppm, or THC at about 8.5 ppm, THC at about 8.4 ppm, or THC at about 8.3 ppm, or THC at about 8.2 ppm, or THC at about 8.1 ppm, THC at about 8.0 ppm, or THC at about 7.9 ppm, or THC at about 7.8 ppm, or THC at about 7.7 ppm, THC at about 7.6 ppm, or THC at about 7.5 ppm, or THC at about 7.4 ppm, or THC at about 7.3 ppm, THC at about 7.2 ppm, or THC at about 7.1 ppm, or THC at about 7.0 ppm, or THC at about 6.9 ppm, THC at about 6.8 ppm, or THC at about 6.7 ppm, or THC at about 6.6 ppm, or THC at about 6.5 ppm, THC at about 6.4 ppm, or THC at about 6.3 ppm, or THC at about 6.2 ppm, or THC at about 6.1 ppm, THC at about 6.0 ppm, or THC at about 5.9 ppm, or THC at about 5.8 ppm, or THC at about 5.7 ppm, THC at about 5.6 ppm, or THC at about 5.5 ppm, or THC at about 5.4 ppm, or THC at about 5.3 ppm, THC at about 5.2 ppm, or THC at about 5.1 ppm, or THC at about 5.0 ppm or below, or THC at about 4.9 ppm, THC at about 4.8 ppm, or THC at about 4.7 ppm, or THC at about 4.6 ppm, or THC at about 4.5 ppm, THC at about 4.4 ppm, or THC at about 4.3 ppm, or THC at about 4.2 ppm, or THC at about 4.1 ppm, THC at about 4.0 ppm or below, or THC at about 3.9 ppm, or THC at about 3.8 ppm, or THC at about 3.7 ppm, or THC at about 3.5 ppm, or THC at about 3.4 ppm, or THC at about 3.3 ppm, or THC at about 3.2 ppm, THC at about 3.1 ppm, or THC at about 3.0 ppm or below, or THC at about 2.9 ppm, or THC at about 2.8 ppm, THC at about 2.7 ppm, or THC at about 2.6 ppm, or THC at about 2.5 ppm, or THC at about 2.4 ppm, THC at about 2.3 ppm, or THC at about 2.2 ppm, or THC at about 2.1 ppm, or THC at about 2.0 ppm or below, THC at about 1.9 ppm, or THC at about 1.8 ppm, or THC at about 1.7 ppm, or THC at about 1.6 ppm, THC at about 1.5 ppm, or THC at about 1.4 ppm, or THC at about 1.3 ppm, or THC at about 1.3 ppm, or THC at about 1.2 ppm, or THC at about 1.1 ppm, or THC at about 1.0 ppm or below, or THC at about 0.9 ppm, THC at about 0.8 ppm, or THC at about 0.7 ppm, or THC at about 0.6 ppm, or THC at about 0.5 ppm, THC at about 0.4 ppm, or THC at about 0.3 ppm or below, or THC at about 0.2 ppm, THC at about 0.2 ppm or below.

In certain embodiments, the ratio of the cannabidiol to THC is increased. In certain embodiments, the ratio of the other cannabinoids present to THC is increased. The increase can be from 5%, 10%, 15%, 20%, 25%, 30%, 35%, 40%, 45%, 50%, 55%, 60%, 65%, 70%, 75%, 80%, 85%, 90%, 95%, 100% or more.

In embodiments, the compositions described herein comprising cannabidiol and less than 10 ppm delta-9-tetrahydrocannabinol further comprise less than 0.15% w/w 3,5-dibromo-5'-methyl-4-pentyl-2'-(prop-1-en-2-yl)-1',2',3',4'-tetrahydro-[1,1'-biphenyl]-2,6-diol and 3-bromo-5'-methyl-4-pentyl-2'-(prop-1-en-2-yl)-1',2',3',4'-tetrahydro-[1,1'-biphenyl]-2,6-diol, and less than 0.5% w/w 4-bromo-5-propylbenzene-1,3-diol and 4,6-di-bromo olivetol. In embodiments, the compositions described herein comprising cannabidiol and less than 10 ppm delta-9-tetrahydrocannabinol further comprise from 0.001 to 0.15% w/w 3,5-dibromo-5'-methyl-4-pentyl-2'-(prop-1-en-2-yl)-1',2',3',4'-tetrahydro-[1,1'-biphenyl]-2,6-diol and 3-bromo-5'-methyl-4-pentyl-2'-(prop-1-en-2-yl)-1',2',3',4'-tetrahydro-[1,1'-biphenyl]-2,6-diol, and from 0.001% to 0.5% w/w 4-bromo-5-propylbenzene-1,3-diol and 4,6-di-bromo olivetol. In embodiments, the compositions described herein comprising cannabidiol and less than 10 ppm delta-9-tetrahydrocannabinol further comprise from 0.0001 to 0.05% w/w 3,5-dibromo-5'-methyl-4-pentyl-2'-(prop-1-en-2-yl)-1',2',3',4'-tetrahydro-[1,1'-biphenyl]-2,6-diol and 3-bromo-5'-methyl-4-pentyl-2'-(prop-1-en-2-yl)-1',2',3',4'-tetrahydro-[1,1'-biphenyl]-2,6-diol, and from 0.0001% to 0.05% w/w 4-bromo-5-propylbenzene-1,3-diol and 4,6-di-bromo olivetol. In embodiments, the compositions described herein comprising cannabidiol and less than 10 ppm delta-9-tetrahydrocannabinol further comprise from 0.0001 to 0.01% w/w 3,5-dibromo-5'-methyl-4-pentyl-2'-(prop-1-en-2-yl)-1',2',3',4'-tetrahydro-[1,1'-biphenyl]-2,6-diol and 3-bromo-5'-methyl-4-pentyl-2'-(prop-1-en-2-yl)-1',2',3',4'-tetrahydro-[1,1'-biphenyl]-2,6-diol, and from 0.0001% to 0.01% w/w 4-bromo-5-propylbenzene-1,3-diol and 4,6-di-bromo olivetol. In certain embodiments, the composition comprising cannabidiol and less than 10 ppm THC is substantially free of a halogenated intermediate, such as those listed above. In certain embodiments, the composition comprising cannabidiol and less than 10 ppm THC is essentially free of a halogenated intermediate.

In certain embodiments, compositions described herein can contain about 10% cannabidiol, a maximum of 10 ppm of THC, for example, 9 ppm, 8 ppm, 7 ppm, 6 ppm, 5 ppm, 4 ppm, 3 ppm, 2 ppm, 1 ppm, or less, and an amount of additional components, to a total of 100%. In certain embodiments, compositions described herein can contain about 20% cannabidiol, a maximum of 10 ppm of THC, and an amount of additional components, to a total of 100%. In certain embodiments, compositions described herein can contain about 30% cannabidiol, a maximum of 10 ppm of THC, and an amount of additional components, to a total of 100%. In certain embodiments, compositions described herein can contain about 40% cannabidiol, a maximum of 10 ppm of THC, and an amount of additional components, to a total of 100%. In certain embodiments, compositions described herein can contain about 50% cannabidiol, a maximum of 10 ppm of THC, and an amount of additional components, to a total of 100%. In certain embodiments, compositions described herein can contain about 60% cannabidiol, a maximum of 10 ppm of THC, and an amount of additional components, to a total of 100%. In certain embodiments, compositions described herein can contain about 70% cannabidiol, a maximum of 10 ppm of THC, and an amount of additional components, to a total of 100%. In certain embodiments, compositions described herein can contain about 80% cannabidiol, a maximum of 10 ppm of THC, and an amount of additional components, to a total of 100%. In certain embodiments, compositions described herein can contain about 90% cannabidiol, a maximum of 10 ppm of THC, and an amount of additional components, to a total of 100%. In certain embodiments, compositions described herein can contain about 91% cannabidiol, a maximum of 10 ppm of THC, and an amount of additional components, to a total of 100%. In certain embodiments, compositions described herein can contain about 92% cannabidiol, a maximum of 10 ppm of THC, and an amount of additional components, to a total of 100%. In certain embodiments, compositions described herein can contain about 93% cannabidiol, a maximum of 10 ppm of THC, and an amount of additional components, to a total of 100%. In certain embodiments, compositions described herein can contain about 94% cannabidiol, a maximum of 10 ppm of THC, and an amount of additional components, to a total of 100%. In certain embodiments, compositions described herein can contain about 96% cannabidiol, a maximum of 10 ppm of THC, and an amount of additional components, to a total of 100%. In certain embodiments, compositions described herein can contain about 97% cannabidiol, a maximum of 10 ppm of THC, and an amount of additional components, to a total of 100%. In certain embodiments, compositions described herein can contain about 98% cannabidiol, a maximum of 10 ppm of THC, and an amount of additional components, to a total of 100%. In certain embodiments, compositions described herein can contain about 99% cannabidiol, a maximum of 10 ppm of THC, and an amount of additional components, to a total of 100%. In certain embodiments, compositions described herein can contain about 99.9% cannabidiol, a maximum of 10 ppm of THC, and an amount of additional components, to a total of 100%. In certain embodiments, compositions described herein can contain about 99.99% cannabidiol, a maximum of 10 ppm of THC, and an amount of additional components, to a total of 100%. In certain embodiments, compositions described herein can contain 99.999% cannabidiol, and 1.0 ppm of THC or other component. In certain embodiments, compositions described herein can contain 99.9999% cannabidiol, and 0.1 ppm of THC or other component.

In embodiments, the subject matter described herein is directed to a composition comprising cannabidiol, delta-9-tetrahydrocannabinol and 4-monobromo-cannabidiol, wherein said delta-9-tetrahydrocannabinol is present in an amount less than 10 ppm and 4-monobromo-cannabidiol is present in an amount less than 400 ppm. In embodiments, the subject matter described herein is directed to a composition comprising cannabidiol, delta-9-tetrahydrocannabinol and 4-monobromo-cannabidiol, wherein said delta-9-tetrahydrocannabinol is present in an amount less than 10 ppm and 4-monobromo-cannabidiol is present in an amount less than 300 ppm. In embodiments, the subject matter described herein is directed to a composition comprising cannabidiol, delta-9-tetrahydrocannabinol and 4-monobromo-cannabidiol, wherein said delta-9-tetrahydrocannabinol is present in an amount less than 10 ppm and 4-monobromo-cannabidiol is present in an amount less than 200 ppm. In embodiments, the subject matter described herein is directed to a composition comprising cannabidiol, delta-9-tetrahydrocannabinol and 4-monobromo-cannabidiol, wherein said delta-9-tetrahydrocannabinol is present in an amount less than 0.001% w/w and 4-monobromo-cannabidiol is present in an amount less than 0.15% w/w. In embodiments, the subject matter described herein is directed to a composition comprising cannabidiol, delta-9-tetrahydrocannabinol and 4-monobromo-cannabidiol, wherein said delta-9-tetrahydrocannabinol is present in an amount less than 0.001% w/w and 4-monobromo-cannabidiol is present in an amount less than 0.03% w/w. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.00001% w/w to about 0.001% w/w and 4-monobromo-cannabidiol is present in an amount from about 0.00001% to about 0.05% w/w. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.00001% w/w to about 0.001% w/w and 4-monobromo-cannabidiol is present in an amount from about 0.00001% to about 0.04% w/w. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.00001% w/w to about 0.001% w/w and 4-monobromo-cannabidiol is present in an amount from about 0.00001% to about 0.03% w/w. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.00001% w/w to about 0.001% w/w and 4-monobromo-cannabidiol is present in an amount from about 0.00001% to about 0.02% w/w. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.00001% w/w to about 0.001% w/w and 4-monobromo-cannabidiol is present in an amount from about 0.00001% to about 0.01% w/w. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.001% w/w to about 5 PPM and 4-monobromo-cannabidiol is present in an amount from about 0.001% w/w to about 100 PPM. In certain embodiments, the subject matter described herein is directed to a composition comprising cannabidiol, delta-9-tetrahydrocannabinol and 4-monobromo-cannabidiol, wherein said delta-9-tetrahydrocannabinol is present in an amount from about 0.001% w/w to about 10 PPM and 4-monobromo-cannabidiol is present in an amount from about 0.001% w/w to about 100 PPM.

In embodiments, the subject matter described herein is directed to a composition comprising cannabidiol, delta-9-tetrahydrocannabinol and olivetol, wherein said delta-9-tetrahydrocannabinol is present in an amount less than 10 ppm and olivetol is present in an amount less than 10 ppm. In embodiments, the subject matter described herein is directed to a composition comprising cannabidiol, delta-9-tetrahydrocannabinol and olivetol, wherein said delta-9-tetrahydrocannabinol is present in an amount less than 0.001% w/w and olivetol is present in an amount less than 0.15% w/w. In embodiments, the subject matter described herein is directed to a composition comprising cannabidiol, delta-9-tetrahydrocannabinol and olivetol, wherein said delta-9-tetrahydrocannabinol is present in an amount less than 0.001% w/w and olivetol is present in an amount less than 0.05% w/w. In certain embodiments, the subject matter described herein is directed to a composition comprising cannabidiol, delta-9-tetrahydrocannabinol and olivetol, wherein said delta-9-tetrahydrocannabinol is present in an amount from about 0.00001% w/w to about 0.001% w/w and olivetol is present in an amount from about 0.00001% to about 0.05% w/w. In certain embodiments, the subject matter described herein is directed to a composition comprising cannabidiol, delta-9-tetrahydrocannabinol and olivetol, wherein said delta-9-tetrahydrocannabinol is present in an amount from about 0.001% w/w to about 5 PPM and olivetol is present in an amount from about 0.001% w/w to about 300 PPM.

In embodiments, the subject matter described herein is directed to a composition comprising cannabidiol, delta-9-tetrahydrocannabinol and delta-8-tetrahydrocannabinol, wherein said delta-9-tetrahydrocannabinol is present in an amount less than 10 ppm and delta-8-tetrahydrocannabinol is present in an amount less than 10 ppm. In embodiments, the subject matter described herein is directed to a composition comprising cannabidiol, delta-9-tetrahydrocannabinol and delta-8-tetrahydrocannabinol, wherein said delta-9-tetrahydrocannabinol is present in an amount less than about 0.001% w/w and delta-8-tetrahydrocannabinol is present in an amount less than about 0.001% w/w. In certain embodiments, the subject matter described herein is directed to a composition comprising cannabidiol, delta-9-tetrahydrocannabinol and delta-8-tetrahydrocannabinol, wherein said delta-9-tetrahydrocannabinol is present in an amount from about 0.00001% w/w to about 0.001% w/w and delta-8-tetrahydrocannabinol is present in an amount from about 0.00001% to about 0.001% w/w. In certain embodiments, the subject matter described herein is directed to a composition comprising cannabidiol, delta-9-tetrahydrocannabinol and delta-8-tetrahydrocannabinol, wherein said delta-9-tetrahydrocannabinol is present in an amount from about 0.001% w/w to about 5 PPM and delta-8-tetrahydrocannabinol is present in an amount from about 0.001% w/w to about 5 PPM. In certain embodiments, the subject matter described herein is directed to a composition comprising cannabidiol, delta-9-tetrahydrocannabinol and delta-8-tetrahydrocannabinol, wherein said delta-9-tetrahydrocannabinol is present in an amount from about 0.001% w/w to about 10 PPM and delta-8-tetrahydrocannabinol is present in an amount from about 0.001% w/w to about 10 PPM.

In embodiments, the compositions described herein comprising cannabidiol and less than 10 ppm delta-9-tetrahydrocannabinol further comprise less than 0.15% w/w 4-monobromo-cannabidiol, less than 0.15% w/w olivetol, and less than 0.10% w/w delta-8-tetrahydrocannabinol. In embodiments, the compositions described herein comprising cannabidiol further comprise about 0.001% w/w to about 10 PPM delta-9-tetrahydrocannabinol, about 0.001% w/w to about 0.03% w/w olivetol, about 0.001% w/w to about 10 PPM delta-8-tetrahydrocannabinol, and about 0.001% w/w to about 0.02% w/w 4-monobromo-cannabidiol. In embodiments, the compositions described herein comprising cannabidiol further comprise about 0.001% w/w to about 5 PPM delta-9-tetrahydrocannabinol, less than 0.03% w/w olivetol, less than 10 PPM delta-8-tetrahydrocannabinol, and less than 0.02% w/w 4-monobromo-cannabidiol.

In embodiments, the crystalline polymorph Form A has particle size distributions. A particle Size distribution of D50 is also known as the median diameter or the medium value of the particle size distribution. It is the value of the particle diameter at 50% in the cumulative distribution. D10 is the diameter at which 10% of the sample's mass is comprised of particles with a diameter less than this value. D90 is the diameter at which 90% of the sample's mass is comprised of particles with a diameter less than this value.

In embodiments, the crystalline polymorph Form A has a d10 particle size ranging from about 1 μm to about 10 μm. In embodiments, the crystalline polymorph Form A has a d10 particle size ranging from about 8 μm to about 40 μm. In embodiments, the crystalline polymorph Form A has a d10 particle size ranging from about 15 μm to about 500 μm. In embodiments, the crystalline polymorph Form A has a d10 particle size ranging from about 1 μm to about 450 μm.

In embodiments, the crystalline polymorph Form A has a d50 particle size ranging from about 8 μm to about 40 μm. In embodiments, the crystalline polymorph Form A has a d50 particle size ranging from about 5 μm to about 600 μm, from about 5 μm to about 100 μm, from about 5 μm to about 75 μm, from about 15 μm to about 50 μm, from about 15 μm to about 30 μm, from about 50 μm to about 600 μm, and from about 2 μm to about 200 μm.

In embodiments, the crystalline polymorph Form A has a d90 particle size ranging from about 8 μm to about 500 μm. In embodiments, the crystalline polymorph Form A has a d90 particle size ranging from about 2 μm to about 400 μm, from about 10 μm to about 350 μm, from about 100 μm to about 200 μm, from about 25 μm to about 150 μm, from about 100 μm to about 150 μm, from about 130 μm to about 180 μm, and from about 100 μm to about 600 μm.

III. Formulations

Pharmaceutical formulations of therapeutic cannabidiol compositions (CBD) as described herein can be prepared for can be prepared for various routes of administration. A CBD having the desired degree of purity is optionally mixed with one or more pharmaceutically acceptable excipients (Remington's Pharmaceutical Sciences (1980) 16th edition, Osol, A. Ed.), in the form of a lyophilized formulation for reconstitution or an aqueous solution.

CBD can be formulated in accordance with standard pharmaceutical practice as a pharmaceutical composition. According to this aspect, there is provided a pharmaceutical composition comprising CBD in association with one or more pharmaceutically acceptable excipients. In embodiments, a cannabidiol formulation comprises cannabidiol and delta-9-tetrahydrocannabinol, wherein said delta-9-tetrahydrocannabinol is present in an amount less than 10 ppm, and a pharmaceutically acceptable excipient.

A typical formulation is prepared by mixing CBD with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the CBD is being applied. Solvents are generally selected based on solvents recognized by persons skilled in the art as safe (GRAS) to be administered to a mammal.

In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the CBD or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The CBD formulations can be sterile. In particular, formulations to be used for in vivo administration must be sterile. Such sterilization is readily accomplished by filtration through sterile filtration membranes.

The CBD ordinarily can be stored as a solid composition, a lyophilized formulation or as an aqueous solution.

The pharmaceutical compositions comprising CBD can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutic amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The CBD can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of CBD that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

Formulations comprising cannabidiol and THC, wherein the THC is present at a level below about 10 ppm can be administered such that a therapeutically effective amount of cannabidiol is given daily although the level of THC administered daily is below 20 µg/day. In certain embodiments, a therapeutically effective amount of cannabidiol is given daily with the level of THC administered daily being below 19 µg/day, 18 µg/day, 17 µg/day, 16 µg/day, 15 µg/day, 14 µg/day, 13 µg/day, 12 µg/day, 11 µg/day, 9 µg/day, 8 µg/day, 7 µg/day, 6 µg/day, 5 µg/day, 4 µg/day, 3 µg/day, 2 µg/day, or 1 µg/day, down to about 0.1 µg/day.

IV. Methods

Indications and Methods of Treatment

It is contemplated that the cannabidiol compositions (CBD) disclosed herein may be used to treat a disease. Exemplary diseases include, but are not limited to, emesis, pain, Huntington's disease, Tourette's syndrome, glaucoma, osteoporosis, schizophrenia, cancer, obesity, autoimmune diseases, diabetic complications, infections against methicillian-resistant *Staphylococcus aureus*, nausea, depression, anxiety, Hypoxia-ischemia injuries, psychosis, and inflammatory diseases.

Autoimmune diseases include, for example, Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, Parkinson's disease, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, inflammatory bowel disease, sepsis, stroke, transplantation of tissue and organs, vasculitis, diabetic retinopathy and ventilator induced lung injury.

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The CBD may be administered by any route appropriate to the condition to be treated, including orally, intravenously, topically, as well as by ophthalmic (eye drops), and transdermal (skin patch) modes.

The CBD can be used either alone or in combination with other agents in a therapy. For instance, the cannabidiol compositions may be co-administered with at least one additional therapeutic agent. Such combination therapies noted above encompass combined administration (where two or more therapeutic agents are included in the same or separate formulations), and separate administration, in which case, administration of the cannabidiol composition can occur prior to, simultaneously, and/or following, administration of the additional therapeutic agent and/or adjuvant.

Methods of Making Cannabidiol (CBD)

Schemes 1-3 display exemplary methods for synthesizing pure cannabidiol compositions.

Scheme 1-Synthetic Route for the Preparation of 4,6-Dibromo Olivetol

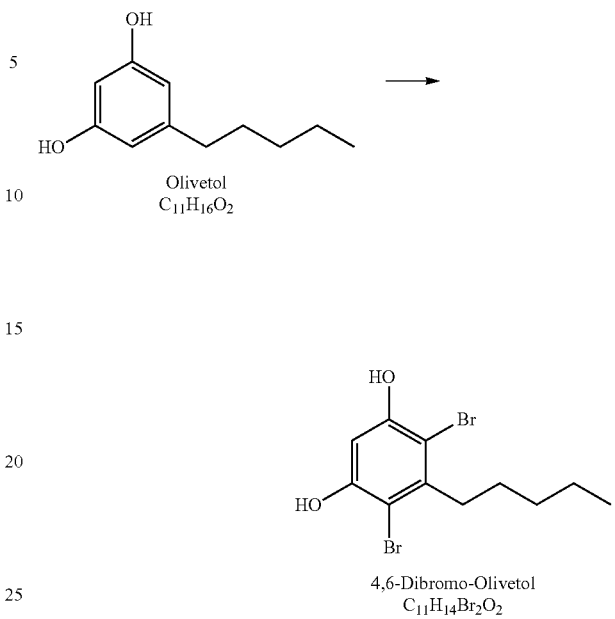

Referring to scheme 1, a method of preparing 4,6-Dibromo Olivetol is provided. The method includes contacting Olivetol with a brominating agent to form 4,6-dibromo-olivetol.

Scheme 2-Synthetic Route for the Preparation of Dibromo-CBD

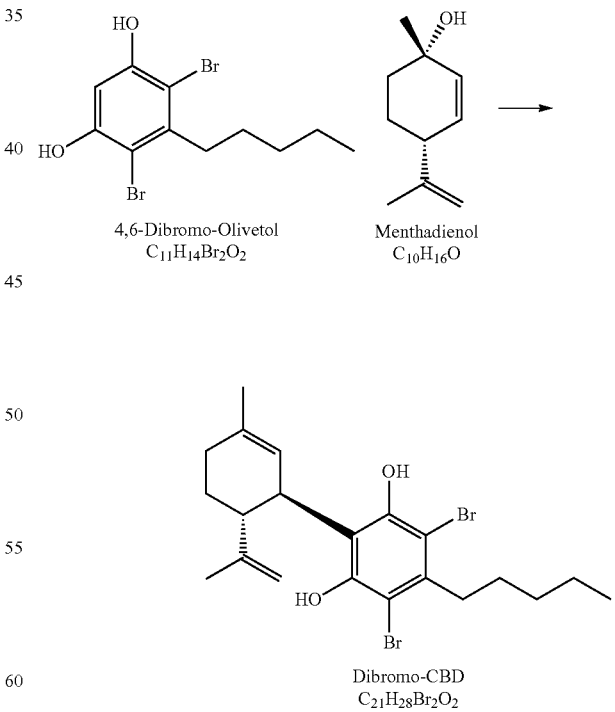

In accordance with Scheme 2, the present disclosure relates to a process for the preparation of Dibromo-CBD; the process can include contacting 4,6-Dibromo-Olivetol with menthadienol in the presence of a protic acid catalyst to form Dibromo-CBD.

Scheme 3- Synthetic Route for the Preparation of CBD

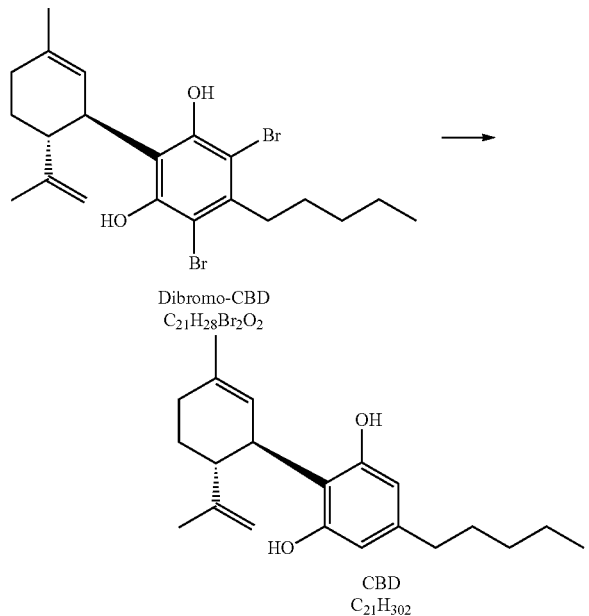

Dibromo-CBD
$C_{21}H_{28}Br_2O_2$

CBD
$C_{21}H_{30}2$

Referring to Scheme 3, the present disclosure further relates to the preparation of cannabidiol; the process can include dissolving Dibromo-CBD in a solvent and treating it with a suitably selected reducing agent, such as sodium sulfite, in the presence of a base to form a first cannabidiol product.

The first cannabidiol product can then be dissolved in a first solvent to form a crystallized second cannabidiol product.

Crystallization/Recrystallization

In another embodiment, the present disclosure relates to the recrystallization of the second cannabidiol product; the process can include dissolving the second cannabidiol product in a second suitable solvent, such as isooctane, heating the solution to about 40° C., cooling the solution to about 32° C., and then seeding said solution at about 32° C. with (−)-Cannabidiol to prepare a suspension; the process further includes allowing said suspension to warm to about 32° C. with stirring, cooling the suspension to −20° C., separating a solid material from said suspension, washing the solid material with isooctane at about −20° C., and then drying the solid material to obtain a crystalline composition comprising cannabidiol and less than 10 ppm delta-9-tetrahydrocannabinol.

The first cannabidiol composition can be crystalized with a suitable organic solvent, such as 2-butanone, ethyl acetate, 1-4-dioxane, diethyl ether, tert-butyl methyl ether, tetrahydrofuran, dichloromethane, chloroform, n-heptane, toluene, isopropyl acetate, isooctane, n-decane, and anisole.

The second cannabidiol composition can be recrystallized with a suitable nonpolar aprotic solvent, such as isooctane, chloroform, n-heptane, dichloromethane, diethyl ether, hexane, n-decane, and pentane.

In each crystallization process, a seed crystal of the desired product may be used to instigate crystallization. In certain embodiments, in the preparation of CBD, the seed crystal is (−)-Cannabidiol generated by Protocol 1, disclosed herein. In certain embodiments, in the preparation of 4,6-dibromo-Olivetol, the seed crystal is 4,6-dibromo-Olivetol generated by Protocol 1, disclosed herein.

General Procedures

In certain embodiments, olivetol can be substituted with Cl, I, or F, in addition to Br, to form a di-halo-Olivetol. Each halogen can be selected from the group consisting of Br, F, I and Cl, more particularly Br, F or Cl, or more particularly Br or F, or even more particularly Br.

In certain embodiments, di-halo olivetol is contacted with menthadienol in the presence of a suitably selected protic acid catalyst. Possible catalysts include p-toluene sulfonic acid, trifluoromethanesulfonic acid, trifluoroacetic acid, acetic acid, and sulfuric acid. The reaction can occur in a suitably selected solvent or mixture of solvents, such as methylene chloride, chloroform, 1,2-dichloroethane, cyclohexane, toluene, methylene bromide, bromoform, hexane, xylene, acetonitrile, tert-butyl methyl ether, or combinations thereof. The reaction can produce di-halo cannabidiol.

The di-halo cannabidiol can then be reduced to remove its halo substituents. The di-halo cannabidiol can undergo reduction by contacting it with a suitably selected reducing agent, for example, sodium sulfite, potassium sulfite, palladium/carbon in combination with hydrogen; in the presence of a suitably selected base, such as sodium hydroxide, triethylamine, sodium carbonate, tripotassium phosphate, and potassium tert-butoxide. The reduction reaction can occur in a suitably selected polar solvent or mixture of polar solvents, or mixture of apolar and polar solvents, for example, methanol or a mixture of methanol and water, acetonitrile, ethanol, acetone, isopropanol, n-butanol, dichloromethane, tetrahydrofuran, tert-butyl methyl ether or a mixture of organic solvent and water. The polar solvent or mixture of polar solvents can also be selected from the group consisting of acetonitrile, methylene chloride, or combinations thereof.

The dihalo-cannabidiol can be contained in non-aqueous solvents or a mixture of solvents such as dichloromethane, toluene, tert-butyl methyl, and n-heptane. The non-aqueous solvent can also contain a desiccating agent. The desiccating agent can be added to remove adventitious moisture from the reaction mixture. The amount of desiccating agent in the dihalo-compound solution can be up to about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% (g of desiccating agent/mL of solvent). These values can be used to define a range, such as about 1% and about 10%, or about 10% and about 20%.

The amount of desiccating agent can be about 5% to about 20% g/mL of anhydrous MgSO4 per mL DCM. For example, a lower amount can be used, e.g., 5% g/mL, if the reagents are anhydrous, e.g., MgSO4, dibromo-Olivetol, pTSA. A higher amount can be used, e.g., 20% g/mL, if the reagents are mono-hydrates, e.g., dibromo-Olivetol and pTSA mono-hydrates. In one embodiment, the amount can be about 14.5% g/mL. In some embodiments, the amount of desiccating agent can be 0% if the compound, e.g., menthadienol, is present in excess amounts, such as greater than about 3 eq.

The amount of desiccating agent per starting material can also be expressed as a molar ratio of desiccating agent to starting material. The amount can be about 1:1, 1.5:1, 2:1, 2.5:1, 3:1, 3.5:1, 4:1, 4.5:1 or about 5:1. These values can be used to define a range, such as about 1.5:1 to about 3.5:1.

The desiccating agent can be any agent or compound that does not interfere with the reaction and can remove moisture from the reaction mixture. The desiccating agent can be selected from the group consisting of an anhydrous inorganic salt, molecular sieve, activated charcoal, silica gel, or combinations thereof. In one embodiment, the desiccating agent is anhydrous magnesium sulfate.

The reaction between the di-halo Olivetol and menthadienol can be carried out with the relative amounts of menthadienol and di-halo Olivetol of about 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4 or 5.5 equivalents of menthadienol to di-halo Olivetol. These values can be used to define a range, such as about 0.5 and about 5 equivalents, or about 0.5 and about 3.5 equivalents or about 1.1 to about 1.7 equivalents.

Menthadienol can be added to di-halo Olivetol, or a solution containing the di-halo Olivetol, slowly. The menthadienol can be added to the compound of di-halo Olivetol, or a solution containing di-halo Olivetol, over 0.1, 0.2, 0.3, 0.4, 0.5, 1, 1.5, 2, 2.5, 3, 3.5, 4, 4.5, 5, 5.5, 6, 7, 8, 9, 10, 11, 12, 16, 20 or about 24 hours. These values can be used to define a range, such about 2 to about 12 hours, or about 4 to about 8 hours. The compound can be added in increments or portions over the time period. For example, the compound can be added over 7 hours as follows: t=0: 0.65 eq; t=1 h: +0.65 eq; t=4 h: +0.3 eq and optionally t=7 h: +0.1 eq.

After addition with menthadienol, the reaction mixture can be stirred for an additional time. The reaction mixture can be stirred for an additional 0.1, 0.2, 0.3, 0.4, 0.5, 0.6, 0.7, 0.8, 0.9, 1, 2, 3, 4, 5, 6, 7, 8, 9, 10, 12, 16, 20, 24, 36 or 48 hours. These values can be used to define a range, such as about 1 to about 3 hours, or about 6 to about 48 hours, or about 12 to about 24 hours, or about 14 to about 18 hours.

One skilled in the art will recognize that the reaction or process step(s) as herein described can proceed for a sufficient period of time until the reaction is complete, as determined by any method known to one skilled in the art, for example, chromatography (e.g., HPLC). In this context a "completed reaction or process step" shall mean that the reaction mixture contains a significantly diminished amount of the starting material(s)/reagent(s)/intermediate(s) and a significantly reduced amount of the desired product(s), as compared to the amounts of each present at the beginning of the reaction.

The amount of the protic acid catalyst, e.g., p-toluenesulfonic acid, in the reaction between menthadienol and the di-halo Olivetol can be about 0.5 mol %, 1 mol %, 2 mol %, 3 mol %, 4 mol %, 5 mol %, 6 mol %, 7 mol %, 8 mol %, 9 mol %, 10 mol %, 20 mol %, 30 mol %, 40 mol %, 50 mol %, 60 mol %, 70 mol %, 80 mol %, 90 mol %, 100 mol %, or about 120 mol % with respect to the di-halo Olivetol. These values can be used to define a range, such as about 4 mol % to about 6 mol %, 20 mol % to about 80 mol %, or about 40 mol % to about 60 mol %.

As used herein, the term "reducing agent" refers to an agent having the ability to add one or more electrons to an atom, ion or molecule. The reducing agent can be a sulfur-containing compound, or Pd/C in the presence of hydrogen. The sulfur containing compound can be a sulfur-containing reducing agent having the ability to reduce C-halogen bonds to form C—H bonds.

The sulfur-containing compound can be a sulfur-containing inorganic acid or salt thereof, including, for example, hydrosulfuric acid ($H_2S$), sulfurous acid ($H_2SO_3$), thiosulfurous acid ($H_2SO_2O_2$), dithionous acid ($H_2S_2O_4$), disulfurous acid ($H_2S_2O_5$), dithionic acid ($H_2S_2O_2$), trithionic acid ($H_2S_3O_6$) and salts thereof. The sulfur-containing inorganic salt can be an alkali metal salt or an alkaline earth metal salt. For example, the salt can be a monovalent or divalent cation selected from $Li^+$, $Na^+$, $K^+$, $Rb^+$, $Cs^+$, $Fr^+$, $Be^{2+}$, $Mg^{2+}$, $Ca^{2+}$, $Sr^{2+}$, $Ba^{2+}$, or $Ra^{2+}$. In one embodiment, the salt can be selected from the group consisting of $Li^+$, $Na^+$, $K^+$, $Mg^{2+}$, and $Ca^{2+}$.

The sulfur-containing inorganic salt can also be an ammonium salt ($NH_4^+$) or a quaternary ammonium salt. For example, the sulfur-containing inorganic acid salt can be a tetra-alkylated ammonium salt, e.g., a quaternary ammonium salt substituted with four alkyl groups. The alkyl groups can be a $C_1$-$C_{18}$. The tetraalkylated ammonium salts can be a tetramethylammonium salt, a tetraethylammonium salt, a tetrapropylammonium salt, a tetrabutylammonium salt, or combinations thereof.

The sulfur-containing inorganic acid or salt thereof can also be one which dissociates into a bisulfite ion ($HSO_3^-$) and/or a sulfite ion ($SO_3^{2-}$) in the reaction mixture. Sulfurous acid ($H_2SO_3$) can generally exist as a solution of $SO_2$ (commonly about 6%) in water.

The molar ratio amount of base The molar ratio amount of base to di-halo cannabidiol in the reduction reaction mixture can be about 0:1, 1:1, 1.5:1, 2:1, 3:1, 4:1, 5:1, 6:1, 7:1, 8:1 or greater. These values can define a range, such as about 3.5:1 to about 4.5:1, or about 4:1 to about 6:1.

The reduction reaction can be carried out at a reflux temperature, including a temperature elevated by high pressure, of the solvent or solvent mixture for a duration of about 1, 2, 3, 4, 5, 6, 7, 8, 9, 10, 12, 16, 20, 24, 28, 30, 32, 36 or about 48 hours; or any amount of time required to reach a desired endpoint (wherein the desired endpoint can be determined by for example, a percent conversion of starting material or an intermediate material).

In certain embodiments, contacting the di-halo cannabidiol with a reducing agent to prepare a first cannabidiol composition further comprises contacting the first cannabidiol composition with activated carbon. In certain embodiments, the activated carbon is loose carbon (Norit CN, Cabot). In certain embodiments, the activated carbon is encapsulated carbon (R55SP or R53SP, Cuno). In certain embodiments, it is preferred that the carbon be encapsulated carbon of the type R55SP, manufactured by Cuno.

The reflux temperature can be at 20° C., Room Temperature, 30° C., 40° C., 50° C., 60° C., 65° C., 70° C., 75° C., 80° C., 85° C., 90° C., 95° C., 100° C., 110° C. or about 120° C. These values can be used to define a range, such as about 20° C. to about 100° C., or about RT to about 50° C., or about 60° C. to about 85° C., or about 72° C. to about 76° C. In some embodiments, subsequent distillation can be performed. The distillation can be performed at the same temperatures listed above, e.g., 85° C.

The reflux pressure can be at atmospheric pressure. In some embodiments, the reflex can be done at a pressure of about 100, 200, 300, 400, 500, 600, 700, 800, 900, 1000, 1500, 2000, 2500, 3000, 3500, or about 4000 mbar. These values can be used to define a range, such as about 900 to about 3000 mbar.

The compounds of the present disclosure may be prepared as individual enantiomers by either enantio-specific synthesis or resolved from an enantiomerically enriched mixture. When the stereochemistry of a disclosed compound is named or depicted, the named or depicted stereoisomer can be at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

The present disclosure can produce the compound of interest, e.g., cannabidiol, etc., in high stereospecificity. The stereospecificity of the processes of the present disclosure can be greater than about 60% ee, 75% ee, 80% ee, 85% ee, 90% ee, 95% ee, 97% ee, 98% ee, 99% ee. These values can define a range, such as about 90% ee and about 99% ee.

The present disclosure can produce the compound of interest, e.g., cannabidiol, in high yield. The yield of the process of the present disclosure can be greater than about 60%, 61%, 62%, 63%, 64%, 65%, 66%, 67%, 68%, 69%, 70%, 71%, 72%, 73%, 74%, 75%, 76%, 77%, 78%, 79%, 80%, 80%, 81%, 82%, 83%, 84%, 85%, 86%, 87%, 88%, 89%, 90%, 91%, 92%, 93%, 94%, 95%, 96%, 97%, 98% or 99%. These values can define a range, such as about 60% to about 85%, or about 90% to about 99%.

In certain embodiments, it is preferred that the coupling temperature is −20° C. or warmer.

In certain embodiments, it is preferred that the synthesis does not include a polymer filtration step.

In certain embodiments, it is preferred that the debromination solvent is no more than about 15 volumes of isopropanol:water (1:1). In certain embodiments, it is preferred that debromination occurs for about 36 hours or more.

In certain embodiments, it is preferred that after debromination, the mixture is contacted with activated carbon.

In certain embodiments, it is preferred that the post acid wash is a buffer solution that is about pH 7.0, such as a phosphate buffer.

In certain embodiments, it is preferred that the post base pH adjustment is water with ascorbate.

In certain embodiments, it is preferred that the organic layer is dried by azeotropic distillation.

In certain embodiments, is preferred that the coupling temperature is −20° C. or warmer; the synthesis does not include a polymer filtration step; the debromination solvent is no more than about 15 volumes of isopropanol:water (1:1); the debromination occurs for about 36 hours or more; after debromination, the mixture is contacted with activated carbon; the post acid wash is a buffer solution that is about pH 7.0, such as a phosphate buffer; the post base pH adjustment is water with ascorbate; and the organic layer is dried by azeotropic distillation.

The subject matter described herein is directed to the following embodiments:

1. A composition comprising cannabidiol and delta-9-tetrahydrocannabinol, wherein said delta-9-tetrahydrocannabinol is present in an amount less than 10 ppm.

2. The composition of embodiment 1, comprising cannabidiol and delta-9-tetrahydrocannabinol, wherein said delta-9-tetrahydrocannabinol is present in an amount less than 8 ppm.

3. The composition of embodiment 1, comprising cannabidiol and delta-9-tetrahydrocannabinol, wherein said delta-9-tetrahydrocannabinol is present in an amount less than 6 ppm.

4. The composition of embodiment 1, comprising cannabidiol and delta-9-tetrahydrocannabinol, wherein said delta-9-tetrahydrocannabinol is present in an amount less than 4 ppm.

5. The composition of embodiment 1, comprising cannabidiol and delta-9-tetrahydrocannabinol, wherein said delta-9-tetrahydrocannabinol is present in an amount less than 3 ppm.

6. The composition of embodiment 1, comprising cannabidiol and delta-9-tetrahydrocannabinol, wherein said delta-9-tetrahydrocannabinol is present in an amount less than 2 ppm.

7. The composition of embodiment 1, comprising cannabidiol and delta-9-tetrahydrocannabinol, wherein said delta-9-tetrahydrocannabinol is present in an amount from about 0.1 ppm to 6 ppm.

8. The composition of embodiment 1, comprising cannabidiol and delta-9-tetrahydrocannabinol, wherein said delta-9-tetrahydrocannabinol is present in an amount from about 1 ppm to 5 ppm.

9. The composition of any one of embodiments 1-8, wherein said cannabidiol is crystalline.

10. The composition of any one of embodiments 1-9, wherein said cannabidiol is crystalline polymorph Form A.

11. The composition of embodiment 10, said crystalline polymorph Form A having an X-ray powder diffraction pattern substantially as depicted in FIG. 11A.

12. The composition of embodiment 10, wherein said crystalline polymorph Form A comprises at least one X-ray powder diffraction peak in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

13. The composition of embodiment 10, wherein said crystalline polymorph Form A comprises at least two X-ray powder diffraction peaks in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

14. The composition of embodiment 10, wherein said crystalline polymorph Form A comprises at least three X-ray powder diffraction peaks in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

15. The composition of embodiment 10, wherein said crystalline polymorph Form A exhibits a characteristic X-ray powder diffraction pattern having peaks in degrees 2θ±0.07 2θ at 9.70, 11.74, 15.08, 17.36, and 18.79.44.

16. The composition of embodiment 10, wherein said crystalline polymorph Form A exhibits a characteristic X-ray powder diffraction pattern having peaks in degrees 2θ±0.07 2θ at 9.70, 11.74, 12.49, 13.12, 13.80, 15.08, 17.36, 18.79, 20.55, and 22.11.

17. The composition of embodiment 10, wherein said crystalline polymorph Form A exhibits a characteristic X-ray powder diffraction pattern with characteristics peaks expressed in 2θ±0.07 at 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

18. The composition of embodiment 10, wherein said crystalline polymorph Form A is characterized by a differential scanning calorimetry thermogram as set forth in FIG. 12.

19. The composition of embodiment 10, wherein said crystalline polymorph Form A is characterized by a differential scanning calorimetry thermogram with an endotherm having an onset of about 67.72° C. and a peak at about 68.12° C.

20. The composition of any one of embodiments 1-19, further comprising at least one compound selected from the group consisting of cannabinol, cannabigerol, delta-8-tetrahydrocannabinol, cannabichromene, cannabicyclol, cannabiyarin, tetrahydrocannabivarin, cannabidivarin, cannabichromevarin, cannabigerovarin, cannabielsoin, cannabicitran, 3,5-dibromo-5'-methyl-4-pentyl-2'-(prop-1-en-2-yl)-1',2',3',4'-tetrahydro-[1,1'-biphenyl]-2,6-diol, 3-bromo-5'-methyl-4-pentyl-2'-(prop-1-en-2-yl)-1',2',3',4'-tetrahydro-[1,1'-biphenyl]-2,6-diol, 4,6-di-bromo olivetol, 4-bromo-5-pentylbenzene-1,3-diol, abnormal cannabidiol (ab-CBD), cannabidiol quinone derivatives (CBQ), 3,5-dibromo-5'-methyl-2'-(prop-1-en-2-yl)-4-propyl-1',2',3',4'-tetrahydro-[1,1'-biphenyl]-2,6-diol, 3,5-dibromo-4-ethyl-5'-methyl-2'-(prop-1-en-2-yl)-1',2',3',4'-tetrahydro-[1,1'-biphenyl]-2,6-diol, 3-bromo-4-ethyl-5'-methyl-2'-(prop-1-en-2-yl)-1',2',3',4'-tetrahydro-[1,1'-biphenyl]-2,6-diol, 4,6-dibromo-5-propylbenzene-1,3-diol, 4-bromo-5-propylbenzene-1,3-diol, 4,6-dibromo-5-ethylbenzene-1,3-diol, 4-bromo-5-ethylbenzene-1,3-diol, 5'-methyl-2'-(prop-1-en-2-yl)-4-propyl-1',2',3',4'-tetrahydro-[1,1'-biphenyl]-2,6-diol, and 4-ethyl-5'-methyl-2'-(prop-1-en-2-yl)-1',2',3',4'-tetrahydro-[1,1'-biphenyl]-2,6-diol.

21. The composition of any one of embodiments 1-20, devoid of plant extract material.

22. A stable composition comprising cannabidiol and delta-9-tetrahydrocannabinol, wherein said delta-9-tetrahydrocannabinol is present in an amount less than 10 ppm upon storage for 2 years or less, for example, at 25° C. at 75% r.h.

23. The stable composition of embodiment 22, wherein said delta-9-tetrahydrocannabinol is present in an amount less than 10 ppm upon storage for 1 year or less.

24. The stable composition of embodiment 22, wherein said delta-9-tetrahydrocannabinol is present in an amount less than 10 ppm upon storage for 6 months or less.

25. The stable composition of embodiment 22, wherein said delta-9-tetrahydrocannabinol is present from about 0.1 ppm to about 9 ppm.

26. The composition of any one of embodiments 22-25, wherein the cannabidiol is crystalline.

27. A composition comprising cannabidiol and less than 10 ppm delta-9-tetrahydrocannabinol, wherein the ratio of cannabidiol to delta-9-tetrahydrocannabinol is less than 1:0.0001 as measured by HPLC.

28. The composition of embodiment 27, wherein the cannabidiol is crystalline.

29. A formulation comprising,
cannabidiol,
delta-9-tetrahydrocannabinol, wherein said delta-9-tetrahydrocannabinol is present in an amount less than 10 ppm, and
a pharmaceutically acceptable excipient.

30. The formulation of embodiment 29, wherein the formulation is in the form of a matrix.

31. The formulation of embodiment 29, wherein the formulation is in the form of a liquid.

32. The formulation of embodiment 31, wherein the liquid is vaporizable.

33. The formulation of embodiment 29, wherein the formulation is in the form of a granule.

34. A method of preparing crystalline cannabidiol characterized by a X-ray powder diffraction pattern substantially as depicted in FIG. 11A and having less than 10 ppm delta-9-tetrahydrocannabinol, comprising crystalizing the cannabidiol from isooctane.

35. A method of preparing a cannabidiol composition, comprising
contacting di-halo olivetol with menthadienol in the presence of a protic acid catalyst to prepare di-halo cannabidiol;
contacting the di-halo cannabidiol with a reducing agent to prepare a first cannabidiol composition;
contacting the first cannabidiol composition with a first solvent; crystallizing a second cannabidiol composition from said solvent; and
recrystallizing crystalline cannabidiol composition having less than 10 ppm delta-9-tetrahydrocannabinol from a second solvent.

36. The method of embodiment 35, wherein the protic acid catalyst is selected from the group consisting of p-toluene sulfonic acid, trifluoromethanesulfonic acid, trifluoroacetic acid, acetic acid, and sulfuric acid.

37. The method of embodiment 35 or 36, wherein the reducing agent is a sulfur-containing compound.

38. The method of any one of embodiments 35-37, wherein the first solvent is selected from the group consisting of water, 2-butanone, ethyl acetate, 1-4-dioxane, diethyl ether, tert-butyl methyl ether, tetrahydrofuran, dichloromethane, chloroform, n-heptane, toluene, isopropyl acetate isooctane, n-decane, and anisole.

39. The method of any one of embodiments 35-38, wherein the second solvent is selected from the group consisting of isooctane, chloroform, n-heptane, dichloromethane, diethyl ether, hexane, n-decane, and pentane.

40. The method of any one of embodiments 35-39, wherein di-halo olivetol is contacted with menthadienol in the presence of a protic acid catalyst at a temperature of about −33° C. to about −27° C.

41. The method of any one of embodiments 35-40, wherein di-halo olivetol is contacted with menthadienol in the presence of a protic acid catalyst at a temperature of about −30° C.

42. A method of recrystallizing cannabidiol from a mixture of cannabinoids to prepare a composition comprising cannabidiol and less than 10 ppm delta-9-tetrahydrocannabinol, said method comprising,
contacting said mixture of cannabinoids with isooctane to form a solution;
heating said solution to about 40° C.;
cooling the solution to about 32° C.;
seeding said solution at about 32° C. with (−)-Cannabidiol to prepare a suspension;
allowing said suspension to warm to about 32° C. with stirring;
cooling the suspension to −20° C.;
separating a solid material from said suspension;
washing solid material with isooctane at about −20° C.; and
drying the solid material to obtain a crystalline composition comprising cannabidiol and less than 10 ppm delta-9-tetrahydrocannabinol.

43. A method of treating a disease in a subject comprising, administering to said subject a composition comprising a therapeutic amount of cannabidiol and an amount of delta-9-tetrahydrocannabinol, wherein said amount of delta-9-tetrahydrocannabinol is less than about 20 µg per day.

44. The method of embodiment 43, wherein the disease is selected from the group consisting of emesis, pain, inflammation, multiple sclerosis, Parkinson's disease, Huntington's disease, Tourette's syndrome, Alzheimer's disease, epilepsy, glaucoma, osteoporosis, schizophrenia, cancer and obesity.

45. The composition of embodiment 10, wherein said crystalline polymorph Form A has at least one of: (a) a d10 particle size ranging from about 1 µm to about 10 µm; (b) a d50 particle size ranging from about 8 µm to about 40 µm; and (c) a d90 particle size ranging from about 8 µm to about 500 µm 46. The composition of embodiment 10, wherein said crystalline polymorph Form A has a d50 particle size ranging from about 8 µm to about 40 µm.

47. The composition of embodiment 10, wherein said crystalline polymorph Form A has a d90 particle size ranging from about 8 µm to about 500 µm.

48. A composition comprising: cannabidiol, halogenated cannabidiol and delta-9-tetrahydrocannabinol, wherein said cannabidiol is present in an amount of at least about 99.999% w/w of the composition, said delta-9-tetrahydrocannabinol is present in an amount less than 10 ppm and said halogenated cannabidiol is present in an amount less than 10 ppm.

49. The composition of embodiment 48, wherein said delta-9-tetrahydrocannabinol is present in an amount less than 8 ppm.

50. The composition of embodiment 48, wherein said delta-9-tetrahydrocannabinol is present in an amount less than 6 ppm.

51. The composition of embodiment 48, wherein said delta-9-tetrahydrocannabinol is present in an amount less than 4 ppm.

52. The composition of any one of embodiments 48-51, wherein said halogenated cannabidiol is a brominated cannabidiol.

53. The composition of embodiment 52, wherein said brominated cannabidiol is 4-monobromo-CBD.

54. The composition of embodiment 53, wherein said 4-monobromo-CBD is present in an amount less than 5 ppm.

55. The composition of embodiment 54, wherein said 4-monobromo-CBD is present in an amount from about 0.1 ppm to about 3 ppm.

56. An enriched composition comprising: at least 99.999% cannabidiol, and total impurities less than 10 ppm, wherein said impurities comprise a halogenated cannabidiol.

57. The composition of embodiment 56, wherein said impurities further comprise delta-9-tetrahydrocannabinol.

58. The composition of embodiment 57, wherein said halogenated cannabidiol and said delta-9-tetrahydrocannabinol are present at a ratio of about 1:1 to about 5:1.

59. A recrystallized composition comprising: cannabidiol, halogenated cannabidiol and delta-9-tetrahydrocannabinol, wherein said cannabidiol is present in an amount at least about 99.999% w/w of the composition, said delta-9-tetrahydrocannabinol is present in an amount less than 5 ppm, and said halogenated cannabidiol is present in an amount less than about 10 ppm, wherein said composition is a solid.

60. The recrystallized composition of embodiment 59, wherein said composition is recrystallized from isooctane.

61. The recrystallized composition of embodiment 59 or 60, wherein said composition is a crystalline powder.

62. A crystalline cannabidiol composition comprising: cannabidiol and halogenated cannabidiol, wherein said composition is free of delta-9-tetrahydrocannabinol.

63. The composition of any one of embodiments 48-59, wherein said composition is free of cannabinoid quinone.

64. The composition of any one of embodiments 45-63, wherein said amounts are present upon storage for 3 months or less.

65. The composition of any one of embodiments 48-62, further comprising a pharmaceutically acceptable excipient.

66. A suspension comprising:
a composition comprising, at least 99.999% cannabidiol, and total impurities less than 10 ppm, wherein said impurities comprise a halogenated cannabidiol; and
a solvent, wherein said composition is insoluble or slightly insoluble in said solvent at 20° C. or below.

67. The suspension of embodiment 66, wherein said solvent is isooctane.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Unless otherwise stated, all reactions described herein were carried out under argon or nitrogen atmosphere.

Example 1—(Protocol 1) Preparation of Cannabidiol, (1'R,2'R)-5'-methyl-4-pentyl-2'-(prop-1-en-2-yl)-1',2',3',4'-tetrahydro-[1,1'-biphenyl]-2,6-diol Cannabidiol was prepared according to the present disclosure.

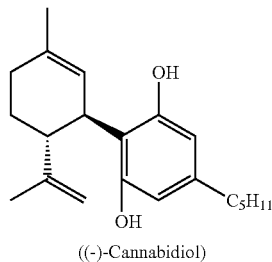

((-)-Cannabidiol)

Scheme 1-1—A Synthetic Route for the Preparation of 4,6-Dibromo-Olivetol

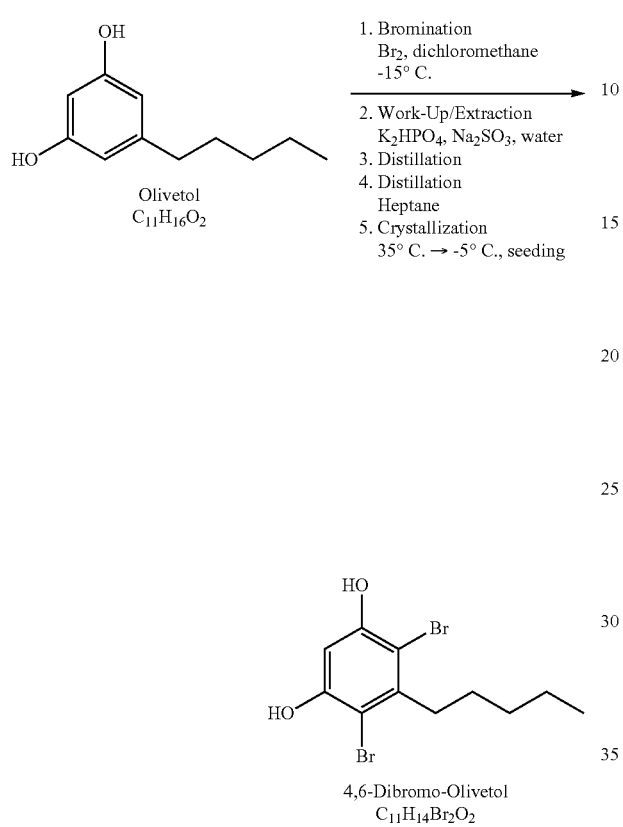

Scheme 1-2—A Synthetic Route for the Preparation of Dibromo-CBD, (1'R,2'R)-3,5-dibromo-5'-methyl-4-pentyl-2'-(prop-1-en-2-yl)-1',2',3',4'-tetrahydro-[1,1'-biphenyl]-2,6-diol

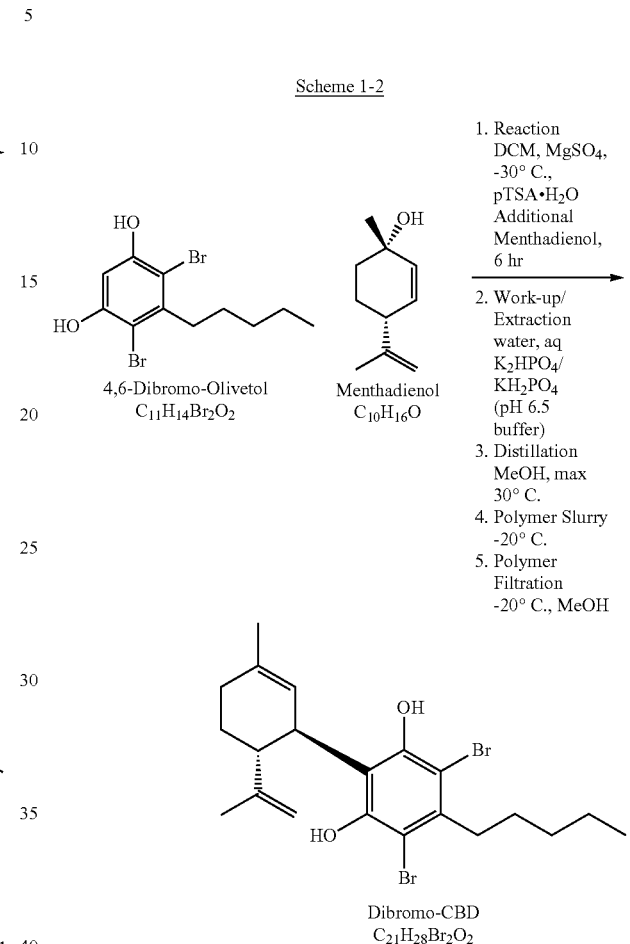

Olivetol (16.2 kg dry basis, 0.0897 kmol) was dissolved in dichloromethane (46 L/kg). The solution was cooled to −15° C., where it turned into a thin white suspension. Bromine (29.8 kg, 2.080 eq. with respect to Olivetol) was then added at −15° C. The reaction mixture transformed into a red solution at the end of the addition; no gas evolution was observed. The mixture dwelled for 5 min.

The process was monitored by IPC (In Process Control). Once the solution was compliant (NMT 0.5%, 4-monobromoolivetol) it was warmed to 0° C. and then poured over a solution of dipotassium hydrogenphosphate (47.2 kg) and sodium sulfite (1.1 kg) in demineralized water (290.9 kg), while maintaining the quench temperature between 0 and 5° C.

The biphasic mixture was warmed to 25° C. and stirred for 30 min, after which the layers settled. The upper aqueous layer was discarded. The organic layer was concentrated to 97 L. Heptane was added (331.6 kg), and then again distilled at 50° C. under partial vacuum down to 339 L.

The solution was cooled to 35° C., seeded with 4,6-dibromo-Olivetol (23 g, 0.10%-wt), and allowed to dwell for 1 h. Finally, the reactor content was cooled to −5° C. in 6 h±30 min to allow for crystallization. The product was isolated, washed with cold (0° C.) heptane (33.2 kg), and dried at 40° C. in full vacuum. Yield: 23.9 kg (79% yield).

A stock solution of dipotassium hydrogenphosphate (2.8 kg) in water (37.3 kg) was prepared. 4,6-dibromo-Olivetol (31.9 kg, 0.0944 kmol), dichloromethane (283.6 kg, 6.7 volumes), and menthadienol (9.3 kg, 0.65 eq.) were charged in a cryogenic reactor. The mixture was stirred to ensure dissolution, and then anhydrous magnesium sulfate (31.6 kg) was added. The suspension was cooled to −30° C., and then p-toluenesulfonic acid hydrate (8.8 kg) was added to trigger the alkylation reaction. The mixture dwelled for 1 h. Menthadienol was added in three portions (9.3 kg, 4.3 kg, and 1.4 kg, i.e. 0.65, 0.30 and 0.10 eq.), at least 2 h, 3 h, and 1 h into the reaction, respectively.

The conversion was checked by IPC (NMT 0.5%, 4,6-dibromo-olivetol); if not compliant, the mixture was further stirred and the IPC repeated. If the IPC was still not compliant, more menthadienol (1.4 kg, 0.10 eq.) was added, stirred, and the IPC repeated.

The mixture was warmed to 0° C. and the suspended solids (Mg sulfate and p-toluenesulfonic acid) were filtered off. The cake was then washed with dichloromethane to recover the product.

The filtrate was quenched with demineralized water while maintaining the temperature below 20° C. The pH was adjusted to 6.5 with the hydrogenphosphate stock solution. Once the temperature was adjusted to 25° C., the phases settled, and the aqueous layer was discarded.

The solution was concentrated under partial vacuum (700 mbar) down to 64 L. Methanol (379 kg) was added, triggering the precipitation of the terpenic polymers. Distillation was continued under a maximum of 30° C.

The resultant white slurry was cooled to −20° C. The polymers were then filtered and the filter was rinsed with methanol. The obtained (1'R,2'R)-3,5-dibromo-5'-methyl-4-pentyl-2'-(prop-1-en-2-yl)-1',2',3',4'-tetrahydro-[1,1'-biphenyl]-2,6-diol solution was obtained in 11% yield.

Scheme 1-3—A Synthetic Route for the Preparation of CBD, (1'R,2'R)-5'-methyl-4-pentyl-2'-(prop-1-en-2-yl)-1',2',3',4'-tetrahydro-[1,1'-biphenyl]-2,6-diol

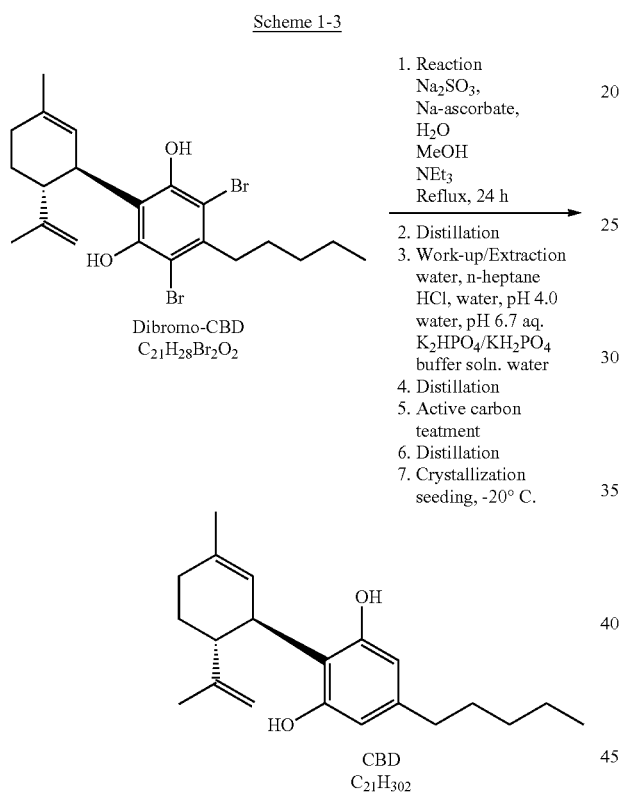

In a glass-lined reactor, sodium sulfite (35.7 kg, 3.00 eq.) and sodium ascorbate (1.6 kg, 0.083 eq) were dissolved in water. The dibromo-CBD solution (the entire lot of which was manufactured from 31.9 kg of 4,6-dibromo-Olivetol synthesized above) was added, followed by methanol if the solution was more than 11% concentrated. Finally, triethylamine (38.2 kg, 4.00 eq.) was added as a base.

The mixture was heated to reflux, where it dwelled for 24 h. Its conversion was then checked by IPC (residual monobromo-cannabidiol max 0.5%). Once the IPC was compliant, the volatiles were removed by distillation until an internal temperature of 85° C. was reached under ambient pressure. A dispersion of product (as oil) in water resulted. Following this, demineralized water (127.6 kg) and n-heptane (319 kg) were added.

The organic layer was extracted with water at pH 4.0 to remove the residual trimethylamine. It was then re-extracted at pH 6.7 with water (159.5 kg) and potassium hydrogenphosphate, and finally washed with water (159.5 kg).

The neutral organic layer was concentrated to 96 L and treated with charcoal (1.6 kg) slurried in n-heptane (32.7 kg) at 50° C. The charcoal was filtered off via polish filtration. Following this, the cake was washed with n-Heptane (21.8 kg).

Figure 2:
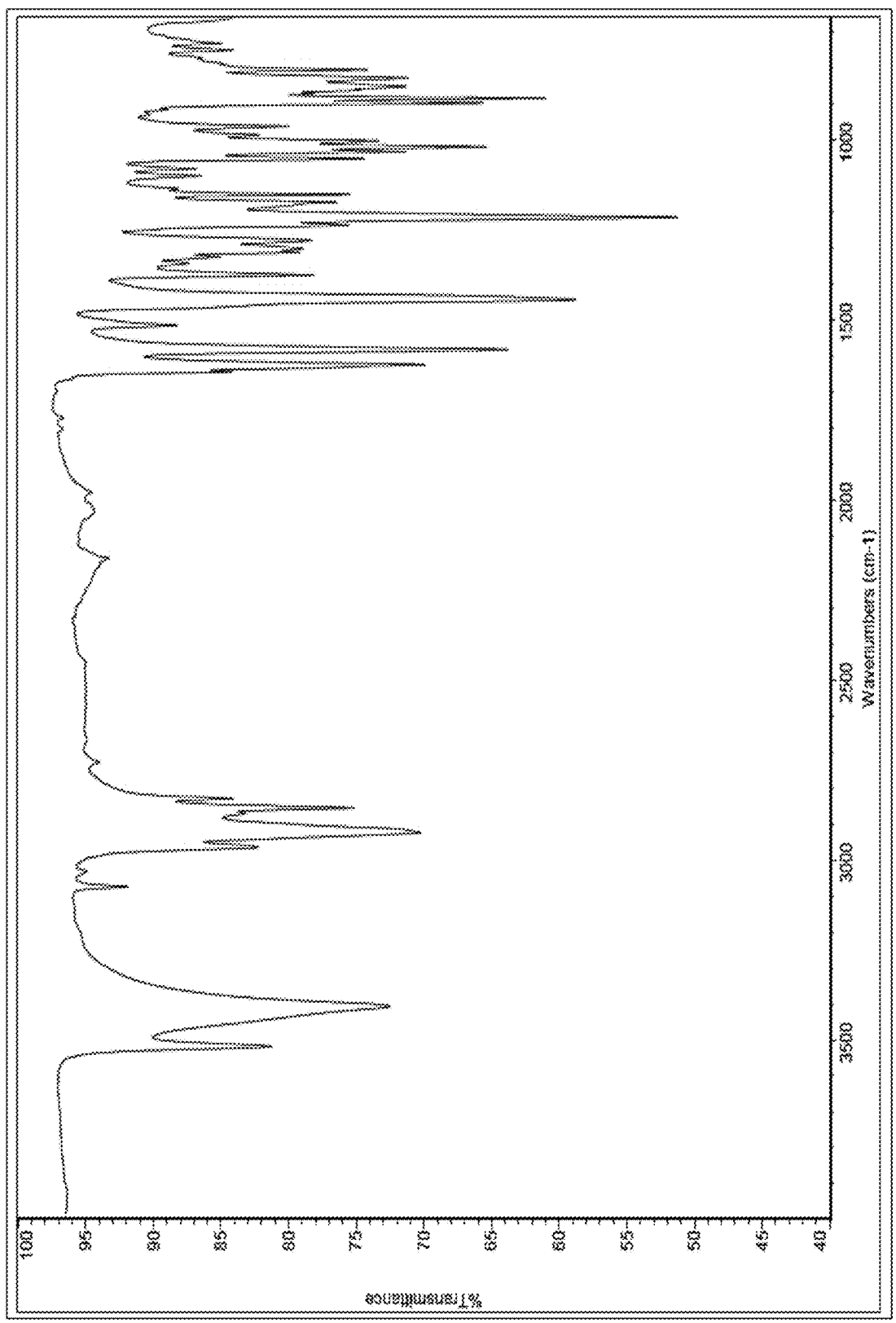
FIG. 2 shows a Fourier Transform Infrared Spectrum of cannabidiol generated by the Protocol 1. The sample underwent recrystallization in n-heptane before analysis.

The solution was concentrated to 96 L and cooled to 20° C. (−)-Cannabidiol was then added as a seed. The suspension was cooled to −20° C. The product was isolated by centrifugation, washed with n-heptane, and dried at 40° C. under full vacuum (drying IPC: max 3000 ppm n-heptane). Yield: 75% (22.3 kg). FIG. 1 and FIG. 2 display a liquid chromatography mass spectrum and Fourier transform infrared spectrum, respectively, of cannabidiol produced by Protocol 1, which underwent recrystallization in n-heptane before analysis. Samples 4, 5, and 6 were produced in accordance with Protocol 1. Chromatograms for Samples 4, 5 and 6 are provided in FIG. 6D, FIG. 6E. and FIG. 6F.

Example 2—(Protocol 2) Preparation of Cannabidiol, (1'R,2'R)-5'-methyl-4-pentyl-2'-(prop-1-en-2-yl)-1',2',3',4'-tetrahydro-[1,1'-biphenyl]-2,6-diol

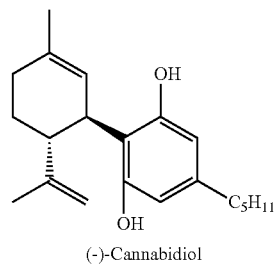

Scheme 2-1—Synthesis of 4,6-dibromo-Olivetol

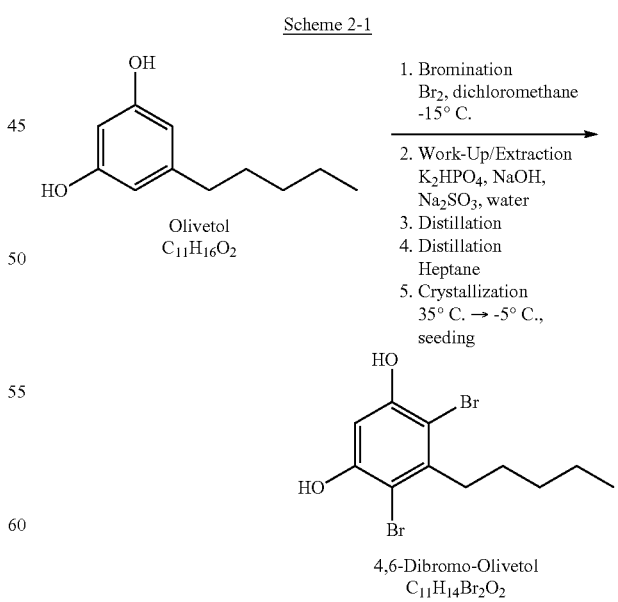

Bromine (1.291 kg, 2.080 eq. with respect to Olivetol) was added to a suspension of Olivetol (0.7 kg, 3.88 mol) in dichloromethane (42 kg, 31.7 L) at −15° C. The reaction mixture was stirred for 5 min and then monitored by IPC to ensure complete conversion (NMT 0.5% 4-monobromoolivetol). An aqueous solution of dipotassium hydrogenphosphate (2.03 kg, 1.5 eq.), sodium hydroxide (0.233 kg, 1.5 eq.), and sodium sulfite (0.049 kg, 0.1 eq.) was then added to the mixture at 20° C. The lower organic phase was separated at 27° C. and dichloromethane was partially distilled off at atmospheric pressure to a volume of ~6 mL/$g_{Olivetol}$. Following this, n-Heptane was added (14.35 kg). The solution was further concentrated at 50° C. (900 to 200 mbar) to distill remaining dichloromethane azeotropically and reach a residual volume of ~20 mL/$g_{Olivetol}$. The solution was seeded at 20 to 40° C., cooled to −5° C. over a period of 6 h, and stirred for at least 1 h. The product was isolated by filtration, washed with cold n-heptane, and dried in vacuo at 40° C. Typical Yield: 70-82% (22-23 g/L).

Scheme 2-2—A Synthetic Route for the Preparation of Dibromo-CBD, (1'R,2'R)-3,5-dibromo-5'-methyl-4-pentyl-2'-(prop-1-en-2-yl)-1',2',3',4'-tetrahydro-[1,1'-biphenyl]-2,6-diol

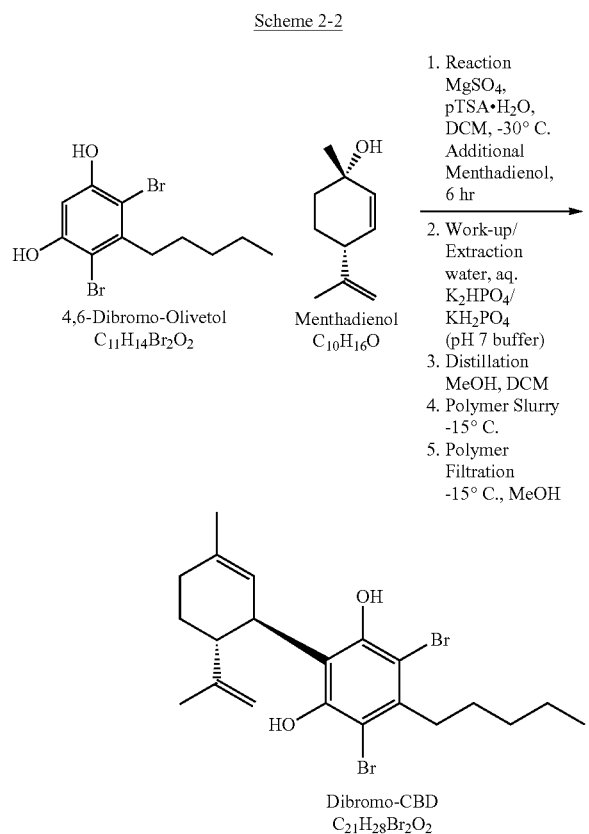

4,6-dibromo-olivetol (100 g), menthadienol (29.3 g, 0.650 mol eq. with respect to 4,5-dibromo-olivetol) and magnesium sulfate (100 g, 2.81 mol eq.) were suspended in dichloromethane (679 mL) in a cryogenic reactor. At −30° C., p-toluenesulfonic acid (28.1 g, 0.50 mol eq.) was added to the solution. Additional amounts of menthadienol were added 1 h (0.650 mol eq. 29.3 g) and 3 h (0.3 mol eq. 13.5 g) once the reaction started. After 6 h into the reaction, the reaction was warmed to 0° C. and quenched with water (800 mL). The layers were separated at 25° C. The organic phase was washed with an aqueous phosphate buffer ($K_2HPO_4$/$KH_2PO_4$, pH 7). The organic phase was concentrated (25 to 40° C., 700 to 1000 mbar) and methanol was added (solvent swap). Remaining dichloromethane was removed by distillation (<30° C., 150 mbar). The mixture was cooled to −15° C. and the white precipitate was filtered off after 1 h. The filter cake was washed with methanol (−15° C.) and discarded. The obtained greenish/yellowish solution of dibromo-CBD in methanol was directly used in the next step. Yield in solution: ~95-99% (75 g/L).

Scheme 3-2—A Synthetic Route for the Preparation of CBD, (1'R,2'R)-5Z'-methyl-4-pentyl-2'-(prop-1-en-2-yl)-1',2',3',4'-tetrahydro-[1,1'-biphenyl]-2,6-diol

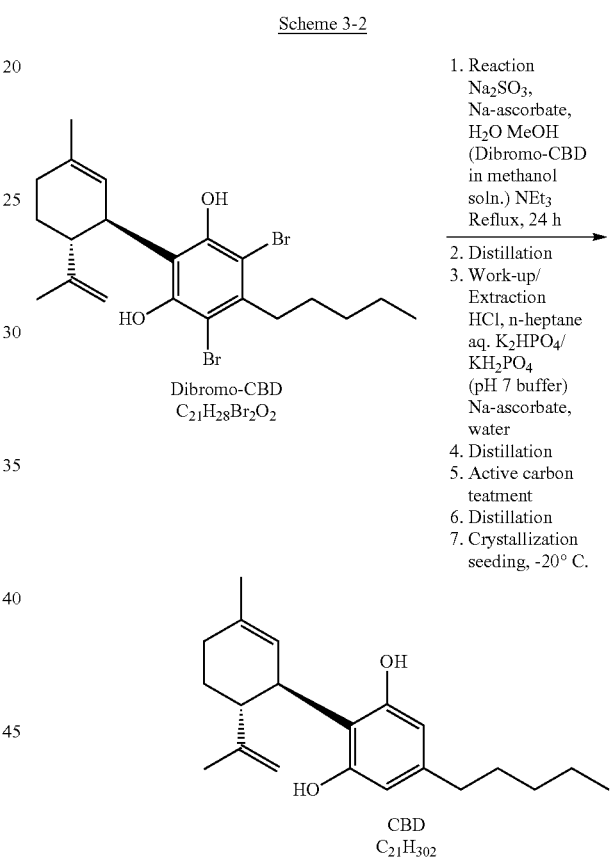

The dibromo-CBD solution in methanol obtained above was added to an aqueous solution of $Na_2SO_3$ (112 g, 3.0 mol eq. with respect to 4,5-dibromo-olivetol) and Na-ascorbate (5 g) at room temperature. Triethylamine (120 g, 4 mol eq.) was added to the off-white suspension and the reaction was stirred at reflux and for approx. 24 h. The reaction solvent (methanol/trimethylamine/water) was partially distilled off at atmospheric pressure and n-heptane (1000 g) was added at 40° C. The suspension was acidified with conc. HCl (18 g) to pH 4.0. After layer separation, the organic layer was washed with a phosphate buffer ($K_2HPO_4$/$KH_2PO_4$, pH 7) and sodium ascorbate and finally with an aqueous sodium ascorbate solution. The organic layer was concentrated, diluted again with n-heptane (684 g), and treated with active carbon for 1 h at 27° C. The suspension was filtered at 27° C. and the charcoal was washed with n-heptane over the reactor. The solution was concentrated in vacuo (target assay: 25 to 30% of CBD in n-heptane) and the remaining organic layer was cooled to 20° C., seeded with (−)-Cannabidiol and stirred at 20° C. for 1 h. The suspension was cooled to 10° C. over 1 h and warmed again to 22° C. over 1 h. The suspension was stirred at 22° C. for 1 h and then further cooled to −20° C. within 6 h. After stirring for 1 h at −20° C., the white suspension was filtered and the wet cake was washed with cold n-heptane over the reactor. The wet product was dried at 40° C. (<10 mbar) for 12 to 24 h. Typical Yield: 75-86% (over two steps) (25 g/L). Sample 3 was produced by Protocol 2. A chromatogram for this Sample is provided in FIG. 6C.

Example 3—(Protocol 3) Preparation of Cannabidiol, (1'R,2'R)-5'-methyl-4-pentyl-2'-(prop-1-en-2-yl)-1',2',3',4'-tetrahydro-[1,1'-biphenyl]-2,6-diol

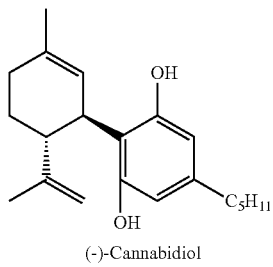

(−)-Cannabidiol

Scheme 3-1—Synthesis of 4,6-dibromo-Olivetol

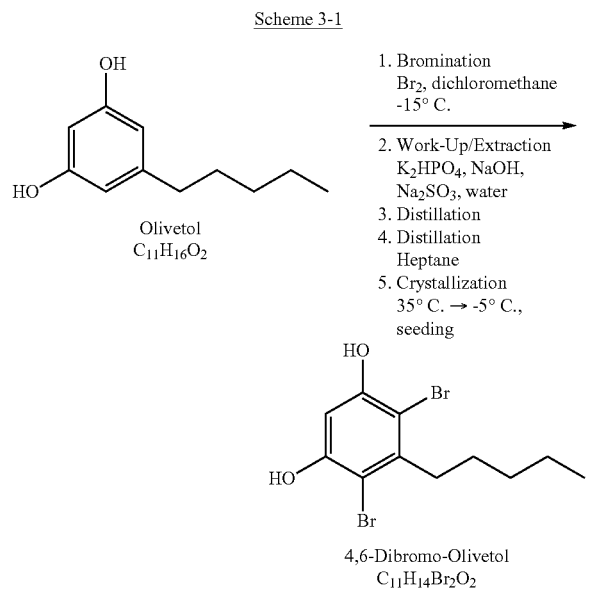

Bromine (1.291 kg, 2.080 eq. with respect to Olivetol) was added to a suspension of Olivetol (0.7 kg, 3.88 mol) in dichloromethane (42 kg, 31.7 L) at −15° C. The reaction mixture was stirred for 5 min and then monitored by IPC to ensure complete conversion (NMT 0.5% 4-monobromoolivetol). An aqueous solution of dipotassium hydrogenphosphate (2.03 kg, 1.5 eq.), sodium hydroxide (0.233 kg, 1.5 eq.), and sodium sulfite (0.049 kg, 0.1 eq.) was added to the reaction mixture at 20° C. The lower organic phase was separated at 27° C. and dichloromethane was partially distilled off at atmospheric pressure to a volume of ~6 mL/g$_{Olivetol}$. Following this, n-heptane was added (14.35 kg). The solution was further concentrated at 50° C. (900 to 200 mbar) to distill the remaining dichloromethane azeotropically and reach a residual volume of 20 mL/g$_{Olivetol}$. The solution was seeded at 20 to 40° C., cooled to −5° C. over a period of 6 h, and stirred for 1 h. The product was isolated by filtration, washed with cold n-heptane, and dried in vacuo at 40° C. Typical Yield: 70-82% (22-23 g/L).

Scheme 3-2—A Synthetic Route for the Preparation of Dibromo-CBD, (1'R,2'R)-3,5-dibromo-5'-methyl-4-pentyl-2'-(prop-1-en-2-yl)-1',2',3',4'-tetrahydro-[1,1'-biphenyl]-2,6-diol

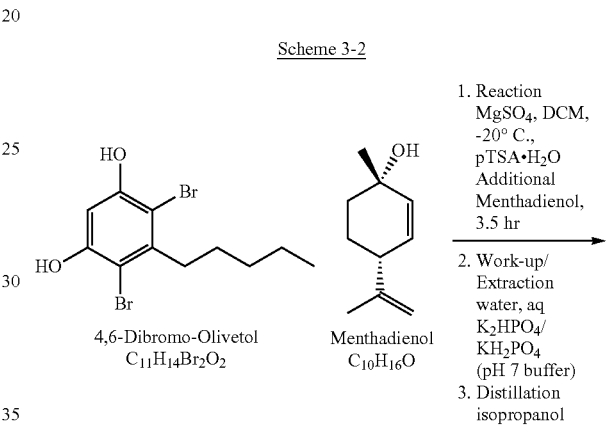

4,6-Dibromo-olivetol (50 g), menthadienol (0.65 eq., 14.6 g) and magnesium sulfate (2.8 eq., 50.0 g) were suspended in dichloromethane (5.5 mL/g, 275 mL) in a cryogenic reactor. At −20° C. p-toluenesulfonic acid (0.2 eq., 5.7 g) was added. Additional amounts of menthadienol were added 0.5 h (0.65 eq., 14.6 g), 1 h (0.4 eq., 7.9 g), and 2 h (0.1 eq., 2.2 g) into the reaction. Approximately 3 h into the reaction, the reaction mixture was warmed to 0° C. and quenched with water (5 mL/g, 250 mL). The layers were separated at 25° C. The organic phase was washed with an aqueous solution of dipotassium hydrogenphosphate (0.13 g/g, 6.5 g) and monopotassium hydrogenphosphate (0.065 g/g, 3.3 g) and water (5 mL/g, 250 mL). The organic phase solvent was swapped to isopropanol (12 mL/g, 600 mL) at reduced pressure (0 to 50° C., 100 to 1000 mbar). The obtained greenish/yellowish solution of dibromo-CBD in isopropanol was directly used in the next step. Estimated Yield in solution: ~95-99%.

Scheme 3-3—A Synthetic Route for the Preparation of CBD, (1'R,2'R)-5'-methyl-4-pentyl-2'-(prop-1-en-2-yl)-1',2',3',4'-tetrahydro-[1,1'-biphenyl]-2,6-diol Scheme 3-3

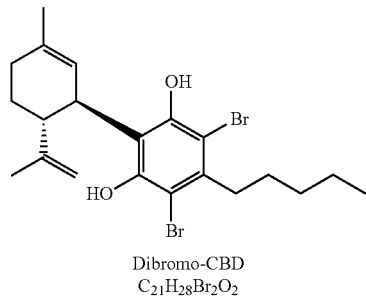

Dibromo-CBD
$C_{21}H_{28}Br_2O_2$

1. Reaction
  $Na_2SO_3$,
  Na-ascorbate,
  $H_2O$
  Isopropanol
  (Dibromo-CBD in isopropanol soln.)
  $NEt_3$
  Reflux, 30-40 h
2. Distillation
3. Work-up/Extraction
  n-heptane
  HCl. pH 4.0 aq.
  $K_2HPO_4/KH_2PO_4$
  (pH 7 buffer)
  Na-ascorbate.
  water
4. Distillation
5. Active carbon teatment
6. Distillation
7. Crystallization
  seeding, -20° C.

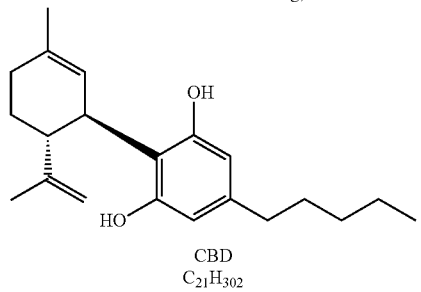

CBD
$C_{21}H_{30}O_2$

The dibromo-CBD solution in isopropanol obtained in step 2 above was combined with an aqueous solution of $Na_2SO_3$ (3.0 eq., 55.9 g/g) and Na-ascorbate (0.05 g/g, 2.5 g) in water (7 mL/g, 350 mL). Triethylamine (4.0 eq., 55.9 g) was added to the off-white suspension and the reaction was stirred at reflux for approximately 36 h. The reaction solvent (isopropanol/trimethylamine/water) was partially distilled off at atmospheric pressure and n-heptane (7 mL/g, 350 mL) was added at 40° C. The suspension was acidified with conc. HCl to pH 4.0. After layer separation, the organic phase was washed with an aqueous solution of dipotassium hydrogenphosphate (0.13 g/g, 6.5 g) and monopotassium hydrogenphosphate (0.065 g/g, 3.3 g) and water (5 mL/g, 250 mL). After layer separation, the organic phase was washed with an aqueous solution of sodium ascorbate (0.05 g/g, 2.5 g) and water (5 mL/g, 250 mL). The organic layer was concentrated, diluted again with n-heptane (4 mL/g, 200 mL) and treated with active carbon at 27° C. The charcoal was washed with n-heptane (3 mL/g, 150 mL) over the reactor. The solution was concentrated in vacuo and the remaining organic layer was cooled to 20° C., seeded with (−)-Cannabidiol and stirred at 20° C. for 1 h. The suspension was cooled to 10° C. over 1 h and warmed again to 22° C. over 1 h. The suspension was stirred at 22° C. for 1 h and then further cooled to −20° C. over a period of 6 h. After stirring for 1 h at −20° C., the white suspension was filtered and the wet cake was washed with cold isooctane (1.5 mL/g, 75 mL) over the reactor. The wet product was dried at 40° C. (<10 mbar) for 12 to 24 h. Typical Yield: 65-75% (over two steps).

Figure 6A:
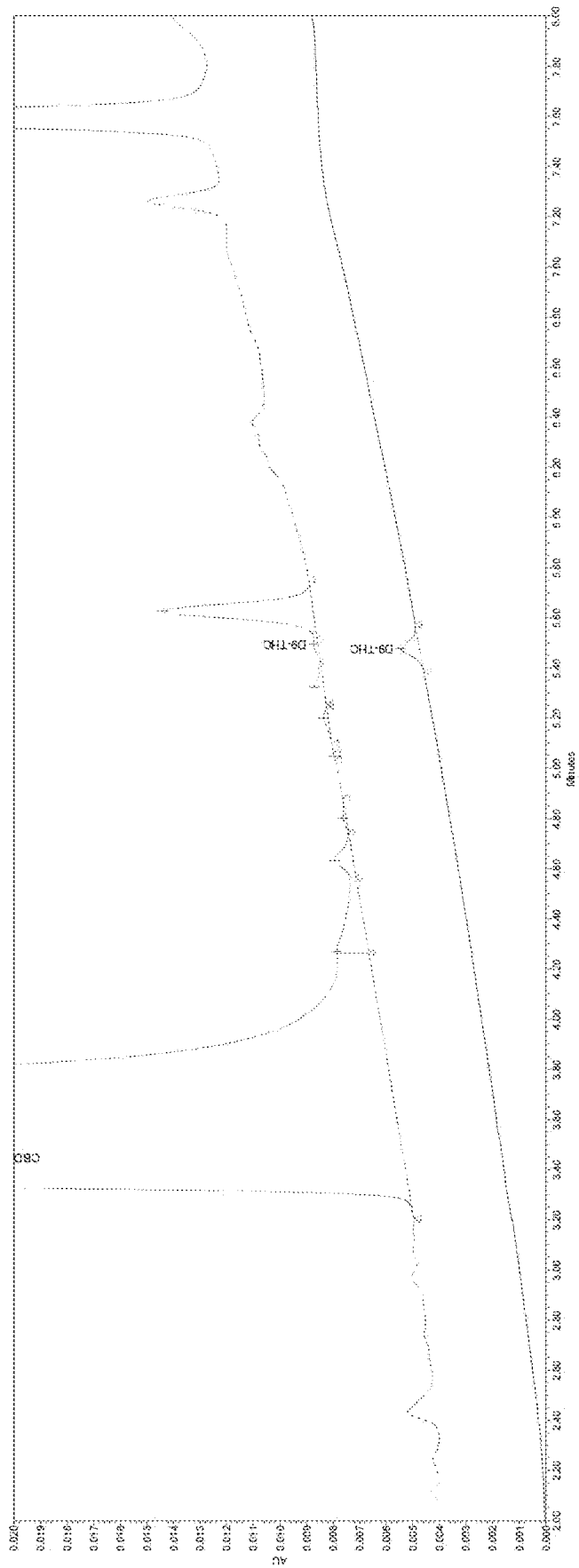
FIG. 6A shows a chromatogram of cannabidiol sample 1, produced by Protocol 3, and which underwent recrystallization in isooctane before HPLC experiments. The chromatogram is placed against that of a 10 PPM THC working standard.
Figure 6B:
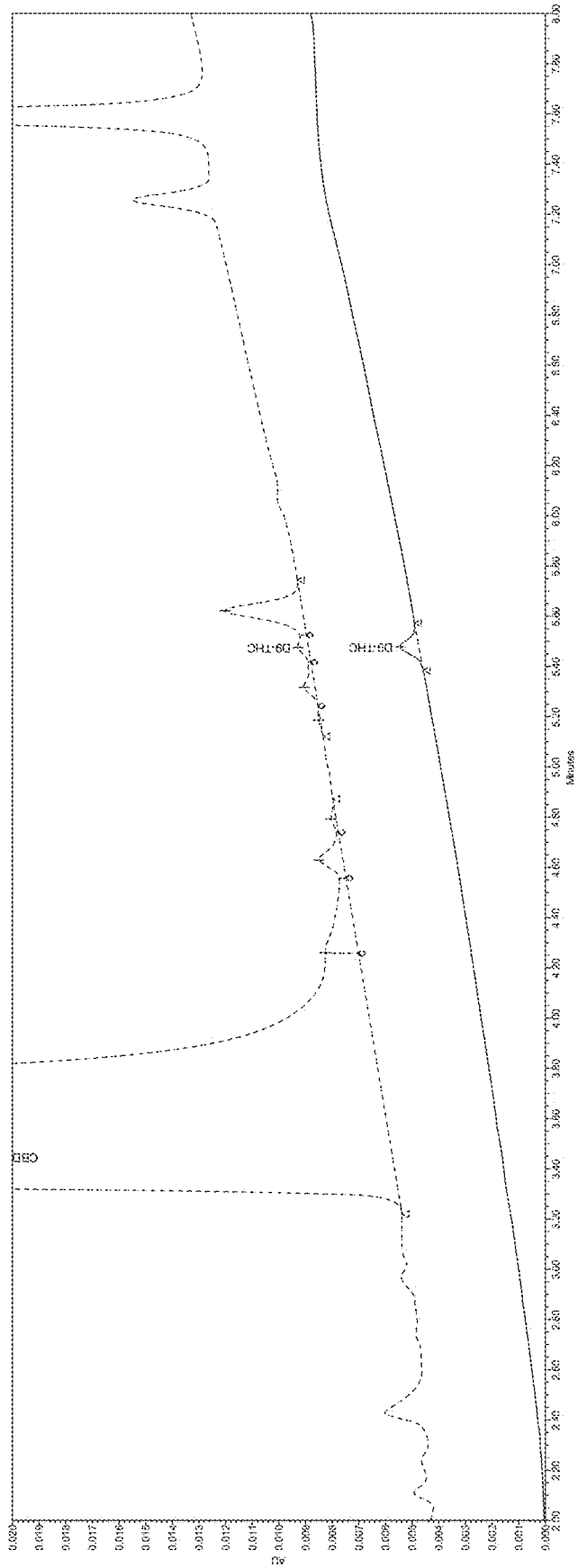
FIG. 6B shows a chromatogram of cannabidiol sample 2, produced by Protocol 3, and which underwent recrystallization in isooctane before HPLC experiments. The chromatogram is placed against that of a 10 PPM THC working standard.
Figure 6C:
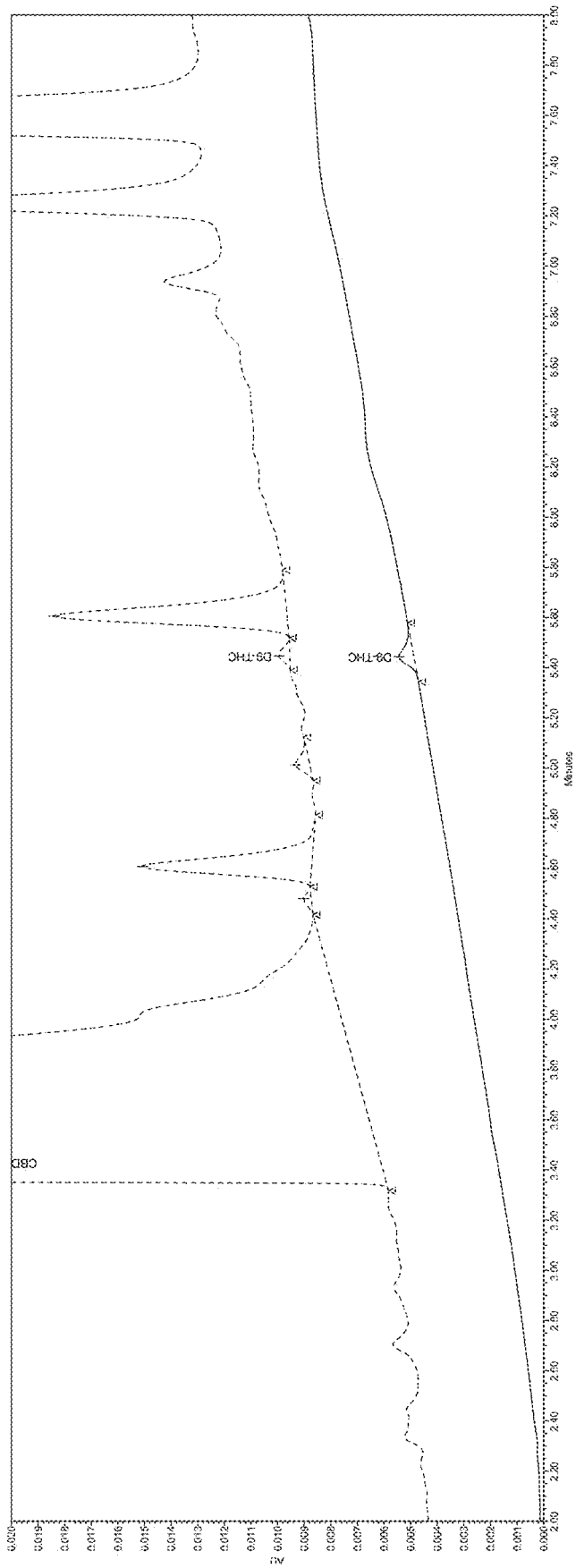
FIG. 6C shows a magnified view of a chromatogram of sample 3, produced by Protocol 2. The chromatogram is placed against that of a 10 PPM THC working standard.
Figure 6D:
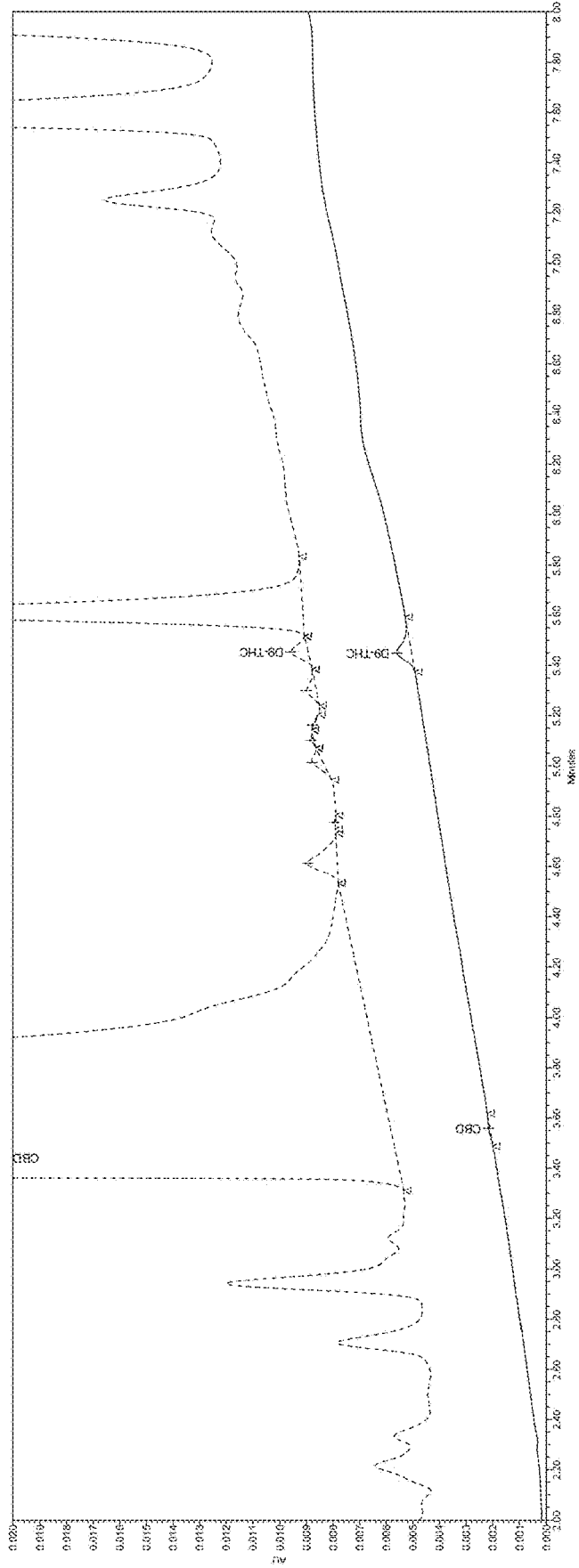
FIG. 6D shows a magnified view of a chromatogram of sample 4, produced by Protocol 1. The chromatogram is placed against that of a 10 PPM THC working standard.
Figure 6E:
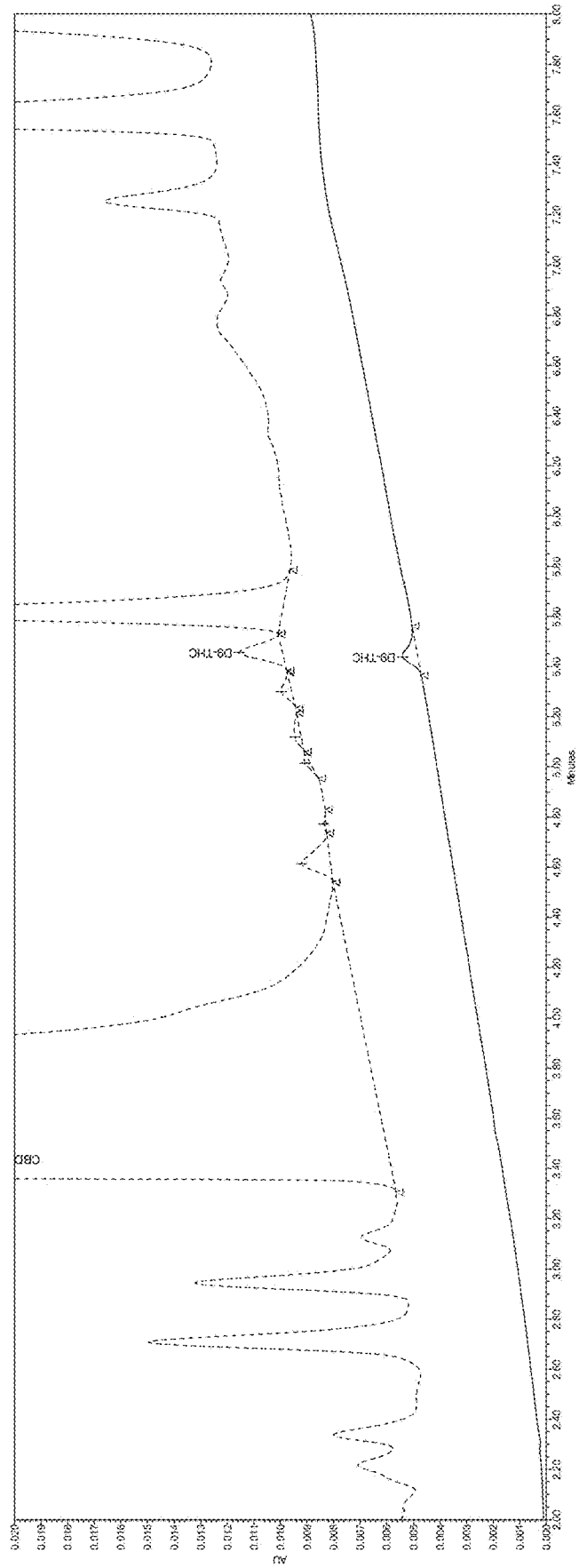
FIG. 6E shows a magnified view of a chromatogram of sample 5, produced by Protocol 1. The chromatogram is placed against that of a 10 PPM THC working standard.
Figure 6F:
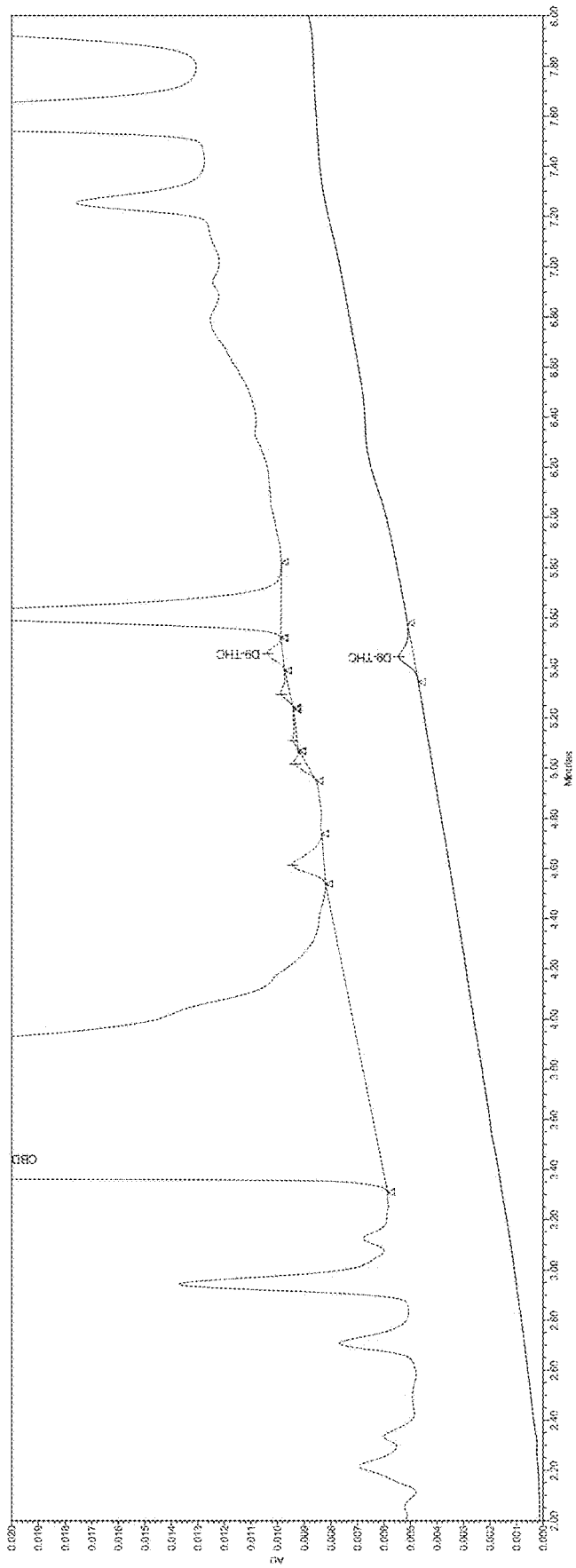
FIG. 6F shows a magnified view of a chromatogram of sample 6, produced by Protocol 1. The chromatogram is placed against that of a 10 PPM THC working standard.

Example 4—Recrystallization (−)-Cannabidiol (20 g) was dissolved in isooctane (80 mL) and heated to 40° C. The solution was cooled to 32° C., seeded with (−)-Cannabidiol (0.20 g), and stirred at 32° C. for 1 h. The suspension was cooled to −20° C. over 3 h and the white suspension was filtered and the wet cake was washed with cold isooctane The wet product was dried at 40° C. (<10 mbar) for 12 to 24 h. Typical Yield: 90-96%. Table 1 shows the Product Characteristics for samples 1 and 2, which were produced by Protocol 3 and underwent recrystallization in isooctane. Chromatograms of these samples are shown in FIG. 6A and FIG. 6B.

TABLE 1

Product Characteristics for Protocol 3 Following Recrystallization

| Analysis | Specification | Sample 1 | Sample 2 |
|---|---|---|---|
| Appearance | White to slightly beige (or slightly yellowish brown/slightly yellow/slightly brown) crystalline powder | white | white |
| Identification | | | |
| IR | Complies with reference | not tested | not tested |
| UPLC | Complies with reference | complies | complies |
| Assay (UPLC) | 97.0% to 102.0% | 101.28 | 100.38 |
| Chromatographic purity (UPLC) | | | |
| Olivetol | NMT 0.15% | ND | 0.01 |
| 4-Monobromo-cannabidiol | NMT 0.15% | 0.01 | ND |
| Delta-9-Tetrahydrocannabinol | MNT 0.10% | ND | ND |
| Each unspecified impurity | NMT 0.10% | 0.03 | 0.02 |
| Total Impurities | NMT 1.0% | 0.06 | 0.07 |
| THC impurity content (HPLC) | | 1.9 | 5.9 |
| Water Content | NMT 0.5% | 0.10 | 0.12 |
| Residue on Ignition (ROI) | NMT 0.2% | 0.0 | 0.0 |
| Specific Optical Rotation (ROS) | −140° to −122° | not tested | not tested |

TABLE 1-continued

Product Characteristics for Protocol 3 Following Recrystallization

| Analysis | Specification | Sample 1 | Sample 2 |
|---|---|---|---|
| Residual Solvents | | | |
| Methanol | NMT 3000 ppm | | |
| n-Heptane | NMT 5000 ppm | | |
| Dichloromethane | NMT 600 ppm | | |
| Triethylamine | NMT 5000 ppm | | |
| Color in Solution | For Information | colorless | colorless |
| Clarity of Solution | For Information | clear | clear |
| XRPD | For Information | not tested | not tested |
| SEC | For Information | | |
| Malvern 2K (dry dispersion) | For Information | D10: 7.8 um D50: 21.8 um D90: 152.9 um | D10: 8.0 um D50: 23.9 um D90: 157.5 um |

Example 5: HPLC Method for Assay/Impurity Testing in Cannabidiol

Figure 3:
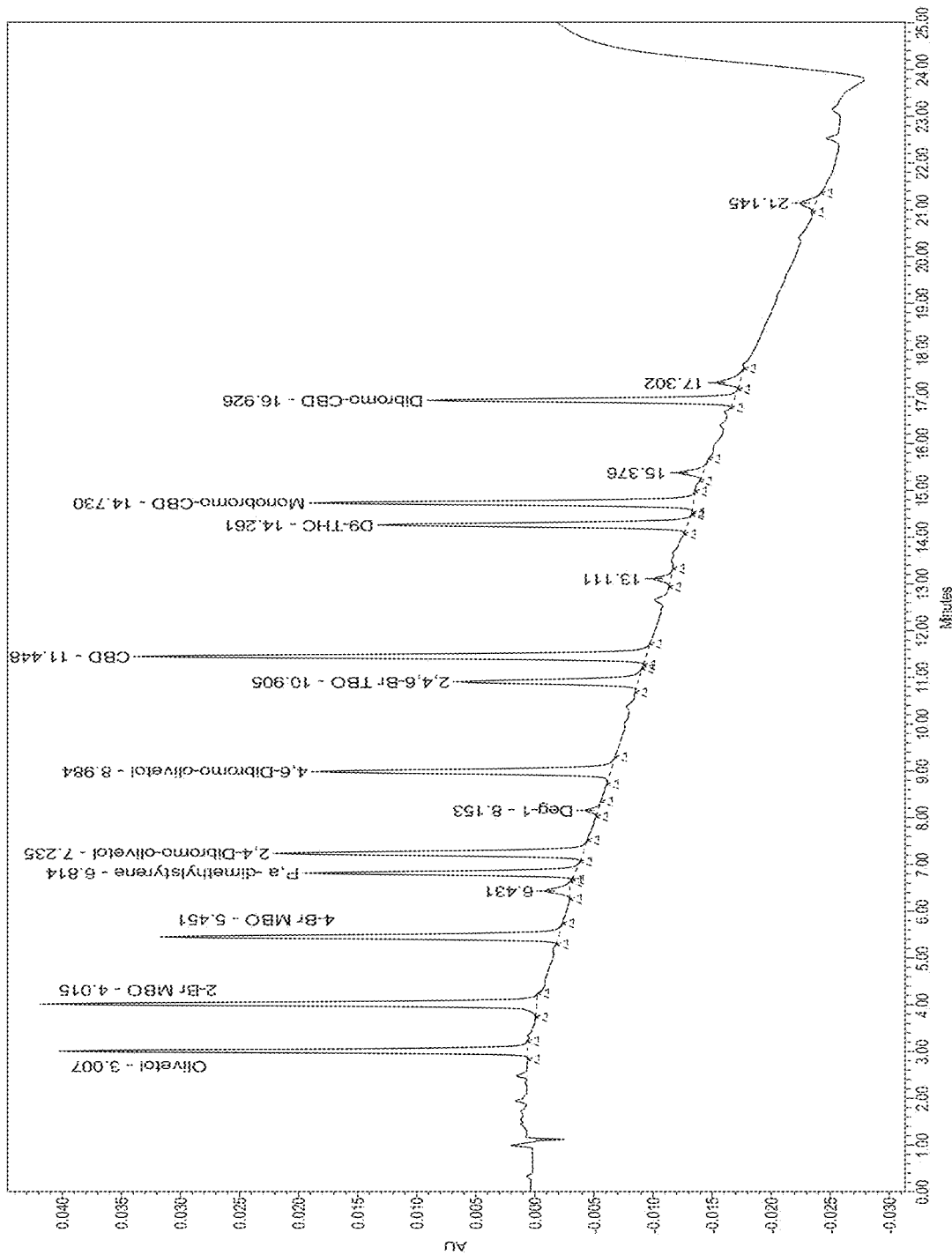
FIG. 3 shows a representative HPLC chromatogram of retention time marker samples.
Figure 4:
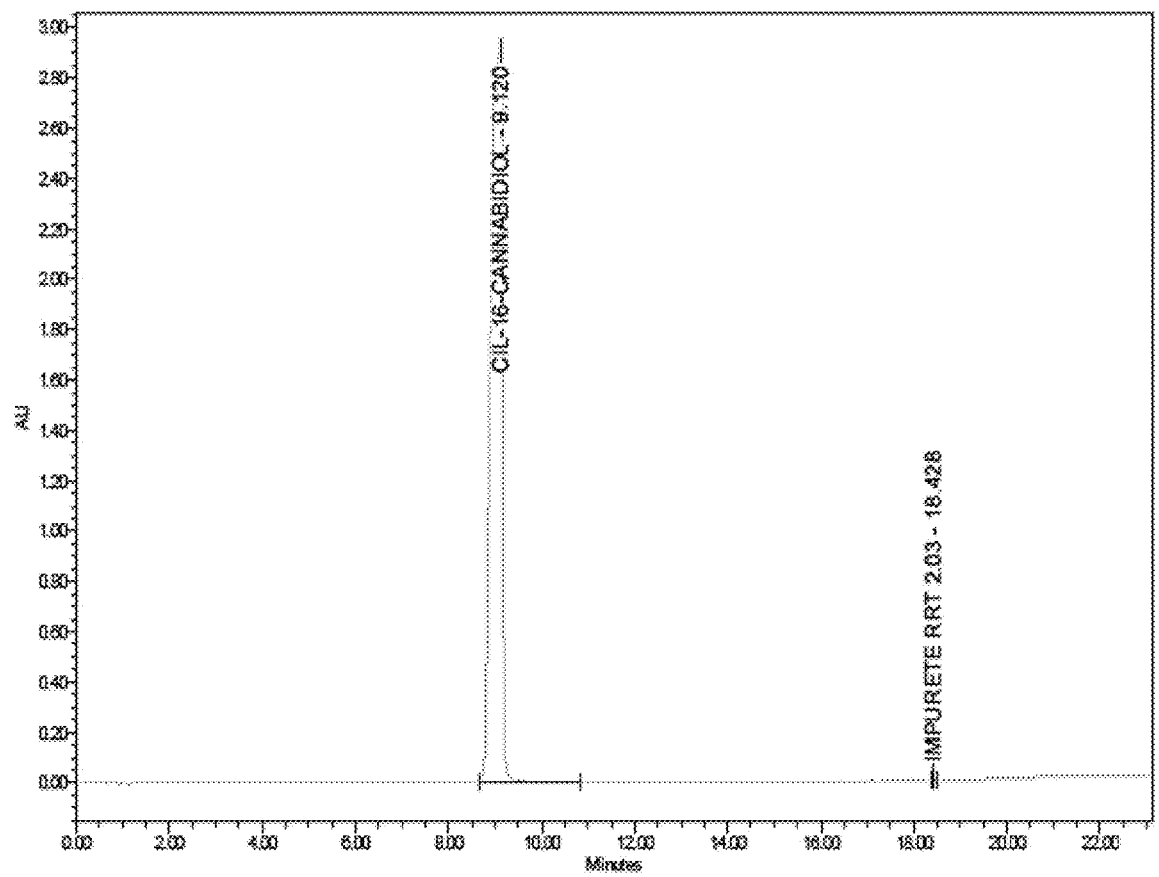
FIG. 4 shows a UPLC chromatogram of cannabidiol obtained by Protocol 2.

A method for assay/impurity testing for cannabidiol was developed. A Waters) (Bridge Shield RP18 3.5 µm, 3.0×150 mm column was used and operated at a column temperature of 35° C. and UV wavelength of 225 nm. Mobile Phase A was 0.05% (v/v) acetic acid in $H_2O$/Acetonitrile 95/5 (v/v), while mobile phase B was methanol. The sample diluent was 30/70 $H_2O$/ACN (v/v) with a sample concentration of 0.3 mg/mL, standard concentration of 0.3 mg/mL, and an injection size of 10 µL. The Mobile Phase Gradient followed is shown in Table 2. FIG. 3 is a representative chromatogram of retention time marker samples obtained using this HPLC method. A UPLC chromatogram of cannabidiol isolated by Protocol 2 is shown in FIG. 4.

TABLE 2

HPLC Mobile Phase Gradient for assay/impurity testing in Cannabidiol

| Time (min) | Flow (mL/min) | % A | % B |
|---|---|---|---|
| 0.0 | 0.7 | 40.0 | 60.0 |
| 19.0 | 0.7 | 10.0 | 95.0 |
| 21.0 | 0.7 | 10.0 | 95.0 |
| 21.1 | 0.7 | 40.0 | 60.0 |
| 25.0 | 0.7 | 40.0 | 60.0 |

Example 6—Ultra Performance Liquid Chromatography of Cannabidiol

Ultra Performance Liquid Chromatography (UPLC) was used to examine the purity of cannabidiol products. An ACQUITY BEH C4 Column was employed, 150 mm length by 2.1 mm. The column temperature was set at 30° C. with a flow rate of 0.4 mL/min, a wavelength of 225 nm, and an injection volume of 4 µL. A linear gradient was programmed as displayed in Table 3.

TABLE 3

Linear Gradient Program Used under UPLC Conditions

| Time (min) | % A (% vol) | % B (% vol) |
|---|---|---|
| 0 | 60 | 40 |
| 15 | 42 | 58 |
| 20 | 10 | 90 |
| 23 | 10 | 90 |
| 23.1 | 60 | 40 |
| 31 | 60 | 40 |

Example 7: Quantifying Low Levels of THC in Cannabidiol

An analytical method using HPLC was developed to determine low levels of delta-9-tetrahydrocannabinol in cannabidiol samples. A Waters XBridge C18 3.5 µm, 3.0×150 mm column was employed and operated at a temperature of 30° C., UV wavelength of 225 nm, and injection size of 20 µL. Mobile Phase A was 0.02% (v/v) acetic acid in $H_2O$, while mobile phase B was 0.02% (v/v) acetic acid in acetonitrile (ACN). The Mobile Phase Gradient followed is shown in Table 4.

TABLE 4

Mobile Phase Gradient for Determining Low Levels of THC in HPLC Experiments

| Time (min) | Flow (mL/min) | % A | % B |
|---|---|---|---|
| 0.0 | 0.8 | 30.0 | 70.0 |
| 5.0 | 0.8 | 10.0 | 90.0 |
| 6.0 | 0.8 | 10.0 | 90.0 |
| 6.1 | 0.8 | 30.0 | 70.0 |
| 10.0 | 0.8 | 30.0 | 70.0 |

Preparation of the THC Stock Solution

An aliquot of 0.5 mL of a D9-THC reference standard (Cerilliant, 1.0 mg/mL MeOH solution) was diluted in a 500-mL volumetric flask using sample diluent (70/30 Acetonitrile/$H_2O$, v/v). The D9-THC concentration was 0.001 mg/mL in the standard stock solution, which corresponded with 200 ppm of D9-THC as compared to the CBD sample solution (nominal CBD concentration was 5.0 mg/mL).

Preparation of the THC Working Standard Solution

An Aliquot of 5 mL of THC Stock Standard Solution was diluted in a 100-mL volumetric flask using the sample diluent. The D9-THC concentration was 0.00005 mg/mL in the working standard solution, corresponding with 10 ppm of D9-THC as compared to the CBD sample solution.

Preparation of the Sample Solution

About 50 mg of cannabidiol sample was weighed into a 10-mL volumetric flask. The volumetric flask was diluted to volume using sample diluent and mixed well.

Sample Set Injection Sequence

A minimum of 6 working standard solutions were injected prior to the sample set. Furthermore, a maximum of 6 injections of CBD sample were injected between bracketing working standard solutions.

Calculations

The amount of THC in each sample was calculated using the following $$THC(ppm) = \frac{THCPeakArea \text{ in SampleSolution}}{Avg. THCPeakArea \text{ in WorkingStds.}} \times$$

$$\frac{10 \text{ (Volume of Sample Solution in mL)}}{Sample \text{ Weight in mg}} \times 0.00005$$

$$(THC \text{ Working Std. Conc. in mg/mL}) \times 1000000$$

Figure 5:
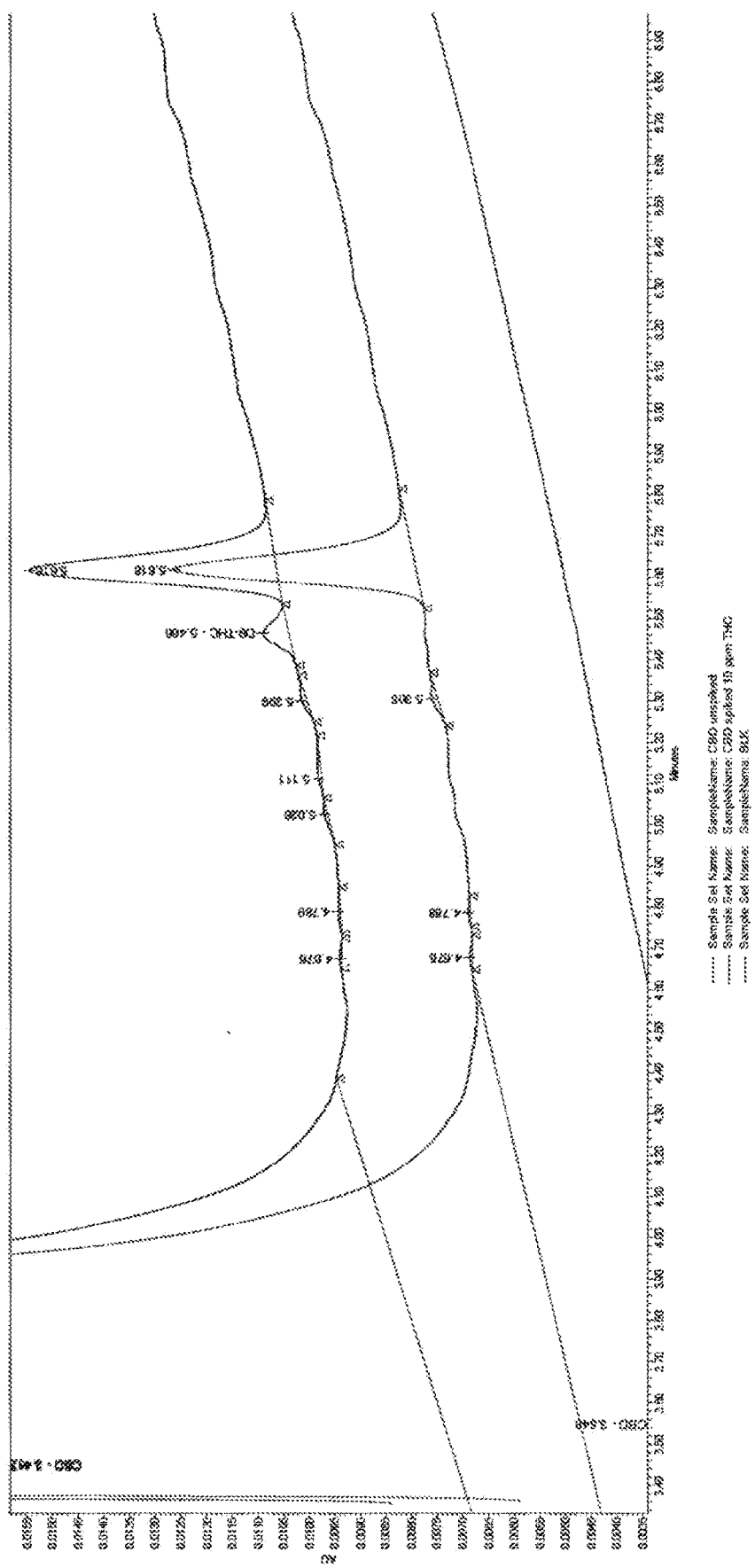
FIG. 5 shows an overlay of HPLC chromatograms of a diluent blank, cannabidiol, and cannabidiol spiked with 10 ppm D9-THC to demonstrate the method sensitivity. The CBD spiked with 10 PPM THC is the top signal showing the greatest intensity, the CBD unspiked sample provides the moderate intensity, while the blank corresponds with the bottom line.

FIG. 5 displays an overlay of HPLC chromatograms of a diluent blank, cannabidiol sample, and cannabidiol sample spiked with 10 ppm D9-THC, demonstrating the method sensitivity. The HPLC chromatograms for several samples and their THC determination are shown in FIG. 6A through FIG. 6E. For reference, each chromatogram in FIG. 6A through FIG. 6F is shown against a 10 ppm THC working standard. For samples 1, 2, and 3, roughly 50.28 mg, 50.77 mg, and 55.60 mg material was used. The results of these HPLC experiments are summarized in Table 5.

TABLE 5

Summary of Cannabidiol HPLC Test Results

| Sample # | Sample Description | Result (D9-THC in ppm) |
|---|---|---|
| 1 | Cannabidiol produced by Protocol 3, recrystallized in isooctane Sample underwent HPLC experiments after stored for 23 days at 55-60° C. | 1.9 |
| 2 | Cannabidiol produced by Protocol 3, recrystallized in isooctane Sample underwent HPLC experiments after stored for 23 days at 55-60° C. | 5.9 |
| 3 | Prepared by Protocol 2, HPLC experiments were run after sample was held in storage for one month at room temperature (25° C.) | 5.1 |
| 4 | Prepared by Protocol 1, HPLC experiment run after sample was held in storage at −16° C. for two years | 8.3 |
| 5 | Prepared by Protocol 1, HPLC experiment run after sample was held in storage at −16° C. for two years | 21.7 |
| 6 | Prepared by the Protocol 1, HPLC experiment run after sample was held in storage at −16° C. for two years | 7.3 |

Samples were analyzed by the low HPLC THC method before and after recrystallization to determine the effect that recrystallization has on purging THC from the sample material. The results are summarized in Table 6. It can be seen that recrystallization provided further purging of THC by ~90%. The levels of THC in "pure" cannabidiol range from about 2-30 PPM.

TABLE 6

Recrystallization Purging Summary

| Protocol | Sample # | THC (PPM) before recrys | THC (PPM) after recrys | Purging % |
|---|---|---|---|---|
| 1 | 4 | 8.3 | Non-Detectable | 100% |
| 3 | 7 | 143.9 | 1.9 | 99% |
|   | 8 | 124.8 | 5.9 | 95% |
|   | 13 | 77.0 | 13.7 | 82% |
|   | 14 | 170.2 | 27.3 | 84% |
|   |   | σ = 129 | σ = 12 |   |

In another series of experiments, cannabidiol samples were spiked with varying amounts of THC. They were analyzed by HPLC before spiking. The spiked samples then underwent recrystallization and were analyzed by HPLC to determine the amount of THC in the recrystallized cannabidiol product. The results of these investigations are provided in Table 7. These spiking experiments demonstrated greater than 95% THC purging.

TABLE 7

Recrystallization Studies with THC Spiking Results

| Protocol and Process | Input CBD THC (PPM) | Post Spike THC (AP) | CBD Product THC (PPM) |
|---|---|---|---|
| Protocol 1 + no spiking | 8.3 PPM | — | ND (100% purge) |
| Protocol 1 + THC spiked to 0.05 AP | 8.3 PPM | 0.06% or 600 PPM | 20.0 PPM (96% purge) |
| Protocol 1 + THC spiked to 0.30 AP | 8.3 PPM | 0.30% or 3000 PPM | 89.5 PPM (97% purge) |

Example 8: Characterization of Cannabidiol by NMR Spectroscopy

Figure 7A:
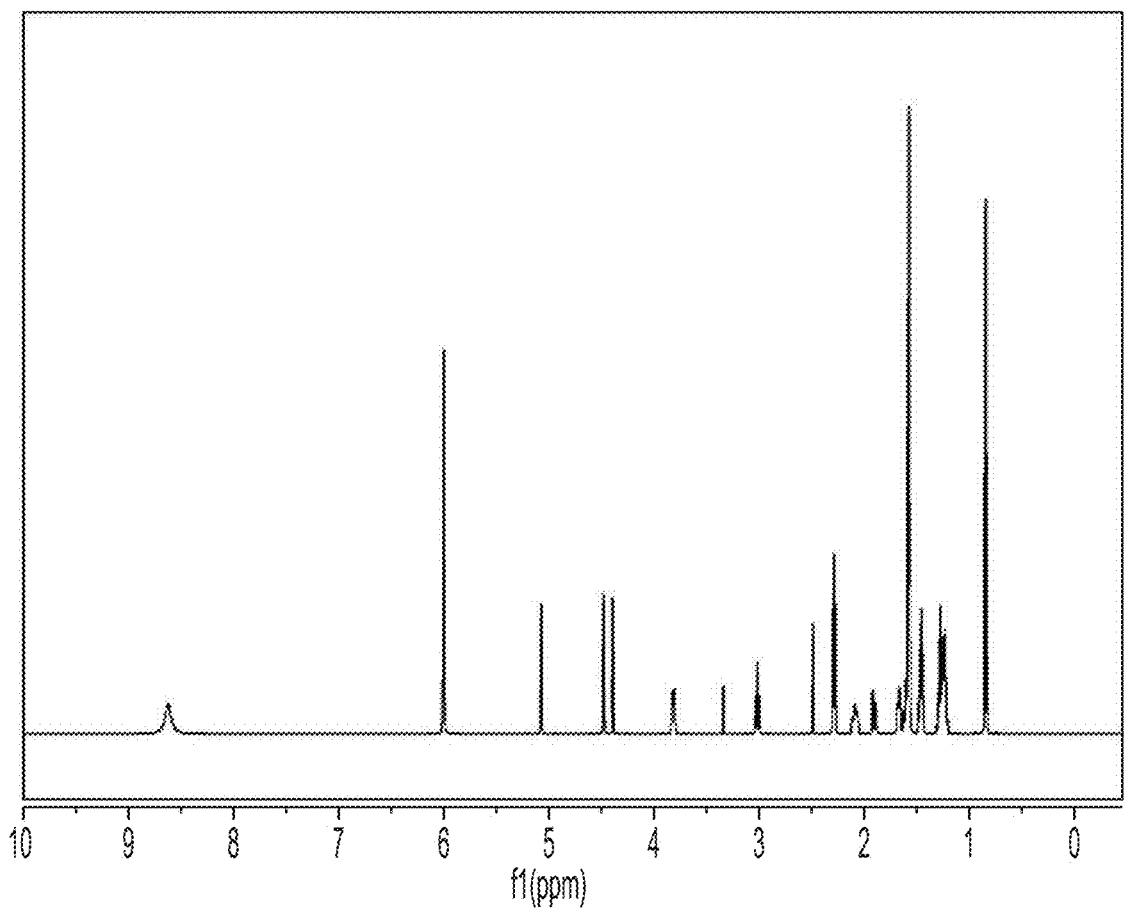
FIG. 7A shows a 1-D proton NMR spectrum of cannabidiol.
Figure 7B:
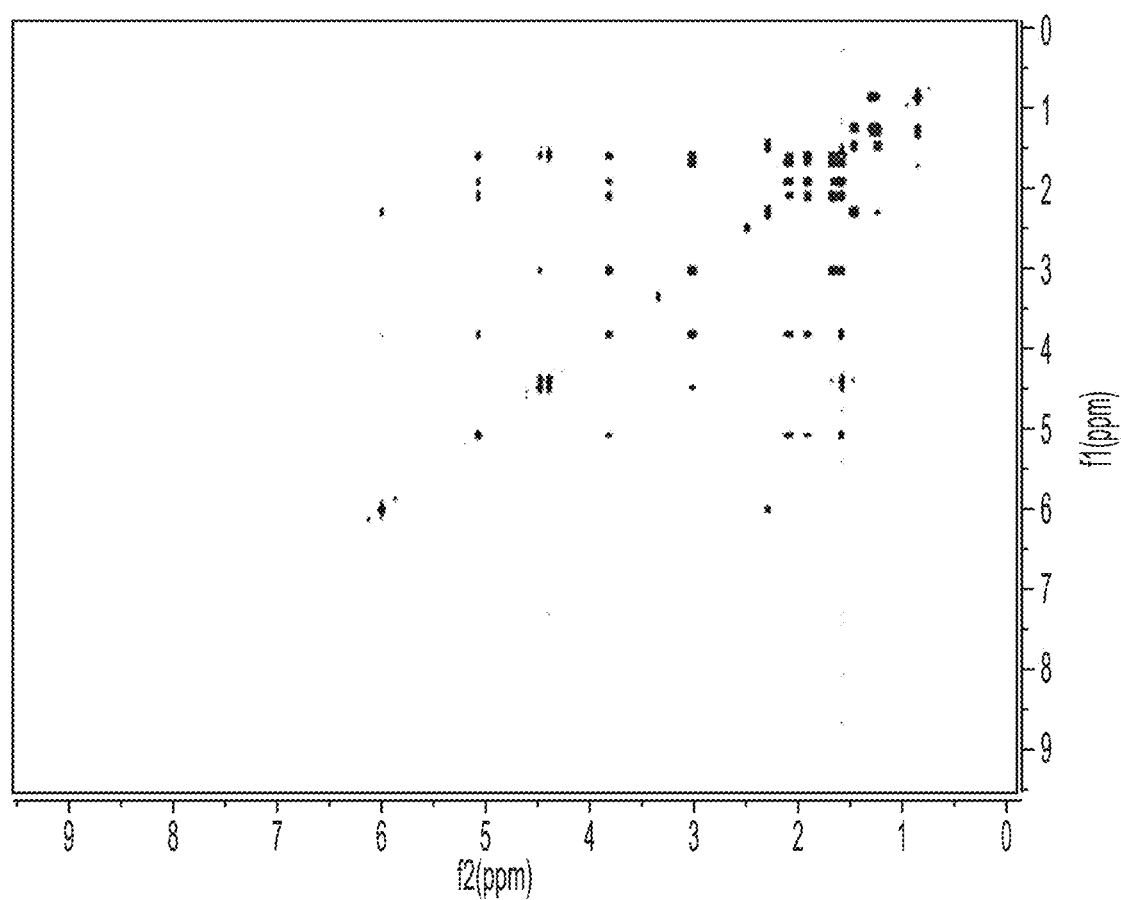
FIG. 7B shows a 2-D gCOSY NMR spectrum of cannabidiol.
Figure 7C:
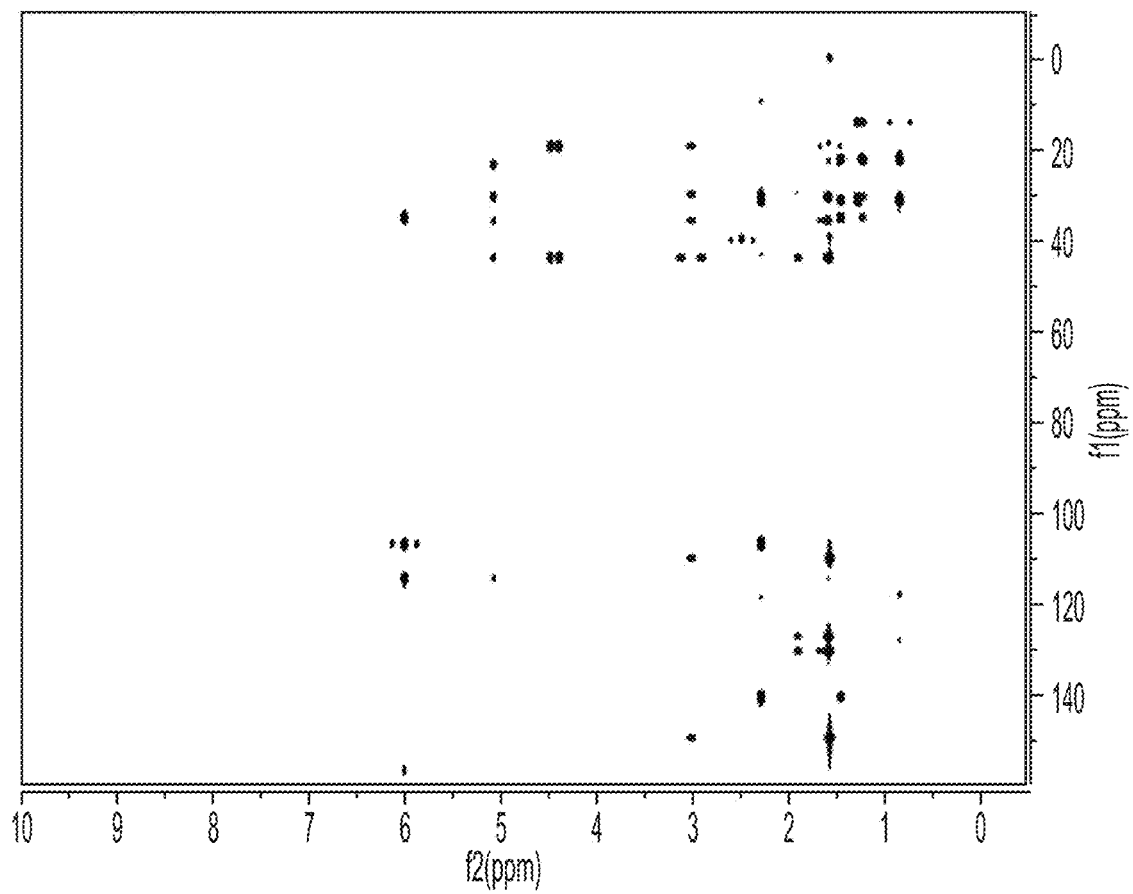
FIG. 7C shows a 2-D gHMBCad NMR spectrum of cannabidiol.
Figure 7D:
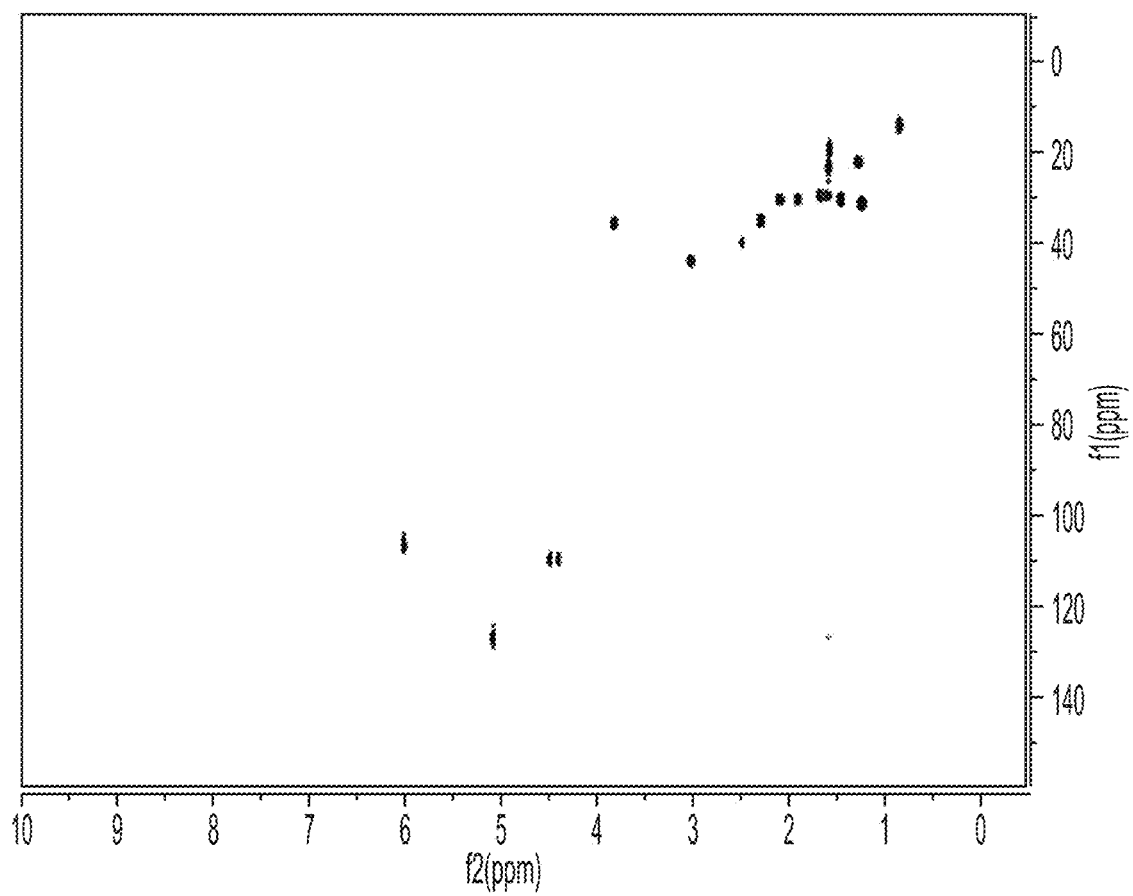
FIG. 7D shows a 2-D gHSQCad NMR spectrum of cannabidiol.
Figure 7E:
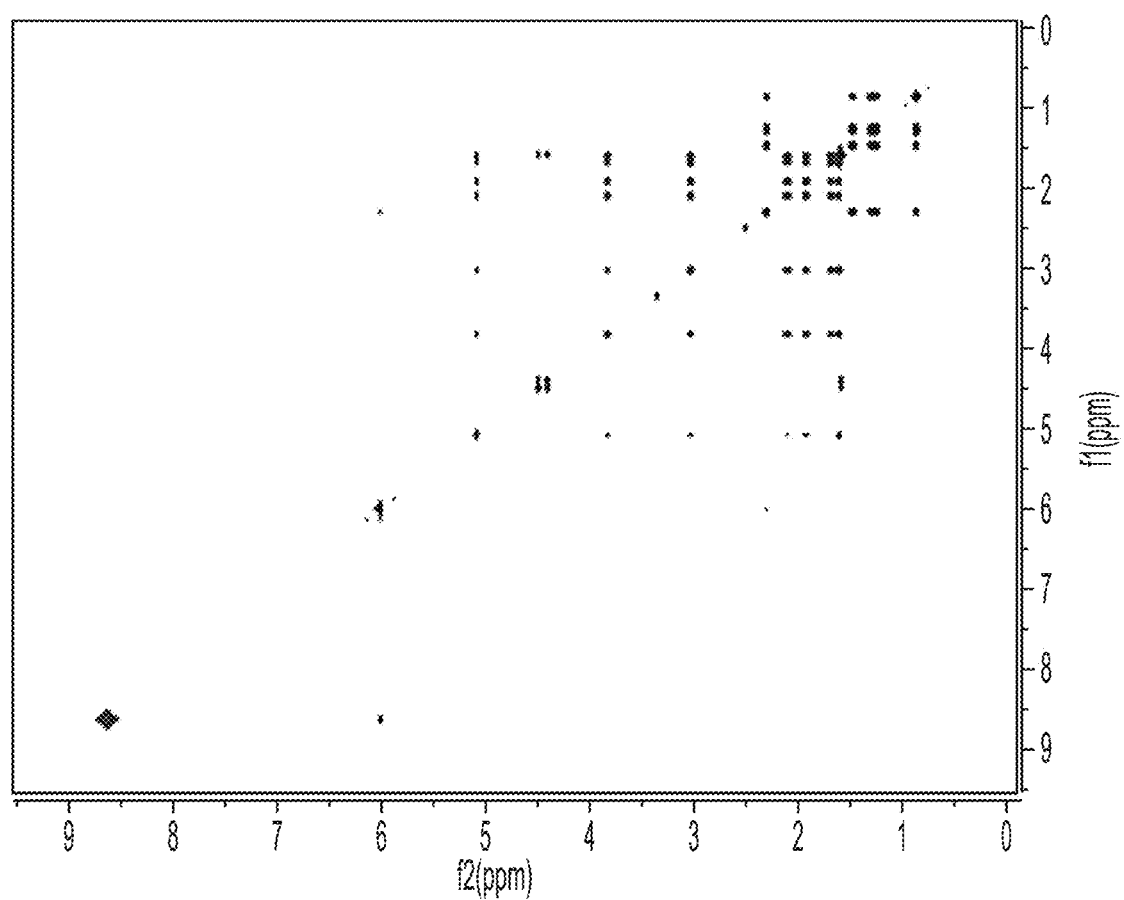
FIG. 7E shows a 2-D ROESYad NMR spectrum of cannabidiol.

For NMR spectroscopy experiments, cannabidiol produced by Protocol 1 that underwent recrystallization in n-heptane was used (Sample 16). The cannabidiol was supplied in a 5-mm NMR tube in DMSO-d6 solution. A 1-D proton spectrum (FIG. 7A), as well as 2-D gCOSY (FIG. 7B), gHMBCad (FIG. 7C) gHSQCad (FIG. 7D), and ROESYad (FIG. 7E) spectra were acquired on an Agilent Inova-600 MHz spectrometer at 25° C. using standard VNMRJ pulse sequences. Proton chemical shifts were measured relative to the residual DMSO-$d_6$ signal (2.50 ppm). Carbon chemical shifts were measured relative to the absolute chemical shifts scale with reference to TMS at 0 ppm and a Ξ value of 0.25145020. For the proton dimension, a spectral width of 6281 Hz was used, which was acquired in 16384 points in the 1-D spectrum and in 1875 points in the 2-D spectra. The pulse width was 7.25 μs. The 2D gCOSY spectrum was acquired in 256 increments of 8 transients each. The gHSQC spectrum was acquired in 96 increments of 16 transients each, and the gHMBC spectrum was acquired in 200 increments of 16 transients each. The spectral width in the indirect dimension was 25633 Hz foe gHSQC (160 ppm) and 34677 Hz (220 ppm) for gHMBC. All spectra were processed using MestreNova Version 11.0.4-18998.

Figure 7F:
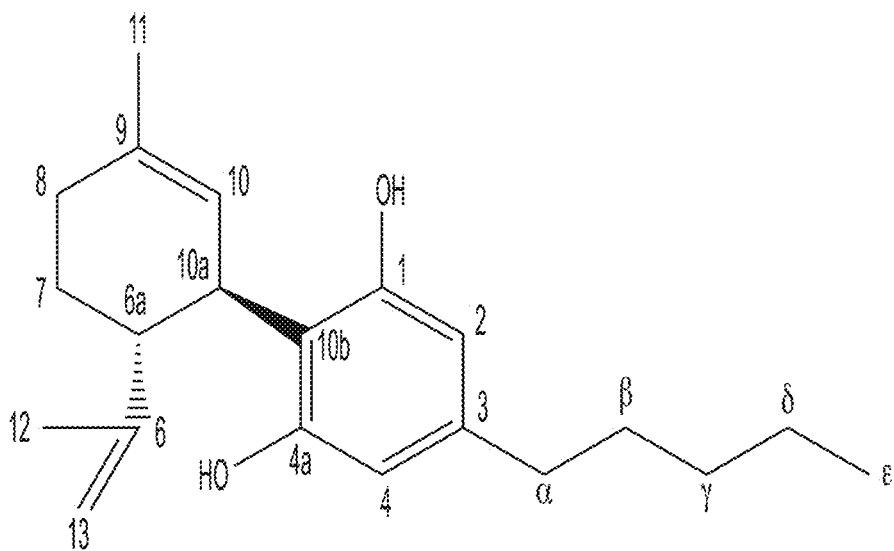
FIG. 7F shows the chemical shift assignment of the cannabidiol sample.

The proposed structure of the sample was confirmed by analysis of the 2-D gCOSY, ROESYad, gHSQC, and gHMBC spectra. The gHSQC spectrum was acquired with multiplicity editing, which provides part of the same information as a 1-D C13 DEPT spectrum, in that methyl and methane groups appear as positive peaks and methylene protons as negative peaks. The gHMBC spectrum provides the chemical shifts of all of the quaternary carbons that are 2-3 bonds apart. The ROESY spectrum shows NOE correlations between protons that are close in space. The NMR analysis led to the chemical shift assignment displayed in FIG. 7F and confirmed the proposed structure of the compound.

Example 9: Particle Size Distribution

Figures 8A, 8B:
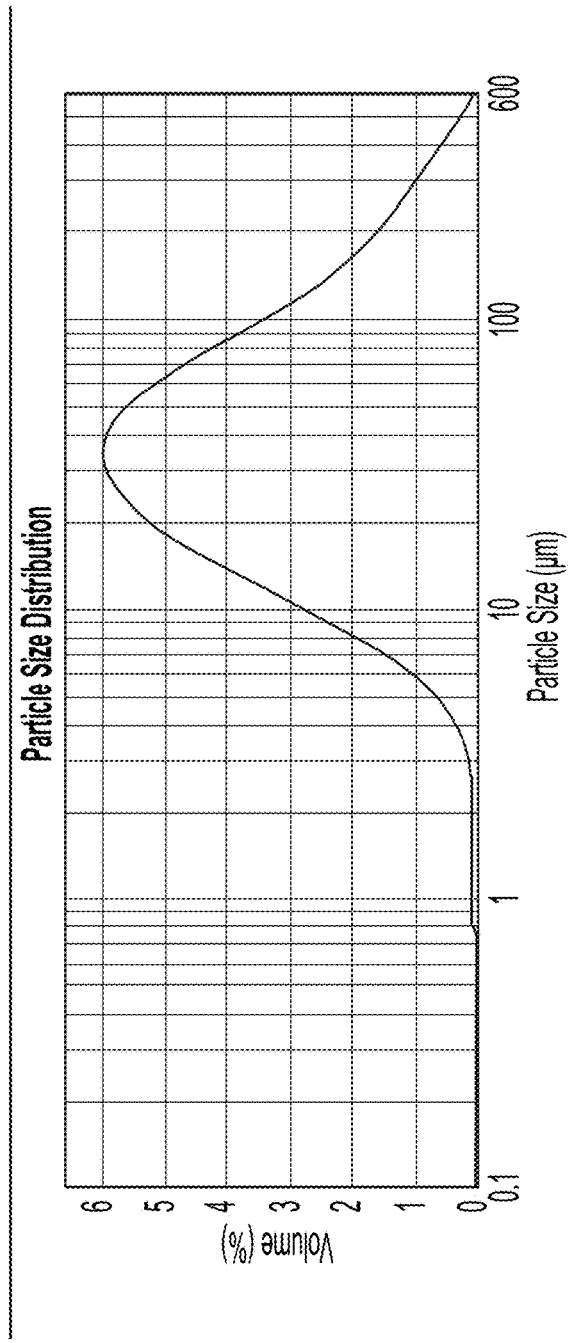
FIG. 8A shows the particle size distribution result analysis report for crude cannabidiol produced by Protocol 3, which did not undergo recrystallization (sample 7).
FIG. 8B shows the particle size graph for the sample analyzed in FIG. 8A.
Figures 8E, 8F:
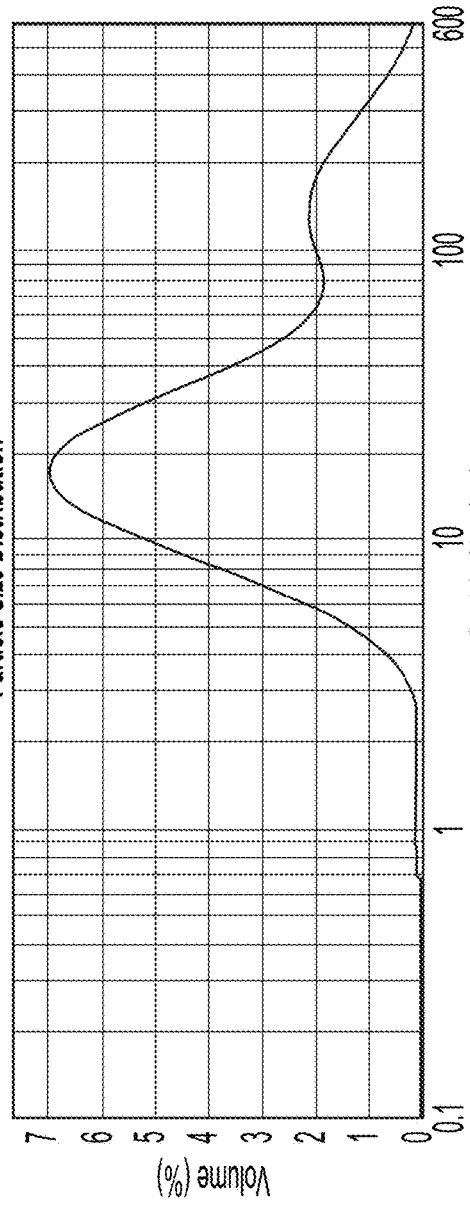
FIG. 8E shows the particle size distribution result analysis report for cannabidiol produced by Protocol 3, which underwent recrystallization in isooctane (sample 1).
FIG. 8F shows the particle size graph for the sample analyzed in FIG. 8E.
Figures 8G, 8H:
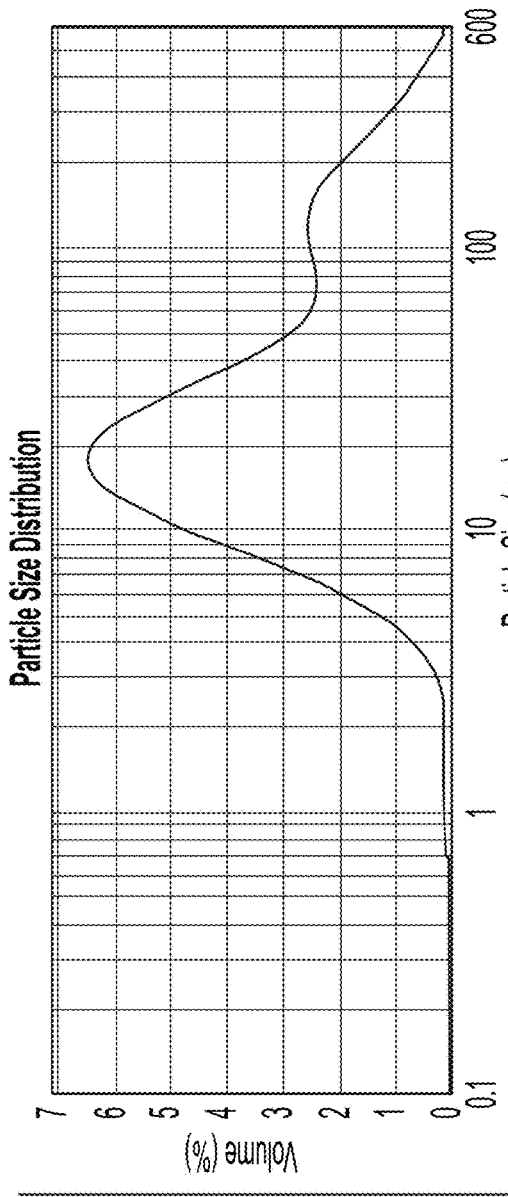
FIG. 8G shows the particle size distribution result analysis report for cannabidiol produced by Protocol 3, which underwent recrystallization in isooctane (sample 2).
FIG. 8H shows the particle size graph for the sample analyzed in FIG. 8G.
Figures 8I, 8J:
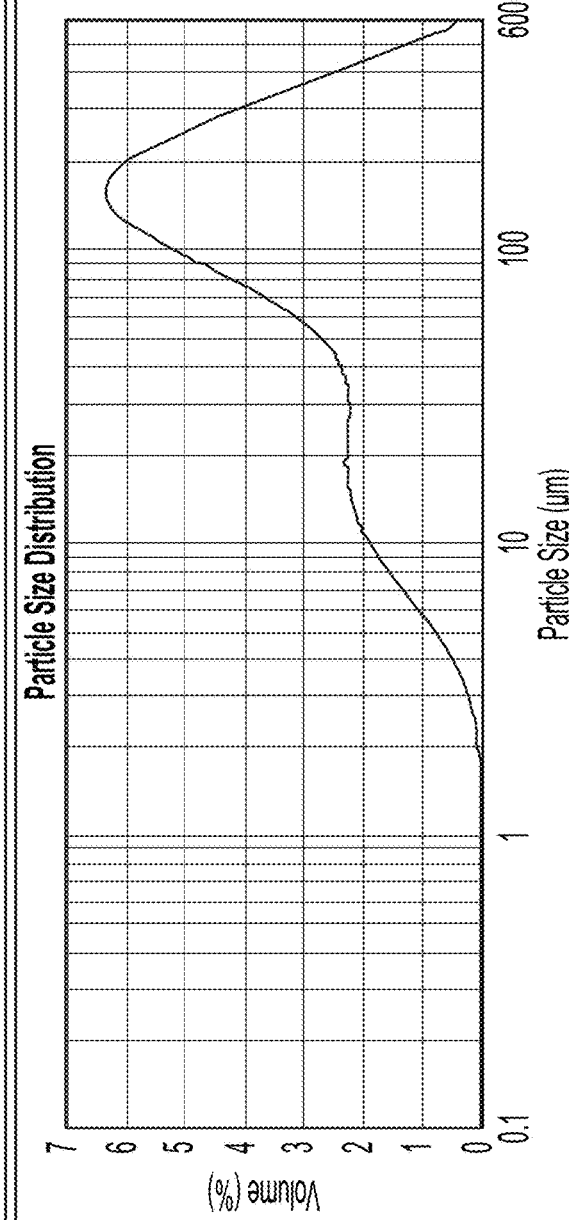
FIG. 8I shows the particle size distribution result analysis report for cannabidiol produced by Protocol 1, which underwent recrystallization in isooctane (sample 9).
FIG. 8J shows the particle size graph for the sample analyzed in FIG. 8I.
Figures 8K, 8L:
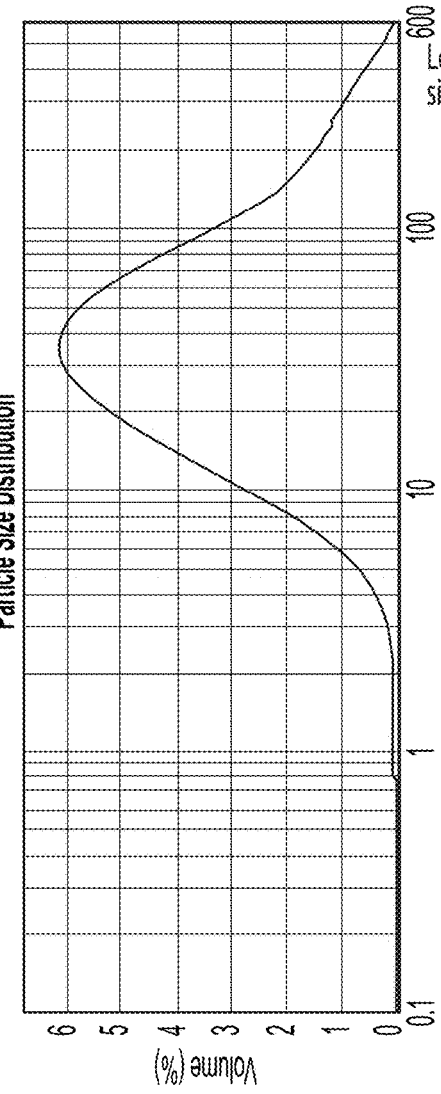
FIG. 8K shows the particle size distribution result analysis report for crude cannabidiol produced by Protocol 3, which did not undergo recrystallization (sample 7). This is a second run for this sample, as shown in FIGS. 8A and 8B, to demonstrate the robustness of the method for measuring particle size.
FIG. 8L shows the particle size graph for the sample analyzed in FIG. 8K.
Figures 8M, 8N:
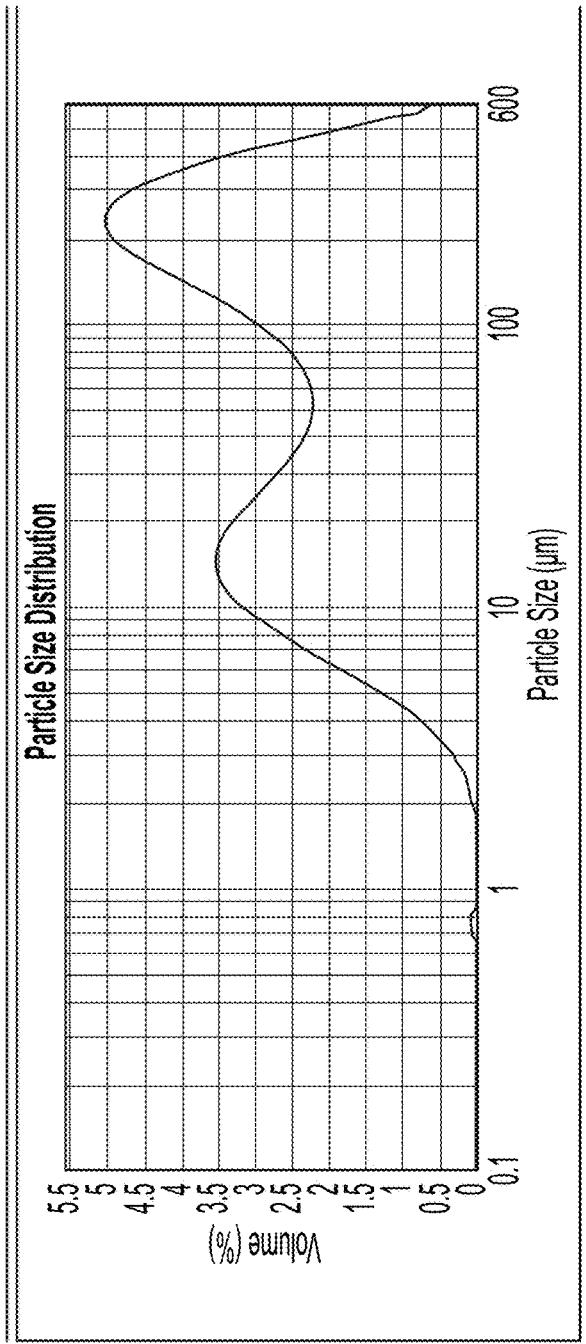
FIG. 8M shows the particle size distribution result analysis report for sample 4 made by Protocol 1, which did not undergo recrystallization.
FIG. 8N shows the particle size graph for sample 4 synthesized by Protocol 1, obtained under the conditions shown in FIG. 8M.
Figures 8O, 8P:
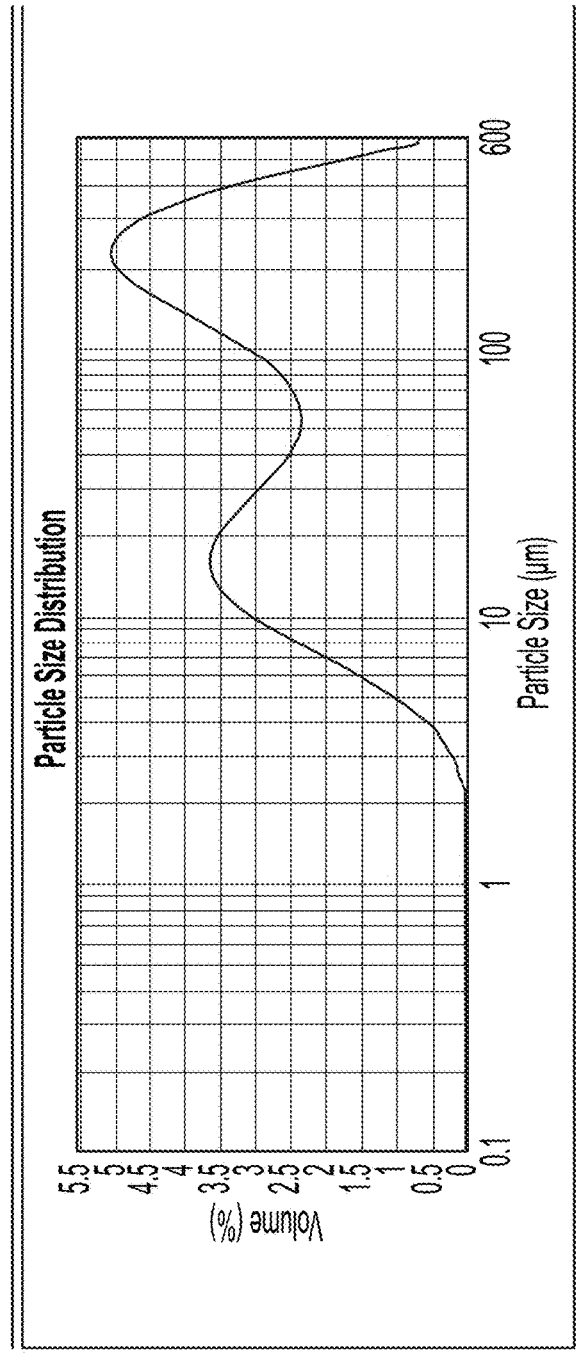
FIG. 8O shows the particle size distribution result analysis report for sample 5 made by Protocol 1, which did not undergo recrystallization.
FIG. 8P shows the particle size graph for sample 5 synthesized by Protocol 1, obtained under the conditions shown in FIG. 8O.
Figures 8Q, 8R:
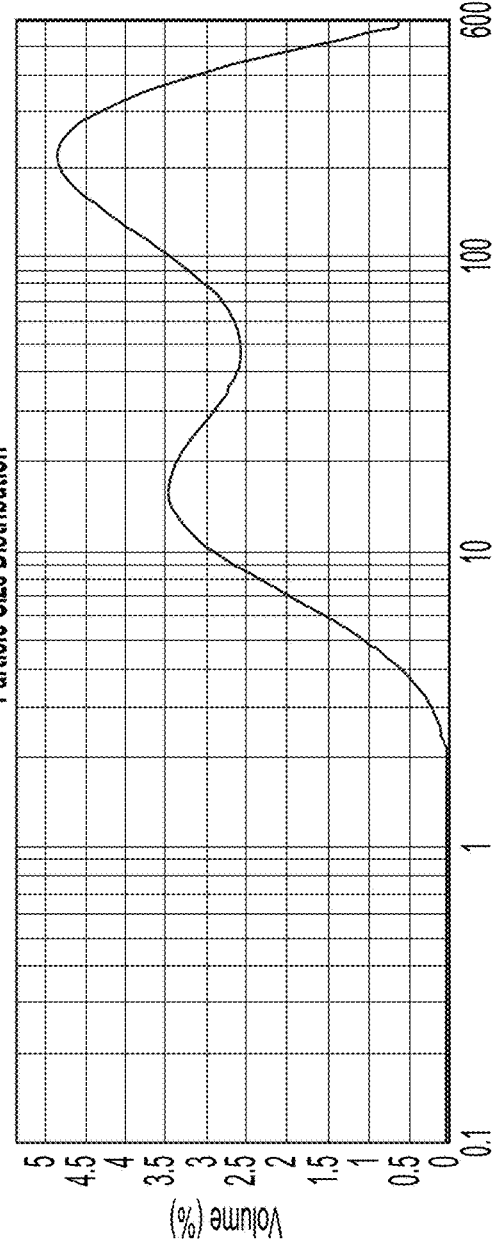
FIG. 8Q shows the particle size distribution result analysis report for sample 6, synthesized by Protocol 1, which did not undergo recrystallization.
FIG. 8R shows the particle size graph for sample 6 synthesized by Protocol 1, obtained under the conditions shown in FIG. 8Q.
Figures 9A, 9B:
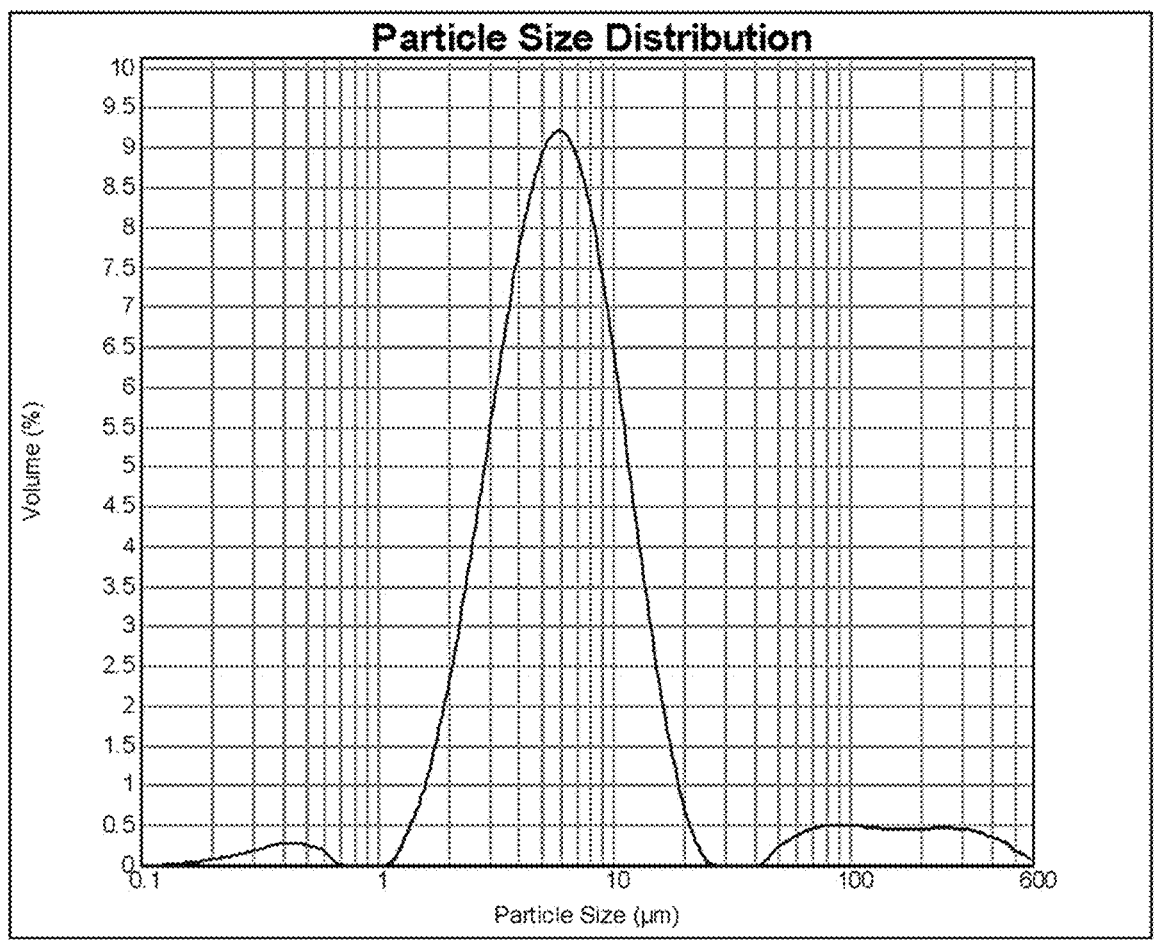
FIG. 9A shows the particle size distribution result analysis report for sample 10, synthesized by Protocol 1, which underwent recrystallization in isooctane.
FIG. 9B shows the particle size graph for sample 10 synthesized by Protocol 1, obtained under the conditions shown in FIG. 9A.
Figures 9C, 9D:
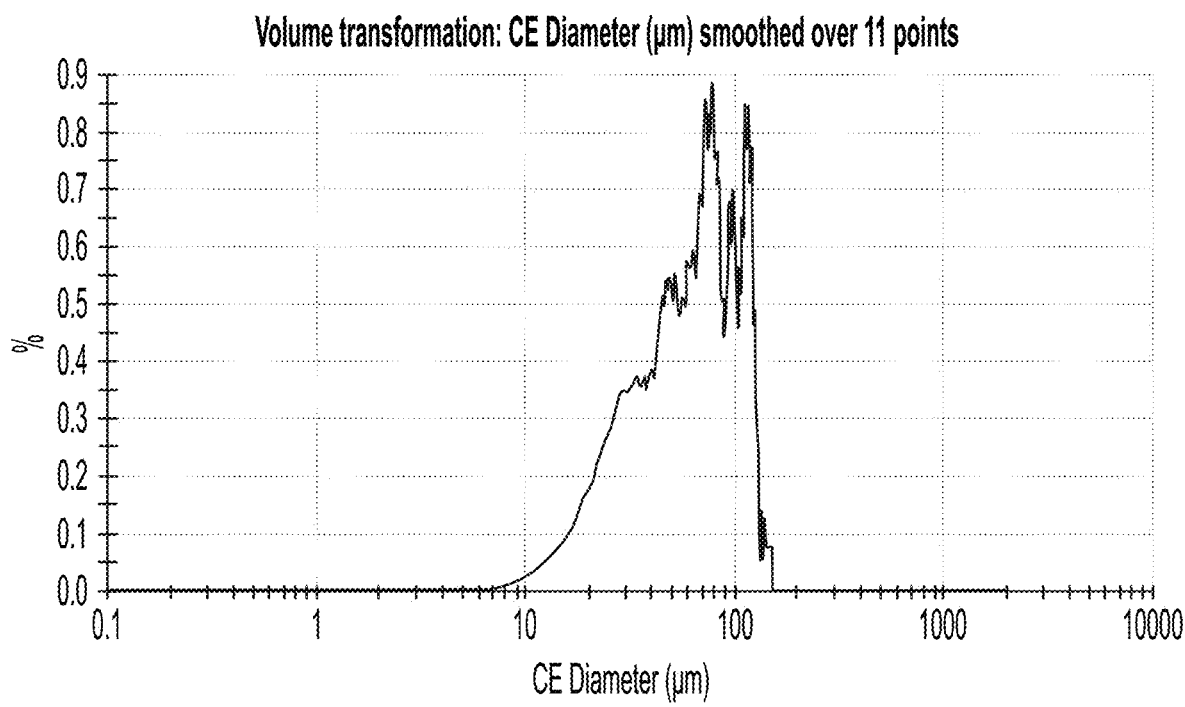
FIG. 9C shows the particle size distribution result analysis report for sample 4, synthesized by Protocol 1, which did not undergo recrystallization.
FIG. 9D shows the particle size graph for sample 4 synthesized by Protocol 1, obtained under the conditions shown in FIG. 9C.
Figures 9E, 9F:
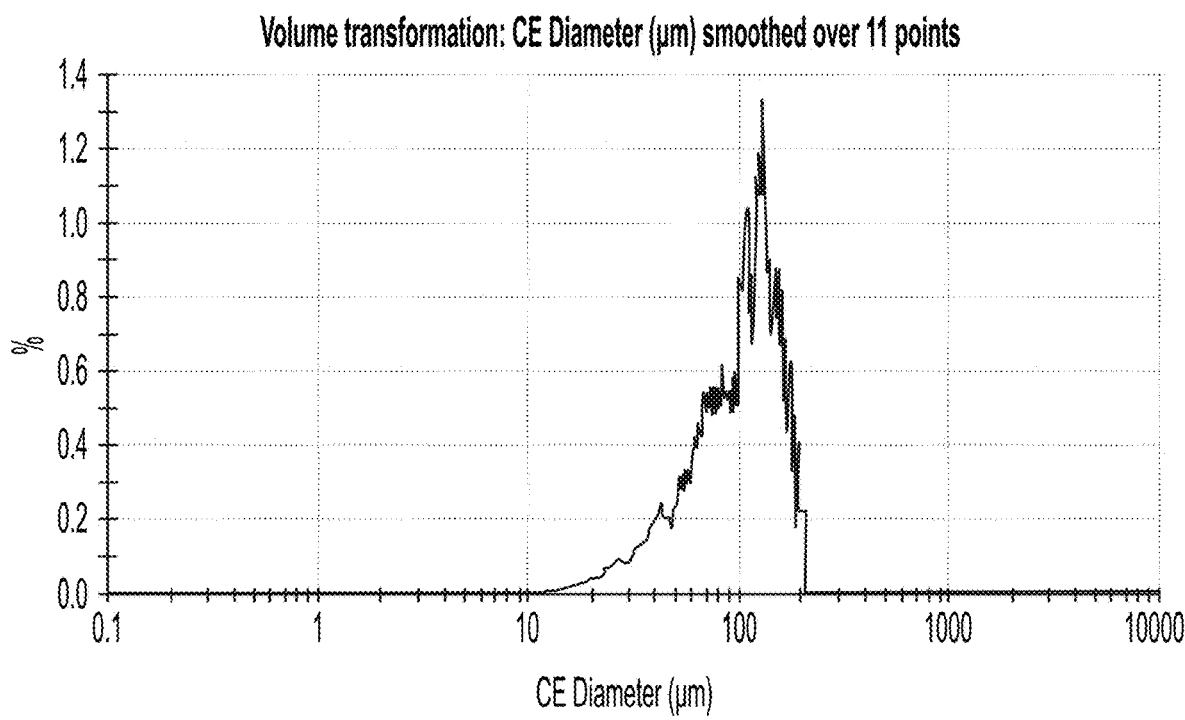
FIG. 9E shows the particle size distribution result analysis report for sample 11, synthesized by Protocol 3, which underwent recrystallization in isooctane.
FIG. 9F shows the particle size graph for sample 11 synthesized by Protocol 3, obtained under the conditions shown in FIG. 9E.
Figures 9G, 9H:
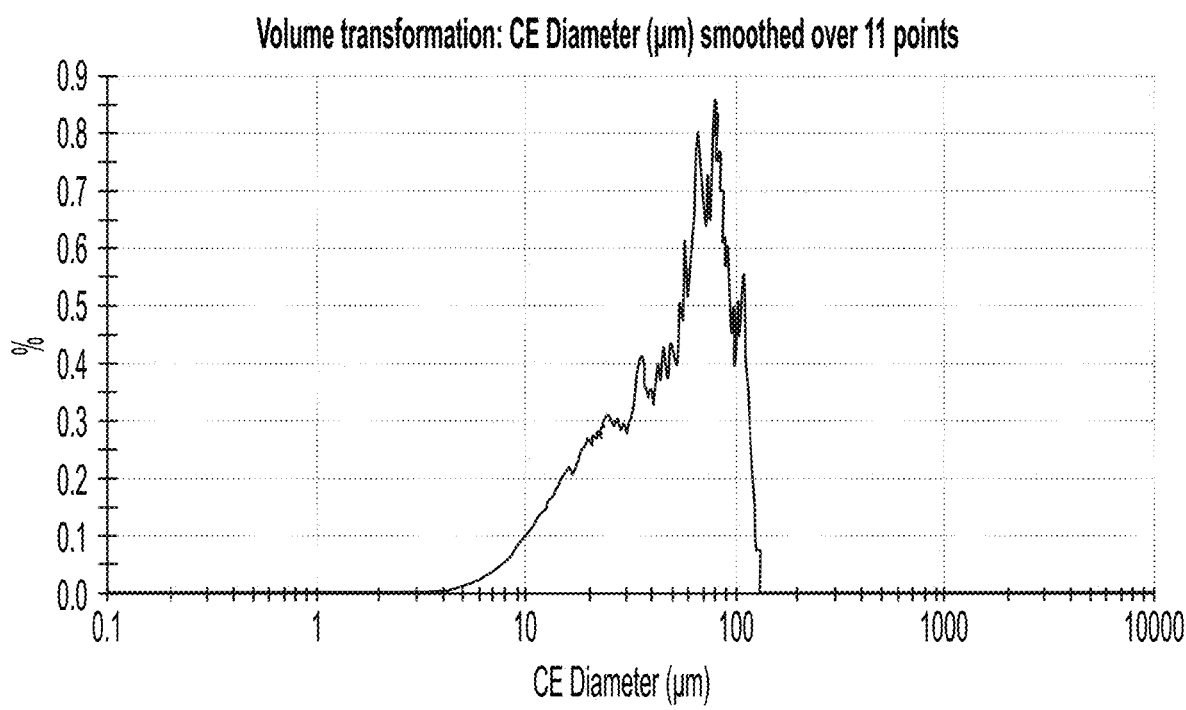
FIG. 9G shows the particle size distribution result analysis report for sample 12, synthesized by Protocol 3, which underwent recrystallization in isooctane.
FIG. 9H shows the particle size graph for sample 12 synthesized by Protocol 3, obtained under the conditions shown in FIG. 9G.
Figures 9I, 9J:
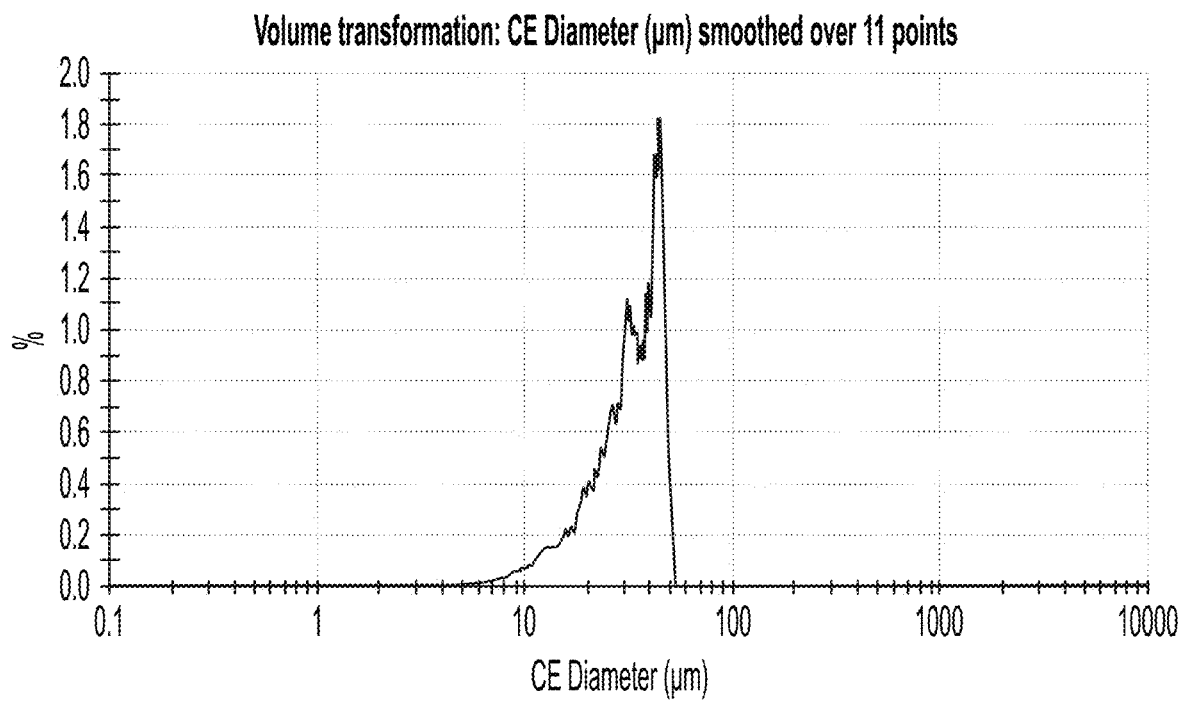
FIG. 9I shows the particle size distribution result analysis report for sample 13, synthesized by Protocol 3, which underwent recrystallization in isooctane.
FIG. 9J shows the particle size graph for sample 13 synthesized by Protocol 3, obtained under the conditions shown in FIG. 9I.
Figures 9K, 9L:
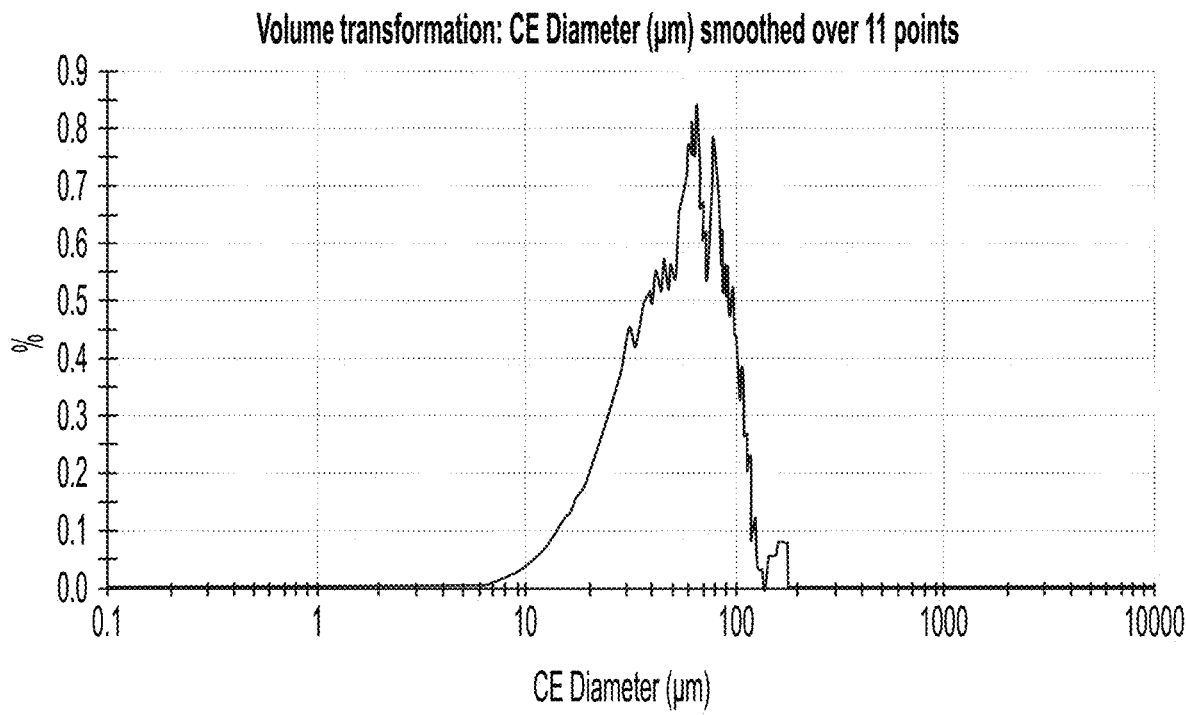
FIG. 9K shows the particle size distribution result analysis report for sample 14, synthesized by Protocol 3, which underwent recrystallization in isooctane.
FIG. 9L shows the particle size graph for sample 14 synthesized by Protocol 14, obtained under the conditions shown in FIG. 9K.
Figures 9M, 9N:
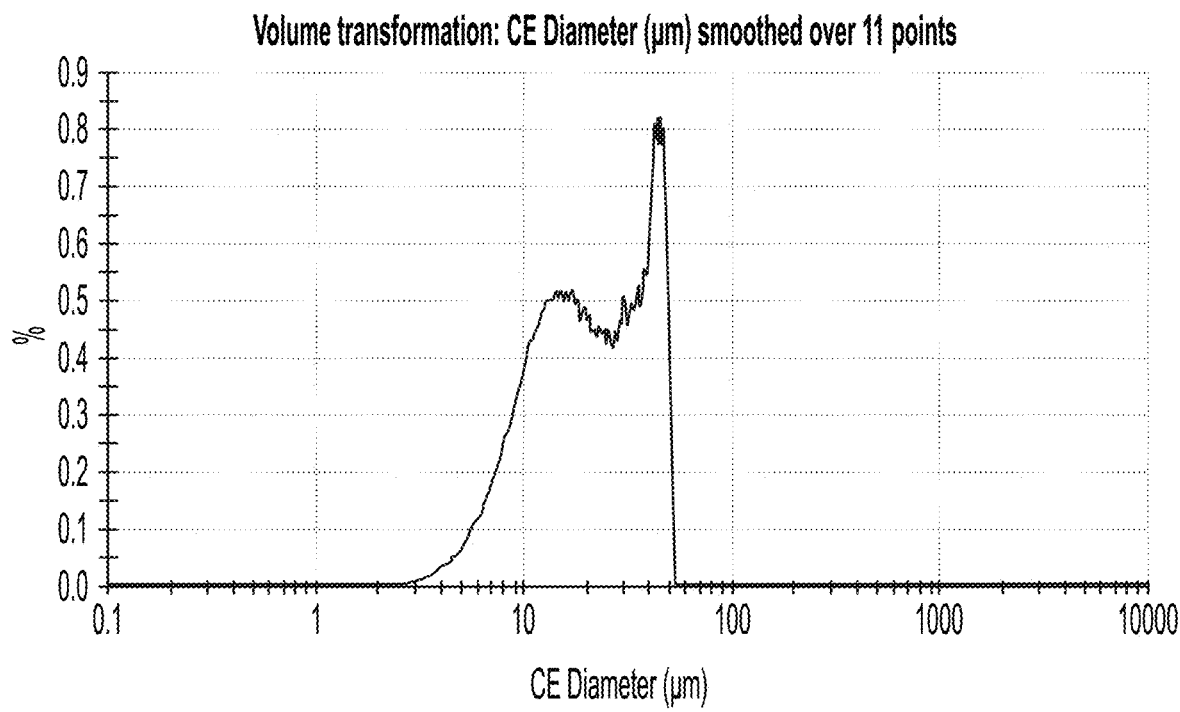
FIG. 9M shows the particle size distribution result analysis report for sample 15, synthesized by Protocol 3, which underwent recrystallization in isooctane.
FIG. 9N shows the particle size graph for sample 15 synthesized by Protocol 3, obtained under the conditions shown in FIG. 9M.
Figures 9O, 9P:
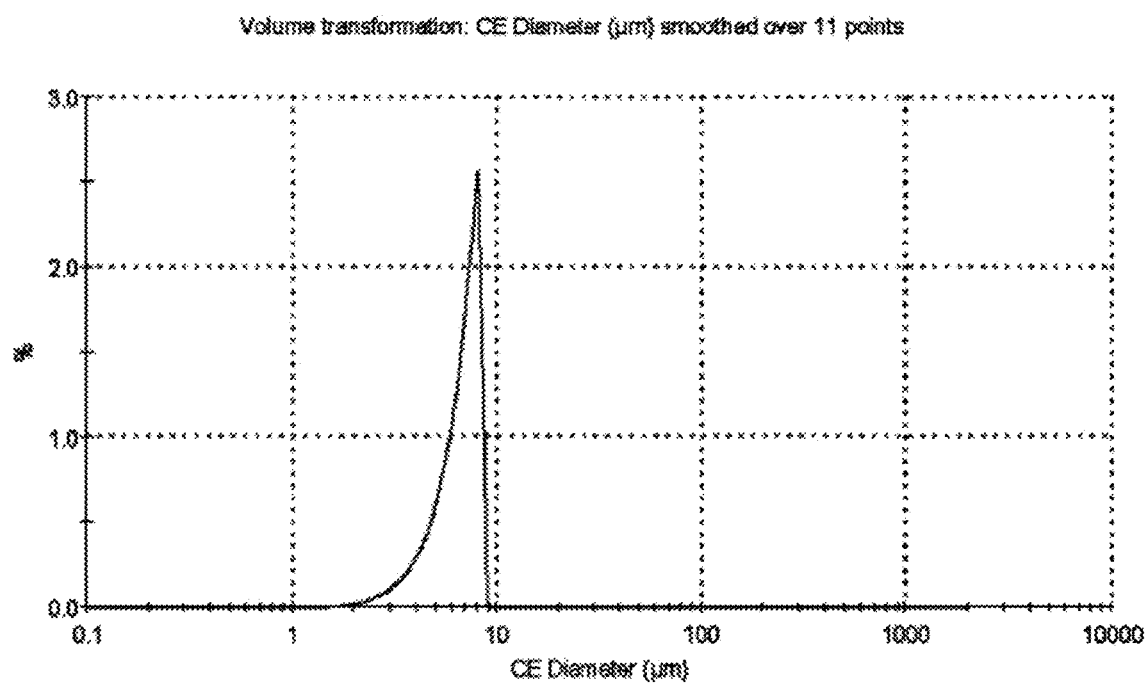
FIG. 9O shows an additional particle size distribution result analysis report for sample 10, synthesized by Protocol 3, which underwent recrystallization in isooctane.
FIG. 9P shows the particle size graph for sample 10 synthesized by Protocol 3, obtained under the conditions shown in FIG. 9O.
Figure 10:
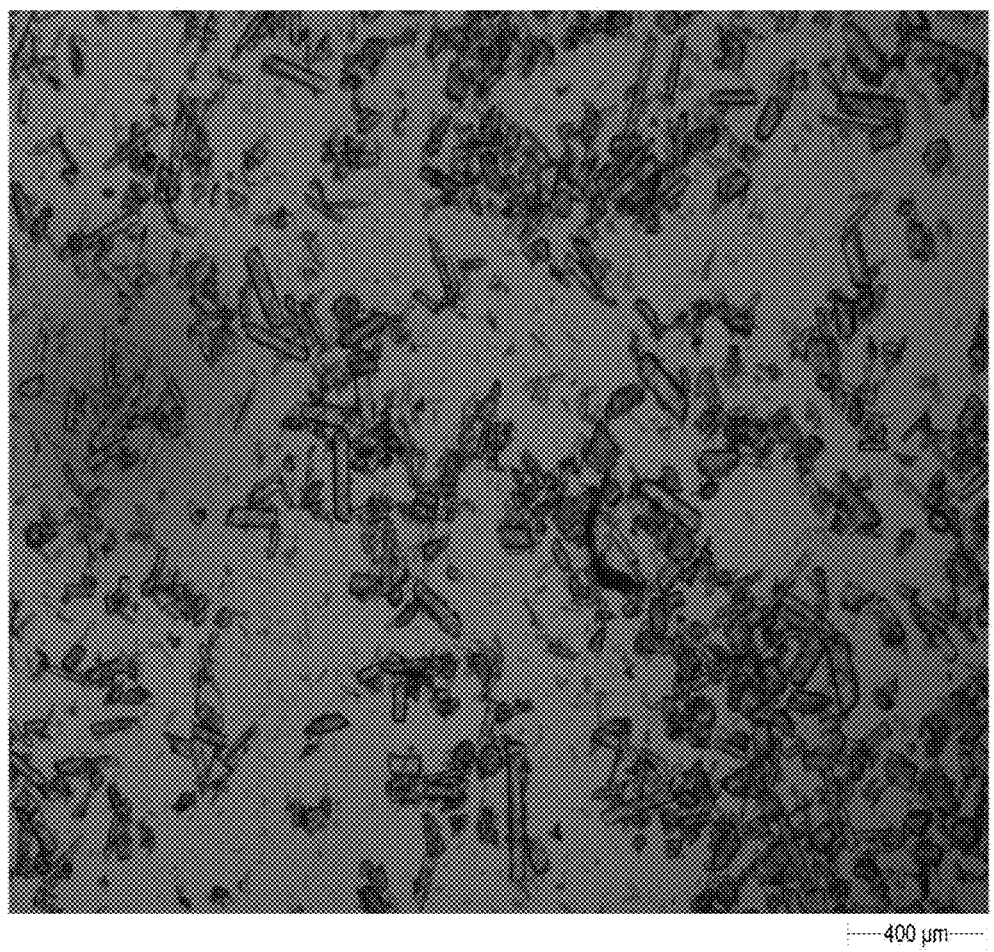
FIG. 10 shows a microscope image of a variety of crude cannabidiol inputs that were recrystallized with isooctane. The image was taken with a light Malvern G3 microscope operating at 2.5× Mag objective.

A Mastersizer 2000 was used to analyze the particle size distribution in cannabidiol samples. This method involved laser diffraction to measure the particle size distribution by the volume standard. Roughly 1 g of each sample was weighed and transferred along the middle of the sample tray. The sample feed gates were 6 mm-8 mm. The instrument software parameters were set to a dispersive air pressure of 3 bar, vibration feed rate of 60%, refractive index of 1.5295, absorption index of 0.01, and size range from 0.020 μm to 2000.000 μm. FIG. 8A-FIG. 8R show the result analysis report for each sample measured as well as their respective particle size distribution graph. Malvern Pananalytical's Morphologi G3 Analyzer was used in another series of experiments to examine sample volume size distribution. The result analysis report for several samples are provided in FIG. 9A through FIG. 9P. These results are summarized in Table 8. FIG. 10 displays a microscope image of a variety of crude cannabidiol inputs that underwent recrystallization in isooctane. The image reveals a rod microstructure for the cannabidiol material.

TABLE 8

Cannabidiol Particle Size Distribution Summary

| Description | No. of samples | d10 (μm) | d50 (μm) | d90 (μm) |
|---|---|---|---|---|
| Protocol 1 | 10 | 2-10 | 6-73 | 8-333 |
| Protocol 2 | 0 | — | — | — |
| Protocol 3 crude CBD crys from n-heptane | 2 | 10-11 | 36-37 | 114-145 |
| Protocol 3 CBD recrys from isooctane | 9 | 8 | 22-24 | 153-158 |

Example 10: Stress Stability Tests

Figure 15A:
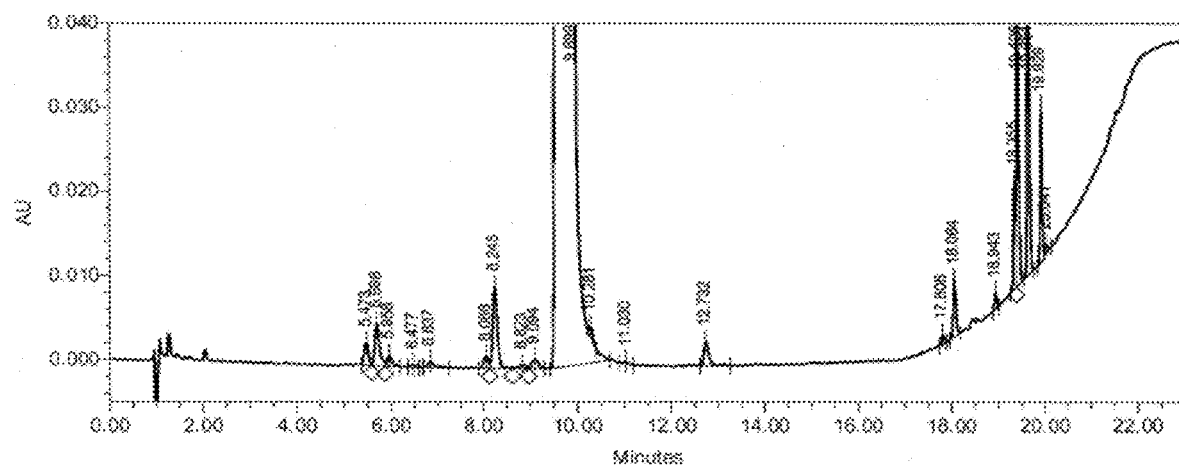
FIG. 15A shows a UPLC chromatogram of an unstressed cannabidiol sample.

Cannabidiol samples obtained by Protocol 1 were subjected to acidic, alkaline, and oxidizing conditions in order to achieve a degradation of at least 3% or a change in appearance. The impact of light, heat, and humidity on the stability of the drug substance was investigated. The assay and purity of samples were analyzed by UPLC. The identity of unknown impurities was examined by LC-MS. The peak purity of cannabidiol after exposure to stress conditions was investigated by comparing the PDA-UV spectrum (photodiode array-ultraviolet) of cannabidiol with the spectrum of the unstressed sample and in addition by LC-MS analysis of the cannabidiol peak. The assay of the unstressed sample in FIG. 15A and FIG. 15B was used as a reference to calculate the extent of degradation of CBD under the representative stress conditions:

Degradation of CBD=(1−[assay of stressed sample]/[assay unstressed sample])*100%

A summary of the results obtained from the stability stress tests can be found in Table 9.

Acidic Stress

Figure 15B:
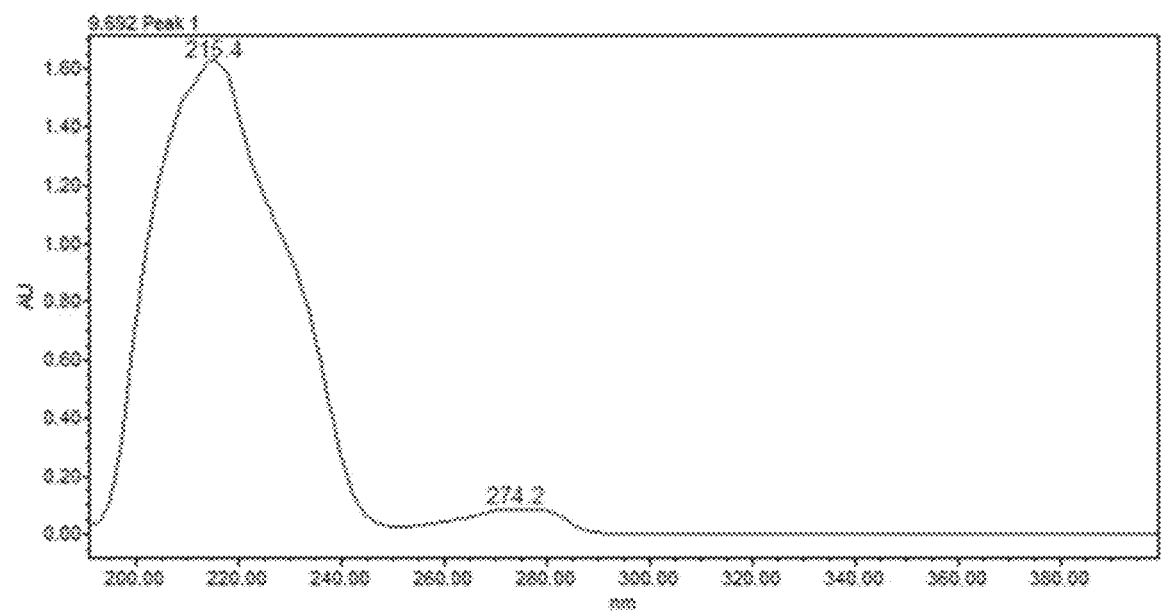
FIG. 15B shows a PDA-UV spectrum of the main component (cannabidiol) of an unstressed cannabidiol sample.
Figure 16:
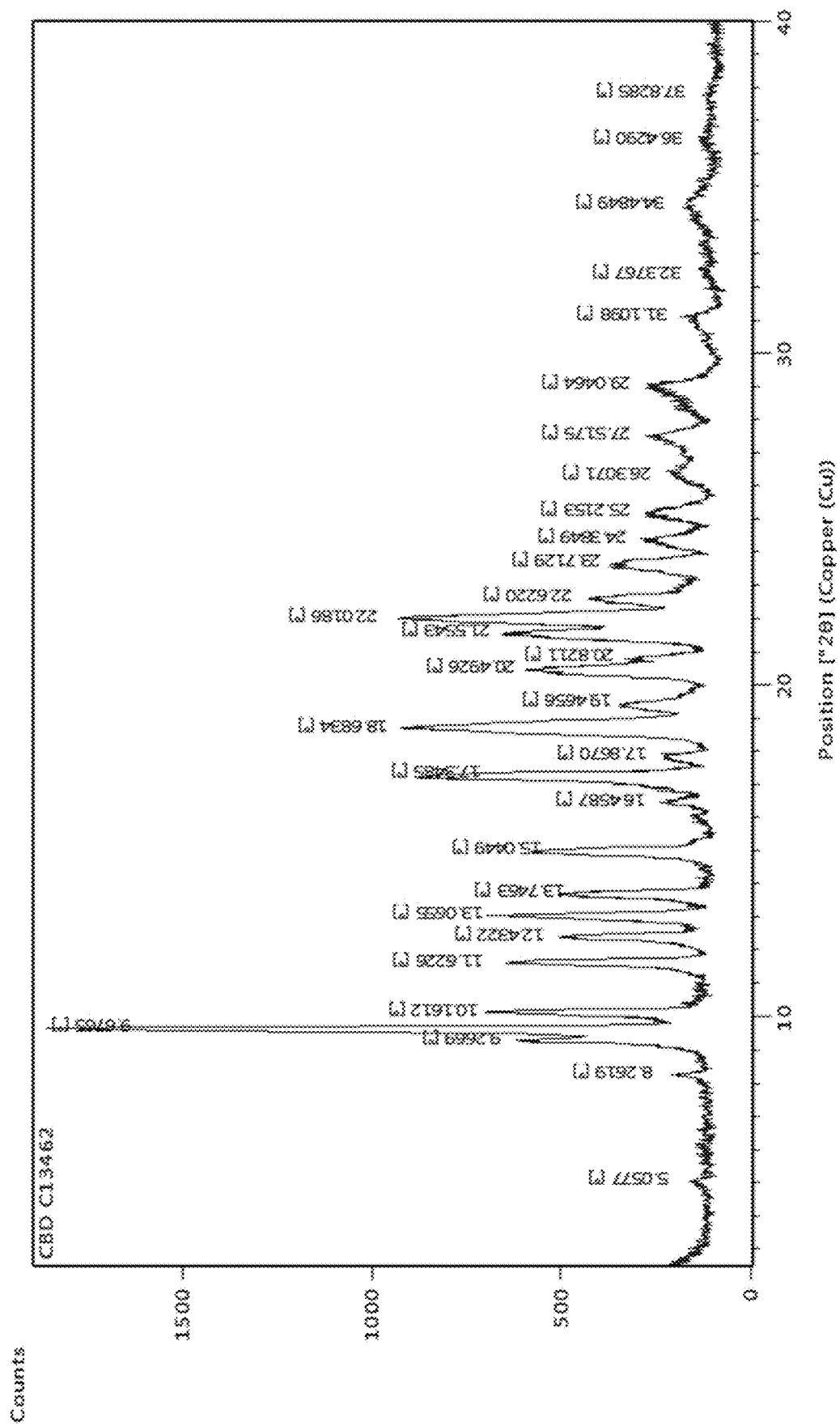
FIG. 16 shows an x-ray powder diffraction pattern of Sample 10, produced by Protocol 1 and which underwent recrystallization in isooctane.
Figure 17:
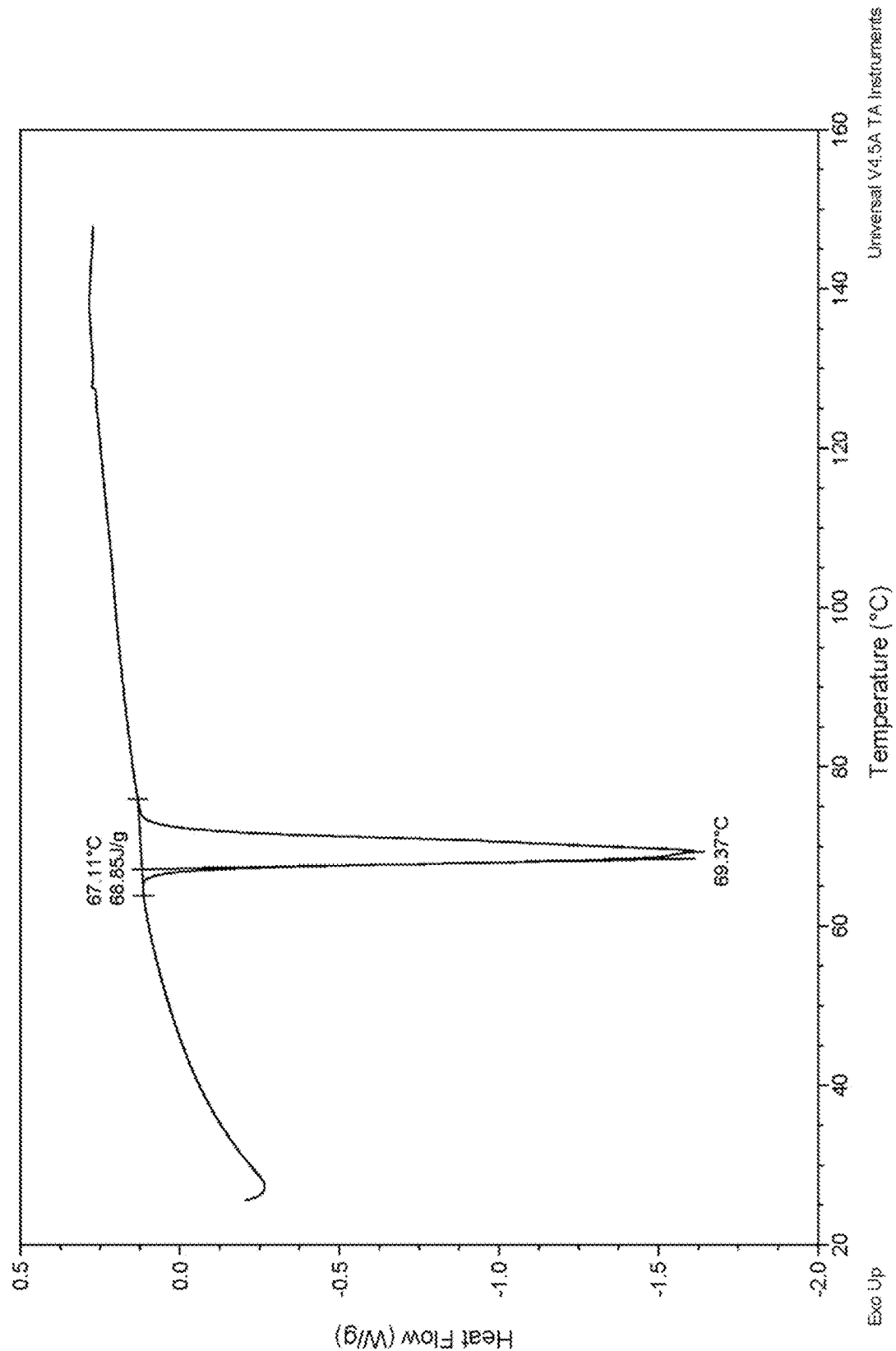
FIG. 17 shows a DSC thermogram of cannabidiol from sample 4, produced by Protocol 1.
Figure 18:
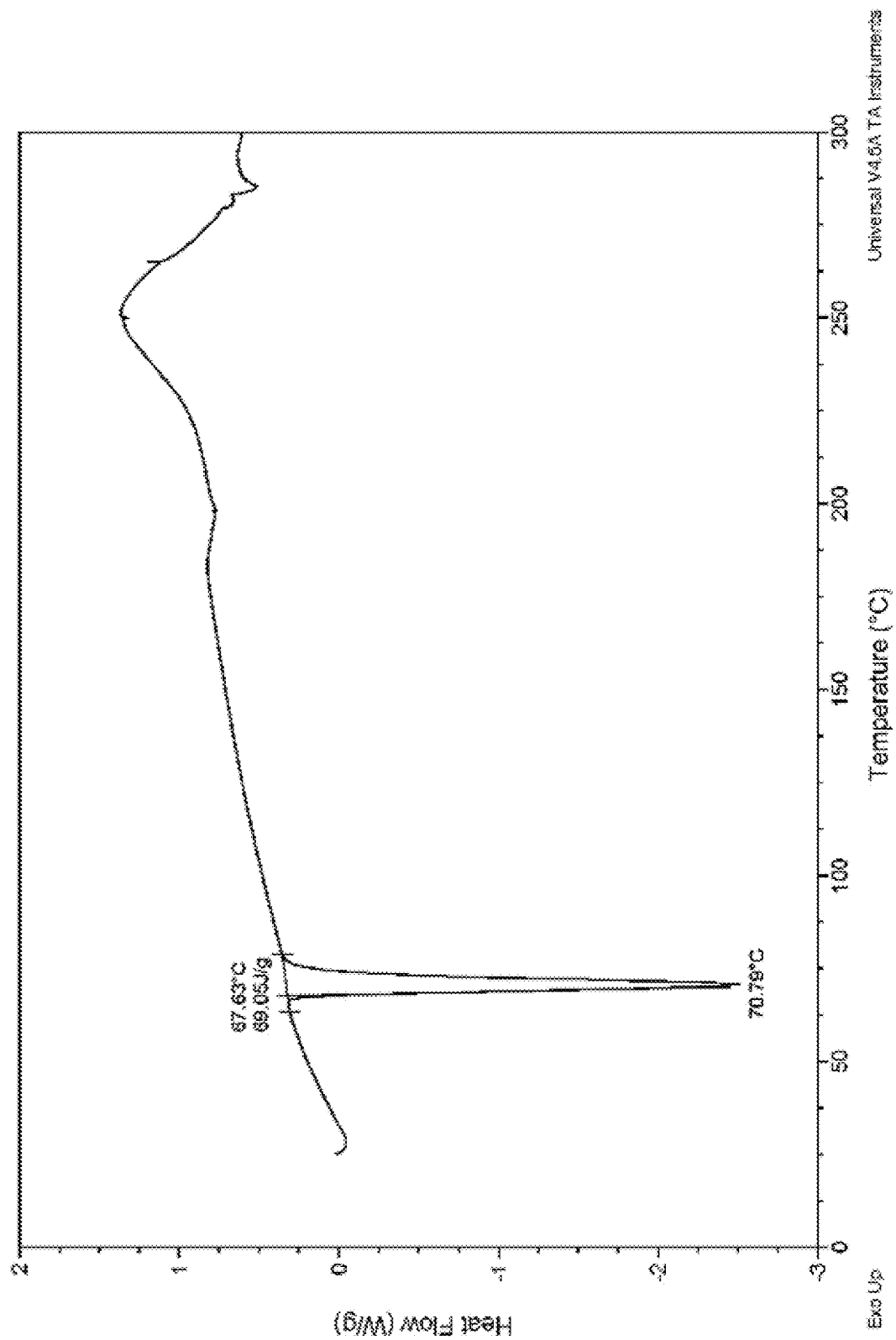
FIG. 18 shows a DSC thermogram of Sample 15, produced by Protocol 3 and which underwent recrystallization in isooctane.
Figure 19:
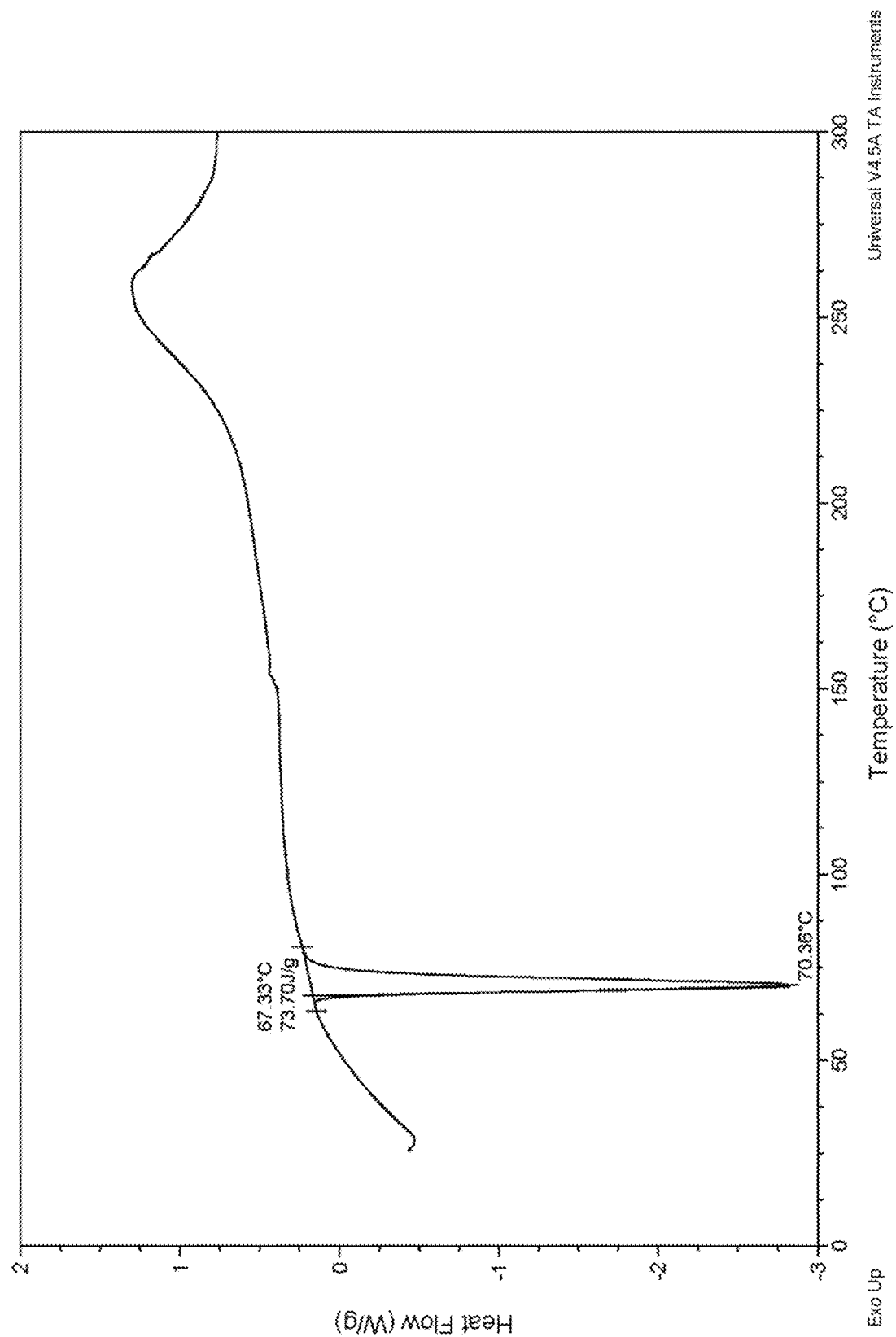
FIG. 19 shows a DSC thermogram of Sample 16, produced by Protocol 3 and which underwent recrystallization in isooctane.
Figure 20:
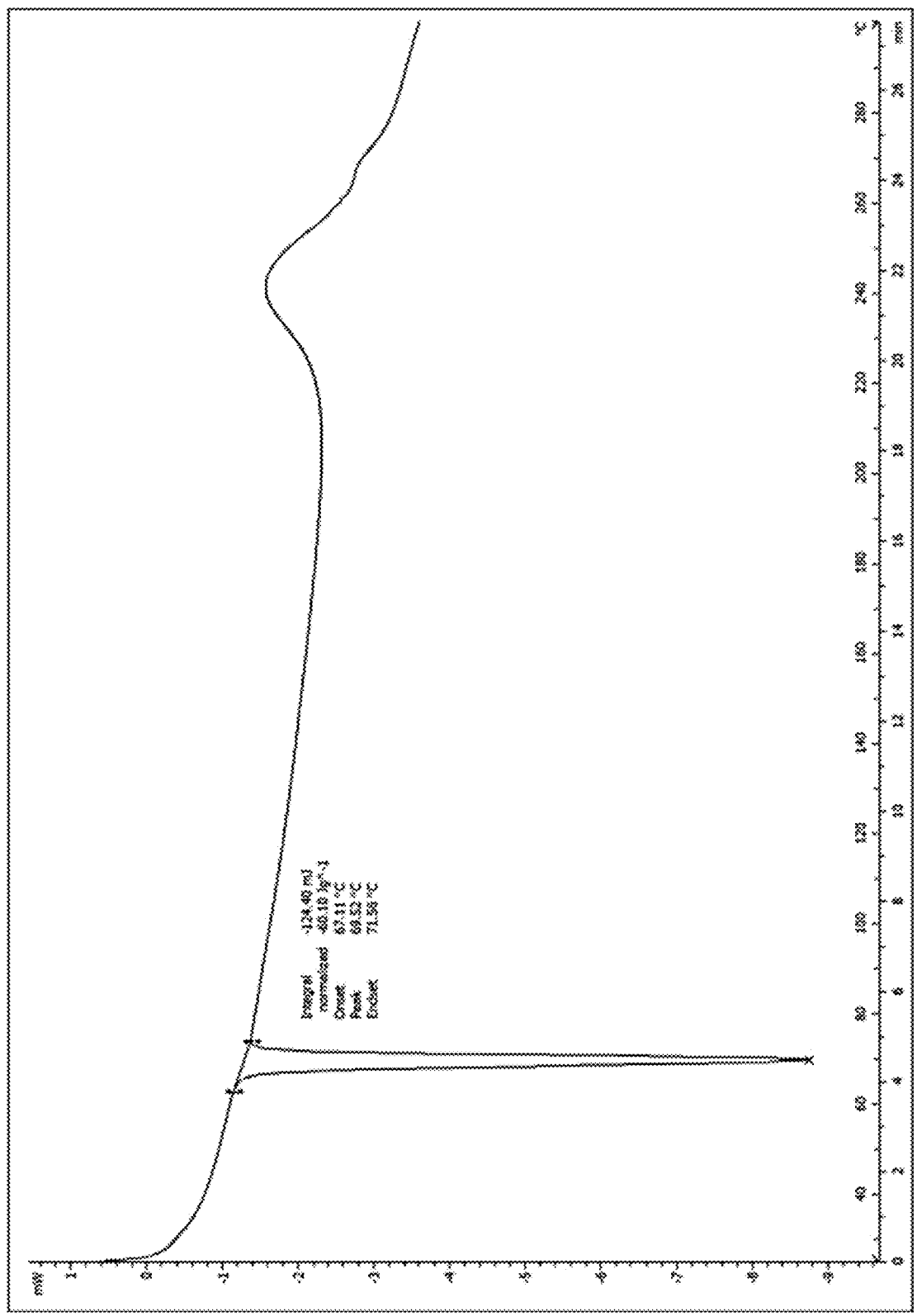
FIG. 20 shows a Differential Scanning calorimetry thermogram of Cannabidiol generated by Protocol 1.
Figure 21:
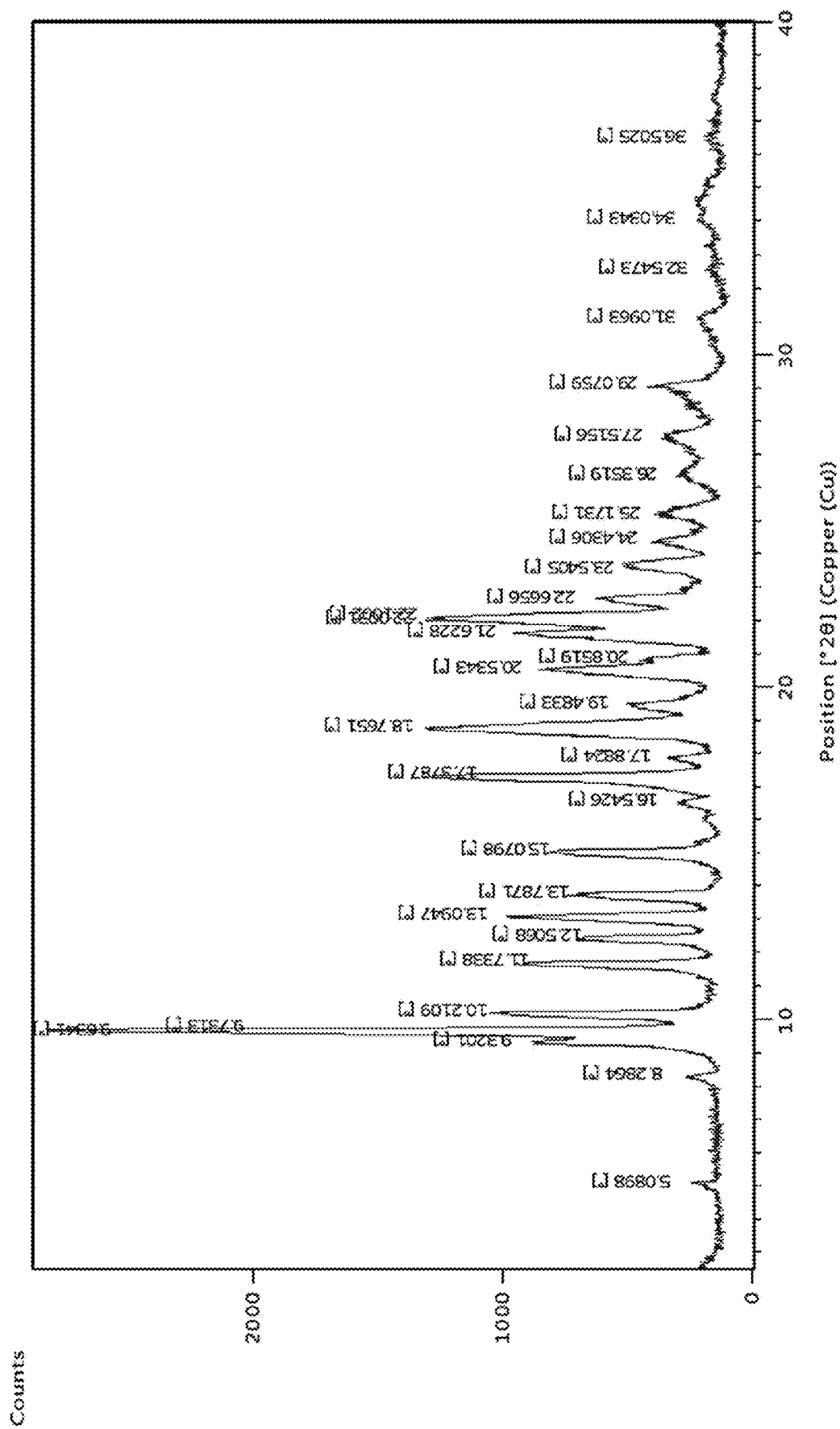
FIG. 21 shows an x-ray pattern for Sample 12, produced by Protocol 3 and which underwent recrystallization in isooctane.
Figure 22:
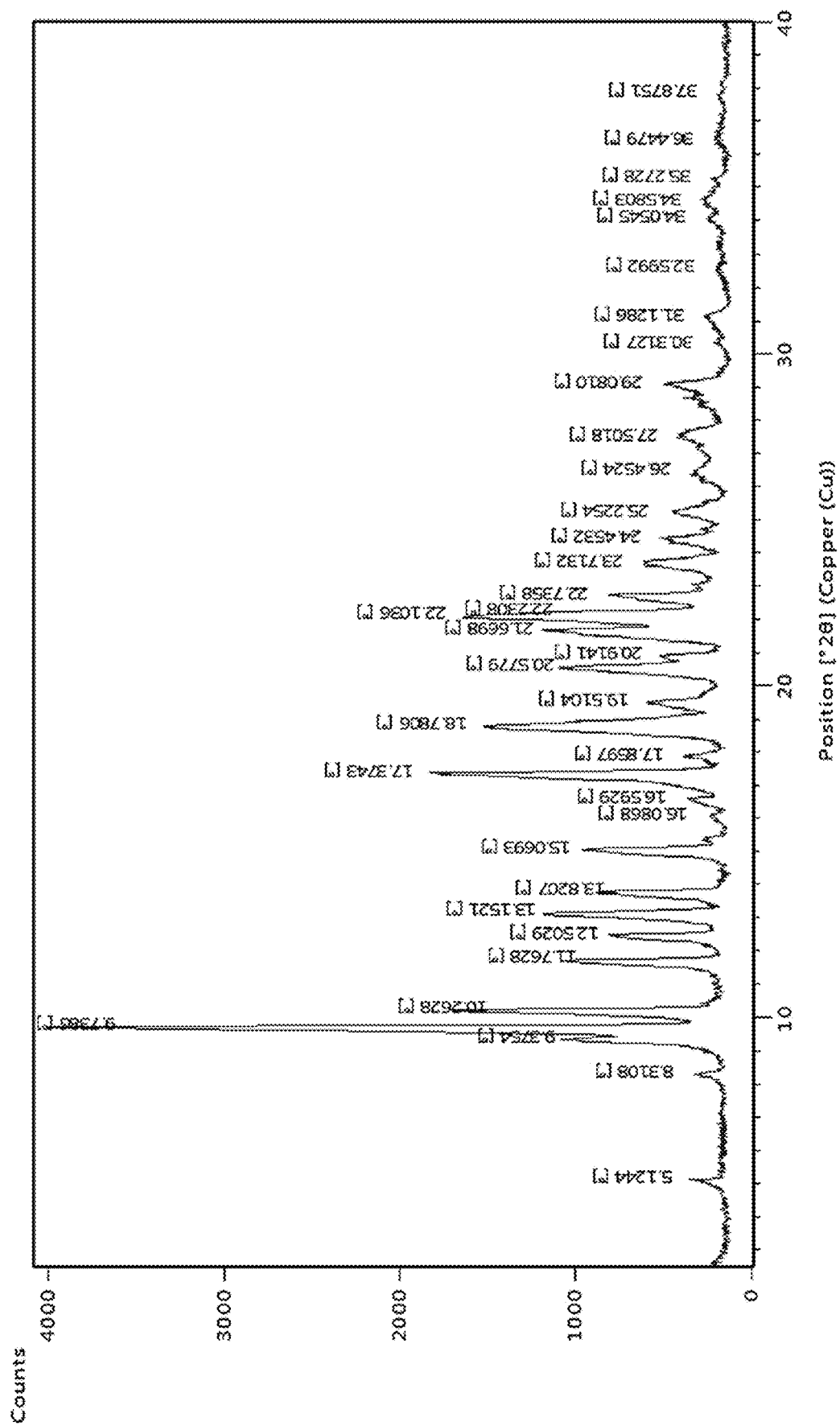
FIG. 22 shows an x-ray pattern for Sample 17, produced by Protocol 3 and which underwent recrystallization in isooctane.
Figure 23:
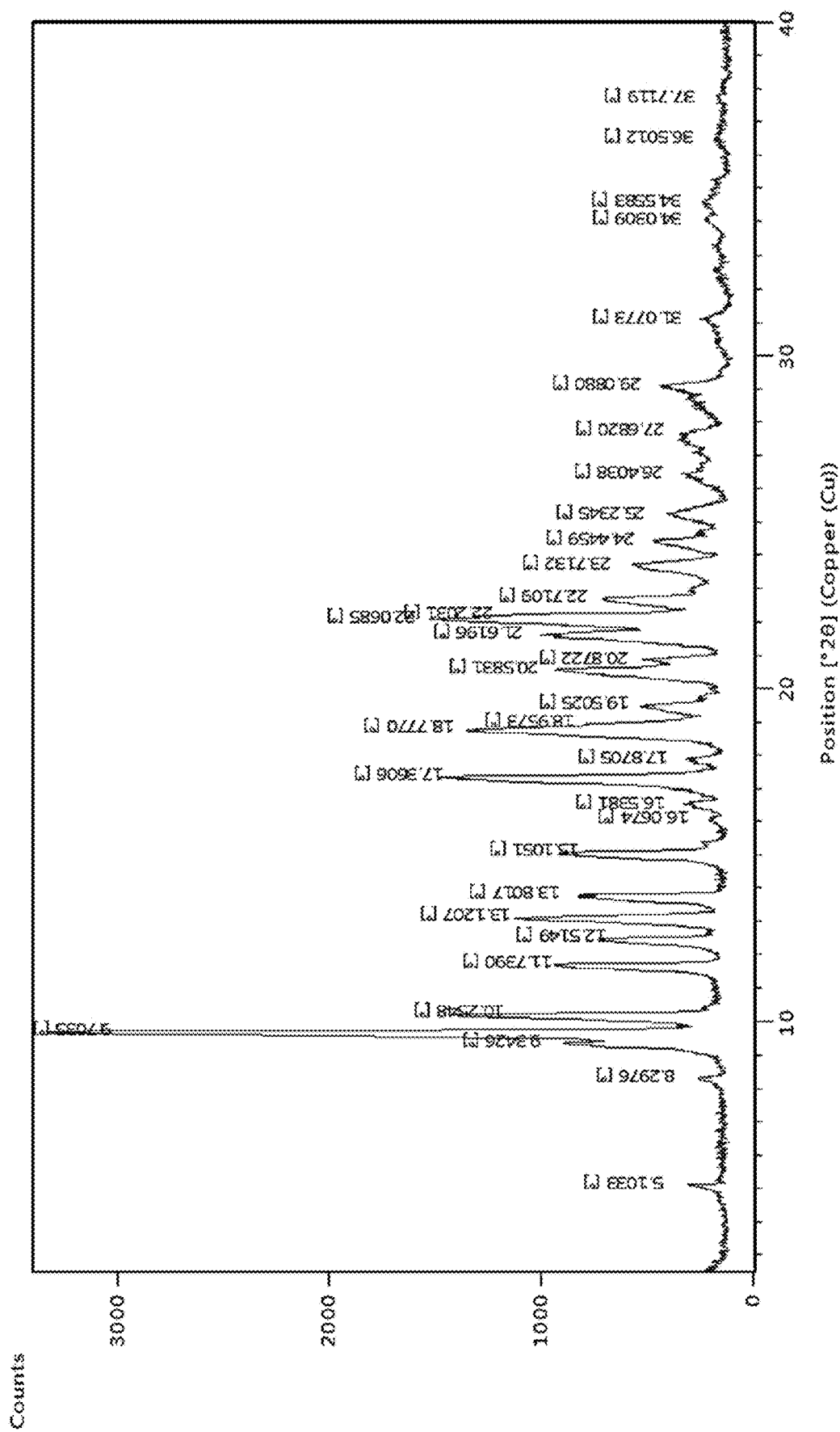
FIG. 23 shows an x-ray pattern for Sample 18, produced by Protocol 3 and which underwent recrystallization in isooctane.
Figure 24:
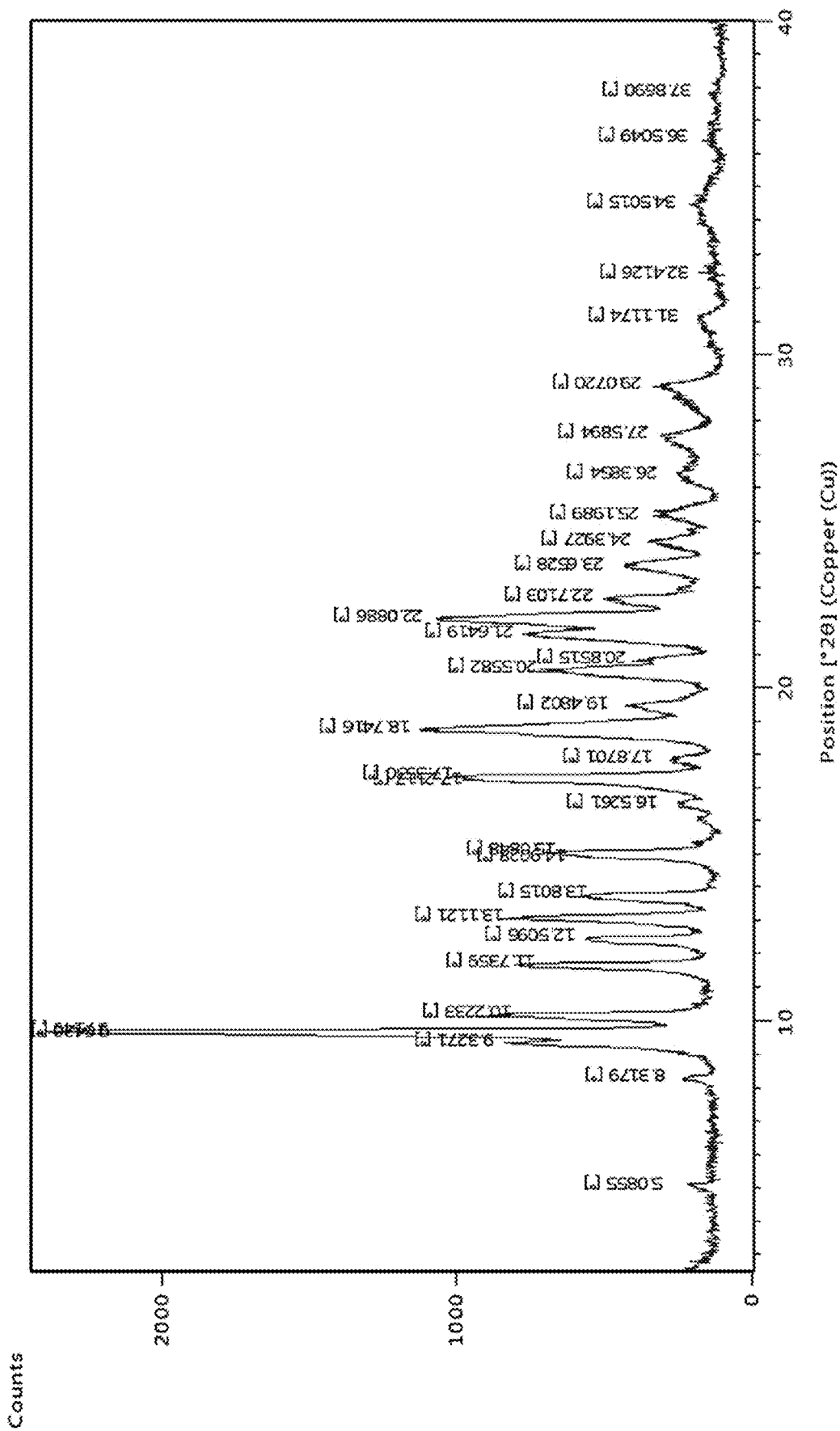
FIG. 24 shows an x-ray pattern for Sample 19, produced by Protocol 3 and which underwent recrystallization in isooctane.
Figure 25A:
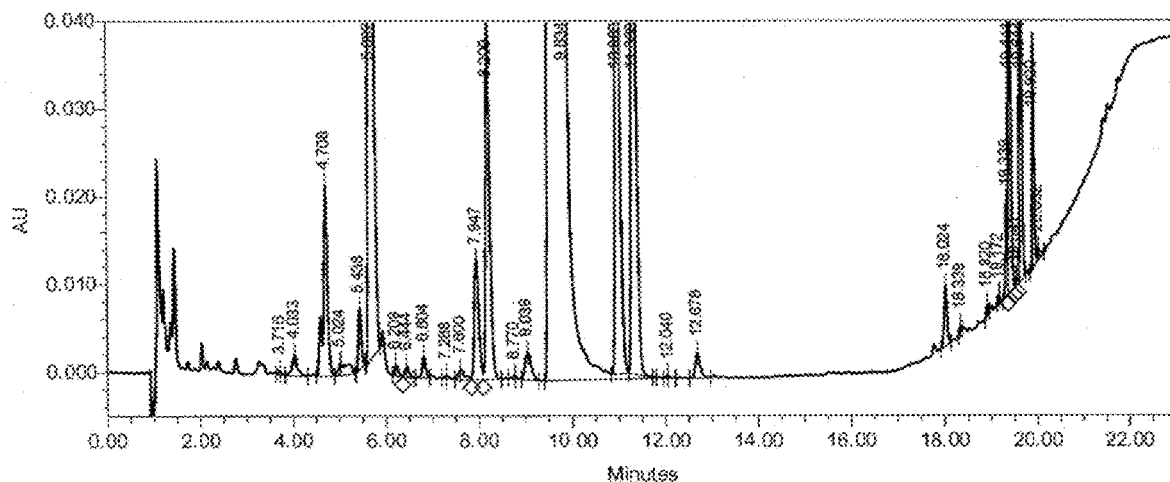
FIG. 25A shows an impurity profile (UHPLC) of a stressed CBD sample after 6 hours of exposure to acidic conditions.
Figure 25B:
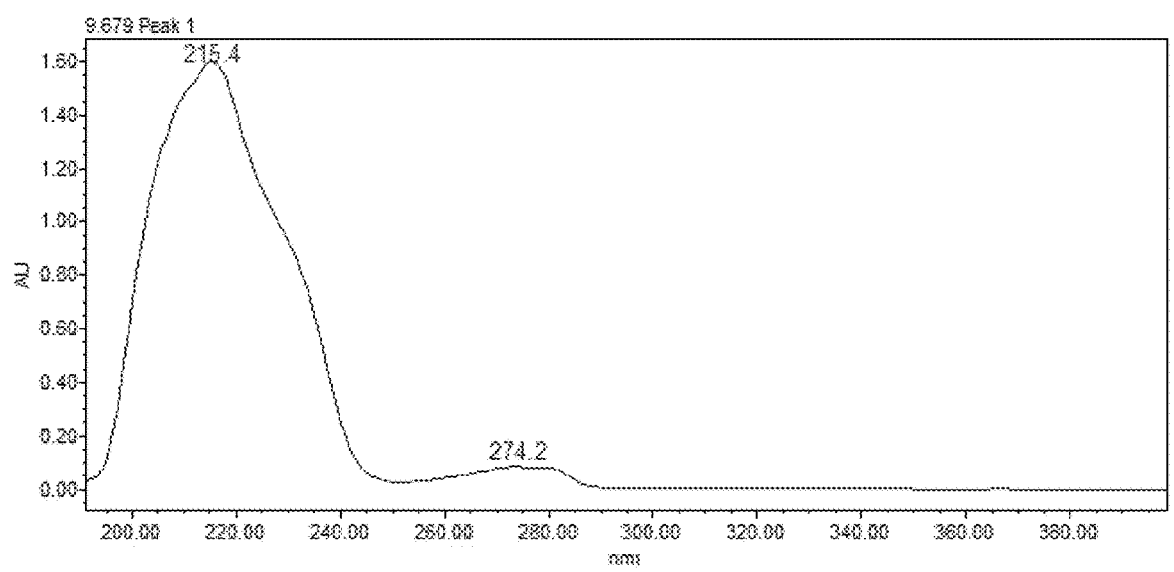
FIG. 25B shows a PDA-UV spectrum of the main compound (CBD) of a stressed sample after 6 h of exposure to acidic conditions.

In a 20 ml GC headspace vial, 150 mg of CBD was suspended in 8 mL of 0.1 M hydrochloric acid and heated to T=80° C. for 2 h, 4 h and 6 h, respectively. Regardless of their reaction time, all samples became a suspension of yellowish melted CBD in a clear colorless aqueous solution. FIG. 25A shows the impurity profile for the CBD sample stressed over a period of 6 h under acidic conditions and heated to 80° C. The PDA-UV spectrum is depicted in FIG. 26, which is comparable to the unstressed CBD sample (FIG. 15B). In addition, LC-MS analysis of the CBD peak confirmed the peak purity, as no co-eluting compound was detected.

Alkaline Stress

Figure 26A:
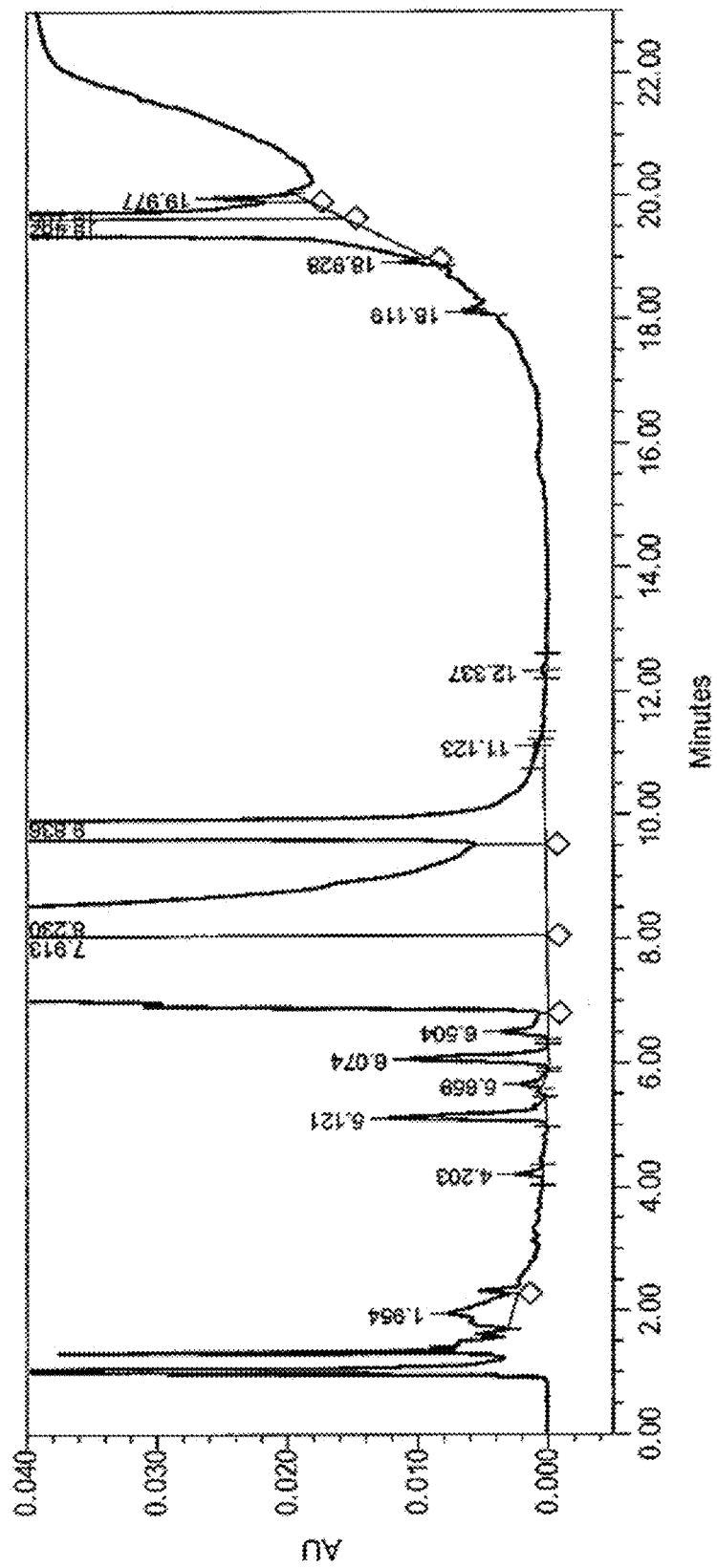
FIG. 26A shows an impurity profile (UHPLC) of a stressed CBD sample after 6 hours of exposure to alkaline conditions.
Figure 26B:
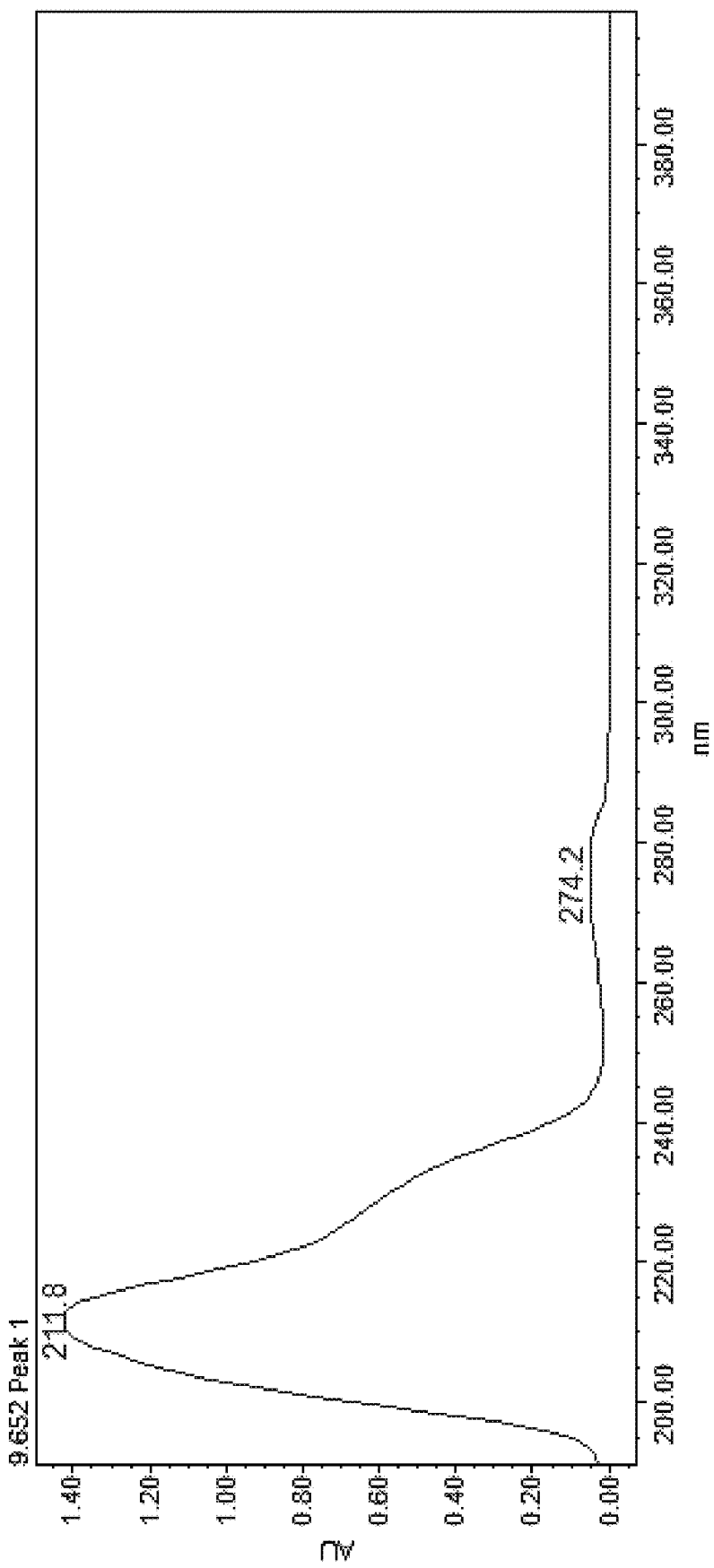
FIG. 26B shows a PDA-UV spectrum of the main compound (CBD) of a stressed sample after 6 h of exposure to alkaline conditions.
Figure 26C:
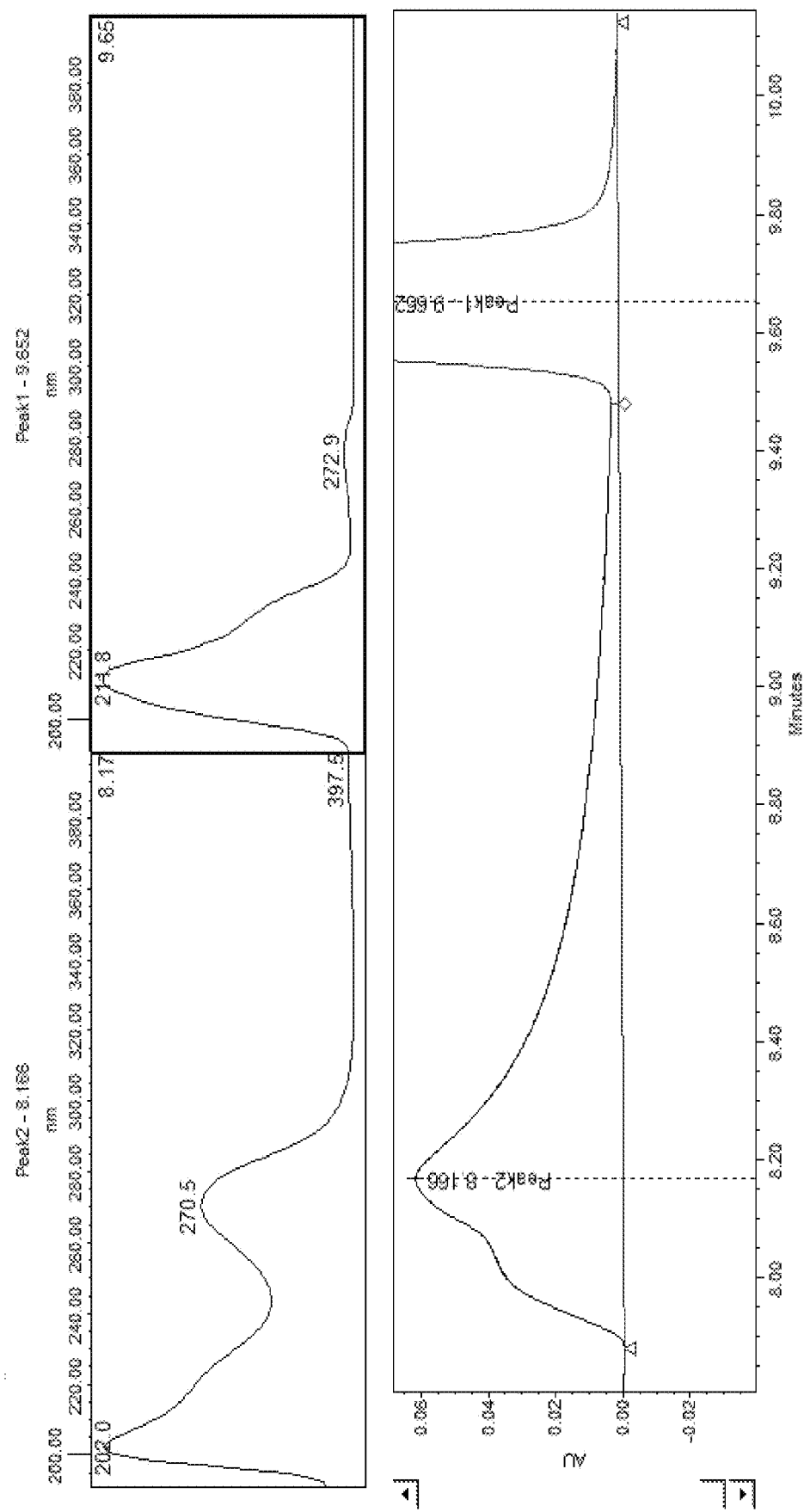
FIG. 26C shows an absorption spectra of CBQ (Peak 2—left) and CBD (Peak 1—right).

In a 20 ml GC headspace vial, 150 mg of CBD was suspended in 8 mL of 0.1 M sodium hydroxide and heated to T=80° C. for 2 h, 4 h and 6 h, respectively. Regardless of their reaction time, all samples became a suspension of yellowish melted CBD in a violet aqueous solution. FIG. 26A shows the impurity profile for the CBD sample stressed over a period of 6 h under basic conditions and heated to 80° C. FIG. 26B shows the PDA-UV-spectrum of the main component (CBD).

Oxidative Stress

Figure 27A:
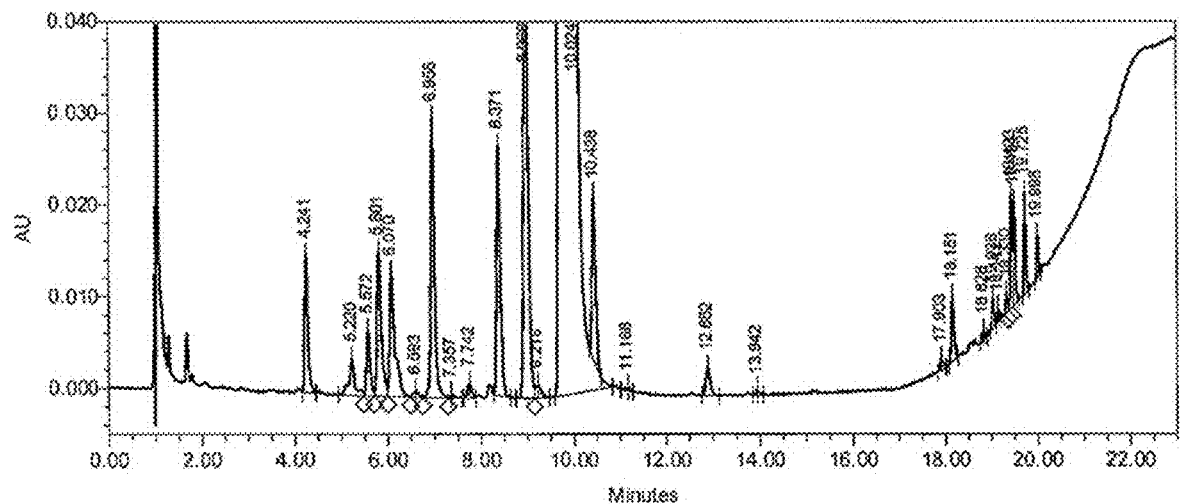
FIG. 27A shows the impurity profile for the CBD sample stressed over a period of 6 h under oxidative conditions and heating to 80° C.
Figure 27B:
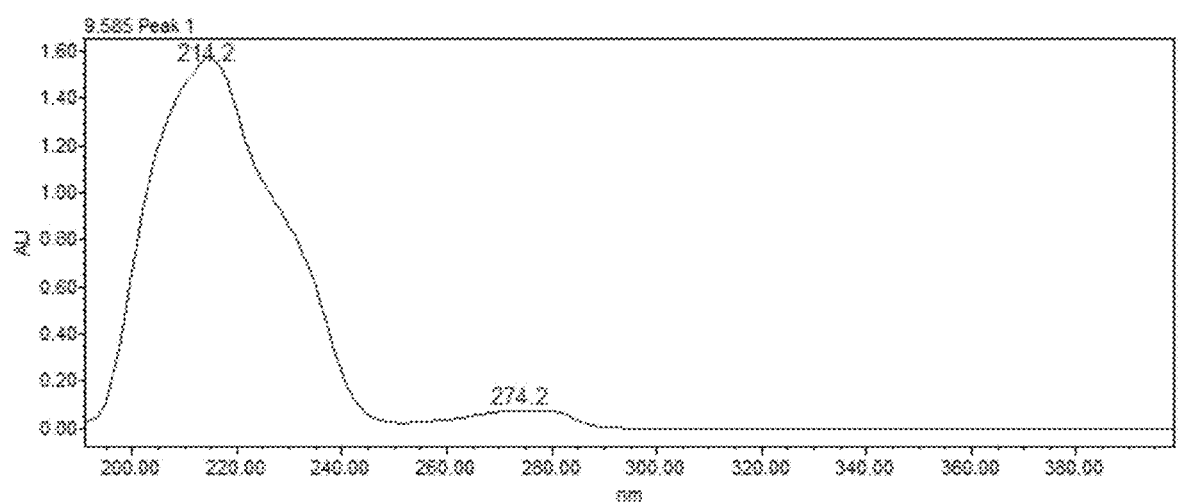
FIG. 27B shows the PDA-UV spectrum of the main compound (CBD) of a stressed sample after 6 h of exposure to oxidative conditions.

In a 20 ml GC headspace vial, 150 mg of CBD was suspended in 8 mL of hydrogen peroxide (0.3% w/w) and heated to T=80° C. for 2 h, 4 h and 6 h, respectively. Regardless of the reaction time, each sample became a suspension of yellowish melted CBD in a clear colorless aqueous solution. FIG. 27A shows the impurity profile for the CBD sample stressed over a period of 6 h under oxidative conditions and heated to 80° C. FIG. 27B shows the PDA-UV spectrum of the main compound (CBD) of a stressed sample after 6 h of exposure to oxidative conditions.

Photodegradation

Figure 28A:
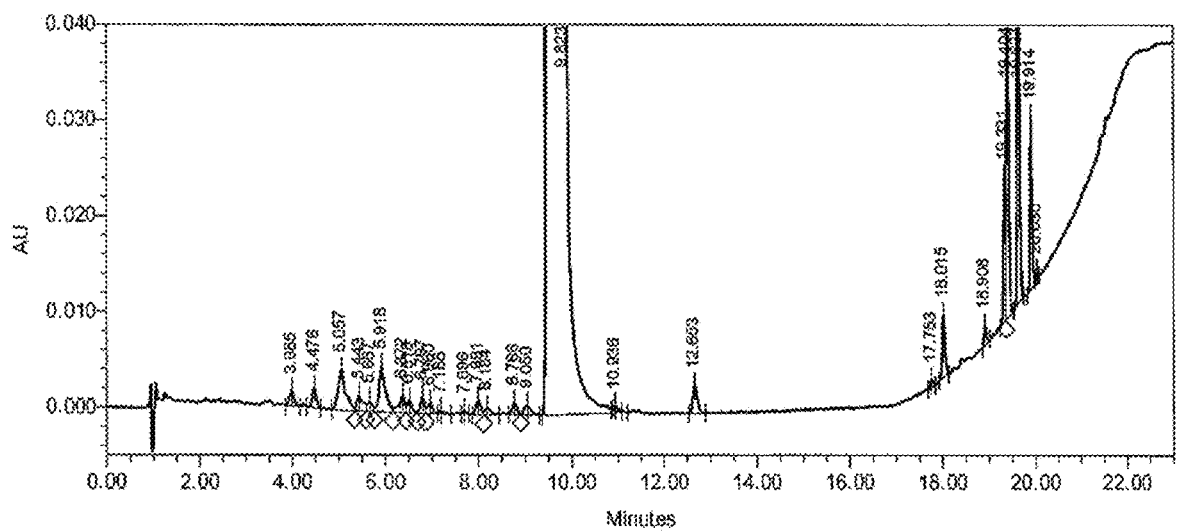
FIG. 28A shows an impurity profile (UHPLC) of a stressed CBD sample after 24 hours of irradiation.
Figure 28B:
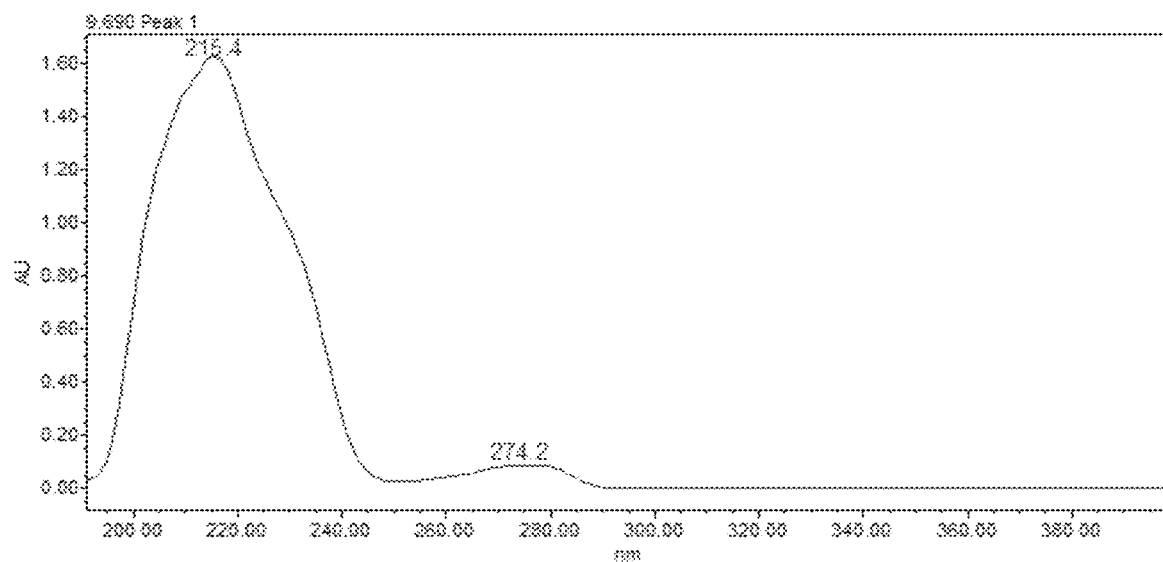
FIG. 28B shows a PDA-UV spectrum of the main compound (CBD) of a stressed sample after 24 h of irradiation.

Approximately 150 mg of CBD was filled into a Duran crystallizing dish and irradiated with light over a period of 24 h in an Atlas SUNTEST CPS+ light cabinet (UV300-400 nm: 500 W/m2; Lux400-800 nm 55 klux, 24 h exposure=1.320 MLux hours). A dark-control for the evaluation of thermally induced degradation was not necessary because the light cabinet was temperated to 24° C. After irradiation, the samples turned slightly yellow. FIG. 28A and FIG. 28B show the corresponding impurity profile and the PDA-UV-spectrum after 24 h of light exposure. The PDA spectrum is comparable to the unstressed CBD sample.

Figure 29A:
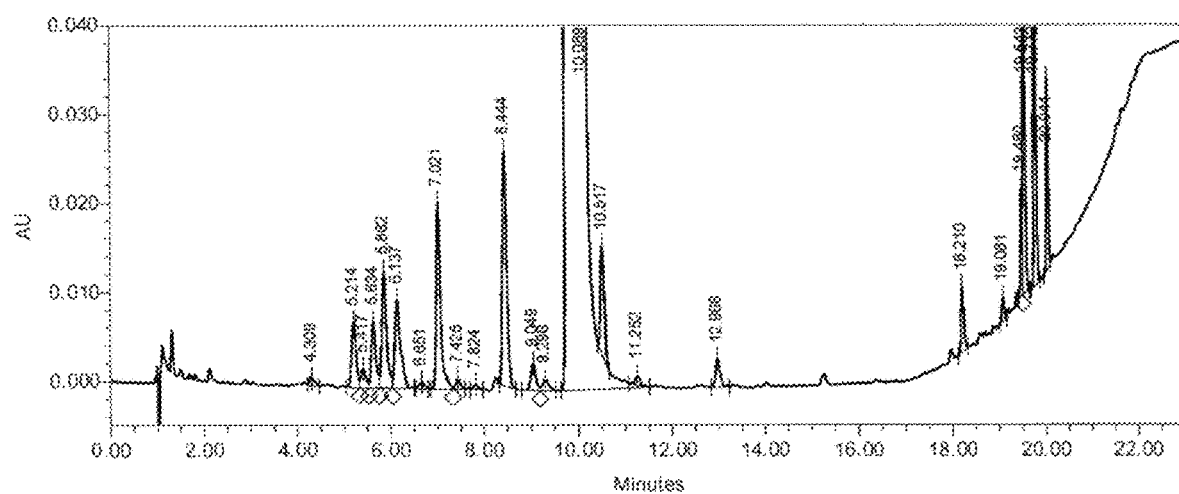
FIG. 29A shows an impurity profile (UHPLC) of a stressed CBD sample after 24 hours of heating to 100° C.
Figure 29B:
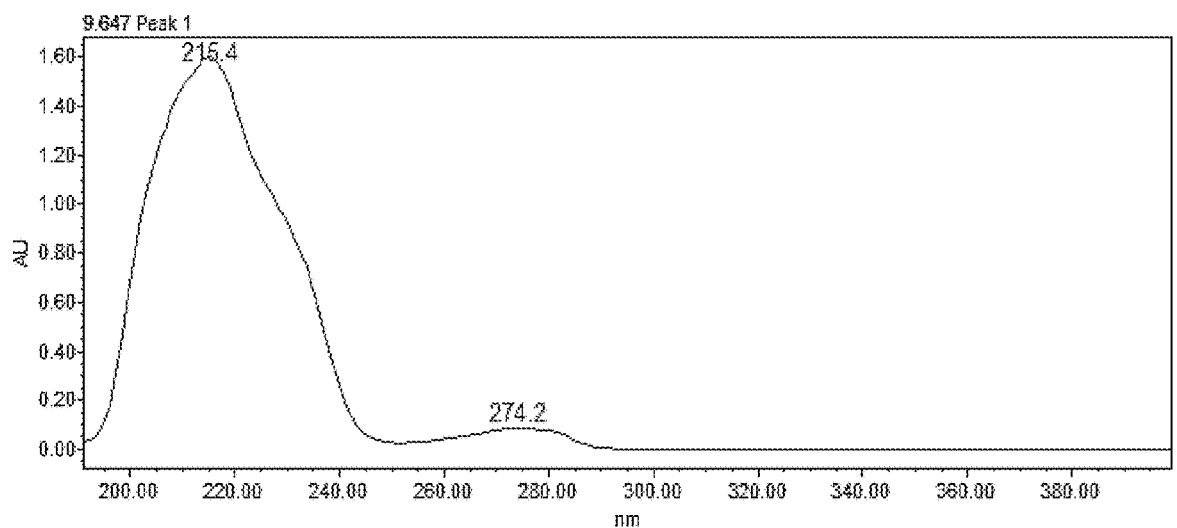
FIG. 29B shows a PDA-UV spectrum of the main compound (CBD) of a stressed sample after 24 h of heating to 100° C.

Elevated Temperature 150 mg of CBD was filled into a 20 mL GC headspace vial and heated to 50, 60, 70, 80, 90 and 100° C. for one hour. Another CBD sample (150 mg) was heated to 100° C. for 24 h. The two samples heated to 50° C. and 60° C. for 1 hour turned slightly yellow but did not change their physical condition. The samples heated to 70° C. were partially melted, whereas all samples heated to 80° C. or higher were fully melted and exhibited a yellow color. FIG. 29A shows the impurity profile for the CBD sample heated for 24 h to 100° C. FIG. 29B demonstrates the peak purity of the main component (CBD).

Figure 30A:
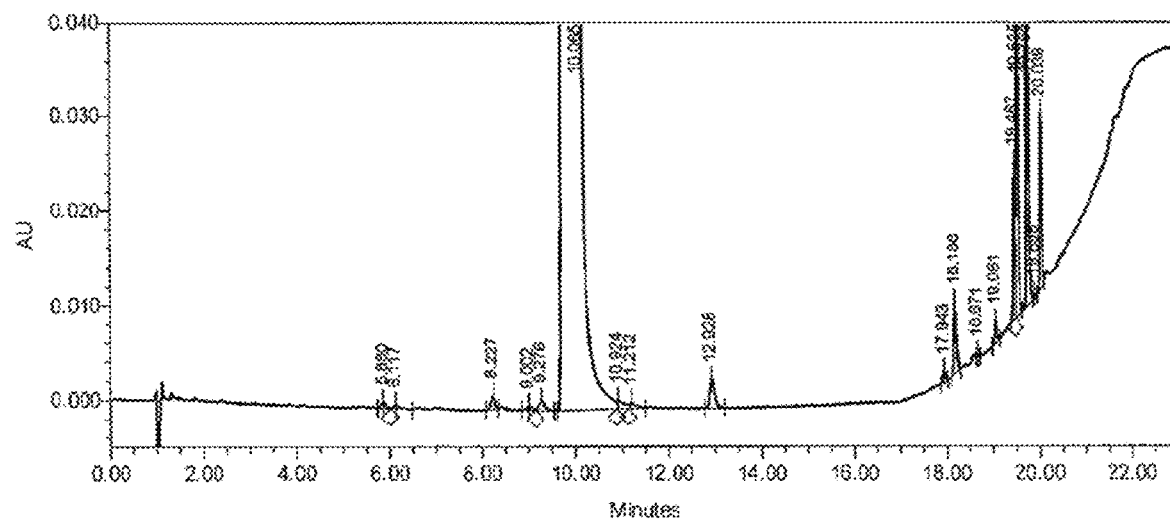
FIG. 30A shows an impurity profile (UHPLC) of a stressed CBD sample after 24 hours at 75% r.h.
Figure 30B:
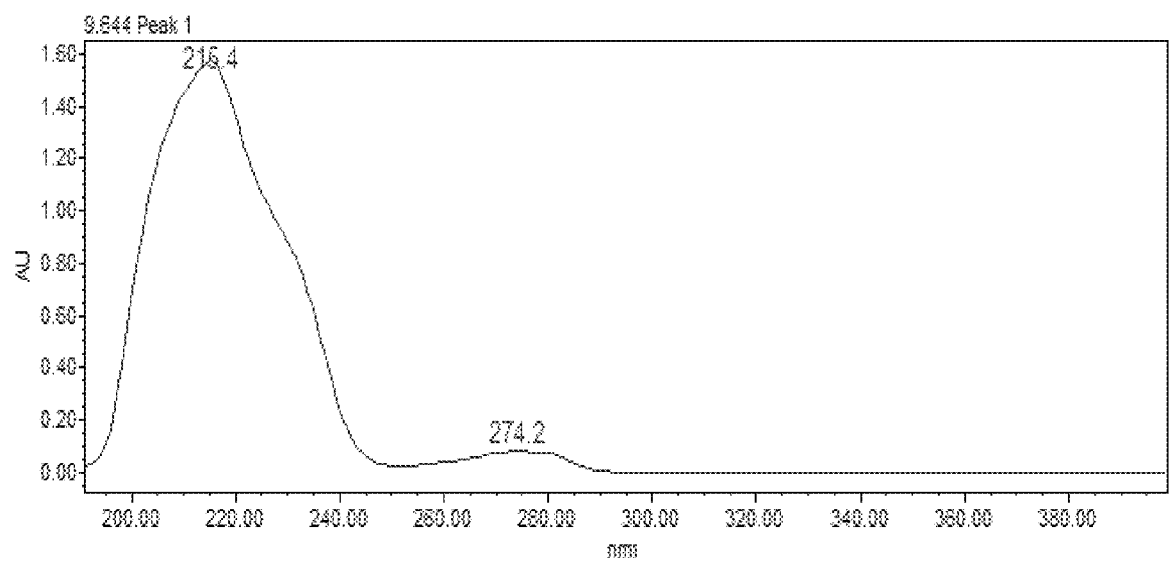
FIG. 30B shows a PDA-UV spectrum of the main compound (CBD) of a stressed sample after 24 h at 75% r.h.

Humidity Degradation 150 mg of CBD was filled into a Duran crystallizing dish and placed into a desiccator containing a dish filled with water. The desiccator was evacuated using a water jet pump and the conditions kept for 24 h. Under humidity treatment, the CBD sample did not change its appearance after 24 h at 75% r.h. FIG. 30A and FIG. 30B show the corresponding impurity profile and PDA-UV spectrum, respectively.

TABLE 9

Results Summary of Stress Tests

| Stress conditions | Degradation of CBD | Proposed main degradation products(s)(CBD) | Peak Purity (CBD) |
|---|---|---|---|
| Acidic, 6 h, 80° C. | 4% | 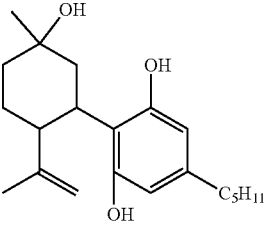 hydrated CBD/THC: 2.25 w/w %<br><br>D9-THC and isomers: 1.63 w/w % | no co-elution |
| Alkaline, 6 h, 80° C. | 38%* | 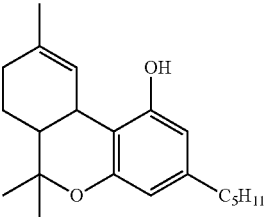 CBQ (isomers): 55.44 w/w % | No co-elution, however slight overlap with CBQ peak tail |
| Oxidative, 6 h 80° C. | 3% | 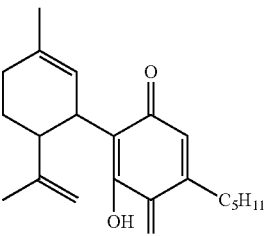 CBD-OH (isomers): 1.01 w/w % | no co-elution |
| Light, 24 h 24° C. | 1% | No prominent degradation product | no co-elution |
| Heat, 24 h, 100° C. | 1% | 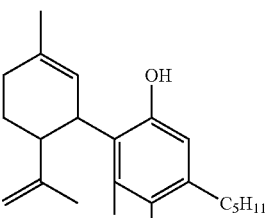 CBD-OH (isomers): 0.30 w/w % | no cp-elution |

TABLE 9-continued

Results Summary of Stress Tests

| Stress conditions | Degradation of CBD | Proposed main degradation products(s)(CBD) | Peak Purity (CBD) |
|---|---|---|---|
| | | 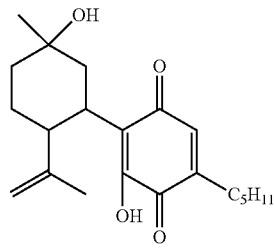<br>Hydrated CBQ: 0.23 w/w % | |
| Humidity, 24 h, 24° C. | 0% | No prominent degradation product | Not tested |

The depicted degradation products are proposed structures based on the LC-MS analysis. Others isomers are possible.
*Level of degradation at the time of the assay analysis. Degradation of cannabidiol progressed in the sample solution after assay analysis.

Under acidic conditions and simultaneous heating (80° C.) of the CBD samples, D9-THC was the main degradant product. In addition, several isomers of the hydration product of CBD and/or THC (m/z=331) were found. In general, only a minor degradation of CBD (4%) was observed.

Under alkaline stress conditions, CBD showed a much more pronounced degradation (>38%) with mainly several isomers of CBQ (=CBD Quinone) being formed. In comparison to the spectrum of the unstressed CBD sample (FIG. 15B) the first absorption maximum at 211.8 nm in FIG. 26B is slightly hypsochromically shifted. Since the absorption maximum (202.0 nm) of the degradation product CBQ (Peak 2 in FIG. 26C) is blue shifted in comparison to the CBD absorption maximum at 215.4 nm, the hypsochromical shift of the CBD absorption maximum (211.8 nm) is likely the result of the CBQ peak tail overlapping with CBD between 9.40 and 10.00 min. Purity analysis of the CBD peak by LC-MS showed (beside m/z=313) a product with m/z=327, which would correspond to CBQ. However, this signal was also detected under non-alkaline (e.g. acidic) conditions and is attributed to the oxidation of CBD in the ionization chamber forming CBQ. The degradation of CBD progressed further in the stock solution after the assay and purity analysis ending up with a degradation>80% at the time of the LC-MS analysis.

Exposure of CBD to oxidative stress conditions ($H_2O_2$) resulted in a slight degradation of CBD (3%) forming Hydroxy-CBD (CBD-OH). This is in agreement with the oxidative conditions induced by elevated temperatures. For example, the sample exposed to 100° C. for 24 h showed oxidized forms of CBD, which could be assigned to Hydroxy-CBD and Hydroxy-CBQ (formally CBD+[O] and CBD+2[O] with m/z=329 and m/z=345). There was no significant degradation observed with temperatures lower than 100° C.

It is generally known that the impurities showing up at relative retention times of about 1.98, 2.00 and 2.03 were formed during UPLC analysis by dimerization of CBD at the column head. Without wishing to be bound by theory, it is understood that the presence of $H_2O_2$ in the sample solution quenches the formation of these isomeric CBD-dimers, as there were only very low quantities of CBD-dimers observed under $H_2O_2$ stress conditions.

Example 11: Cannabidiol Stability Studies of CBD Prepared Via Protocol 1

Three different cannabidiol batches obtained by Protocol 1 were packaged into two LD-polyethylene bags in a HD-polyethylene drum and stored under four different storage conditions. Samples were checked against the specification limits shown in Table 10. The results of the stability experiments are summarized in Table 11 through Table 22.

TABLE 10

Specifications for Evaluating Samples in Stability Tests

| Test Parameters | Specification Limits |
|---|---|
| 1. Appearance | White to slightly beige (or slightly yellowish brown/slightly yellow/slightly brown) crystalline powder |
| 2. UHPLC-Assay in w/w % | ≥97.0-102.0 |
| 3. UHPLC-Purity in w/w % | |
| 3.1. Olivetol | ≤0.15 |
| 3.2. 4-Monobromo-CBD | ≤0.15 |
| 3.3. D9-THC | ≤0.10 |
| 3.4. Each unspecified impurity | ≤0.10 |
| 3.5. Total impurities | ≤1.0 |
| 4. Water content in w/w % | ≤0.2 |
| 5. Color of solution | For information |
| 6. Clarity of solution | For information |

The appearance was stable within specification over 12 months at all storage conditions. However, a slight color change from almost white to slightly yellowish brown was observed after 9 months of storage time with all batches and independent from the storage conditions.

The UPLC assay was stable and within specification over a period of 12 months for all batches and storage conditions. No trending was observed for the batches stored at 5° C., 25° C., and 30° C. Batches stored at 40° C. showed a slightly decreasing trend in assay for the tested 6 month-period.

The UPLC purity was stable over 12 months, if stored at 5° C. and 25° C./60% r.h. No trending was observed.

The UPLC purity was also stable and within specification over a period of 6 months when stored at elevated temperatures, 30° C./75% r.h.

At the higher temperature (40° C./75% r.h.), all batches showed higher levels of Δ9-THC after 3 months and 6 months. Also, the amount of each unspecified impurity (after 3 months) and the total amount of impurities (after 6 months) was higher at 40° C./75% r.h. A decreasing trend in purity at 40° C./75% r.h was observed for all batches, mainly due to an increasing trend in the formation of Δ9-THC.

The water content was stable and within specification for all batches and storage conditions over a period of 6 months at 30° C./75% or 40° C./75% r.h. and over 12 months if stored at 5° C. or 25° C./60% r.h.

TABLE 11

Analytical results of sample 5 (Protocol 1) stored at 5 ° C.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Appearance | White to slightly beige (or slightly yellowish brown/ slightly yellow/ slightly brown) crystalline powder | almost white crystalline powder | almost white crystalline powder | almost white crystalline powder | Slightly yellowish brown crystalline powder | Slightly yellowish brown crystalline powder |
| Clarity of solution | For information | n.t. | clear | clear | clear | clear |
| Color of solution | For information | n.t. | colorless | brownish | brownish | brownish |
| Water content in % w/w | ≤0.2 | ≤0.1 | ≤0.1 | ≤0.1 | ≤0.1 | ≤0.1 |
| UHPLC Assay in % w/w | ≥97.0-102.0 | 99.4 | 100.5 | 101.5 | 101.2 | 100.8 |
| UHPLC Purity in % w/w | | | | | | |
| Olivetol | ≤0.15 | n.d. | n.d. | n.d. | n.d. | n.d. |
| D9-THC | ≤0.10 | n.d. | n.d. | n.d. | n.d. | n.d. |
| 4-Monobromo-CBD | ≤0.15 | n.d. | 0.03 | 0.03 | 0.03 | 0.03 |
| Each unspecified impurity | ≤0.10 | 0.06 | 0.08 | 0.06 | 0.04 | 0.07 |
| Total impurities | ≤1.0 | 0.10 | 0.43 | 0.25 | 0.25 | 0.20 | n.t.: not tested
n.d.: not detected or not determined (because < LoQ)

TABLE 12

Analytical results of sample 5 (Protocol 1) stored at 25° C./60% r.h.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Appearance | White to slightly beige (or slightly yellowish brown/ slightly yellow/ slightly brown) crystalline powder | almost white crystalline powder | almost white crystalline powder | almost white crystalline powder | Slightly yellowish brown crystalline powder | Slightly yellowish brown crystalline powder |
| Clarity of solution | For information | n.t. | clear | clear | clear | clear |
| Color of solution | For information | n.t. | colorless | brownish | brownish | brownish |
| Water content in % w/w | ≤0.2 | ≤0.1 | ≤0.1 | ≤0.1 | ≤0.1 | ≤0.1 |
| UHPLC Assay in % w/w | ≥97.0-102.0 | 99.4 | 100.7 | 99.6 | 99.4 | 101.0 |
| UHPLC Purity in % w/w | | | | | | |
| Olivetol | ≤0.15 | n.d. | n.d. | n.d. | n.d. | n.d. |
| D9-THC | ≤0.10 | n.d. | n.d. | n.d. | n.d. | n.d. |
| 4-Monobromo-CBD | ≤0.15 | n.d. | 0.03 | 0.03 | 0.03 | 0.03 |

TABLE 12-continued

Analytical results of sample 5 (Protocol 1) stored at 25° C./60% r.h.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Each unspecified impurity | ≤0.10 | 0.06 | 0.04 | 0.05 | 0.04 | 0.07 |
| Total impurities | ≤1.0 | 0.10 | 0.35 | 0.30 | 0.28 | 0.20 | n.d.: not detected or not determined (because < LoQ)

TABLE 13

Analytical results of sample 5 (Protocol 1) stored at 30° C./75% r.h.

| Test | Limit | 0 months (October 16) | 3 months (January 17) | 6 months (April 17) |
|---|---|---|---|---|
| Appearance | White to slightly beige (or slightly yellowish brown/ slightly yellow/ slightly brown) crystalline powder | almost white crystalline powder | almost white crystalline powder | almost white crystalline powder |
| Clarity of solution | For information | n.t. | clear | clear |
| Color of solution | For information | n.t. | colorless | brownish |
| Water content in % w/w | ≤0.2 | ≤0.1 | ≤0.1 | ≤0.1 |
| UHPLC Assay in % w/w | ≥97.0-102.0 | 99.4 | 99.7 | 100.6 |
| UHPLC Purity in % w/w | | | | |
| Olivetol | ≤0.15 | n.d. | n.d. | n.d. |
| D9-THC | ≤0.10 | n.d. | 0.00 | 0.01 |
| 4-Monobromo-CBD | ≤0.15 | n.d. | 0.03 | 0.03 |
| Each unspecified impurity | ≤0.10 | 0.06 | 0.05 | 0.05 |
| Total impurities | ≤1.0 | 0.10 | 0.35 | 0.28 | n.d.: not detected or not determined (because <LoQ)

TABLE 14

Analytical results of sample 5 (Protocol 1) stored at 40° C./75% r.h.

| Test | Limit | 0 months (October 16) | 3 months (January 17) | 6 months (April 17) |
|---|---|---|---|---|
| Appearance | White to slightly beige (or slightly yellowish brown/ slightly yellow/ slightly brown) crystalline powder | almost white crystalline powder | almost white crystalline powder | almost white crystalline powder |
| Clarity of solution | For information | n.t. | clear | clear |
| Color of solution | For information | n.t. | colorless | brownish |
| Water content in % w/w | ≤0.2 | ≤0.1 | ≤0.1 | ≤0.1 |
| UHPLC Assay in % w/w | ≥97.0-102.0 | 99.4 | 99.6 | 99.0 |
| UHPLC Purity in % w/w | | | | |
| Olivetol | ≤0.15 | n.d. | n.d. | n.d. |
| D9-THC | ≤0.10 | n.d. | 0.04 | 0.11 |
| 4-Monobromo-CBD | ≤0.15 | n.d. | 0.03 | 0.03 |
| Each unspecified impurity | ≤0.10 | 0.06 | 0.04 | 0.10 |
| Total impurities | ≤1.0 | 0.10 | 0.48 | 0.58 | n.d.: not detected or not determined (because <LoQ)

TABLE 15

Analytical results of sample 6 (Protocol 1) stored at 5° C.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Appearance | White to slightly beige (or slightly yellowish brown/ slightly yellow/ slightly brown) crystalline powder | almost white crystalline powder | almost white crystalline powder | almost white crystalline powder | Slightly yellowish brown crystalline powder | Slightly yellowish brown crystalline powder |
| Clarity of solution | For information | n.t. | clear | clear | clear | clear |
| Color of solution | For information | n.t. | colorless | brownish | brownish | brownish |
| Water content in % w/w | ≤0.2 | ≤0.1 | ≤0.1 | ≤0.1 | ≤0.1 | ≤0.1 |
| UHPLC Assay in % w/w | ≥97.0-102.0 | 99.9 | 100.5 | 100.1 | 99.7 | 101.0 |
| UHPLC Purity in % w/w | | | | | | |
| Olivetol | ≤0.15 | n.d. | n.d. | n.d. | n.d. | n.d. |
| D9-THC | ≤0.10 | n.d. | n.d. | n.d. | n.d. | n.d. |
| 4-Monobromo-CBD | ≤0.15 | n.d. | 0.02 | 0.02 | 0.02 | 0.02 |
| Each unspecified impurity | ≤0.10 | 0.07 | 0.05 | 0.06 | 0.04 | 0.07 |
| Total impurities | ≤1.0 | 0.10 | 0.32 | 0.26 | 0.24 | 0.20 | n.d.: not detected or not determined (because < LoQ)

TABLE 16

Analytical results of sample 6 (Protocol 1) stored at 25° C./60% r.h.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Appearance | White to slightly beige (or slightly yellowish brown/ slightly yellow/ slightly brown) crystalline powder | almost white crystalline powder | almost white crystalline powder | almost white crystalline powder | Slightly yellowish brown crystalline powder | Slightly yellowish brown crystalline powder |
| Clarity of solution | For information | at. | clear | clear | clear | clear |
| Color of solution | For information | at. | colorless | brownish | brownish | brownish |
| Water content in % w/w | ≤0.2 | ≤0.1 | ≤0.1 | ≤0.1 | ≤0.1 | ≤0.1 |
| UHPLC Assay in % w/w | ≥97.0-102.0 | 99.9 | 99.9 | 99.0 | 99.8 | 100.3 |
| UHPLC Purity in % w/w | | | | | | |
| Olivetol | ≤0.15 | n.d. | n.d. | n.d. | n.d. | n.d. |
| D9-THC | ≤0.10 | n.d. | n.d. | n.d. | n.d. | n.d. |
| 4-Monobromo-CBD | ≤0.15 | n.d. | 0.02 | 0.02 | 0.02 | 0.02 |
| Each unspecified impurity | ≤0.10 | 0.07 | 0.05 | 0.08 | 0.04 | 0.07 |
| Total impurities | ≤1.0 | 0.10 | 0.32 | 0.29 | 0.28 | 0.21 | n.d.: not detected or not determined (because < LoQ)

TABLE 17

Analytical results of sample 6 (Protocol 1) stored at 30° C./75% r.h.

| Test | Limit | 0 months (October 16) | 3 months (January 17) | 6 months (April 17) |
| --- | --- | --- | --- | --- |
| Appearance | White to slightly beige (or slightly yellowish brown/ slightly yellow/ slightly brown) crystalline powder | almost white crystalline powder | almost white crystalline powder | almost white crystalline powder |
| Clarity of solution | For information | n.t. | clear | clear |
| Color of solution | For information | n.t. | colorless | brownish |
| Water content in % w/w | ≤0.2 | ≤0.1 | ≤0.1 | ≤0.1 |
| UHPLC Assay in % w/w | ≥97.0-102.0 | 99.9 | 100.1 | 99.8 |
| UHPLC Purity in % w/w | | | | |
| Olivetol | ≤0.15 | n.d. | n.d. | n.d. |
| D9-THC | ≤0.10 | n.d. | 0.00 | 0.02 |
| 4-Monobromo-CBD | ≤0.15 | n.d. | 0.02 | 0.02 |
| Each unspecified impurity | ≤0.10 | 0.07 | 0.05 | 0.06 |
| Total impurities | ≤1.0 | 0.10 | 0.30 | 0.31 | n.d.: not detected or not determined (because <LoQ)

TABLE 18

Analytical results of sample 6 (Protocol 1) stored at 40° C./75% r.h.

| Test | Limit | 0 months (October 16) | 3 months (January 17) | 6 months (April 17) |
| --- | --- | --- | --- | --- |
| Appearance | White to slightly beige (or slightly yellowish brown/ slightly yellow/ slightly brown) crystalline powder | almost white crystalline powder | almost white crystalline powder | almost white crystalline powder |
| Clarity of solution | For information | n.t. | clear | clear |
| Color of solution | For information | n.t. | colorless | brownish |
| Water content in % w/w | ≤0.2 | ≤0.1 | ≤0.1 | ≤0.1 |
| UHPLC Assay in % w/w | ≥97.0-102.0 | 99.9 | 99.7 | 100.1 |
| UHPLC Purity in % w/w | | | | |
| Olivetol | ≤0.15 | n.d. | n.d. | 0.00 |
| D9-THC | ≤0.10 | n.d. | 0.13 | 0.25 |
| 4-Monobromo-CBD | ≤0.15 | n.d. | 0.02 | 0.02 |
| Each unspecified impurity | ≤0.10 | 0.07 | 0.11 | 0.24 |
| Total impurities | ≤1.0 | 0.10 | 0.67 | 1.04 | n.d.: not detected or not determined (because <LoQ)

TABLE 19

Analytical results of sample 4 (Protocol 1) stored at 5° C.

| Test | Limit | 0 months (Oct. 16) | 3 months (Jan. 17) | 6 months (Apr. 17) | 9 months (Jul. 17) | 12 months (Oct. 17) |
| --- | --- | --- | --- | --- | --- | --- |
| Appearance | White to slightly beige (or slightly yellowish brown/ slightly yellow/ slightly brown) crystalline powder | almost white crystalline powder | almost white crystalline powder | almost white crystalline powder | Slightly yellowish brown crystalline powder | Slightly yellowish brown crystalline powder |

TABLE 19-continued

Analytical results of sample 4 (Protocol 1) stored at 5° C.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Clarity of solution | For information | at. | clear | clear | clear | clear |
| Color of solution | For information | n.t. | colorless | brownish | brownish | brownish |
| Water content in % w/w | ≤0.2 | ≤0.1 | ≤0.1 | ≤0.1 | ≤0.1 | ≤0.1 |
| UHPLC Assay in % w/w | ≥97.0-102.0 | 100.6 | 100.5 | 100.4 | 99.3 | 101.2 |
| UHPLC Purity in % w/w | | | | | | |
| Olivetol | ≤0.15 | n.d. | n.d. | n.d. | n.d. | n.d. |
| D9-THC | ≤0.10 | n.d. | n.d. | n.d. | n.d. | n.d. |
| 4-Monobromo-CBD | ≤0.15 | 0.03 | 0.03 | 0.03 | 0.03 | 0.03 |
| Each unspecified impurity | ≤0.10 | 0.06 | 0.05 | 0.06 | 0.05 | 0.07 |
| Total impurities | ≤1.0 | 0.10 | 0.33 | 0.26 | 0.26 | 0.20 | n.d.: not detected or not determined (because < LoQ)

TABLE 20

Analytical results of sample 4 (Protocol 1) stored at 25° C./60% r.h.

| Test | Limit | 0 months (Oct. 16) | 3 months (Jan. 17) | 6 months (Apr. 17) | 9 months (Jul. 17) | 12 months (Oct. 17) |
|---|---|---|---|---|---|---|
| Appearance | White to slightly beige (or slightly yellowish brown/ slightly yellow/ slightly brown) crystalline powder | almost white crystalline powder | almost white crystalline powder | almost white crystalline powder | Slightly yellowish brown crystalline powder | Slightly yellowish brown crystalline powder |
| Clarity of solution | For information | at. | clear | clear | clear | clear |
| Color of solution | For information | at. | colorless | brownish | brownish | brownish |
| Water content in % w/w | ≤0.2 | ≤0.1 | ≤0.1 | ≤0.1 | ≤0.1 | ≤0.1 |
| UHPLC Assay in % w/w | ≤97.0-102.0 | 100.6 | 100.1 | 99.7 | 99.8 | 100.5 |
| UHPLC Purity in % w/w | | | | | | |
| Olivetol | ≤0.15 | n.d. | n.d. | n.d. | n.d. | n.d. |
| D9-THC | ≤0.10 | n.d. | n.d. | n.d. | n.d. | n.d. |
| 4-Monobromo-CBD | ≤0.15 | 0.03 | 0.03 | 0.02 | 0.03 | 0.03 |
| Each unspecified impurity | ≤0.10 | 0.06 | 0.05 | 0.07 | 0.04 | 0.07 |
| Total impurities | ≤1.0 | 0.10 | 0.32 | 0.38 | 0.29 | 0.20 | n.d.: not detected or not determined (because < LoQ)

TABLE 21

Analytical results of sample 4 (Protocol 1) stored at 30° C./75% r.h.

| Test | Limit | 0 months (October 16) | 3 months (January 17) | 6 months (April 17) |
|---|---|---|---|---|
| Appearance | White to slightly beige (or slightly yellowish | almost white crystalline powder | almost white crystalline powder | almost white crystalline powder |

TABLE 21-continued

Analytical results of sample 4 (Protocol 1) stored at 30° C./75% r.h.

| Test | Limit | 0 months (October 16) | 3 months (January 17) | 6 months (April 17) |
|---|---|---|---|---|
| | brown/slightly yellow/slightly brown) crystalline powder | | | |
| Clarity of solution | For information | n.t. | clear | clear |
| Color of solution | For information | n.t. | colorless | brownish |
| Water content in % w/w | ≤0.2 | ≤0.1 | ≤0.1 | ≤0.1 |
| UHPLC Assay in % w/w | ≥97.0-102.0 | 100.6 | 99.8 | 101.0 |
| UHPLC Purity in % w/w | | | | |
| Olivetol | ≤0.15 | n.d. | n.d. | n.d. |
| D9-THC | ≤0.10 | n.d. | 0.00 | 0.01 |
| 4-Monobromo-CBD | ≤0.15 | 0.03 | 0.02 | 0.03 |
| Each unspecified impurity | ≤0.10 | 0.06 | 0.05 | 0.05 |
| Total impurities | ≤1.0 | 0.10 | 0.36 | 0.30 | n.d.: not detected or not determined (because <LoQ)

TABLE 22

Analytical results of sample 4 (Protocol 1) stored at 40° C./75% r.h.

| Test | Limit | 0 months (October 16) | 3 months (January 17) | 6 months (April 17) |
|---|---|---|---|---|
| Appearance | White to slightly beige (or slightly yellowish brown/ slightly yellow/ slightly brown) crystalline powder | almost white crystalline powder | almost white crystalline powder | almost white crystalline powder |
| Clarity of solution | For information | n.t. | clear | clear |
| Color of solution | For information | n.t. | colorless | brownish |
| Water content in % w/w | ≤0.2 | ≤0.1 | ≤0.1 | ≤0.1 |
| UHPLC Assay in % w/w | ≥97.0-102.0 | 100.6 | 99.8 | 98.0 |
| UHPLC Purity in % w/w | | | | |
| Olivetol | ≤0.15 | n.d. | n.d. | n.d. |
| D9-THC | ≤0.10 | n.d. | 0.15 | 0.30 |
| 4-Monobromo-CBD | ≤0.15 | 0.03 | 0.02 | 0.03 |
| Each unspecified impurity | ≤0.10 | 0.06 | 0.12 | 0.27 |
| Total impurities | ≤1.0 | 0.10 | 0.81 | 1.26 | n.d.: not detected or not determined (because <LoQ)

Example 12: Confirmation of Cannabidiol Crystal Structure from Cannabidiol Recrystallized in Isooctane from Protocol 1

Figure 11B:
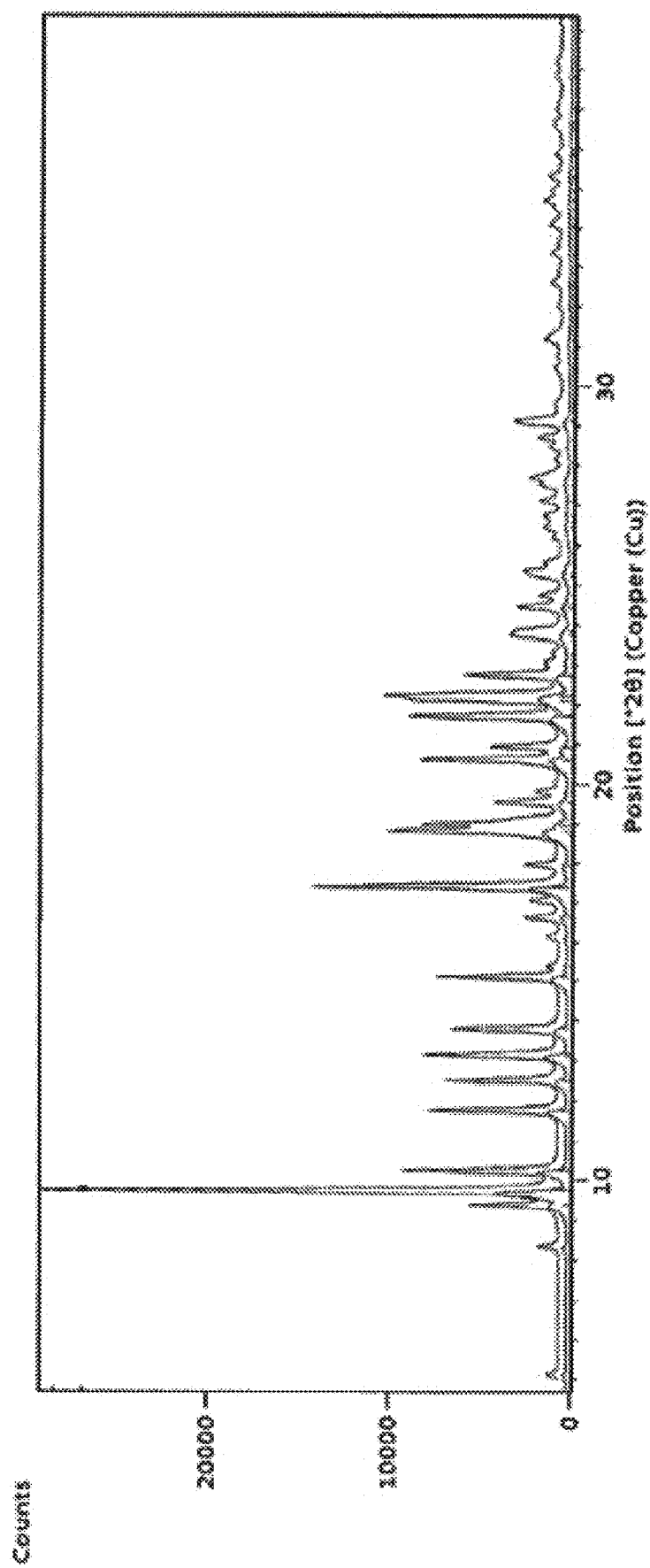
FIG. 11B shows overlays of a simulated x-ray data (higher intensity pattern) and experimentally derived x-ray data (lower intensity pattern) of Cannabidiol Form A, produced by Protocol 1, and which underwent recrystallization in isooctane.

High resolution X-ray powder diffraction patterns were collected on a D8 Advance system equipped with LynxEye solid-state detector. The radiation used for collecting the data was CuKα1 (λ=1.54056 Å) monochromatized by germanium crystal. The patterns were collected in the range 4 to 50° 2θ, with a step in the range of 0.016° 2θ without further processing. All patterns were taken at approximately 295 K. FIG. 11A shows an X-ray pattern of the recrystallized CBD. FIG. 11B shows overlays of simulated X-ray single crystal diffraction (top pattern) and experimentally derived XRPD diffractograms (bottom pattern) of cannabidiol. Comparison of the simulated x-ray data with the experimentally derived diffractograms indicates that the cannabidiol batch is phase pure and consists only of Form A. Cannabidiol crystallizes in the P2$_1$ space group. FIG. 16, FIG. 21, FIG. 22, FIG. 23, and FIG. 24 show additional x-ray powder diffraction patterns of cannabidiol samples.

Example 13: Differential Scanning Calorimetry Experiments

Sample 2, prepared by Protocol 3 and which underwent recrystallization in isooctane, was used for DSC experiments. Melting properties were obtained from DSC thermograms, recorded with a heat flux DSC822e instrument (Mettler-Toledo GmbH, Switzerland). The DSC822e was calibrated for temperature and enthalpy with a small piece of indium (melting point at 156.6° C.; ΔHf=28.45 J·g−1). Samples were sealed in standard 40 μl aluminum pans, pin-holed and heated in the DSC from 25° C. to 300° C., at a heating rate of 10° C. min-1. Dry N$_2$ gas, at a flow rate of 50 ml min-1 was used to purge the DSC equipment during measurement. FIG. 12 shows a DSC thermogram of cannabidiol sample 2, which was produced under Protocol 3 and underwent recrystallization in isooctane. A single endothermic event is observed at 68.12° C. in FIG. 12, corresponding with melting of the API. Additional DSC thermograms are provided in FIG. 17, FIG. 18, FIG. 19, and FIG. 20.

Example 14: Thermogravimetric Mass Analysis

Figure 13A:
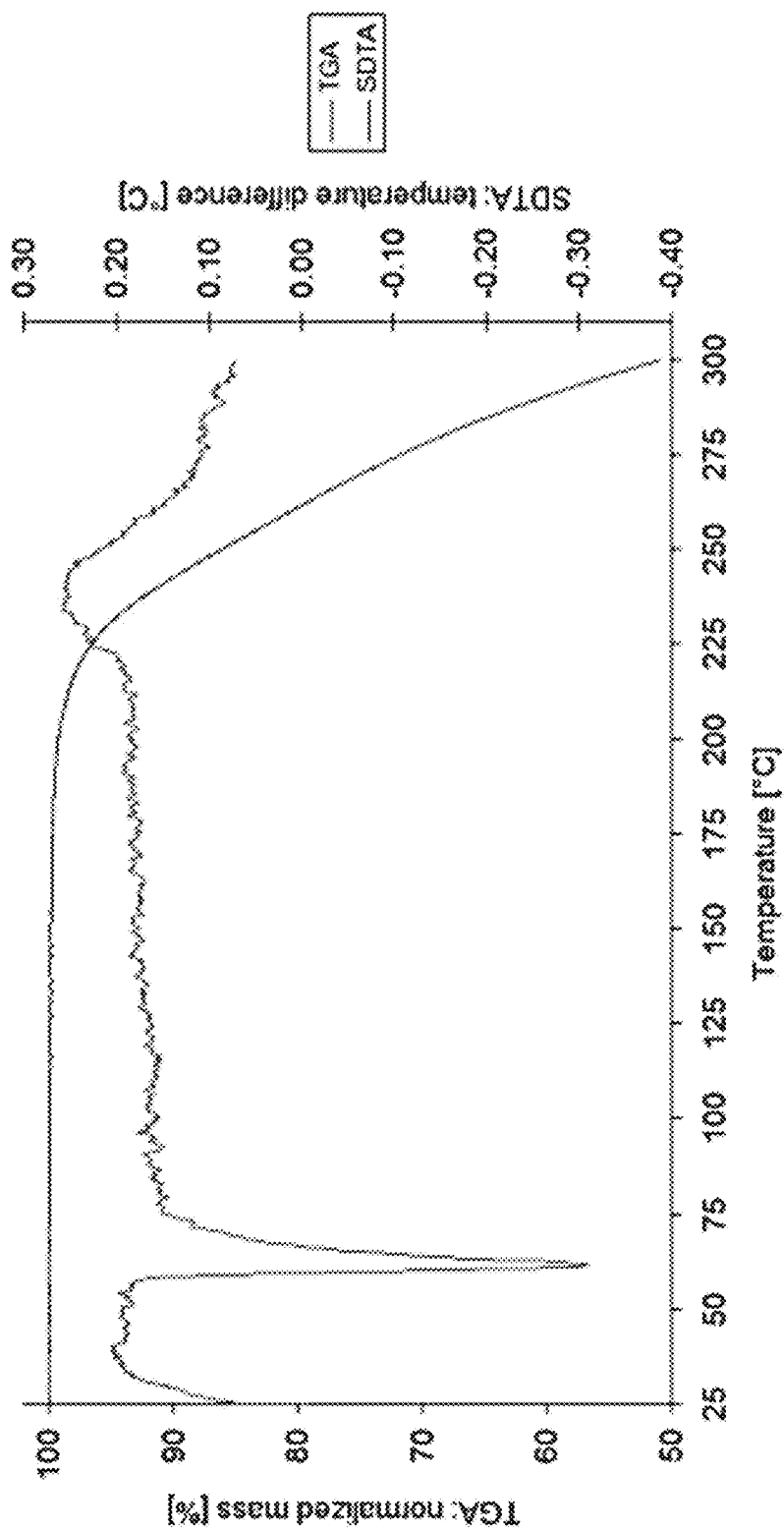
FIG. 13A shows a TGA/SDTA analysis of cannabidiol.
Figure 13B:
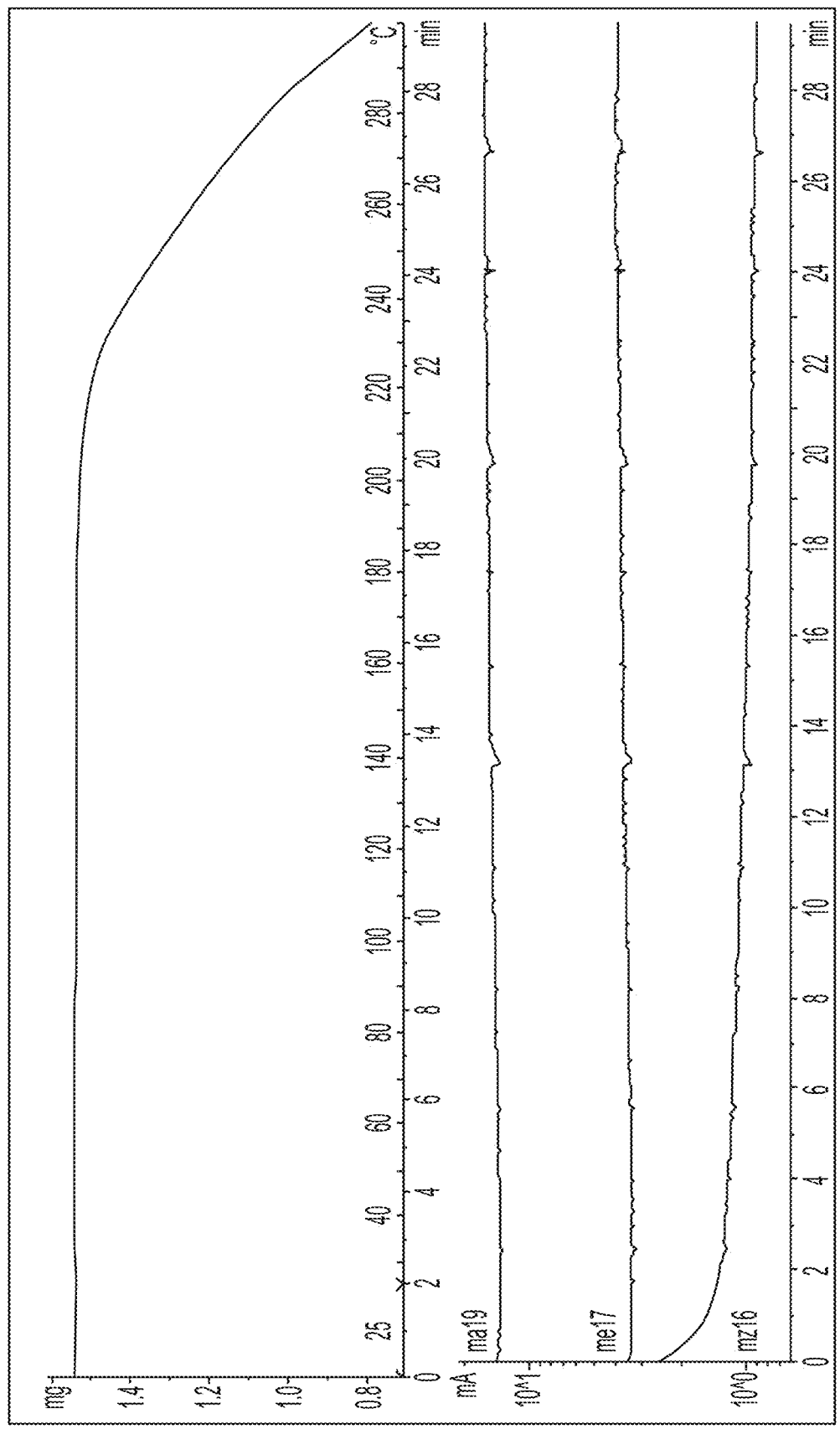
FIG. 13B shows a TGA-MS analysis of cannabidiol.

Mass loss due to solvent or water loss from the crystals was determined by TGA/SDTA. Monitoring the sample weight, during heating in a TGA/SDTA851e instrument (Mettler-Toledo GmbH, Switzerland), resulted in a weight vs. temperature curve. The TGA/SDTA851e was calibrated for temperature with indium and aluminum. Samples were weighed into 100 μl aluminum crucibles and sealed. The seals were pin-holed and the crucibles heated in the TGA from 25 to 300° C. at a heating rate of 10° C. min-1. Dry $N_2$ gas was used for purging. The gases evolved from the TGA samples were analyzed by a mass spectrometer Omnistar GSD 301 T2 (Pfeiffer Vacuum GmbH, Germany). The latter is a quadrupole mass spectrometer which analyses masses in the range of 0-200 amu. TGA/SDTA and TGA-MS analyses of Cannabidiol are shown in FIG. 13A and FIG. 13B, respectively. No significant mass loss was observed prior to the thermal decomposition. The SDTA signal showed an endothermic event at 62° C., attributed to the melting of the API.

Example 15: Investigating Other Impurities

Figure 14:
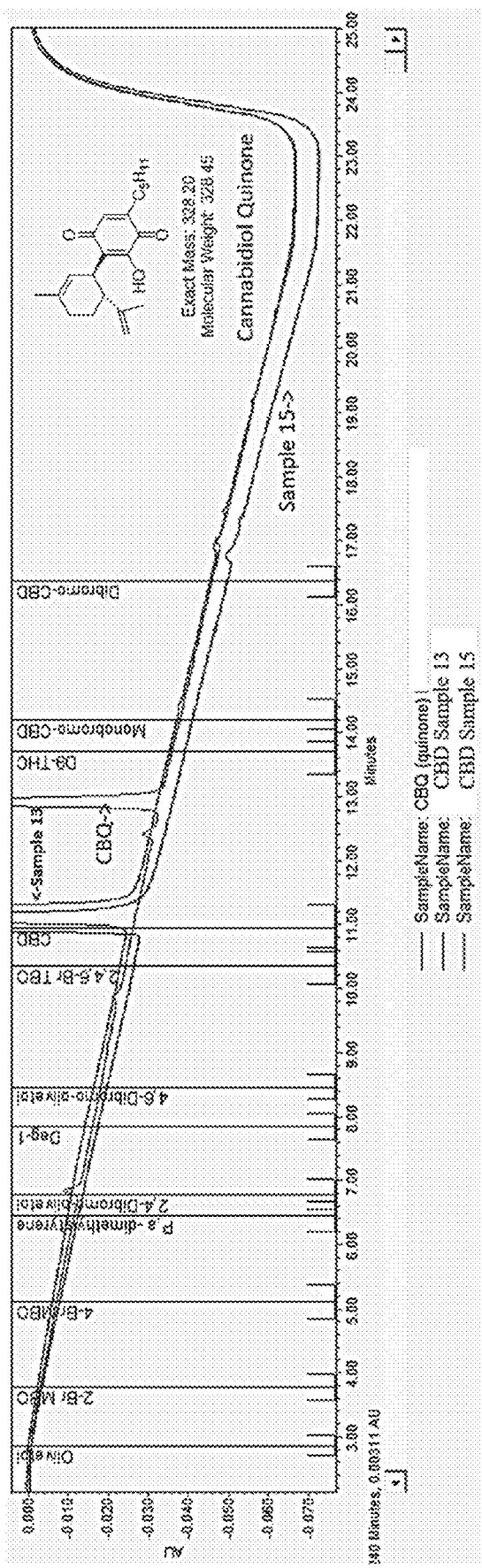
FIG. 14 shows a chromatograph of a cannabidiol quinone standard (CBQ) and two cannabidiol samples, indicating that the cannabidiol samples are essentially free of CBQ.

The presence of other impurities in the CBD samples was further investigated. FIG. 14 shows a chromatograph of a cannabidiol quinone standard (CBQ) against two cannabidiol samples prepared by Protocol 3. It can be seen that the CBD samples are free of the CBQ oxidation product.

Example 16: Solubility Experiments

A quantitative thermodynamic solubility determination was performed on crude cannabidiol obtained via Protocol 2 to aid in the selection of solvents for crystallization experiments. The results of the solubility determination performed at ambient temperature are summarized in Table 23. The clear solutions obtained from each solubility determination experiment were evaporated and the obtained solids were analyzed by XRPD.

When the material precipitated as a solid, it was classified as Form A. However, in 11 experiments, the material obtained after evaporation was oil-like in appearance and could not be analyzed by XRPD. When no XRPD record was generated, the field was defined as "Not Applicable" (N/A).

TABLE 23

| Solubility (mg/mL) | Solvent | XRPD |
| --- | --- | --- |
| <0.13 | Water | Form A |
| 64.6 | Heptane | Form A |
| >100 | 2-propanol | N/A |
| >100 | 1-Propanol | N/A |
| >100 | Anisole | N/A |
| >100 | Tetrahydrofuran | Form A |
| >100 | Toluene | Form A |
| >100 | Cumene | N/A |
| >100 | Ethyl Formate | Form A |
| >100 | Diethyl ether | Form A |
| >100 | 1,2-Dimethoxyethane | N/A |

TABLE 23-continued

| Solubility (mg/mL) | Solvent | XRPD |
| --- | --- | --- |
| >100 | Acetone | N/A |
| >100 | Ethyl Acetate | Form A |
| >100 | Isobutanol | N/A |
| >100 | Chloroform | Form A |
| >100 | Dichloromethane | Form A |
| >100 | Acetonitrile | N/A |
| >100 | Isopropyl acetate | Form A |
| >100 | Cyclohexane | Form A |
| >100 | Methanol | N/A |
| >100 | Ethanol | N/A |
| >100 | p-Xylene | N/A |
| >100 | 1,4-Dioxane | Form A |
| >100 | 2-Butanone | Form A |
| >100 | Tert-Butyl methyl ether | Form A |

Example 17: Crude CBG Crystallization Experiments

Seeding was implemented in the crystallization of CBD, as supersaturated solutions often require very cold temperatures or long times to induce self-nucleation. Various temperature cycles were investigated, typically proceeding within the 20-30° C. range with seeding advancing within that range as well (Protocols 1-3), followed by cooling to about −20° C. As shown in Protocol 4, Example 21, a temperature cycle was applied in the crystallization of the crude product by cooling from the seeding temperature 26° C. to 10° C., warming to 24° C., and final cooling to the isolation temperature, −20° C. Without wishing to be bound by theory, this temperature cycle was believed to help reduce the crusting, i.e., solids adhering to the walls of the crystal just above the liquid level, and there was evidence that this temperature cycle improved the purging of some impurities. CBD was finally cooled to a very cold temperature, −20° C., to maximize the yield. As shown in Example 16, long chain hydrocarbons, such as heptane, isooctane, and decane, were found to have the lowest solubility of CBD, but even in these solvents, high losses of CBD could be realized if the crystallization was not concentrated and cooled to low temperatures.

Seeding Temperature and Isolation Temperature

Figure 31:
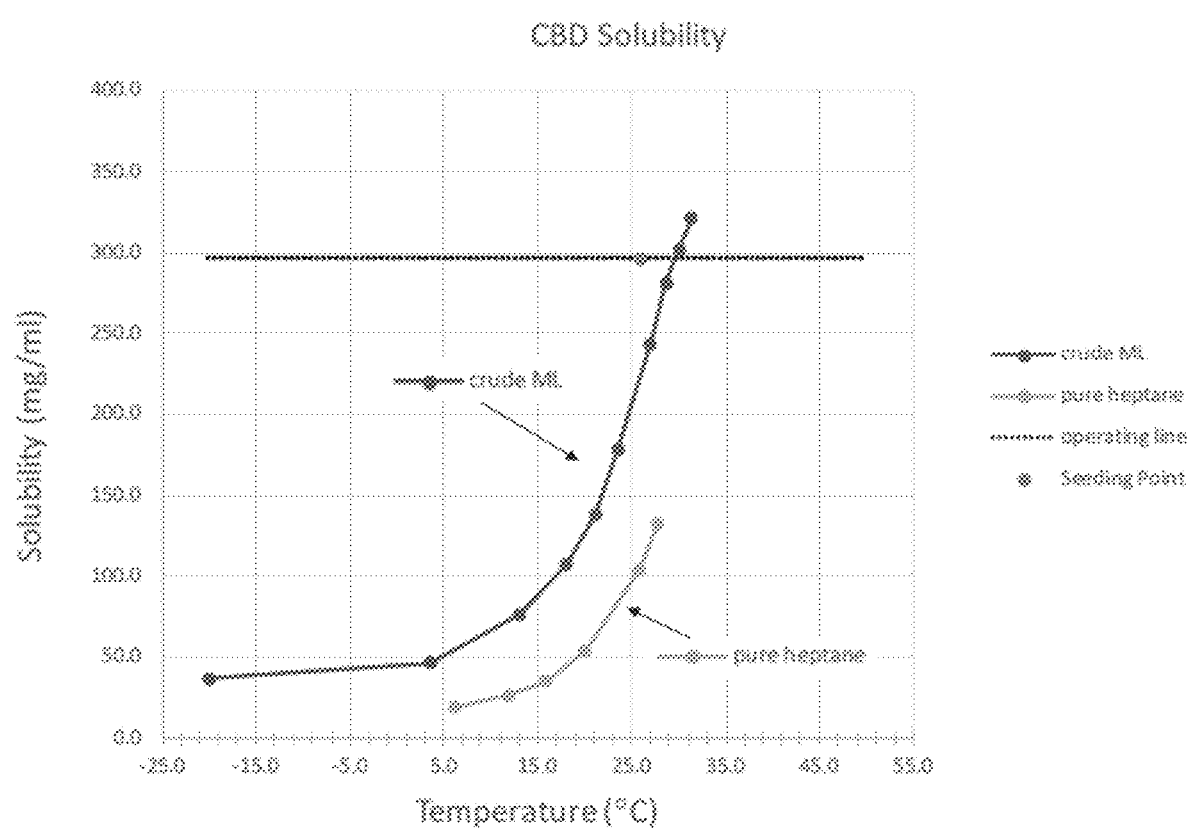
FIG. 31 shows a solubility curve of CBD in crude CBD mother liquor and heptane.

To determine an appropriate seeding temperature of CBD, a Crystal 16 instrument was employed to measure the solubility in crude CBD mother liquor, a mixture of heptane and process impurities, and pure heptane. FIG. 31 shows the solubility data measured as a function of temperature. As shown, the crude CBD mother liquor had a significantly higher solubility than pure heptane, which may have been due to impurities present in the mother liquor. The minimum volume for the crystallization was determined by balancing the volumetrics of the process, the expected yield at a certain concentration, and the practicality of the seeding temperature. A crystallization at a volume of 3.5 L/kg was determined to be appropriate, as this would result in a CBD concentration of ca. 296 mg/ml, as shown by the operating line in FIG. 31. At this concentration, the solubility temperature of CBD was 29-30° C. Therefore, a seeding temperature of 26° C. was considered suitable to afford a supersaturated solution of CBD and provide a reasonable operating window, with respect to the parameters of temperature and crystallization volume, where CBD would robustly crystallize when seeded (Protocol 4, Example 21).

To maximize the yield, it was found helpful to cool the crystallization slurry to a very cold temperature, ca. −20° C., as exemplified in Protocols 1-3 and Protocol 4 (Example 21). Replacing n-heptane with isooctane was briefly considered and studied; however, the yield increase was negligible when replacing n-heptane with isooctane in the crude crystallization, likely due to the presence of impurities in the crude mother that strongly impact the solubility of CBD.

Temperature Cycle

Figure 32:
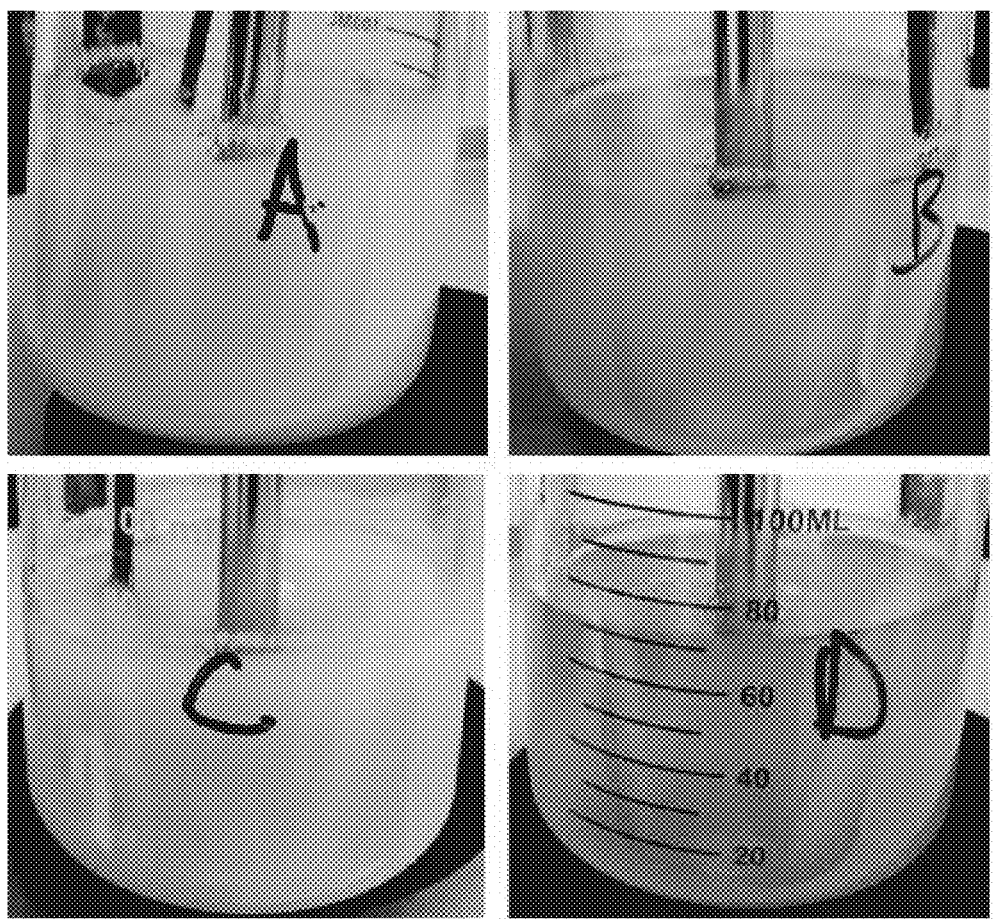
FIG. 32 shows images of the crusting that forms after seed age during a temperature cycle study in the crystallization of crude CBD.

A temperature cycle during the crystallization was used to reduce the observed crusting that occurred above the liquid level of the crystallization slurry. A series of experiments was conducted where the volume of the crystallization was altered, a temperature cycle or straight ramp cool was either applied, and the seeding temperature was modified. The results are summarized in Table 24. As shown, the seeding temperature appeared to have a significant impact on the amount of crust formed. FIG. 32 shows pictures of the crust that formed after seeding for each of the experiments. To reduce the relative supersaturation, the seeding temperature could be increased such that the seeding point was closer to the solubility curve.

Additionally, as shown in Table 24, a temperature cycle appeared to significantly improve the purging of an unknown impurity at 1.98 RRT (Example 21). RRT 1.98 was observed in crude CBD. Analysis of the impurity by mass suggested it could be a CBD analog coupled with two menthadienol molecules. This impurity purged at 77-79% when the crystallization did not apply a temperature cycle, versus 86-88% when a temperature cycle was applied. As such, a temperature cycle was considered advantageous to reduce this impurity to levels comfortably with the specification for unknown impurities (NMT 0.10%).

Figure 33:
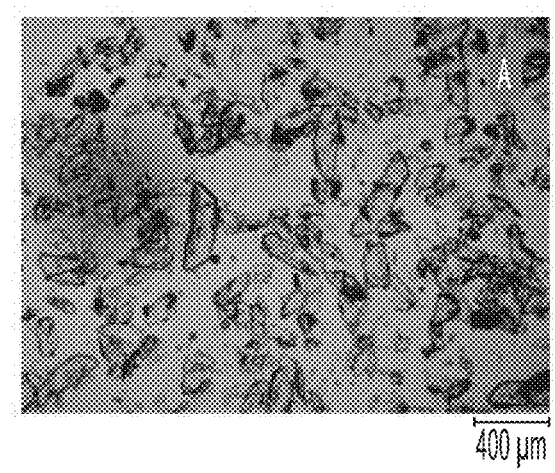
FIG. 33 shows microscope images (2.5×) of crude CBD after a temperature cycle study.
Figure 33:
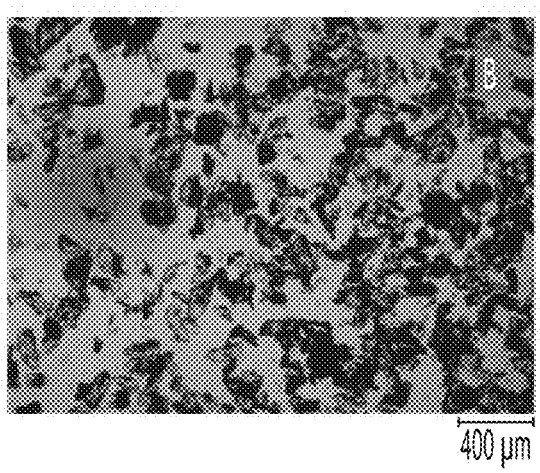
Figure 33:
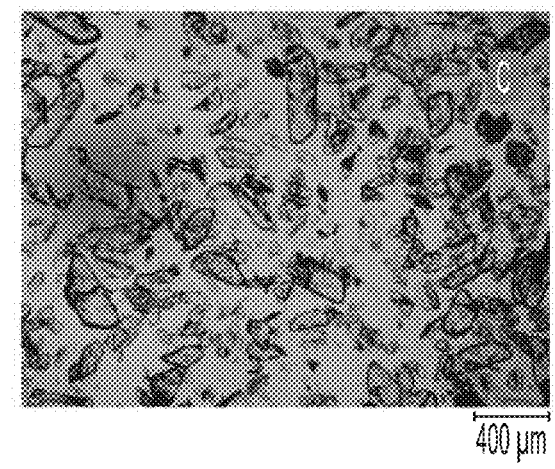
Figure 33:
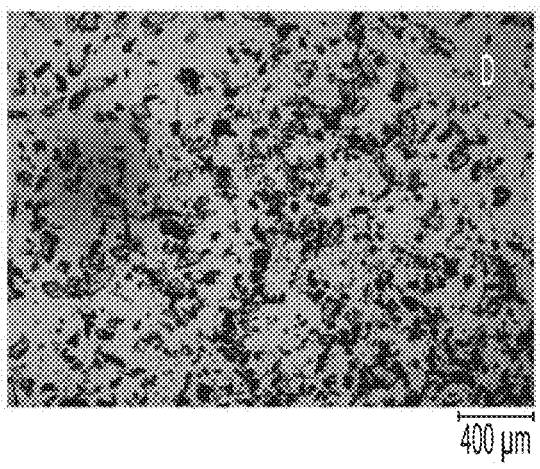

The temperature cycle also impacted the particle size and the settling rate of the slurry. Without wishing to be bound by theory, temperature cycling is known to increase the particle size distribution due to the dissolution of smaller particles when reheating the slurry. An increase in the particle size was also observed in these experiments when a temperature cycle was applied (FIG. 33) and this also appeared to impact the settling rate as the large particles settled much faster based on visual observation.

Example 18: Recrystallization Experiments

Recrystallization experiments were conducted to screen for potential CBD polymorphs and evaluate the ability of the recrystallized CBD to expel impurities. The following recrystallization methods were undertaken:
evaporative crystallization from solvent mixtures;
antisolvent crystallization;
cooling crystallization;
single solvent drop grinding;
crystallization by crash-cooling;
vapor-diffusion-into-solution crystallization; and
crystallization by liquid diffusion.

In each method, the starting material consisted of crystallized CBD of form A.

Evaporative Crystallization from Solvent Mixtures

Without wishing to be bound by theory, the general principle behind evaporative crystallization using solvent anti-solvent mixtures is that the solvent evaporates, first causing the API to precipitate to some extent, and this material then acts as a seed, when the anti-solvent is evaporated. The first evaporation step is slow and is followed by a faster final evaporation phase. The solvent mixtures and respective vapor pressures together with the XRPD analysis of the solids are presented in Table 25. All crystalline samples were Form A both before and after the solids were exposed to accelerated ageing conditions. An oil-like substance was obtained from an acetonitrile/water solvent mixture that could not be analyzed by XRPD; therefore, this sample was not exposed to accelerated aging conditions.

TABLE 25

| Solvent | Vapor pressure KPa, 25° C. | Anti-solvent | Vapor pressure KPa, 25° C. | Form by HT-XRPD Before AAC | Form by HT-XRPD After AAC |
|---|---|---|---|---|---|
| Ethanol | 8 | Heptane | 6 | A | A |
| Chloroform | 207 | Hexane | 20 | A | A |
| Acetonitrile | 12 | Water | 3 | Oily | N/A |
| Tetrahydrofuran | 23 | Trimethylpentane | 7 | A | A |
| Acetone | 30 | Decane | 0.2 | A | A |
| Hexane | 34 | tert-Butyl methyl ether | 20 | A | A |
| 2-Butanone | 12 | Heptane | 6 | A | A |
| 1,4-Dioxane | 5 | Decane | 0.2 | A | A |
| Methanol | 17 | Water | 3 | A | A |

TABLE 24

| Parameter | Experiment A | Experiment B | Experiment C | Experiment D |
|---|---|---|---|---|
| Volume | 4.0 L/kg | 4.0 L/kg | 3.5 L/kg | 3.5 L/kg |
| Temperature Cycle | Yes | No (seed at 24° C.) | Yes | No (seed at 26° C.) |
| Crusting (Visual Rank) | 4 (most crust) | 2 | 3 | 1 (least crust) |
| Crusting (Quant., mol %) | 6.0% | 0.3% | 0.5% | 0.2% |
| Mother Liquor Loss, % | 13.1% | 9.4% | 7.4% | 8.0% |
| cCBD Quality, cCBD AP | 99.85 | 99.79 | 99.83 | 99.82 |
| cCBD Quality, 1.98 RRT Purging | 0.05 88% | 0.09 79% | 0.06 86% | 0.10 77% |
| cCBD Quality, THC (ppm) | 53 | 28 | 51 | 27 |
| pCBD Quality, 1.98 RRT Purging | 0.03 40% | 0.07 20% | not tested | 0.07 30% |
| Other, Settling | Fast to settle | Slow to settle | Fast to settle | Slow to settle |
| Other, Particle Size | 1 (largest) | 3 | 2 | 4 (smallest) |

TABLE 25-continued

| Solvent | Vapor pressure KPa, 25° C. | Anti-solvent | Vapor pressure KPa, 25° C. | Form by HT-XRPD Before AAC | After AAC |
|---|---|---|---|---|---|
| 1.2-Dimethoxyethane | 6 | Water | 3 | A | A |

Results of the evaporative crystallization experiments from solvent mixtures. Cannabidiol was dissolved in a mixture of solvent and anti-solvent (50/50, v/v). The solvent was allowed to slowly evaporate, after which the anti-solvent evaporated more rapidly. The obtained solids were analyzed by XRPD before and after exposure to 40° C./75% RH (AAC) for two days. Experiments that yielded an oily material were not analyzed by XRPD and therefore, not exposed to AAC (defined as N/A).

Anti-Solvent Crystallization

For the anti-solvent crystallization experiments, clear solutions of CBD of approximately 60 mg/mL were prepared. Briefly, 1 volume of cannabidiol solution was added to 4 volumes of anti-solvent. If solids were precipitated, they were collected by centrifugation. The solid was analyzed by XRPD after being dried under ambient conditions and following drying under deep vacuum. The mother liquors were allowed to evaporate until completely dry and the remaining solids analyzed as well. All solids were analyzed by XRPD before and after exposure to accelerated aging conditions (40° C./75% RH) for two days. The results of the XRPD analysis of the precipitated solids are outlined in Table 26. The XRPD results of the evaporation of the mother liquors are presented in Table 27.

Solids precipitated immediately from the combination of methanol with water. To facilitate precipitation, the samples were placed at 5° C. for 24 hours. Under these conditions, the sample from dichloromethane with 2,2,4-trimethylepentane showed precipitation. The XRPD analysis was indicative of Form A. Evaporation of all other samples resulted in either Form A or in oil-like substances that could not be analyzed by XRPD. When no XRPD record was generated, the field is defined as "Not Applicable" (N/A).

TABLE 27

| Solvent | Anti-solvent | AS:S ratio 4:1 Precipitation? | Form (evap. ML) | Form (evap. ML) after AAC |
|---|---|---|---|---|
| 1,4-Dioxane | Water | No | A | A |
| 1,2-Dimethoxyethane | Decane | No | Oily | N/A |
| Tetrahydrofuran | Water | No | A | A |
| Methanol | Water | Yes | A | A |
| Ethanol | Decane | No | Oily | N/A |
| Acetonitrile | Decane | No | Oily | N/A |
| 2-Butanone | Water | No | A | A |
| Toluene | Decane | No | Oily | N/A |
| Ethyl acetate | 2,2,4-Trimethylepentane | No | A low yield | A low yield |
| Tetrahydrofuran | Decane | No | A | A |
| Acetone | 2,2,4-Trimethylepentane | No | Oily | N/A |
| Dichloromethane | 2,2,4-Trimethylepentane | No | N/A | N/A |
| Isopropyl acetate | 2,2,4-Trimethylepentane | No | Oily | N/A |
| 1,4-Dioxane | 2,2,4-Trimethylepentane | No | A | A |
| 1,2-Dimethoxyethane | Water | No | A | A |

Cooling Crystallization

Cooling crystallizations were performed by preparing clear solutions of CBD with a maximum concentration of approximately 60 mg/mL. The solutions were slowly cooled to 0° C. and kept at this temperature for 48 hours. Precipitated solids were collected, dried under ambient conditions, and analyzed by XRPD. If no solids had precipitated, the mother liquors were allowed to slowly evaporate and the remaining solids were analyzed by XRPD. All solids were exposed to accelerated aging conditions for 48 hours and analyzed again by XRPD. The results are presented in Table 28. Cannabidiol precipitated upon cooling from pentane and heptane. XRPD analysis revealed that these solids were identical to starting material Form A. Precipitation of the mother liquors resulted in either crystalline samples with Form A or in oil-like samples. Exposure to the accelerated aging conditions had no effect on the crystallinity, nor did

TABLE 26

| Solvent | Anti-solvent | AS:S ratio 4:1 Precipitation | Solid form by HT-XRPD | | | |
|---|---|---|---|---|---|---|
| | | | Ambient | Ambient (after AAC) | Vacuum | Vacuum (after AAC) |
| 1,4-Dioxane | Water | No | N/A | N/A | N/A | N/A |
| 1,2-Dimethovethane | Decane | No | N/A | N/A | N/A | N/A |
| Tetrahydrofuran | Water | No | N/A | N/A | N/A | N/A |
| Methanol | Water | Yes | A | A | A | A |
| Ethanol | Decane | No | N/A | N/A | N/A | N/A |
| Acetonitrile | Decane | No | N/A | N/A | N/A | N/A |
| 2-Butanone | Water | No | N/A | N/A | N/A | N/A |
| Toluene | Decane | No | N/A | N/A | N/A | N/A |
| Ethyl acetate | 2,2,4-Trimethylepentane | No | N/A | N/A | N/A | N/A |
| Tetrahydrofuran | Decane | No | N/A | N/A | N/A | N/A |
| Acetone | 2,2,4-Trimethylepentane | No | N/A | N/A | N/A | N/A |
| Dichloromethane | 2,2,4-Trimethylepentane | No[1] | A | A low yield | A | A |
| Isopropyl acetate | 2,2,4-Trimethylepentane | No | N/A | N/A | N/A | N/A |
| 1,4-Dioxane | 2,2,4-Trimethylepentane | No | N/A | N/A | N/A | N/A |
| 1,2-Dimethoxyethane | Water | No | N/A | N/A | N/A | N/A |

Results of the reverse anti-solvent crystallization experiments. 1 volume of a clear solution was added to 4 volumes of anti-solvent. The precipitated solids were collected for analysis. Solids were dried under ambient conditions and under deep vacuum before analysis by XRPD. When no XRPD record was produced, the field is defined as "Not Applicable" (N/A).
[1]Solids were obtained after storing the sample at 5° C..

any of the oils crystallize. When no XRPD record was generated, the field is defined as "Not Applicable" (N/A).

TABLE 28

| Solvent | Dissolved at initial T? | Solids after T profile | Form by HT-XRPD Dry solids | Form by HT-XRPD Dry after AAC |
|---|---|---|---|---|
| Acetonitrile | Yes | No | Oily | N/A |
| Acetone | Yes | No | Oily | N/A |
| 1,4-Dioxane | Yes | No | A | A |
| Tetrahydrofuran | Yes | No | Oily | N/A |
| Ethanol | Yes | No | A | A |
| Chloroform | Yes | No | Oily | N/A |
| Ethyl acetate | Yes | No | Oily | N/A |
| Heptane | Yes | No | Oily | N/A |
| Pentane | No | Yes | A | A |
| Hexane | No | Yes | A | A |
| Cyclohexane | Yes | No | A | A |
| 2,2,4-Trimethylpentane | No | No | A | A |
| Water | No | No | Low yield | |
| Diethylene glycol | Yes | No | Oily | N/A |
| 1,2-Dimethoxyethane | Yes | No | A | A |

Crash Cooling Crystallization

As a variation on the above cooling crystallization experiments, several crash cooling crystallization were performed. In order to modulate the solubility of cannabidiol, crash cooling experiments were performed in solvent mixtures. Clear solutions of 50 mg/mL of cannabidiol were prepared in solvent mixtures and rapidly cooled in an ice bath. Vials were then placed at −20° C. for 48 hours. Precipitated solids and mother liquors were treated as described above for the ordinary cooling crystallization experiments. The results are depicted in Table 29. Only from heptane/pentane cooling did there result in the precipitation of a solid. The solid appeared of the same polymorphic form as the starting material Form A. Evaporation of the other mother liquors also resulted in Form A or in oil-like substances. Exposure to accelerated aging conditions (40° C./75% RH) for two days had no effect on the physical appearance of the samples. When no XRPD record was generated, the field is defined as "Not Applicable" (N/A) in Table 29.

Crystallization by Single Solvent Drop Grinding

For the grinding experiments, 40 mg cannabidiol was placed in a stainless steel container with 10 μL solvent and two steel beads. The vials were shaken for 1 hour at 30 Hz, after which the solids were collected for XRPD analysis. The results of these experiments are outlined in Table 30. All of the samples were classified as Form A based on HT-XRPD analysis. Exposure to accelerated aging conditions for two days did not lead to any physical changes.

TABLE 30

| Solvent | Volume (μL) | Form by HT-XRPD Dry | Form by HT-XRPD After AAC |
|---|---|---|---|
| Water | 10 | A | A |
| Decane | 10 | A | A |
| Hexane | 10 | A | A |
| Pentane | 10 | A | A |
| 2,2,4-Trimethylpentane | 10 | A | A |
| Heptane | 10 | A | A |
| Acetone | 10 | A | A |
| Ethanol | 10 | A | A |
| Ethyl acetate | 10 | A | A |
| Tetrahydrofuran | 10 | A | A |

Result of the single solvent drop grinding experiments. 40 mg cannabidiol was grounded in the presence of 10 μL of solvent for 1 hour at 30 Hz.

Vapor-Diffusion-into-Solution Crystallization

Clear solutions of cannabidiol (about 100 mg/mL) were prepared in the solvents indicated in Table 31. The open vials were placed in a larger container with anti-solvent and the vapors were allowed to diffuse into the cannabidiol solution for two weeks. The effect of the anti-solvent, however, was too low to induce any precipitation of cannabidiol and, therefore, it was decided to evaporate the mother liquors and analyze the remaining solids. The results are presented in Table 31. Crystalline solid was only found after evaporation of the Toluene/2,2,4-Trimethylepentane solution. XRPD analysis of this solid confirmed that it was Form A. All other samples resulted in an oily substance. Exposure to accelerated aging conditions had no effect on the physical appearance of the samples.

TABLE 29

| Solvent mixtures (v/v) | Dissolved at start | Solids after T profile | Solid form by HT-XRPD Precipitated solid Before | Solid form by HT-XRPD Precipitated solid After AAC | Solid form by HT-XRPD Evaporation of ML Before | Solid form by HT-XRPD Evaporation of ML After AAC |
|---|---|---|---|---|---|---|
| Acetonitrile/Water (80/20) | Yes | No | N/A | N/A | A | A |
| Acetone/Water (80/20) | Yes | No | N/A | N/A | Oily | N/A |
| 1,4-Dioxane/Water (80/20) | Yes | No | N/A | N/A | A | A |
| Tetrahydrofuran/Water (80/20) | Yes | No | N/A | N/A | Oily | N/A |
| Acetone/2,2,4-Trimethylpentane | Yes | No | N/A | N/A | A | A |
| Ethyl formate/Decane | Yes | No | N/A | N/A | Oily | N/A |
| Chloroform/Hexane (50/50) | Yes | No | N/A | N/A | A | A |
| Heptane/Pentane (50/50) | Yes | Yes | A | A | N/A | N/A |
| Isopropanol/Decane (50/50) | Yes | No | N/A | N/A | A | A |
| Ethanol/2,2,4-Trimethylpentane | Yes | No | N/A | N/A | A | A |

Results of the crash cooling crystallization experiments. Solutions of 50 mg/mL were prepared and rapidly cooled in an ice bath. Subsequently vials were stored at −20° C. for 48 hours. Precipitated solids were collected, dried, and analyzed by XRPD before and after exposure to AAC for 2 days. The mother liquors of the samples not precipitated were allowed to evaporate and the solids analyzed before and after AAC by XRPD. When no XRPD record was generated, the field is defined as "Not Applicable" (N/A).

TABLE 31

| Solvent | Anti-solvent | Precipitation? | Solid form after evaporation Before AAC | Solid form after evaporation After AAC |
|---|---|---|---|---|
| 1,4-Dioxane | 2,2,4-Trimethylpentane | No | Oil | Oil |
| 1,4-Dioxane | Water | No | Oil | Oil |
| Acetonitrile | Water | No | Oil | Oil |
| Isopropanol | Water | No | Oil | Oil |
| Isobutanol | Water | No | Oil | Oil |
| Toluene | 2,2,4-Trimethylpentane | No | A | A |
| Ethyl acetate | 2,2,4-Trimethylpentane | No | Oil | Oil |
| 4-methyl-2-pentanone | 2,2,4-Trimethylpentane | No | Oil | Oil |
| Tetrahydrofuran | Water | No | Oil | Oil |
| 2-Methoxyethanol | 2,2,4-Trimethylpentane | No | Oil | Oil |

Result of the vapor diffusion into solution experiments. A vial with a clear solution of Cannabidiol was placed in a larger container filled with anti-solvent. After two weeks, no precipitaton had occurred and the mother liquors were evaporated. The remaining solids were analyzed by XRPD before and after exposure to AAC.

Liquid Diffusion Crystallization

The results of the diffusion experiments are given in Table 32. A solution of cannabidiol of about 75 mg/mL was prepared and a layer of anti-solvent was carefully added to the vial. These experiments were performed with water as anti-solvent because of the larger difference in density between solvent and anti-solvent. With the exception of the experiments from 1,4-dioxane, diethylene glycol, DMSO and diethanolamine, the outcome resulted in crystalline precipitation. XRPD analysis of these solids was indicative of Form A. Exposure of the solids to accelerated aging conditions for 2 days had no effect on the solid form.

TABLE 32

| Solvent | Anti-solvent | Solids after? | Solid form by HT-XRPD Before AAC | Solid form by HT-XRPD After AAC | Solid form by HT-XRPD Vacuum |
|---|---|---|---|---|---|
| 1,4-Dioxane | Water | No | oily | oily | Oily |
| Diethylene glycol | Water | Yes | A | A | Oily |
| Dimethyl sulfoxide | Water | Yes | A | A | Oily |
| Diethanolamine | Water | Yes | A | A | Oily |

Results of the liquid diffusion experiments. A vial with a clear solution of Cannabidiol was prepared and a layer of the anti-solvent was carefully added. The material precipitated in the inter phase between the solvent and the anti-solvent was separated from the liquid and analyzed by XRPD before and after exposure to AAC.

Example 19: Recrystallization of Pure Cannabidiol in Isooctane

Figure 34:
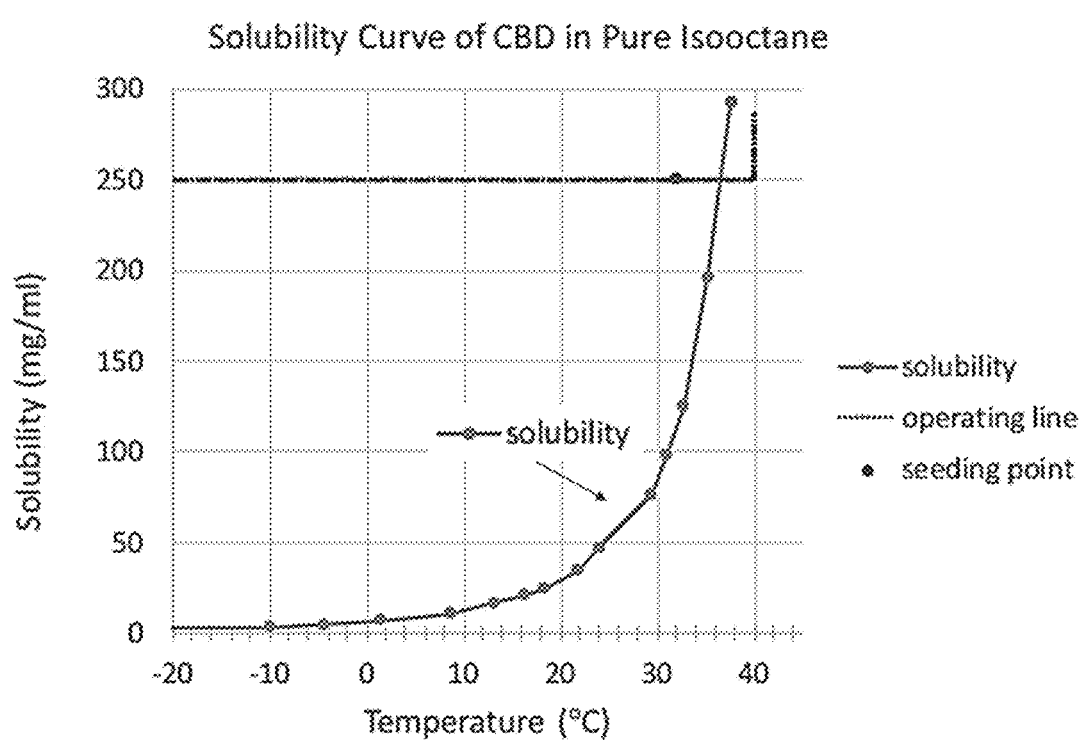
FIG. 34 shows the solubility of CBD in pure isooctane and the typical operating line for the final crystallization.

Isooctane was selected as the final crystallization solvent due the low solubility and similar properties to heptane, i.e., low viscosity and boiling point relative to other higher hydrocarbons (Table 33). The crystallization with isooctane was designed by mapping the solubility curve, as shown in FIG. 34. Based on the solubility and desire to maximize yield, an isooctane volume of 4.0 L/kg was selected as an appropriate crystallization concentration. Prior to crystallization, it was desired to fully dissolve the CBD in isooctane and filter the process stream. This dissolution and filtration was performed by charging 3.5 L/kg isooctane (286 mg/ml CBD concentration), heating to 40° C., and filtering the process stream to ensure that the filtration stream did not fall below 38° C., where crystallization could occur. Based on the solubility curve in FIG. 34, an appropriate temperature for robustly seeding the crystallization was 32° C. before cooling to −20° C. for isolation. The isolation temperature of −20° C. was chosen to maximize the yield of the CBD from the final crystallization.

TABLE 33

Cannabidiol Solubility in Neat Solvents and Mixtures

| Solvent | Solubility at RT mg/ml | Solvent | Solubility at RT mg/ml |
|---|---|---|---|
| Water | <0.13 | IPOAc | >100 |
| Silcone oil | 9.7 | Cyclohexane | >100 |
| n-decane | 36.8 | MeOH | >100 |
| Isooctane | 43.9 | EtOH | >100 |
| Heptane | 64.6 | p-xylene | >100 |
| IPA | >100 | 1,4-dioxane | >100 |
| 1-propanol | >100 | 2-butanone | >100 |
| Anisole | >100 | MTBE | >100 |
| THF | >100 | n-hexane | >100 |
| Toluene | >100 | NMPO | >100 |
| Cumene | >100 | Methylcyclohexane | >100 |
| Ethyl Formate | >100 | MeTHF | >100 |
| Diethyl Ether | >100 | MeTHF saturated with water | >100 |
| 1,2-Dimethoxyethane | >100 | 60/40 Water/Methanol | 0 |
| Acetone | >100 | 50/50 Water/Methanol | 0.3 |
| EtOAc | >100 | 45/65 Water Methanol | 3.4 |
| Isobutanol | >100 | 40/60 Water Methanol | oil partitioning |
| CIP 100 | <1 | 10/90 Water/Ethanol | >100 |
| CIP 200 | <1 | 30/70 Water/Ethanol | 20 to 70 |
| Chloroform | >100 | 50/50 Water/Ethanol | <5 |
| DCM | >100 | 30/70 Water/IPA | >20 |
| ACN | >100 | 50/50 Water/IPA | 10 to 20 |

Example 20: Stability Studies of CBD Prepared Via Protocol 3

Cannabidiol prepared via Protocol 3 underwent stability investigations. One batch each of Cannabidiol (crude), Cannabidiol API (pure) and Cannabidiol (2× recrystallized) were packaged into bulk containers of double low-density polyethylene (LDPE) bags in a high-density polyethylene brown bottle. The stability of the material was then evaluated at several different storage conditions (5° C., 25° C./60% RH and 40° C./75% RH). For 3 months of stability, the acceptance criteria were met for the 25° C./60% RH and 40° C./75% RH conditions. For 5 months stability, only the 40° C./75% RH condition was tested. All the acceptance criteria were met. The cannabidiol was evaluated against the specifications in Table 34. The results for each of the three samples are provided in Table 35 through Table 40.

TABLE 34

| Proposed Regulatory Parameters | Regulatory Acceptance Criteria |
|---|---|
| 1. Appearance (visual) | White to off-white to beige solid |
| 2. Assay by HPLC (on dried basis) | 97.0% w/w-102.0% w/w |
| 3. Related substances by HPLC | |
| a. Olivetol | NMT 0.15% w/w |
| b. 4-Monobromo-cannabidiol | NMT 0.15% w/w |
| c. Δ9-Tetrahydrocannabinol | NMT 0.10% w/w |
| d. Δ8-Tetrahydrocannabinol | FIO |
| e. Each unknown impurity | NMT 0.10% w/w |
| f. Total impurities | NMT 1.0% w/w |
| 4. Related substances by HPLC | |
| a. Δ9-Tetrahydrocannabinol | FIO (ppm) |
| b. Δ8-Tetrahydrocannabinol | FIO (ppm) |
| 5. Water Content | NMT 0.5% |

TABLE 35

Crude CBD under 25° C./60% RH

| Test | Limit | 0 month (Nov. 18) | 1 month (Dec. 18) | 2 months (Jan. 19) | 3 months (Feb. 18) |
|---|---|---|---|---|---|
| Appearance | FIO at crude (White to slightly brown crystalline powder) | White | Off-White Powder | Off-White Powder | Off-white |
| Assay by HPLC | FIO at crude (97.0%-102.0%) | 99.9% | 98.2% | 99.5% | 98.1% |
| Related substances by HPLC | | | | | |
| Olivetol | FIO at crude (≤0.15%) | <0.03% (ND) | <0.03% (ND) | <0.03% (0.02%) | <0.03% (ND) |
| Δ9-Tetrahydrocannabinol | FIO at crude (≤0.10%) | <0.02% (ND) | <0.02% (ND) | <0.02% (ND) | <0.02% (ND) |
| Δ8-Tetrahydrocannabinol | FIO at crude (≤0.10%) | — | <0.02% (ND) | <0.02% (ND) | <0.02% (ND) |
| 4-Monobromo-CBD | FIO at crude (≤0.15%) | <0.03% (0.02%) | <0.03% (0.02) | <0.03% (0.02%) | <0.03% (0.02%) |
| Each unspecified impurity | FIO at crude (≤0.10%) | RRT~1.540: 0.06% RRT~1.690: 0.11% | RRT~1.927: 0.07% RRT~2.146: 0.12% | RRT~1.931: 0.06% RRT~2.151: 0.09% | RRT~1.983: 0.05% RRT~2.260: 0.10% |
| Sum of impurities, ≥0.05% | FIO at crude (≤1.0%) | 0.17% | 0.19% | 0.15% | 0.15% |
| Related substances by HPLC (low level) | | | | | |
| Δ9-Tetrahydrocannabinol | FIO | 26 ppm | 29 ppm | 27 ppm | 13 ppm |
| Δ8-Tetrahydrocannabinol | FIO | — | 6 ppm | 5 ppm | 8 ppm |
| Water content in % w/w | FIO at crude (≤0.5%) | — | — | — | — |

ND*: not detected

TABLE 36

Crude CBD under 40 ° C./75% RH

| Test | Limit | 0 month (Nov. 18) | 1 month (Dec. 18) | 2 months (Jan. 19) | 3 months (Feb. 18) | 5 months (Apr. 2019) |
|---|---|---|---|---|---|---|
| Appearance | FIO at crude (White to slightly brown crystalline powder) | White | Yellow Powder | Off-White | Off-white | Beige/off-white |
| Assay by HPLC | FIO at crude (97.0% - 102.0%) | 99.9% | 98.7% | 99.6% | 99.0% | 98.6% |
| Related substances by HPLC | | | | | | |
| Olivetol | FIO at crude (≤0.15%) | <0.03% (ND) | <0.03% (ND) | <0.03% (ND) | <0.03% (ND) | <0.03% (ND) |
| Δ9-Tetrahydrocannabinol | FIO at crude (≤0.10%) | <0.02% (ND) | <0.02% (ND) | <0.02% (ND) | <0.02% (ND) | <0.02% (ND) |
| Δ8-Tetrahydrocannabinol | FIO at crude (≤0.10%) | — | <0.02% (ND) | <0.02% (ND) | <0.02% (ND) | <0.02% (ND) |
| 4-Monobromo-CBD | FIO at crude (≤0.15%) | <0.03% (0.02%) | <0.03% (0.02) | <0.03% (0.02) | <0.03% (0.02) | <0.03% (ND) |
| Each unspecified impurity | FIO at crude (≤0.10%) | RRT~1.540: 0.06% RRT~1.690: 0.11% | RRT~1.928: 0.06% RRT~2.150: 0.11% | RRT~1.931: 0.06% RRT~2.151: 0.07% | RRT~1.982: 0.05% RRT~2.258: 0.09% | Methadienol deg-1: 0.03% RRT~0.956: 0.04% RRT~1.918: 0.05% |

TABLE 36-continued

| | | Crude CBD under 40 ° C./75% RH | | | | |
|---|---|---|---|---|---|---|
| Test | Limit | 0 month (Nov. 18) | 1 month (Dec. 18) | 2 months (Jan. 19) | 3 months (Feb. 18) | 5 months (Apr. 2019) |
| Sum of impurities, ≥0.05% Related substances by HPLC (low level) | FIO at crude (≤1.0%) | 0.17% | 0.17% | 0.13% | 0.14% | 0.05% |
| Δ9-Tetrahydrocannabinol | FIO | 26 ppm | 28 ppm | 27 ppm | 17 ppm | 24 ppm |
| Δ8-Tetrahydrocannabinol | FIO | — | 7 ppm | 4 ppm | 8 ppm | 36 ppm |
| Water content in % w/w | FIO at crude (≤0.5%) | — | — | — | — | — |

ND*: not detected

TABLE 37

| | | Pure CBD Under 25° C./60% RH | | | |
|---|---|---|---|---|---|
| Test | Limit | 0 months (Nov. 18) | 1 month (Dec. 18) | 2 months (Jan. 19) | 3 months (Feb. 18) |
| Appearance | White to slightly brown crystalline powder | — | Off-White Powder | Off-White Powder | Off-white |
| Assay by HPLC | 97.0%-102.0% | — | 99.7% | 100.3% | 98.5% |
| Related substances by HPLC | | | | | |
| Olivetol | ≤0.15% | — | <0.03% (ND) | <0.03% (ND) | <0.03% (ND) |
| Δ9-Tetrahydrocannabinol | ≤0.10% | — | <0.02% (ND) | <0.02% (ND) | <0.02% (ND) |
| Δ8-Tetrahydrocannabinol | FIO (≤0.10%) | — | <0.02% (ND) | <0.02% (ND) | <0.02% (ND) |
| 4-Monobromo-CBD | ≤0.15% | — | <0.03% (ND) | <0.03% (ND) | <0.03% (ND) |
| Each unspecified impurity | ≤0.10% | — | RRT~1.927: 0.06% | RRT~1.935: 0.08% | RRT~1.982: 0.03% |
| Sum of impurities, ≤0.05% Related substances by HPLC (low level) | ≤1.0% | — | 0.06% | 0.08% | <0.05% |
| Δ9-Tetrahydrocannabinol | FIO | 26 ppm | 21 ppm | 14 ppm | <4 ppm (2 ppm) |
| Δ8-Tetrahydrocannabinol | FIO | — | 25 ppm | 21 ppm | 36 ppm |
| Water content in % w/w | ≤0.5% | <0.05% (0.02%) | — | — | — |

ND*: not detected

TABLE 38

| | | Pure CBD Under 40 ° C./75% RH | | | | |
|---|---|---|---|---|---|---|
| Test | Limit | 0 months (Nov. 18) | 1 month (Dec. 18) | 2 months (Jan. 19) | 3 months (Feb. 19) | 5 months (Apr. 2019) |
| Appearance | White to slightly brown crystalline powder | — | Off-White Powder | Off-White Powder | Off-white | Off-white |
| Assay by HPLC | 97.0%-102.0% | — | 99.5% | 100.2% | 98.8% | 99.9% |
| Related substances by HPLC | | | | | | |
| Olivetol | ≤0.15% | — | <0.03% (ND) | <0.03% (ND) | <0.03% (ND) | <0.03% (ND) |
| Δ9-Tetrahydrocannabinol | ≤0.10% | — | <0.02% (ND) | <0.02% (ND) | <0.02% (ND) | <0.02% (ND) |

TABLE 38-continued

Pure CBD Under 40° C./75% RH

| Test | Limit | 0 months (Nov. 18) | 1 month (Dec. 18) | 2 months (Jan. 19) | 3 months (Feb. 19) | 5 months (Apr. 2019) |
|---|---|---|---|---|---|---|
| Δ8-Tetrahydrocannabinol | FIO (≤0.10%) | — | <0.02% (ND) | <0.02% (ND) | <0.02% (ND) | <0.02% (ND) |
| 4-Monobromo-CBD | ≤0.15% | — | <0.03% (ND) | <0.03% (ND) | <0.03% (ND) | <0.03% (ND) |
| Each unspecified impurity | ≤0.10% | — | RRT~1.929: 0.05% | RRT~1.932: 0.07% | RRT~1.983: 0.03% | RRT~1.918: 0.04% |
| Sum of impurities, ≥0.05% | ≤1.0% | — | 0.05% | 0.07% | <0.05% | <0.05% |
| Related substances by HPLC (low level) | | | | | | |
| Δ9-Tetrahydrocannabinol | FIO | 26 ppm | 14 ppm | 9 ppm | <4 ppm (ND) | 6 ppm |
| Δ8-Tetrahydrocannabinol | FIO | — | 22 ppm | 20 ppm | 30 ppm | 36 ppm |
| Water content in % w/w | ≤0.5% | <0.05% (0.02%) | — | — | — | — |

ND*: not detected

TABLE 39

Pure CBD (Recrystallized Twice) Under 25° C./60% RH

| Test | Limit | 0 months (Nov. 18) | 1 month (Dec. 18) | 2 months (Jan. 19) | 3 months (Feb. 18) |
|---|---|---|---|---|---|
| Appearance | White to slightly brown crystalline powder | — | Off-White Powder | Off-White Powder | White |
| Assay by HPLC | 97.0%-102.0% | — | 100.2% | 99.9% | 98.4% |
| Related substances by HPLC | | | | | |
| Olivetol | ≤0.15% | — | <0.03% (ND) | <0.03% (ND) | <0.03% (ND) |
| Δ9-Tetrahydrocannabinol | ≤0.10% | — | <0.02% (ND) | <0.02% (ND) | <0.02% (ND) |
| Δ8-Tetrahydrocannabinol | FIO (≤0.10%) | — | <0.02% (ND) | <0.02% (ND) | <0.02% (ND) |
| 4-Monobromo-CBD | ≤0.15% | — | <0.03% (ND) | <0.03% (ND) | <0.03% (ND) |
| Each unspecified impurity | ≤0.10% | — | <0.03% (ND) | <0.03% (ND) | RRT~1.980: 0.03% |
| Sum of impurities, ≥0.05% | ≤1.0% | — | <0.05% (ND) | <0.05% (ND) | <0.05% |
| Related substances by HPLC (low level) | | | | | |
| Δ9-Tetrahydrocannabinol | FIO | 11 ppm | 6 ppm | 4 ppm | <4 ppm |
| Δ8-Tetrahydrocannabinol | FIO | — | 9 ppm | 7 ppm | 13 ppm |
| Water content in % w/w | ≤0.5% | <0.05% (0.01%) | — | — | — |

ND*: not detected

TABLE 40

Pure CBD (Recrystallized Twice) Under 40° C./75%RH

| Test | Limit | 0 months (Nov. 18) | 1 month (Dec. 18) | 2 months (Jan. 19) | 3 months (Feb. 18) | 5 months (Apr. 2019) |
|---|---|---|---|---|---|---|
| Appearance | White to slightly brown crystalline powder | — | Off-White Powder | Off-White Powder | Off-white | Off-white |
| Assay by HPLC | 97.0%-102.0% | — | 99.5% | 101.7% | 99.4% | 98.9% |
| Related substances by HPLC | | | | | | |
| Olivetol | ≤0.15% | — | <0.03% (ND) | <0.03% (ND) | <0.03% (ND) | <0.03% (ND) |
| Δ9-Tetrahydrocannabinol | ≤0.10% | — | <0.02% (ND) | <0.02% (ND) | <0.02% (ND) | <0.02% (ND) |
| Δ8-Tetrahydrocannabinol | FIO (≤0.10%) | — | <0.02% (ND) | <0.02% (ND) | <0.02% (ND) | <0.02% (ND) |

TABLE 40-continued

Pure CBD (Recrystallized Twice) Under 40° C./75%RH

| Test | Limit | 0 months (Nov. 18) | 1 month (Dec. 18) | 2 months (Jan. 19) | 3 months (Feb. 18) | 5 months (Apr. 2019) |
|---|---|---|---|---|---|---|
| 4-Monobromo-CBD | ≤0.15% | — | <0.03% (ND) | <0.03% (ND) | <0.03% (ND) | <0.03% (ND) |
| Each unspecified impurity | ≤0.10% | — | <0.03% (ND) | <0.03% (ND) | RRT~1.981: 0.03% | RRT~0.956: 0.04% |
| Sum of impurities, ≤0.05% | ≤1.0% | — | <0.05% (ND) | <0.05% (ND) | <0.05% | <0.05% |
| Related substances by HPLC (low level) | | | | | | |
| 49-Tetrahydrocannabinol | FIO | 11 ppm | 4 ppm | <4 ppm (3 ppm) | <4 ppm | <4 ppm |
| Δ8-Tetrahydrocannabinol | FIO | — | 6 ppm | 6 ppm | 14 ppm | 21 ppm |
| Water content in % w/w | ≤0.5% | <0.05% (0.01%) | — | — | — | |

ND*: not detected

As shown by the above stability data, the appearance analyses, HPLC assay analyses, and impurity results were all within specification. Additionally, no growth in Δ9-THC was observed at the ppm levels. Furthermore, based on previous stability studies, the water content was not considered to be a stability indicating test, as CBD is not hygroscopic. Thus, water content was not consistently tested through the stability program.

Example 21: Protocol 4

Bromine (102.4 kg, 1.07 molar equivalents) was added to a suspension of Olivetol (55 kg, basis) in dichloromethane (3366 kg) at −15° C. and the reaction mixture was stirred. Reaction completion was confirmed by HPLC (IPC). The reaction was quenched by the transfer into an aqueous (947 L) solution of potassium phosphate dibasic (79.8 kg), sodium hydroxide (61.1 kg) and sodium sulfite (3.85 kg). The solution was warmed, and the organic phase was separated. Dichloromethane was partially distilled off at atmospheric pressure. n-Heptane (1650 L) was added and the solution was further concentrated under reduced pressure to remove residual dichloromethane. The intermediate was crystallized by the addition of water (110 L) and cooling. The solids were filtered, washed with n-heptane, and dried to give 4,6-dibromo-olivetol.

4,6-Dibromo-olivetol (500 g, basis), menthadienol (146 g, 0.65 molar equivalents), and magnesium sulfate (499 g, 2.8 molar equivalents) were suspended in dichloromethane (2.5 L) and cooled to −25° C. The p-toluenesulfonic acid catalyst (56 g, 0.2 molar equivalents) was added to initiate the reaction. Further portions of menthadienol were added at 0.5 h (146 g, 0.65 molar equivalents) and 1.0 h (90 g, 0.40 molar equivalents) after the reaction start. Reaction completion was confirmed by HPLC (IPC). Following complete reaction conversion, the reaction was warmed and quenched with water (4 L). The layers were separated. The organic phase was washed with an aqueous phosphate buffer of pH 7 (2.5 L). The organic phase solvent was switched to isopropanol under reduced pressure while maintaining a constant volume (solvent swap). The dibromo-CBD solution in isopropanol was combined with an aqueous (3.5 L) solution of sodium sulfite (559 g, 3.0 molar equivalents) and sodium-L-ascorbate (25 g). Triethylamine (599 g, 4.0 molar equivalents) was added and the reaction was stirred at reflux (~80° C.) for approximately 36 h (30 to 42 h). Reaction completion was confirmed by HPLC (IPC). The reaction solvent (isopropanol/trimethylamine/water) was partially distilled off at atmospheric pressure to 8.0 volumes and n-heptane (3 L) was added. The suspension was acidified with concentrated HCl to pH 4.0. After layer separation, the organic layer was washed with a sodium ascorbate/phosphate buffer of pH 7 (2.5 L) and with an aqueous sodium ascorbate solution (2.5 L). The organic layer was concentrated by distillation (reduced pressure) and treated with active carbon. The solution was concentrated by distillation (reduced pressure) to 3.5 volumes. The organic solution was cooled to 26° C., seeded with cannabidiol (5.0 g) and stirred at 26° C. for 1 h. The suspension was cooled to 10° C. and warmed again to 24° C. The suspension was stirred at 24° C. for 1 h and then further cooled to −20° C. over 3 h. The white suspension was filtered and the wet cake was washed with cold isooctane (1.5 L). The wet product was dried to give crude cannabidiol.

Cannabidiol (100 g) was dissolved in isooctane (400 mL) and heated to 40° C. The solution was cooled to 32° C., seeded with cannabidiol (1 g) and stirred at 32° C. for 1 h. The suspension was cooled to −20° C. over 3 h and the white suspension was filtered and the wet cake was washed with cold isooctane (400 mL). The wet product was dried at 40° C. (<10 mbar) until drying was complete to give Cannabidiol API.

Confirmation batches for three representative lots of starting material prepared by Protocol 4 are provided in Tables 41 and 42. An analysis of potential impurities is provided in Table 43.

TABLE 41

Crude CBD Generated by Protocol 4

| Information | | confirmation 1 | confirmation 2 | confirmation 3 |
|---|---|---|---|---|
| scale (input DBO) | — | 50 g (1-L vessel) | 50 g (1-L vessel) | 500 g (10-L vessel) |
| yield (% yield) | — | 28.5 g (61.3%) | 29.1 g (62.7%) | 336 9 (72.2%) |

TABLE 41-continued

Crude CBD Generated by Protocol 4

| Information | | confirmation 1 | confirmation 2 | confirmation 3 |
|---|---|---|---|---|
| Proposed Regulatory Parameters | acceptance criteria | | | |
| appearance | white to off-white to beige solid | off-white | off-white | off-white |
| ID by HPLC retention time | corresponds to reference | pass | pass | pass |
| purity by HPLC | NMT 97.0% | 99.62% (assay) | 99.95% (assay) | 100.07% (assay) |
| related substances by HPLC | | | | |
| olivetol | NMT 0.15% w/w | <0.03% (ND) | <0.03% (ND) | <0.03% (ND) |
| total impurities | NMT 3.0% w/w | 0.17% | 0.16% | 0.09% |
| Proposed In-House Parameters | acceptance criteria | | | |
| related substances by HPLC | | | | |
| 4-monobromo-CBD | NMT 0.70% w/w | 0.08% | 0.05% | 0.03% |
| Δ9-tetrahydrocannabinol | NMT 0.30% w/w | <0.02% (ND) | <0.02% (ND) | <0.02% (ND) |
| RRT 1.98 | NMT 0.10% w/w | 0.09% | 0.06% | 0.09% |
| RRT 2.24 | NMT 0.25% w/w | 0.03% | 0.06% | 0.04% |
| Individual unspecified | NMT 0.10% w/w | 0.09% | 0.06% | 0.09% |
| FIO Testing (API Parameters) | acceptance criteria | | | |
| identity (IR) | FIO (matches reference) | pass | pass | pass |
| water content | FIO (NMT 0.5%) | 0.0% (0.03%) | 0.0% (0.02%) | 0.0% (0.02%) |
| residue on ignition | FIO (NMT 0.2%) | 0.0% (0.02%) | 0.1% (0.09%) | 0.1% (0.00%) |
| assay by HPLC | FIO (97.0 to 102.0%) | 99.62% (assay) | 99.95% (assay) | 100.07% (assay) |
| Δ9-THC impurity (HPLC Ppm) | FIO | <4 ppm (2 ppm) | <4 ppm (ND) | 57 ppm |
| Δ8-THC impurity (HPLC ppm) | FIO | <4 ppm (2 ppm) | 4 ppm | 37 ppm |
| THC stability at 55° C. | FIO | 2 ppm/day | 33 ppm/day | 17 ppm/day |
| sample number | — | C14306 | C14307 | C14328 |
| residual solvents by GC | | | | |
| 2-propanol | FIO (NMT 5000 ppm) | <300 ppm (ND) | <300 ppm (ND) | <300 ppm (ND) |
| n-heptane | FIO (NMT 5000 ppm) | 1488 ppm | 1403 ppm | 2620 ppm |
| dichloromethane | FIO (NMT 600 ppm) | <60 ppm (ND) | <60 ppm (ND) | <60 ppm (ND) |
| isooctane | FIO (NMT 5000 ppm) | <500 ppm (99 ppm) | <500 ppm (135 ppm) | <500 ppm (225 ppm) |
| triethylamine | FIO (NMT 5000 ppm) | <500 ppm (60 ppm) | <500 ppm (79 ppm) | <500 ppm (53 ppm) |

TABLE 42

Recrystallized CBD Generated by Protocol 4

| Information | | confirmation 1 | confirmation 2 | confirmation 3 |
|---|---|---|---|---|
| scale (input CBD) | — | 10 g (100 mL vessel) | 10 g (100 mL vessel) | 100 g (1-L vessel) |
| yield (% yield) | — | 9.4 g (94%) | 9.4 g (94%) | 94.0 g (94.0%) |
| Proposed Regulatory Parameters | acceptance criteria | | | |
| appearance | white to off-white to beige solid | off-white | off-white | off-white |
| identification by IR | FIO (matches reference) | pass | pass | Pass |
| identification by HPLC retention time | corresponds to reference | pass | pass | Pass |
| water content | FIO (NMT 0.5%) | 0.0% (0.03%) | 0.0% (0.02%) | 0.0% (0.03%) |
| residue on ignition | FIO (NMT 0.2%) | 0.0% (0.00%) | 0.1% (0.07%) | 0.1% (0.06%) |
| assay by HPLC | FIO (97.0 to 102.0%) | 100.35% (assay) | 101.02% (assay) | 101.15% (assay) |
| related substances by HPLC | | | | |
| olivetol | NMT 0.15% w/w | <0.03% (ND) | <0.03% (ND) | <0.03% (ND) |
| 4-monobromo-CBD | NMT 0.15%w/w | <0.03% (ND) | <0.03% (ND) | <0.03% (ND) |
| Δ9-tetrahydrocannabinol | NMT 0.10% w/w | ND (<0.02%) | ND (<0.02%) | ND (<0.02%) |
| Individual unspecified | NMT 0.10% w/w | 0.06% | 0.05% | 0.07% |
| total impurities | NMT 1.0% w/w | 0.06% | 0.05% | 0.07% |

TABLE 42-continued

Recrystallized CBD Generated by Protocol 4

| Information | | confirmation 1 | confirmation 2 | confirmation 3 |
|---|---|---|---|---|
| residual solvents by GC | | | | |
| 2-propanol | FIO (NMT 5000 ppm) | <300 ppm (ND) | <300 ppm (ND) | <300 ppm (ND) |
| n-heptane | FIO (NMT 5000 ppm) | <500 ppm (8 ppm) | <500 ppm (2 ppm) | <500 ppm (3 ppm) |
| dichloromethane | FIO (NMT 600 ppm) | <60 ppm (ND) | <60 ppm (ND) | <60 ppm (ND) |
| isooctane | FIO (NMT 5000 ppm) | 502 ppm | <500 ppm (367 ppm) | <500 ppm (467 ppm) |
| triethylamine | FIO (NMT 5000 ppm) | <500 ppm (32 ppm) | <500 ppm (45 ppm) | <500 ppm (33 ppm) |
| specific optical rotation | FIO (−140° to −122°) | TBD | TBD | TBD |
| sample number | — | C14330 | C14331 | C14332 |
| Proposed In-House Parameters | acceptance criteria | | | |
| Δ9-THC impurity (HPLC ppm) | FIO | <4 ppm (ND) | <4 ppm (ND) | <4 ppm (ND) |
| THC stability at 55° C. | FIO | 9 ppm/day | 4 ppm/day | 1 ppm/day |
| insoluble matter | FIO (NSFM) | TBD | TBD | TBD |
| particle size | FIO | TBD | TBD | TBD |
| clarity of solution | FIO | TBD | TBD | TBD |
| FIO Testing | acceptance criteria | | | |
| related substances by HPLC | | | | |
| RRT 1.98 | FIO (NMT 0.10%) | 0.06 | 0.05 | 0.07 |
| RRT 2.24 | FIO (NMT 0.10%) | ND | ND | ND |
| Δ8-THC impurity (HPLC ppm) | FIO | <4 ppm (ND) | <4 ppm (ND) | <4 ppm (ND) |
| XRPD | FIO | TBD | TBD | TBD |

TABLE 43

| Impurity | Structure | Resolution in cCBD |
|---|---|---|
| Olivetol | (structure: 5-pentylbenzene-1,3-diol) | Olivetol formed in the cCBD step by the debromination of unreacted DBO and the impurity 2,4,6-tribromo-olivetol. The olivetol content was reduced after treatment with carbon. In situ levels of olivetol prior to carbon treatment were 0.5-1.5% and nondetectable after, with typical levels of nondetectable (<0.03%) in the isolated products cCBD and CBD. |
| 4-Monobromo-cannabinol | (structure of 4-monobromo-CBD with Br substituent) | 4-Monobromo-CBD (MB-CBD) formed as an in situ intermediate during the debromination of 4,6-dibromo-cannabidiol (DB-CBD)-MB-CBD was controlled by the debromination conditions and by IPC. Residual levels were reduced by crystallization and isolation, with typical levels <0.05% in cCBD and nondetectable in CBD. |
| Δ9-Tetrahydro-cannabinol | (structure of Δ9-THC) | Δ9-THC formed by the ring closure of CBD in the presence of heat and a catalyst (protic acid, Lewis acid, etc.). Levels of Δ9-THC were reduced by crystallization and isolation. Typical levels observed in situ were <0.2%, and nondetectable (<0.02%) in cCBD and CBD. |
| RRT 1.98 | NA (unconfirmed) | RRT 1.98 was observed in crude CBD. Analysis of the impurity by mass suggested that it could be a CBD analog coupled with two menthadienol molecules.<br>The presence of RRT 1.98 was primarily reduced in the filtrate during |

TABLE 43-continued

| Impurity | Structure | Resolution in cCBD |
|---|---|---|
| RRT 2.24 | NA (unconfirmed) | isolation. Typical levels of RRT 1.98 in cCBD were 0.04 to 0.08%. RRT 1.98 was observed up to 0.10% in CBD in some processing conditions but was usually <0.05% in the isolated product. RRT 2.24 was observed in crude CBD. Analysis of the impurity by mass suggested it could be a CBD analog coupled with two menthadienol molecules. The presence of RRT 2.24 was primarily reduced in the filtrate during isolation. Typical levels of RRT 2.24 in cCBD were 0.03% to 0.15% and <0.05% in CBD. |

Example 22: Protocol 5

Cannabidiol obtained via protocol 2 underwent a rework procedure. Briefly, cannabidiol (100 kg) was dissolved in isopropanol (298.7 kg) and combined with an aqueous (4.0 L) solution of Na-ascorbate (5.0 kg) at room temperature (15 to 60° C.). Triethylamine (64.4 kg) was added and the reaction was stirred at reflux (79 to 81° C.) for approximately 1 h. The reaction solvent (isopropanol/triethylamine/water) was partially distilled off at atmospheric pressure to 5 volumes and n-heptane (342 kg) was added (25 to 40° C.). The suspension was acidified with concentrated HCl to pH 4.0. After layer separation, the organic layer was washed with a sodium ascorbate/phosphate buffer (pH 7) and finally with an aqueous (4.0 L) sodium ascorbate (5.0 kg) solution. The organic layer was diluted with n-heptane (136.8 kg) and passed through a polishing filter. The solution was concentrated by distillation (200 mbar vacuum) to 4 volumes. The organic solution was cooled to approximately 30° C., seeded with CBD, and stirred at seeding temperature for 1 h. The suspension was cooled to −10° C. over 3 h. After stirring for 1 h at −10° C., the white suspension was filtered, and the wet cake was washed with cold isooctane over the reactor. The wet product was (optionally) dried at 40° C. (<10 mbar) for 12 to 24 h.

CBD (wet or dried) from the previous step was dissolved in isooctane (259.1 kg) and heated to 40° C. The solution was cooled to 32° C., seeded with CBD (1.0 kg) and stirred at 32° C. for 1 h. The suspension was cooled to −10° C. over 3 h and the white suspension was filtered and the wet cake was washed with cold isooctane. The wet product was dried at 40° C. (<10 mbar) for 12 to 24 h.

Example 23: Stability Studies of CBD Prepared Via Protocol 5

Four different batches of CBD prepared by Protocol 5 were packaged into double low-density polyethylene (LDPE) bags in a high-density polyethylene brown bottle. The stability of the material was then evaluated at different storage conditions (5° C., 25° C./60% RH and 40° C./75% RH). The specification against which the samples were evaluated is provided in Table 44. The results for each of the four samples are provided in Tables 45-48.

TABLE 44

| Parameters | Specification | Test Method | Method |
|---|---|---|---|
| Appearance | White to off-white to beige crystalline powder | Visual | Compendial |
| Identity by HPLC | Retention time corresponds to reference | in House Method | Qualified |
| HPLC Purity in % w/w: | | In House Method | Qualified |
| Olivetol | ≤0.15% w/w | | |
| 4-Mono-Bromo-CBD | ≤0.15% w/w | | |
| D9 THC | ≤0.10% w/w (PPM: Level: FIO) | | |
| Each unspecified impurity | ≤0.10% w/w | | |
| Sum of impurities | ≤1.0% relative | | |
| HPLC Assay (anhydrous basis) | 97.0-102.0% w/w | In House Method | Qualified |
| Water Content | ≤0.5% | USP <921> | Compendial |
| Specific Optical Rotation | −140° to −122° | USP <781> | Compendial |

TABLE 45

| Test | Specification | 0 month | 1 month 5° C. | 1 month 25° C./60% RH | 1 month Accelerated 40° C./75% RH | 1.5 months 25° C./60% RH | 1.5 months Accelerated 40° C./75% RH |
|---|---|---|---|---|---|---|---|
| Appearance | White to off-white to beige crystalline powder | White crystalline powder | White crystalline powder | White crystalline powder | Almost white crystalline powder | Almost white crystalline powder | Almost white crystalline powder |

TABLE 45-continued

| Identification by HPLC | Retention time corresponds to reference | Corresponds to reference | Corresponds to reference | Corresponds to reference | Corresponds to reference | Corresponds to reference | Corresponds to reference |
|---|---|---|---|---|---|---|---|
| Assay by HPLC (on dried basis) Chromatographic Purity | 97.0% to 102.0% w/w | 99.4% | 99.8% | 100.0% | 99.8% | 99.5% | 100.4% |
| Olivetol | ≤0.15% w/w | <0.03% (ND*) | <0.03% (ND*) | <0.03% (ND*) | <0.03% (ND*) | <0.03% (ND*) | <0.03% (ND*) |
| Δ9-Tetrahydrocannabinol | ≤0.10% w/w | <0.02% (ND*) | <0.02% (ND*) | <0.02% (ND*) | <0.02% (ND*) | <0.02% (ND*) | <0.02% (ND*) |
| Δ8-Tetrahydrocannabinol | ≤0.10% w/w | <0.02% (ND*) | <0.02% (ND*) | <0.02% (ND*) | <0.02% (ND*) | <0.02% (ND*) | <0.02% (ND*) |
| 4-Monobromo-cannabidiol | ≤0.15% w/w | <0.03% (ND*) | <0.03% (ND*) | <0.03% (ND*) | <0.03% (ND*) | <0.03% (ND*) | <0.03% (ND*) |
| Individual unspecified impurity | ≤0.10% relative | <0.03% (ND*) | <0.03% (ND*) | <0.03% (ND*) | <0.03% (ND*) | <0.03% (ND*) | <0.03% (ND*) |
| Sum of impurities Chromatographic Purity (Low level) | ≤1.0% w/w | <0.05% (ND*) | <0.05% (ND*) | <0.05% (ND*) | <0.05% (ND*) | <0.05% (ND*) | <0.05% (ND*) |
| Δ9-Tetrahydrocannabinol | For information only | <4 ppm (ND*) | <4 ppm (ND*) | <4 ppm (ND*) | <4 ppm (ND*) | <4 ppm (ND*) | <4 ppm (ND*) |
| Δ8-Tetrahydrocannabinol | For information only | <4 ppm (ND*) | <4 ppm (ND*) | <4 ppm (ND*) | <4 ppm (ND*) | <4 ppm (ND*) | <4 ppm (ND*) |
| Water Content (Coulometer) | ≤0.5% | <0.05% (ND*) | 0.1% | 0.1% | <0.05% (ND*) | <0.05% (0.01%) | <0.05% (ND*) |

| Test | Specification | 2 months Accelerated 40° C./75% RH | 3 months Accelerated 40° C./75% RH | 5 months Accelerated 40° C./75% RH | 6 months 25° C./60% RH | 6 months Accelerated 40° C./75% RH |
|---|---|---|---|---|---|---|
| Appearance | White to off-white to beige crystalline powder | Almost white crystalline powder | Almost white crystalline powder | Almost white crystalline powder | Almost white crystalline powder | Almost white crystalline powder |
| Identification by HPLC | Retention time corresponds to reference | Corresponds to reference | Corresponds to reference | Corresponds to reference | Corresponds to reference | Corresponds to reference |
| Assay by HPLC (on dried basis) Chromatographic Purity | 97.0% to 102.0% w/w | 100.1% | 99.1% | 100.4% | 100.0% | 99.4% |
| Olivetol | ≤0.15% w/w | <0.03% (ND*) | <0.03% (ND*) | <0.03% (ND*) | <0.03% (ND*) | <0.03% (ND*) |
| Δ9-Tetrahydrocannabinol | ≤0.10% w/w | <0.02% (ND*) | <0.02% (ND*) | <0.02% (ND*) | <0.02% (ND*) | <0.02% (ND*) |
| Δ8-Tetrahydrocannabinol | ≤0.10% w/w | <0.02% (ND*) | <0.02% (ND*) | <0.02% (ND*) | <0.02% (ND*) | <0.02% (ND*) |
| 4-Monobromo-cannabidiol | ≤0.15% w/w | <0.03% (ND*) | <0.03% (ND*) | <0.03% (ND*) | <0.03% (ND*) | <0.03% (ND*) |
| Individual unspecified impurity | ≤0.10% relative | <0.03% (ND*) | <0.03% (0.01%) | <0.03% (ND*) | <0.03% (ND*) | <0.03% (ND*) |
| Sum of impurities Chromatographic Purity (Low level) | ≤1.0% w/w | <0.05% (ND*) | <0.05% | <0.05% (ND*) | <0.05% (ND*) | <0.05% (ND*) |
| Δ9-Tetrahydrocannabinol | For information only | <4 ppm (ND*) | <4 ppm (ND*) | <4 ppm (ND*) | <4 ppm (ND*) | <4 ppm (ND*) |
| Δ8-Tetrahydrocannabinol | For information only | <4 ppm (ND*) | <4 ppm (ND*) | <4 ppm (ND*) | <4 ppm (ND*) | <4 ppm (ND*) |

TABLE 45-continued

| | | | | | | |
|---|---|---|---|---|---|---|
| Water Content (Coulometer) | ≤0.5% | <0.05% (0.01%) | <0.05% (0.01%) | <0.05% (0.02%) | <0.05% (0.02%) | <0.05% (0.01%) |

TABLE 46

| Test | Specification | 0 month | 1 month 5° C. | 1 month 25° C./60% RH | 1 month Accelerated 40° C./75% RH | 2 months Accelerated 40° C./75% RH | 3 months Accelerated 40° C./75% RH | 6 months 25° C./60% RH | 6 months Accelerated 40° C./75% RH |
|---|---|---|---|---|---|---|---|---|---|
| Appearance | White to off-white to beige crystalline powder | White crystalline powder | White crystalline powder | White crystalline powder | Almost white crystalline powder | Almost white crystalline powder | Almost white crystalline powder | Almost white crystalline powder | Almost white crystalline powder |
| Identification by HPLC | Retention time corresponds to reference | Corresponds to reference | Corresponds to reference | Corresponds to reference | Corresponds to reference | Corresponds to reference | Corresponds to reference | Corresponds to reference | Corresponds to reference |
| Assay by HPLC (on dried basis) | 97.0% to 102.0% w/w | 99.8% | 100.1% | 99.9% | 99.5% | 99.9% | 98.8% | 100.0% | 99.9% |
| Chromatographic Purity | | | | | | | | | |
| Olivetol | ≤0.15% w/w | <0.03% (ND*) | <0.03% (ND*) | <0.03% (ND*) | <0.03% (ND*) | <0.03% (ND*) | <0.03% (ND*) | <0.03% (ND*) | <0.03% (ND*) |
| Δ9-Tetrahydrocannabinol | ≤0.10% w/w | <0.02% (ND*) | <0.02% (ND*) | <0.02% (ND*) | <0.02% (ND*) | <0.02% (ND*) | <0.02% (ND*) | <0.02% (ND*) | <0.02% (ND*) |
| Δ8-Tetrahydrocannabinol-THC | ≤0.10% w/w | <0.02% (ND*) | <0.02% (ND*) | <0.02% (ND*) | <0.02% (ND*) | <0.02% (ND*) | <0.02% (ND*) | <0.02% (ND*) | <0.02% (ND*) |
| 4-Monobromo-cannabidiol | ≤0.15% w/w | <0.03% (ND*) | <0.03% (ND*) | <0.03% (ND*) | <0.03% (ND*) | <0.03% (ND*) | <0.03% (ND*) | <0.03% (ND*) | <0.03% (ND*) |
| Individual unspecified impurity | ≤0.10 % relative | <0.03% (ND*) | <0.03% (ND*) | <0.03% (ND*) | <0.03% (ND*) | <0.03% (ND*) | <0.03% (0.01%) | <0.03% (ND*) | <0.03% (ND*) |
| Sum of impurities | ≤1.0% w/w | <0.05% (ND*) | <0.05% (ND*) | <0.05% (ND*) | <0.05% (ND*) | <0.05% (ND*) | <0.05% | <0.05% (ND*) | <0.05% (ND*) |
| Chromatographic Purity (Low level) | | | | | | | | | |
| Δ9-Tetrahydrocannabinol | For information only | <4 ppm (ND*) | <4 ppm (ND*) | <4 ppm (ND*) | <4 ppm (ND*) | <4 ppm (ND*) | <4 ppm (ND*) | <4 ppm (ND*) | <4 ppm (ND*) |
| Δ8-Tetrahydrocannabinol | For information only | <4 ppm (ND*) | <4 ppm (ND*) | <4 ppm (ND*) | <4 ppm (ND*) | <4 ppm (ND*) | <4 ppm (ND*) | <4 ppm (ND*) | <4 ppm (ND*) |
| Water Content (Coulometer) | ≤0.5% | <0.05% (ND*) | 0.1% | 0.1% | 0.1% | <0.05% (0.01%) | <0.05% (0.01%) | <0.05% (0.01%) | <0.05% (0.01%) |

ND* not detected

TABLE 47

| Test | Specification | 0 month | 1 month 5° C. | 1 month 25° C./60% RH | 1 month Accelerated 40° C./75% RH | 2 months Accelerated 40° C./75% RH | 3 months Accelerated 40° C./75% RH | 6 months 25° C./60% RH | 6 months Accelerated 40° C./75% RH |
|---|---|---|---|---|---|---|---|---|---|
| Appearance | White to off-white to beige crystalline powder | Almost White crystalline powder | Almost White crystalline powder | Almost White crystalline powder | Almost White crystalline powder | Almost White crystalline powder | Almost White crystalline powder | Almost White crystalline powder | Almost White crystalline powder |
| Identification by HPLC | Retention time corresponds to reference | Corresponds to reference | Corresponds to reference | Corresponds to reference | Corresponds to reference | Corresponds to reference | Corresponds to reference | Corresponds to reference | Corresponds to reference |
| Assay by HPLC (on dried basis) | 97.0% to 102.0% w/w | 99.9% | 100.4% | 98.3% | 100.3% | 99.8% | 99.4% | 99.6% | 99.8% |

TABLE 47-continued

| Test | Specification | 0 month | 1 month 5° C. | 1 month 25° C./60% RH | 1 month Accelerated 40° C./75% RH | 2 months Accelerated 40° C./75% RH | 3 months Accelerated 40° C./75% RH | 6 months 25° C./60% RH | 6 months Accelerated 40° C./75% RH |
|---|---|---|---|---|---|---|---|---|---|
| Chromatographic Purity | | | | | | | | | |
| Olivetol | ≤0.15% w/w | <0.03% | <0.03% | <0.03% | <0.03% | <0.03% | <0.03% | <0.03% | <0.03% |
| Δ9-Tetrahydrocannabinol | ≤0.10% w/w | <0.02% (ND*) | <0.02% (ND*) | <0.02% (ND*) | <0.02% (ND*) | <0.02% (ND*) | <0.02% (ND*) | <0.02% (ND*) | <0.02% (ND*) |
| Δ8-Tetrahydrocannabinol-THC | ≤0.10% w/w | <0.02% (ND*) | <0.02% (ND*) | <0.02% (ND*) | <0.02% (ND*) | <0.02% (ND*) | <0.02% (ND*) | <0.02% (ND*) | <0.02% (ND*) |
| 4-Monobromo-cannabidiol | ≤0.15% w/w | <0.03% (ND*) | <0.03% (ND*) | <0.03% (ND*) | <0.03% (ND*) | <0.03% (ND*) | <0.03% (ND*) | <0.03% (ND*) | <0.03% (ND*) |
| Individual unspecified impurity | ≤0.10% relative | <0.03% (ND*) | <0.03% (ND*) | <0.03% (ND*) | <0.03% (ND*) | <0.03% (ND*) | <0.03% (ND*) (0.01%) | <0.03% (ND*) | <0.03% (ND*) |
| Sum of impurities | ≤1.0% w/w | <0.05% (ND*) | <0.05% (ND*) | <0.05% (ND*) | <0.05% (ND*) | <0.05% (ND*) | <0.05% | <0.05% (ND*) | <0.05% (ND*) |
| Chromatographic Purity (Low level) | | | | | | | | | |
| Δ9-Tetrahydrocannabinol | For information only | 10 ppm | 8 ppm | 6 ppm | 5 ppm | 6 ppm | 5 ppm | <4 ppm (ND*) | <4 ppm (ND*) |
| Δ8-Tetrahydrocannabinol | For information only | 6 ppm | <4 ppm (ND*) | <4 ppm (ND*) | <4 ppm (ND*) | <4 ppm (ND*) | <4 ppm (ND*) | <4 ppm (ND*) | <4 ppm (ND*) |
| Water Content (Coulometer) | ≤0.5% | <0.05% (ND*) | 0.1% | 0.1% | 0.1% | <0.05% (0.01%) | <0.05% (0.01%) | <0.05% (0.01%) | <0.05% (0.02%) |

ND*: not detected

TABLE 48

| Test | Specification | 0 month | 1 month 5° C. | 1 month 25° C./60% RH | 1 month Accelerated 40° C./75% RH | 2 months Accelerated 40° C./75% RH | 3 months Accelerated 40° C./75% RH | 6 months 25° C./60% RH | 6 months Accelerated 40° C./75% RH |
|---|---|---|---|---|---|---|---|---|---|
| Appearance | White to off-white to beige crystalline powder | Almost White crystalline powder | Almost White crystalline powder | Almost White crystalline powder | Almost White crystalline powder | Almost White crystalline powder | Almost White crystalline powder | Almost White crystalline powder | Almost White crystalline powder |
| Identification by HPLC | Retention time corresponds to reference | Corresponds to reference | Corresponds to reference | Corresponds to reference | Corresponds to reference | Corresponds to reference | Corresponds to reference | Corresponds to reference | Corresponds to reference |
| Assay by HPLC (on dried basis) | 97.0% to 102.0% w/w | 100.1% | 100.3% | 99.5% | 99.9% | 100.0% | 98.2% | 99.5% | 99.4% |
| Chromatographic Purity | | | | | | | | | |
| Olivetol | <0.15% | <0.03% | <0.03% | <0.03% | <0.03% | <0.03% | <0.03% | <0.03% | <0.03% |
| Δ9-Tetrahydrocannabinol | ≤0.10% w/w | <0.02% (ND*) | <0.02% (ND*) | <0.02% (ND*) | <0.02% (ND*) | <0.02% (ND*) | <0.02% (ND*) | <0.02% (ND*) | <0.02% (ND*) |
| Δ8-Tetrahydrocannabinol-THC | ≤0.10% w/w | <0.02% (ND*) | <0.02% (ND*) | <0.02% (ND*) | <0.02% (ND*) | <0.02% (ND*) | <0.02% (ND*) | <0.02% (ND*) | <0.02% (ND*) |
| 4-Monobromo-cannabidiol | ≤0.15% w/w | <0.03% (ND*) | <0.03% (ND*) | <0.03% (ND*) | <0.03% (ND*) | <0.03% (ND*) | <0.03% (ND*) | <0.03% (ND*) | <0.03% (ND*) |
| Individual unspecified impurity | ≤0.10% rew/w | <0.03% (ND*) | <0.03% (ND*) | <0.03% (ND*) | <0.03% (ND*) | <0.03% (ND*) | <0.03% (ND*) (0.01%) | <0.03% (ND*) | <0.03% (ND*) |
| Sum of impurities | ≤1.0% w/w | <0.05% | <0.05% | <0.05% | <0.05% | <0.05% | <0.05% | <0.05% | <0.05% |
| Chromatographic Purity (Low level) | | | | | | | | | |
| Δ9-Tetrahydrocannabinol | For information only | 10 ppm | 9 ppm | 10 ppm | 6 ppm | 7 ppm | 6 ppm | <4 ppm (ND*) | <4 ppm (ND*) |

TABLE 48-continued

| Test | Specification | 0 month | 1 month 5° C. | 1 month 25° C./60% RH | 1 month Accelerated 40° C./75% RH | 2 months Accelerated 40° C./75% RH | 3 months Accelerated 40° C./75% RH | 6 months 25° C./60% RH | 6 months Accelerated 40° C./75% RH |
|---|---|---|---|---|---|---|---|---|---|
| Δ8-Tetrahydrocannabinol | For information only | 6 ppm | <4 ppm (3 ppm) | 4 ppm | <4 ppm (ND*) | <4 ppm (2 ppm) | <4 ppm (ND*) | <4 ppm (ND*) | <4 ppm (ND*) |
| Water Content (Coulometer) | <0.5% | <0.05% (ND*) | 0.1% | 0.1% | 0.1% | <0.05% (0.01%) | <0.05% (0.01%) | <0.05% (0.01%) | <0.05% (0.01%) |

ND*: not detected

As shown by the data in Tables 45-48, the appearance analyses, HPLC assays, and impurity results were within specification. The water content was also within specification.

Example 24: Carbon Treatment Experiments

Figure 35:
FIG. 35 shows CBD treated with active carbon (left) and CBD not treated with active carbon (right).
Figure 36:
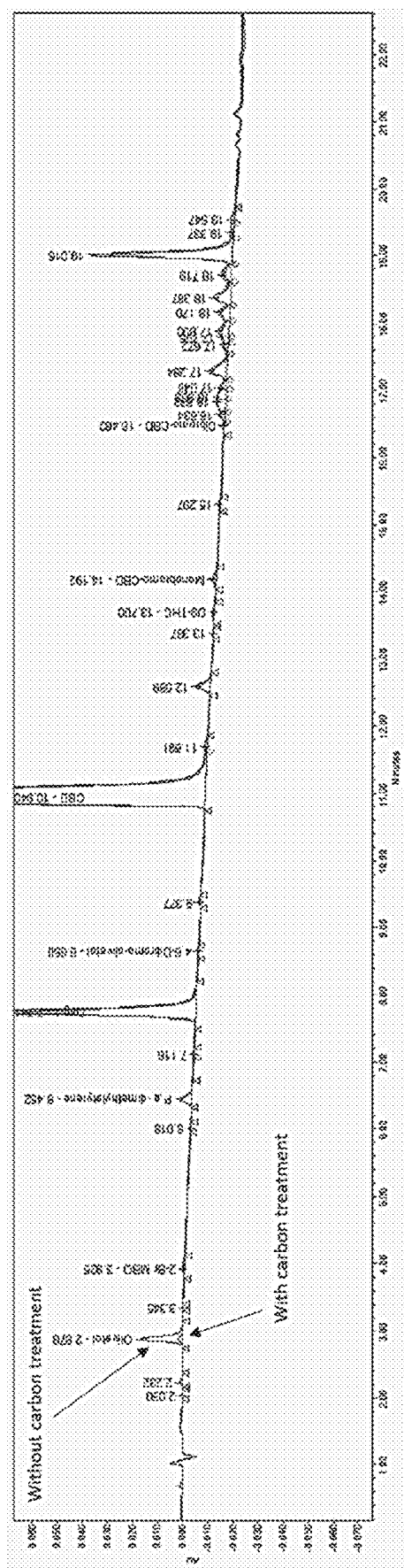
FIG. 36 shows the impurity profile of the pre-crystallization CBD reaction mixture pre-carbon and post-carbon treatment.

Carbon treatment was utilized to (i) improve the color of the CBD product and (ii) to remove olivetol (an impurity that purges poorly during the crystallization) prior to the crystallization of crude CBD. FIG. 35 displays the color improvement of the crude CBD product after treatment with carbon. This color was found to persist in the final crystallization of pure CBD. FIG. 36 shows the impurity profile, by HPLC, pre- and post-carbon treatment. The impurity profile exhibits a reduction in olivetol. It was concluded that activated carbon is a strong adsorbent for olivetol and an effective means to reduce the presence of this impurity from the process.

A variety of activated carbon types were tested in the CBD synthesis. In several experiments, loose carbon (Norit® CN, Cabot) was charged to the reactor, agitated in the reactor with the CBD solution in heptane, and filtered prior to crystallization. In other preparations of CBD, carbon treatment with encapsulated carbon was trialed and developed. In these experiments, Cuno encapsulated carbon of type R55SP was utilized. Treatment with this carbon type was found to be very effective. Another Cuno carbon type, R53SP, was tested, although it did not prove to be as effective as R55SP. Without wishing to be bound by theory, it is generally understood that different carbon types can adsorb impurities at different efficiencies. Table 49 summarizes the carbon types trialed in the CBD process.

TABLE 49

| Carbon Type | Manufacturer | Decrease in Olivetol |
|---|---|---|
| Norit ® CN | Cabot | Olivetol: 0.26% → 0.02% |
| R55SP | Cabot | Olivetol: 0.91% → 0.07% |
| R53SP | Cabot | Olivetol: 0.90% → 0.21% |

Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A composition comprising cannabidiol and delta-9-tetrahydrocannabinol, wherein said delta-9-tetrahydrocannabinol is present in an amount less than 10 ppm.

2. The composition of claim 1, comprising cannabidiol and delta-9-tetrahydrocannabinol, wherein said delta-9-tetrahydrocannabinol is present in an amount less than 6 ppm.

3. The composition of claim 1, comprising cannabidiol and delta-9-tetrahydrocannabinol, wherein said delta-9-tetrahydrocannabinol is present in an amount less than 2 ppm.

4. The composition of claim 1, comprising cannabidiol and delta-9-tetrahydrocannabinol, wherein said delta-9-tetrahydrocannabinol is present in an amount from about 0.1 ppm to 6 ppm.

5. The composition of claim 1, wherein said cannabidiol is crystalline.

6. The composition of claim 1, wherein said cannabidiol is crystalline polymorph Form A.

7. The composition of claim 1, wherein said crystalline polymorph Form A comprises at least one X-ray powder diffraction peak in degrees 2θ±0.07 selected from the group consisting of 5.07, 8.28, 9.30, 9.70, 10.20, 11.74, 12.49, 13.12, 13.80, 15.08, 15.35, 16.05, 16.57, 17.36, 17.93, 18.79, 18.96, 19.44, 19.79, 20.55, 20.82, 21.61, 22.11, 22.63, 22.99, 23.68, 24.40, 25.28, 26.45, 26.76, 27.46, 27.70, 28.45, 29.06, 31.07, 32.60, 33.31, 34.03, 34.57, 35.31, 36.49, and 37.79.

8. The composition of claim 6, wherein said crystalline polymorph Form A exhibits a characteristic X-ray powder diffraction pattern having peaks in degrees 2θ±0.07 2θ at 9.70, 11.74, 15.08, 17.36, and 18.79.

9. The composition of claim 6, wherein said crystalline polymorph Form A is characterized by a differential scanning calorimetry thermogram with an endotherm having an onset of about 67.72° C. and a peak at about 68.12° C.

10. The composition of claim 1, further comprising at least one compound selected from the group consisting of cannabinol, cannabigerol, delta-8-tetrahydrocannabinol, cannabichromene, cannabicyclol, cannabiyarin, tetrahydrocannabivarin, cannabidivarin, cannabichromevarin, cannabigerovarin, cannabielsoin, cannabicitran, 3,5-dibromo-5'-methyl-4-pentyl-2'-(prop-1-en-2-yl)-1',2',3',4'-tetrahydro-[1,1'-biphenyl]-2,6-diol, 3-bromo-5'-methyl-4-pentyl-2'-(prop-1-en-2-yl)-1',2',3',4'-tetrahydro-[1,1'-biphenyl]-2,6-diol, 4,6-di-bromo olivetol, 4-bromo-5-pentylbenzene-1,3-diol, abnormal cannabidiol (ab-CBD), cannabidiol quinone derivatives (CBQ), 3,5-dibromo-5'-methyl-2'-(prop-1-en-2-yl)-4-propyl-1',2',3',4'-tetrahydro-[1,1'-biphenyl]-2,6-diol, 3,5-dibromo-4-ethyl-5'-methyl-2'-(prop-1-en-2-yl)-1',2',3',4'-tetrahydro-[1,1'-biphenyl]-2,6-diol, 3-bromo-4-ethyl-5'-methyl-2'-(prop-1-en-2-yl)-1',2',3',4'-tetrahydro-[1,1'-biphenyl]-2,6-diol, 4,6-dibromo-5-propylbenzene-1,3-diol, 4-bromo-5-propylbenzene-1,3-diol, 4,6-dibromo-5-ethylbenzene-1,3-diol, 4-bromo-5-ethylbenzene-1,3-diol, 5'-methyl-2'-(prop-1-en-2-yl)-4-propyl-1',2',3',4'-tetrahydro-[1,1'-biphenyl]-2,6-diol, and 4-ethyl-5'-methyl-2'-(prop-1-en-2-yl)-1',2',3',4'-tetrahydro-[1,1'-biphenyl]-2,6-diol.

11. The composition of claim 1, devoid of plant extract material.

12. A stable composition comprising cannabidiol and delta-9-tetrahydrocannabinol, wherein said delta-9-tetrahydrocannabinol is present in an amount less than 10 ppm upon storage for 2 years or less.

13. The stable composition of claim 12, wherein said delta-9-tetrahydrocannabinol is present from about 0.1 ppm to about 9 ppm.

14. The stable composition of claim 12, wherein the cannabidiol is crystalline.

15. A composition comprising cannabidiol and less than 10 ppm delta-9-tetrahydrocannabinol, wherein the ratio of cannabidiol to delta-9-tetrahydrocannabinol is less than 1:0.0001 as measured by UPLC.

16. The composition of claim 15, wherein the cannabidiol is crystalline.

17. A formulation comprising,
cannabidiol,
delta-9-tetrahydrocannabinol, wherein said delta-9-tetrahydrocannabinol is present in an amount less than 10 ppm, and
a pharmaceutically acceptable excipient.

18. The formulation of claim 17, wherein the formulation is in the form of a matrix, a liquid, or a granule.

19. A method of preparing a cannabidiol composition, comprising
contacting di-halo olivetol with menthadienol in the presence of a protic acid catalyst to prepare di-halo cannabidiol;
contacting the di-halo cannabidiol with a reducing agent to prepare a first cannabidiol composition;
contacting the first cannabidiol composition with a first solvent;
crystallizing a second cannabidiol composition from said solvent; and
recrystallizing crystalline cannabidiol composition having less than 10 ppm delta-9-tetrahydrocannabinol from a second solvent.

20. A method of recrystallizing cannabidiol from a mixture of cannabinoids to prepare a composition comprising cannabidiol and less than 10 ppm delta-9-tetrahydrocannabinol, said method comprising,
contacting said mixture of cannabinoids with isooctane to form a solution;
heating said solution to about 40° C.;
cooling the solution to about 32° C.;
seeding said solution at about 32° C. with (−)-Cannabidiol to prepare a suspension;
allowing said suspension to warm to about 32° C. with stirring;
cooling the suspension to −20° C.;
separating a solid material from said suspension;
washing solid material with isooctane at about −20° C.; and
drying the solid material to obtain a crystalline composition comprising cannabidiol and less than 10 ppm delta-9-tetrahydrocannabinol.

* * * * *

UNITED STATES PATENT AND TRADEMARK OFFICE
CERTIFICATE OF CORRECTION

PATENT NO. : 12,144,795 B2
APPLICATION NO. : 17/273643
DATED : November 19, 2024
INVENTOR(S) : Daniel M. Hallow et al.

It is certified that error appears in the above-identified patent and that said Letters Patent is hereby corrected as shown below:

In the Claims

In Column 99, Line 9, Claim 7, delete "claim 1," and insert -- claim 6, --, therefor.

Signed and Sealed this
Sixth Day of May, 2025

Coke Morgan Stewart
*Acting Director of the United States Patent and Trademark Office*